(12) United States Patent
Muehlebach et al.

(10) Patent No.: US 8,084,649 B2
(45) Date of Patent: Dec. 27, 2011

(54) HERBICIDES

(75) Inventors: Michel Muehlebach, Stein (CH);
William Lutz, Riehen (CH); Jean Wenger, Wallbach (CH); John Finney, Bracknell (GB); Christopher John Mathews, Bracknell (GB); Delphine Raymonde Suzanne Fawke, Bracknell (GB)

(73) Assignee: Syngenta Crop Protection, inc., Greensboro, NC (US)

( * ) Notice: Subject to any disclaimer, the term of this patent is extended or adjusted under 35 U.S.C. 154(b) by 0 days.

(21) Appl. No.: 12/530,472

(22) PCT Filed: Mar. 7, 2008

(86) PCT No.: PCT/EP2008/001841
§ 371 (c)(1),
(2), (4) Date: Jan. 19, 2010

(87) PCT Pub. No.: WO2008/110308
PCT Pub. Date: Sep. 18, 2008

(65) Prior Publication Data
US 2010/0173774 A1 Jul. 8, 2010

(30) Foreign Application Priority Data
Mar. 9, 2007 (GB) .................................. 0704652.7

(51) Int. Cl.
C07C 49/403 (2006.01)
C07C 321/10 (2006.01)
C07D 211/82 (2006.01)
C07D 211/96 (2006.01)
C07D 333/00 (2006.01)
A01N 35/06 (2006.01)

(52) U.S. Cl. ............ 568/376; 568/377; 568/31; 568/42; 549/23; 549/331; 546/340; 504/103; 504/246; 504/268; 504/248

(58) Field of Classification Search .................. 568/376, 568/377, 31, 42; 549/23, 331; 546/340; 504/103, 244, 288, 292, 348
See application file for complete search history.

(56) References Cited

U.S. PATENT DOCUMENTS

| 4,209,532 | A | 6/1980 | Wheeler | |
|---|---|---|---|---|
| 5,416,061 | A | 5/1995 | Hewett et al. | |
| 6,376,429 | B1 | 4/2002 | Van Almsick et al. | |
| 6,417,370 | B1 | 7/2002 | Lieb et al. | |
| 2003/0216260 | A1* | 11/2003 | Ruther et al. | 504/283 |
| 2005/0164883 | A1 | 7/2005 | Maetzke et al. | |
| 2007/0135630 | A1 | 6/2007 | Fischer et al. | |
| 2010/0087320 | A1 | 4/2010 | Lieb et al. | |
| 2010/0113270 | A1 | 5/2010 | Mathews et al. | |
| 2010/0210466 | A1 | 8/2010 | Muehlebach et al. | |

FOREIGN PATENT DOCUMENTS

| CA | 2041793 | 11/1991 |
|---|---|---|
| CA | 2322158 | 8/2000 |
| CA | 2325526 | 9/2000 |
| CA | 2443642 | 10/2003 |
| CA | 2456776 | 2/2004 |
| CA | 2346796 | 1/2009 |
| DE | 2641343 | 4/1977 |
| EP | 0253537 | 6/1987 |
| EP | 0456089 | 4/1991 |
| RU | 2254328 | 6/2005 |
| WO | 9943649 | 9/1999 |
| WO | 9948869 | 9/1999 |
| WO | 0021924 | 4/2000 |
| WO | 0174770 | 10/2001 |
| WO | 03013249 | 2/2003 |
| WO | 2004022559 | 3/2004 |
| WO | 2004085661 | 10/2004 |
| WO | 2004087650 | 10/2004 |
| WO | 2008071405 | 6/2008 |
| WO | 2008110307 | 9/2008 |

OTHER PUBLICATIONS

Mai, Antonello et al: "5-Alkyl-2-alkylamino-6-(2,6-difluorophenylalkyl)-3,4-dihydropyrimidin-4(3H)-ones, a new series of potent, broad-spectrum non-nucleoside reverse transcriptase inhibitors belonging to the DABO family," Bioorganic & Medicinal Chemistry, vol. 13, No. 6, 2005, pp. 2065-2077, XP004759007.

Negishi, Eiichi et al: "Palladium-catalyzed carbonylative cyclization via trapping of acylpalladium derivatives with itnernal enolates. Its scope and factors affecting the C-to-O ratio;" Tetrahedron, vol. 50, No. 2, 1994, pp. 425-436, XP002498419, p. 428.

Monostroy et al: "New derivatives on carbon atom 6 of 2-thiouracil with antithyroidal effects;" Anales De La Asociatcion Quimica Argentina, vol. 40, Jan. 1, 1952, pp. 99-108, XP009106453.

* cited by examiner

Primary Examiner — Sikarl Witherspoon
(74) Attorney, Agent, or Firm — James Cueva

(57) ABSTRACT

Cyclohexanedione compounds, and derivatives thereof, which are substituted in 5-position, are suitable for use as herbicides. The cyclohexanedione compounds and derivatives of the invention are compounds of formula (I)

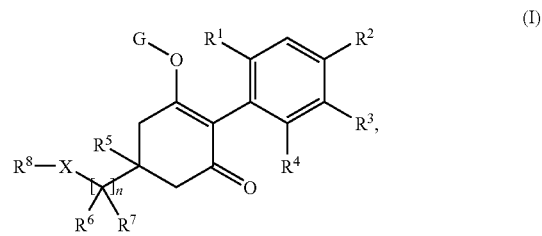

wherein the substituents are as defined in the description.

47 Claims, No Drawings

HERBICIDES

This application is a 371 of International Application No. PCT/EP2008/001841 filed Mar. 7, 2008, which claims priority to GB 0704652.7 filed Mar. 9, 2007, the contents of which are incorporated herein by reference.

The present invention relates to novel, herbicidally active cyclic diones, and derivatives thereof, to processes for their preparation, to compositions comprising those compounds, and to their use in controlling weeds, especially in crops of useful plants, or in inhibiting plant growth.

Cyclic diones having herbicidal action are described, for example, in WO 01/74770.

Novel cyclohexanedione compounds, and derivatives thereof, having herbicidal and growth-inhibiting properties have now been found.

The present invention accordingly relates to compounds of formula (I)

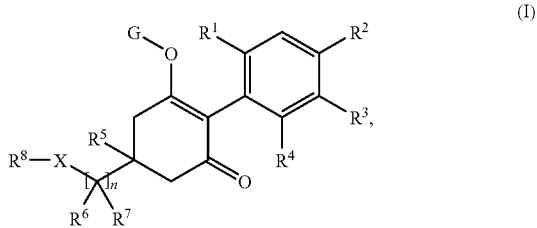

wherein
$R^1$ is methyl, ethyl, n-propyl, iso-propyl, cyclopropyl, halomethyl, haloethyl, halogen, vinyl, ethynyl, methoxy, ethoxy, halomethoxy or haloethoxy, $R^2$ and $R^3$ are, independently of each other hydrogen, halogen, $C_1$-$C_6$alkyl, $C_1$-$C_6$haloalkyl, $C_1$-$C_6$alkoxy, $C_1$-$C_6$haloalkoxy, $C_2$-$C_6$alkenyl, $C_2$-$C_6$haloalkenyl, $C_2$-$C_6$alkynyl, $C_3$-$C_6$alkenyloxy, $C_3$-$C_6$haloalkenyloxy, $C_3$-$C_6$alkynyloxy, $C_3$-$C_6$cycloalkyl, $C_1$-$C_6$alkylthio, $C_1$-$C_6$alkylsulfinyl, $C_1$-$C_6$alkylsulfonyl, $C_1$-$C_6$alkylsulfonyloxy, $C_1$-$C_6$haloalkylsulfonyloxy, cyano, nitro, phenyl, phenyl substituted by $C_1$-$C_4$alkyl, $C_1$-$C_3$haloalkyl, $C_1$-$C_3$alkoxy, $C_1$-$C_3$haloalkoxy, cyano, nitro, halogen, $C_1$-$C_3$alkylthio, $C_1$-$C_3$alkylsulfinyl or $C_1$-$C_3$alkylsulfonyl, or heteroaryl or heteroaryl substituted by $C_4$alkyl, $C_1$-$C_3$haloalkyl, $C_1$-$C_3$alkoxy, $C_1$-$C_3$haloalkoxy, cyano, nitro, halogen, $C_1$-$C_3$alkylthio, $C_1$-$C_3$alkylsulfinyl or $C_1$-$C_3$alkylsulfonyl, $R^4$ is hydrogen, methyl, ethyl, n-propyl, iso-propyl, halomethyl, haloethyl, halogen, vinyl, ethynyl, methoxy, ethoxy, halomethoxy or haloethoxy, n is 0, 1, 2 or 3,
X is O, S, S(O) or S(O)$_2$,
$R^5$ is hydrogen or methyl,
$R^6$ and $R^7$ are independently of each other hydrogen, methyl or ethyl, where, when n is 2 or 3, the meanings of the 4 or 6 substituents $R^6$ and $R^7$ do not have to be the same, $R^8$ is $C_1$-$C_{18}$alkyl, $C_1$-$C_{18}$haloalkyl, $C_3$-$C_7$cycloalkyl, $C_3$-$C_7$cycloalkyl substituted by methyl or ethyl, $C_1$-$C_6$alkoxyC$_1$-$C_{12}$alkyl, $C_1$-$C_6$alkylthioC$_1$-$C_{12}$alkyl, $C_{3-18}$ alkenyl or $C_3$-$C_{18}$ alkenyl substituted by halogen, $C_3$-$C_{18}$alkynyl or $C_3$-$C_{18}$alkynyl substituted by halogen, or $R^5$, when n denotes 1 or 2, and $R^8$ together form a $C_2$-$C_5$ alkylene chain, which is unsubstituted or substituted by methyl or ethyl, or an $C_2$-$C_5$alkenylene chain, which is unsubstituted or substituted by methyl or ethyl, where, when n is 2, the meanings of the 4 substituents $R^6$ and $R^7$ do not have to be the same, or $R^6$, when n denotes 1, and one of $R^5$, $R^7$ and $R^8$ together form a $C_2$-$C_5$alkylene chain, which is unsubstituted or substituted by methyl or ethyl, or an $C_2$-$C_5$alkenylene chain, which is unsubstituted or substituted by methyl or ethyl, and G is hydrogen, an alkali metal, alkaline earth metal, sulfonium, ammonium or a latentiating group.

In the substituent definitions of the compounds of the formula (I), the alkyl substituents and alkyl moieties of alkoxy, alkylamino etc. having 1 to 6 carbon atoms are preferably methyl, ethyl, propyl, butyl, pentyl and hexyl as well as straight and branched isomers thereof. Higher alkyl groups of up to 18 carbon atoms comprise preferably octyl, nonyl, decyl, undecyl and dodecyl. The alkenyl and alkynyl radicals having 2 to 6 carbon atoms as well as up to 18 carbon atoms can be straight or branched and can contain more than 1 double or triple bond, respectively. Examples are vinyl, allyl, propargyl, butenyl, butynyl, pentenyl and pentynyl. Suitable cycloalkyl groups contain 3 to 7 carbon atoms and are for example cyclopropyl, cyclobutyl, cyclopentyl, cyclohexyl and cycloheptyl. Cyclopropyl, cyclobutyl, cyclopentyl and cyclohexyl are preferred. Preferred examples of heteroaryls are thienyl, furyl, pyrrolyl, oxazolyl, thiazolyl, pyrazolyl, imidazolyl, triazolyl, tetrazolyl, pyridyl, pyrimidinyl, pyrazinyl, triazinyl, benzofuryl, benzothienyl, benzothiazolyl, benzoxazolyl, indolyl, quinolinyl and quinoxalinyl groups, and, where appropriate, N-oxides and salts thereof. The group G is hydrogen or an alkali metal, alkaline earth metal, sulfonium (—S($C_1$-$C_6$alkyl$_3$)$^+$), ammonium (—NH$_4^+$ or N($C_1$-$C_6$alkyl)$_4^+$) or a latentiating group. This latentiating group G is selected to allow its removal by one or a combination of biochemical, chemical or physical processes to afford compounds of formula I where G is H before, during or following application to the treated area or plants. Examples of these processes include enzymatic cleavage, chemical hydrolysis and photolysis. Compounds bearing latentiating groups G may offer certain advantages, such as improved penetration of the cuticula of the plants treated, increased tolerance of crops, improved compatibility or stability in formulated mixtures containing other herbicides, herbicide safeners, plant growth regulators, fungicides or insecticides, or reduced leaching in soils. A large number of latentiating groups, which are known in the art, can be used in the new compounds.

The latentiating group G is preferably selected from $C_1$-$C_8$ alkyl, $C_2$-$C_8$ haloalkyl, phenylC$_1$-$C_8$alkyl (wherein the phenyl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$ alkylsulfonyl, halogen, cyano or by nitro), heteroarylC$_1$-$C_8$alkyl (wherein the heteroaryl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$ alkylsulfonyl, halogen, cyano or by nitro), $C_3$-$C_8$ alkenyl, $C_3$-$C_8$ haloalkenyl, $C_3$-$C_8$ alkynyl, C(X$^a$)—R$^a$, C(X$^b$)—X$^c$—R$^b$, C(X$^d$)—N(R$^c$)—R$^d$, —SO$_2$—R$^e$, —P(X$^e$)(R$^f$)—R$^g$ or CH$_2$—X$^f$—R$^h$, wherein X$^a$, X$^b$, X$^c$, X$^d$, X$^e$ and X$^f$ are independently of each other oxygen or sulfur;

$R^a$ is hydrogen, $C_1$-$C_{18}$alkyl, $C_2$-$C_{18}$alkenyl, $C_2$-$C_{18}$alkynyl, $C_1$-$C_{10}$haloalkyl, $C_1$-$C_{10}$cyanoalkyl, $C_1$-$C_{10}$nitroalkyl, $C_1$-$C_{10}$aminoalkyl, $C_2$-$C_8$dialkylaminoC$_1$-$C_5$alkyl, $C_3$-$C_7$cycloalkylC$_1$-$C_5$alkyl, $C_1$-$C_5$alkoxyC$_1$-$C_5$alkyl, $C_3$-$C_5$alkenyloxyC$_1$-$C_5$alkyl, $C_3$-$C_5$alkynylC$_1$-$C_5$oxyalkyl, $C_1$-$C_5$alkylthioC$_1$-$C_5$alkyl, $C_1$-$C_5$alkylsulfonyl$C_1$-$C_5$alkyl,
$C_2$-$C_8$alkylideneaminoxy$C_1$-$C_5$alkyl,
$C_1$-$C_5$alkylcarbonyl$C_1$-$C_5$alkyl, $C_1$-$C_5$alkoxycarbonyl$C_1$-$C_5$alkyl, aminocarbonyl$C_1$-$C_5$alkyl,
$C_1$-$C_5$alkylaminocarbonyl$C_1$-$C_5$alkyl,
$C_2$-$C_8$dialkylaminocarbonyl$C_1$-$C_5$alkyl,
$C_1$-$C_5$alkylcarbonylamino$C_1$-$C_5$alkyl, N—$C_1$-$C_5$alkylcarbonyl-N—$C_1$-$C_5$alkylamino$C_1$-$C_5$alkyl,
$C_3$-$C_5$-trialkylsilyl$C_1$-$C_5$alkyl, phenyl$C_1$-$C_5$alkyl (wherein the phenyl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), heteroaryl$C_1$-$C_5$alkyl, (wherein the heteroaryl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), $C_2$-$C_8$haloalkenyl, $C_3$-$C_8$cycloalkyl, phenyl or phenyl substituted by $C_1$-$C_3$alkyl, $C_1$-$C_3$haloalkyl, $C_1$-$C_3$alkoxy, $C_1$-$C_3$haloalkoxy, halogen, cyano or nitro, heteroaryl or heteroaryl substituted by $C_1$-$C_3$ alkyl, $C_1$-$C_3$haloalkyl, $C_1$-$C_3$alkoxy, $C_1$-$C_3$haloalkoxy, halogen, cyano or nitro, $R^b$ is $C_1$-$C_{18}$alkyl, $C_3$-$C_{18}$alkenyl, $C_3$-$C_{18}$alkynyl, $C_2$-$C_{10}$haloalkyl, $C_1$-$C_{10}$cyanoalkyl, $C_{10}$nitroalkyl, $C_2$-$C_{10}$-aminoalkyl, $C_1$-$C_5$alkylamino$C_1$-$C_0$lkyl, $C_2$-$C_8$dialkylamino$C_1$-$C_5$alkyl, $C_3$-$C_7$cycloalkyl$C_1$-$C_5$alkyl, $C_1$-$C_5$alkoxy$C_1$-$C_5$alkyl, $C_3$-$C_5$alkenyloxy$C_1$-$C_5$alkyl, $C_3$-$C_5$alkynyloxy$C_1$-$C_1$-$C_3$alkylsulfinyl$C_1$-$C_3$alkyl,
$C_1$-$C_5$alkylsulfonyl$C_1$-$C_8$alkyl,
$C_2$-$C_8$alkylideneaminoxy$C_1$-$C_5$alkyl,
$C_1$-$C_5$alkylcarbonyl$C_1$-$C_8$alkyl, $C_1$-$C_5$alkoxycarbonyl$C_1$-$C_5$alkyl, aminocarbonyl$C_1$-$C_8$alkyl,
$C_1$-$C_5$alkylaminocarbonyl$C_1$-$C_5$alkyl,
$C_2$-$C_8$dialkylaminocarbonyl$C_1$-$C_5$alkyl,
$C_1$-$C_8$alkylcarbonylamino$C_1$-$C_5$alkyl, N—$C_1$-$C_5$alkylcarbonyl-N—$C_1$-$C_5$alkylamino$C_1$-$C_5$alkyl, phenyl$C_1$-$C_5$alkyl (wherein the phenyl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), heteroaryl$C_1$-$C_5$alkyl, (wherein the heteroaryl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), $C_3$-$C_5$haloalkenyl, $C_3$-$C_5$cycloalkyl, phenyl or phenyl substituted by $C_1$-$C_3$alkyl, $C_1$-$C_3$haloalkyl, $C_1$-$C_3$alkoxy, $C_1$-$C_3$haloalkoxy, halogen, cyano or nitro, heteroaryl or heteroaryl substituted by $C_1$-$C_3$ alkyl, $C_1$-$C_3$haloalkyl, $C_1$-$C_3$alkoxy, $C_1$-$C_3$haloalkoxy, halogen, cyano or nitro, $R^c$ and $R^d$ are each independently of each other hydrogen, $C_1$-$C_{10}$alkyl, $C_3$-$C_{10}$alkenyl, $C_3$-$C_{10}$alkynyl, $C_2$-$C_{10}$haloalkyl, $C_1$-$C_{10}$cyanoalkyl, $C_1$-$C_{10}$nitroalkyl, $C_1$-$C_{10}$aminoalkyl, $C_1$-$C_5$alkylamino$C_1$-$C_5$alkyl, $C_2$-$C_5$dialkylamino$C_1$-$C_5$alkyl, $C_3$-$C_7$cycloalkyl$C_1$-$C_5$alkyl, $C_1$-$C_5$alkoxy$C_1$-$C_5$alkyl, $C_3$-$C_5$alkenyloxy$C_1$-$C_5$alkyl, $C_3$-$C_5$alkynyloxy$C_1$-$C_5$alkyl, $C_1$-$C_5$alkylthio$C_1$-$C_5$alkyl, $C_1$-$C_5$alkylsulfinyl$C_1$-$C_5$alkyl,
$C_1$-$C_5$alkylsulfonyl$C_1$-$C_5$alkyl,
$C_2$-$C_5$alkylideneaminoxy$C_1$-$C_5$alkyl,
$C_1$-$C_5$alkylcarbonyl$C_1$-$C_5$alkyl, $C_1$-$C_5$alkoxycarbonyl$C_1$-$C_5$alkyl, aminocarbonyl$C_1$-$C_5$alkyl,
$C_1$-$C_5$alkylaminocarbonyl$C_1$-$C_5$alkyl,
$C_2$-$C_5$dialkylaminocarbonyl$C_1$-$C_5$alkyl,
$C_1$-$C_5$alkylcarbonylamino$C_1$-$C_5$alkyl, N—$C_1$-$C_5$alkylcarbonyl-N—$C_2$-$C_5$alkylaminoalkyl, $C_3$-$C_6$-trialkylsilyl$C_1$-$C_5$alkyl, phenyl$C_1$-$C_5$alkyl (wherein the phenyl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), heteroaryl$C_1$-$C_5$alkyl, (wherein the heteroaryl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), $C_2$-$C_5$haloalkenyl, $C_3$-$C_5$cycloalkyl, phenyl or phenyl substituted by $C_1$-$C_3$alkyl, $C_1$-$C_3$haloalkyl, $C_1$-$C_3$alkoxy, $C_1$-$C_3$haloalkoxy, halogen, cyano or nitro, heteroaryl or heteroaryl substituted by $C_1$-$C_3$ alkyl, $C_1$-$C_3$haloalkyl, $C_1$-$C_3$alkoxy, $C_1$-$C_3$haloalkoxy, halogen, cyano or nitro, heteroarylamino or heteroarylamino substituted by $C_1$-$C_3$ alkyl, $C_1$-$C_3$haloalkyl, $C_1$-$C_3$alkoxy, $C_1$-$C_3$haloalkoxy, halogen, cyano or nitro, diheteroarylamino or diheteroarylamino substituted by $C_1$-$C_3$ alkyl, $C_1$-$C_3$haloalkyl, $C_1$-$C_3$alkoxy, $C_1$-$C_3$haloalkoxy, halogen, cyano or nitro, phenylamino or phenylamino substituted by $C_1$-$C_3$alkyl, $C_1$-$C_3$haloalkyl, $C_1$-$C_3$alkoxy, $C_1$-$C_3$haloalkoxy, halogen, cyano or by nitro, diphenylamino or diphenylamino substituted by $C_1$-$C_3$alkyl, $C_1$-$C_3$haloalkyl, $C_1$-$C_3$alkoxy, $C_1$-$C_3$haloalkoxy, halogen, cyano or by nitro or $C_3$-$C_7$cycloalkylamino, di-$C_3$-$C_7$cycloalkylamino or $C_3$-$C_7$cycloalkoxy or $R^c$ and $R^d$ may join together to form a 3-7 membered ring, optionally containing one heteroatom selected from O or S, $R^e$ is $C_1$-$C_{10}$alkyl, $C_2$-$C_{10}$alkenyl, $C_2$-$C_{10}$alkynyl, $C_1$-$C_{10}$haloalkyl, $C_1$-$C_{10}$cyanoalkyl, $C_1$-$C_{10}$nitroalkyl, $C_1$-$C_{10}$aminoalkyl, $C_1$-$C_5$alkylamino$C_1$-$C_5$alkyl, $C_2$-$C_5$dialkylamino$C_1$-$C_5$alkyl, $C_3$-$C_7$cycloalkyl$C_1$-$C_5$alkyl, $C_1$-$C_5$alkoxy$C_1$-$C_5$alkyl, $C_3$-$C_5$alkenyloxy$C_1$-$C_5$alkyl, $C_3$-$C_5$alkynyloxy$C_1$-$C_5$alkyl, $C_1$-$C_5$alkylthio$C_1$-$C_5$alkyl, $C_1$-$C_5$alkylsulfinyl$C_1$-$C_5$alkyl,
$C_1$-$C_5$alkylsulfonyl$C_1$-$C_5$alkyl,
$C_2$-$C_8$alkylideneaminoxy$C_1$-$C_5$alkyl,
$C_1$-$C_5$alkylcarbonyl$C_1$-$C_5$alkyl, $C_1$-$C_5$alkoxycarbonyl$C_1$-$C_5$alkyl, aminocarbonyl$C_1$-$C_5$alkyl,
$C_1$-$C_5$alkylaminocarbonyl$C_1$-$C_5$alkyl,
$C_2$-$C_5$dialkylaminocarbonyl$C_1$-$C_5$alkyl,
$C_1$-$C_5$alkylcarbonylamino$C_1$-$C_5$alkyl, N—$C_1$-$C_5$alkylcarbonyl-N—$C_1$-$C_5$alkylamino$C_1$-$C_5$alkyl,
$C_3$-$C_6$-trialkylsilyl$C_1$-$C_5$alkyl, phenyl$C_1$-$C_5$alkyl (wherein the phenyl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), heteroaryl$C_1$-$C_5$alkyl (wherein the heteroaryl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), $C_2$-$C_5$haloalkenyl, $C_3$-$C_8$cycloalkyl, phenyl or phenyl substituted by $C_1$-$C_3$alkyl, $C_1$-$C_3$haloalkyl, $C_1$-$C_3$alkoxy, $C_1$-$C_3$haloalkoxy, halogen, cyano or nitro, heteroaryl or heteroaryl substituted by $C_1$-$C_3$ alkyl, $C_1$-$C_3$haloalkyl, $C_1$-$C_3$alkoxy, $C_1$-$C_3$haloalkoxy, halogen, cyano or by nitro, heteroarylamino or heteroarylamino substituted by $C_1$-$C_3$ alkyl, $C_1$-$C_3$haloalkyl, $C_1$-$C_3$alkoxy, $C_1$-$C_3$haloalkoxy, halogen, cyano or by nitro, diheteroarylamino or diheteroarylamino substituted by $C_1$-$C_3$ alkyl, $C_1$-$C_3$haloalkyl, $C_1$-$C_3$alkoxy, $C_1$-$C_3$haloalkoxy, halogen, cyano or nitro, phenylamino or phenylamino substituted by $C_1$-$C_3$alkyl, $C_1$-$C_3$haloalkyl, $C_1$-$C_3$alkoxy, $C_1$-$C_3$haloalkoxy, halogen, cyano or nitro, diphenylamino, or diphenylamino substituted by $C_1$-$C_3$alkyl, $C_1$-$C_3$haloalkyl, $C_1$-$C_3$alkoxy, $C_1$-$C_3$haloalkoxy, halogen, cyano or nitro, or $C_3$-$C_7$cycloalkylamino, di$C_3$-

$C_7$cycloalkylamino or $C_3$-$C_7$cycloalkoxy, $C_1$-$C_{10}$alkoxy, $C_1$-$C_{10}$haloalkoxy, $C_1$-$C_5$alkylamino or $C_2$-$C_8$dialkylamino, $R^f$ and $R^g$ are each independently of each other $C_1$-$C_{10}$alkyl, $C_2$-$C_{10}$alkenyl, $C_2$-$C_{10}$alkynyl, $C_1$-$C_{10}$alkoxy, $C_1$-$C_{10}$haloalkyl, $C_1$-$C_{10}$cyanoalkyl, $C_1$-$C_{10}$nitroalkyl, $C_1$-$C_{10}$aminoalkyl, $C_1$-$C_5$alkylamino$C_1$-$C_5$alkyl, $C_2$-$C_8$dialkylamino$C_1$-$C_5$alkyl, $C_3$-$C_7$cycloalkyl$C_1$-$C_5$alkyl, $C_1$-$C_5$alkoxy$C_1$-$C_5$alkyl, $C_3$-$C_5$alkenyloxy$C_1$-$C_5$alkyl, $C_3$-$C_5$alkynyloxy$C_1$-$C_5$alkyl, $C_1$-$C_5$alkylthio$C_1$-$C_5$alkyl, $C_1$-$C_5$alkylsulfinyl$C_1$-$C_5$alkyl, $C_1$-$C_5$alkylsulfonyl$C_1$-$C_5$alkyl, $C_2$-$C_0$alkylideneaminoxy$C_1$-$C_5$alkyl, $C_1$-$C_5$alkylcarbonyl$C_1$-$C_5$alkyl, $C_1$-$C_5$alkoxycarbonyl$C_1$-$C_5$alkyl, aminocarbonyl$C_1$-$C_5$alkyl, $C_1$-$C_5$alkylaminocarbonyl$C_1$-$C_5$alkyl, $C_2$-$C_8$dialkylaminocarbonyl$C_1$-$C_5$alkyl, $C_1$-$C_5$alkylcarbonylamino$C_1$-$C_5$alkyl, N—$C_1$-$C_5$alkylcarbonyl-N—$C_2$-$C_5$alkylaminoalkyl, $C_3$-$C_6$-trialkylsilyl$C_1$-$C_5$alkyl, phenyl$C_1$-$C_5$alkyl (wherein the phenyl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), heteroaryl$C_1$-$C_5$alkyl (wherein the heteroaryl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), $C_2$-$C_5$haloalkenyl, $C_3$-$C_8$cycloalkyl, phenyl or phenyl substituted by $C_1$-$C_3$alkyl, $C_1$-$C_3$haloalkyl, $C_1$-$C_3$alkoxy, $C_1$-$C_3$haloalkoxy, halogen, cyano or nitro, heteroaryl or heteroaryl substituted by $C_1$-$C_3$ alkyl, $C_1$-$C_3$haloalkyl, $C_1$-$C_3$alkoxy, $C_1$-$C_3$haloalkoxy, halogen, cyano or by nitro, heteroarylamino or heteroarylamino substituted by $C_1$-$C_3$ alkyl, $C_1$-$C_3$haloalkyl, $C_1$-$C_3$alkoxy, $C_1$-$C_3$haloalkoxy, halogen, cyano or by nitro, diheteroarylamino or diheteroarylamino substituted by $C_1$-$C_3$ alkyl, $C_1$-$C_3$haloalkyl, $C_1$-$C_3$alkoxy, $C_1$-$C_3$haloalkoxy, halogen, cyano or nitro, phenylamino or phenylamino substituted by $C_1$-$C_3$alkyl, $C_1$-$C_3$haloalkyl, $C_1$-$C_3$alkoxy, $C_1$-$C_3$haloalkoxy, halogen, cyano or nitro, diphenylamino, or diphenylamino substituted by $C_1$-$C_3$alkyl, $C_1$-$C_3$haloalkyl, $C_1$-$C_3$alkoxy, $C_3$haloalkoxy, halogen, cyano or nitro, or $C_3$-$C_7$cycloalkylamino, di$C_3$-$C_7$cycloalkylamino or $C_3$-$C_7$cycloalkoxy, $C_1$-$C_{10}$haloalkoxy, $C_1$-$C_5$alkylamino or $C_2$-$C_8$dialkylamino, benzyloxy or phenoxy, wherein the benzyl and phenyl groups may in turn be substituted by $C_1$-$C_3$alkyl, $C_1$-$C_3$haloalkyl, $C_1$-$C_3$alkoxy, $C_1$-$C_3$haloalkoxy, halogen, cyano or nitro, and $R^h$ is $C_1$-$C_{10}$alkyl, $C_3$-$C_{10}$alkenyl, $C_3$-$C_{10}$alkynyl, $C_1$-$C_{10}$haloalkyl, $C_1$-$C_{10}$cyanoalkyl, $C_1$-$C_{10}$nitroalkyl, $C_2$-$C_{10}$aminoalkyl, $C_1$-$C_5$alkylamino$C_1$-$C_5$alkyl, $C_2$-$C_5$dialkylamino$C_1$-$C_5$alkyl, $C_3$-$C_7$cycloalkyl$C_1$-$C_5$alkyl, $C_1$-$C_5$alkoxy$C_1$-$C_5$alkyl, $C_3$-$C_5$alkenyloxy$C_1$-$C_5$alkyl, $C_3$-$C_5$alkynyloxy$C_1$-$C_5$alkyl, $C_1$-$C_5$alkylthio$C_1$-$C_5$alkyl, $C_1$-$C_5$alkylsulfinyl$C_1$-$C_5$alkyl, $C_1$-$C_5$alkylsulfonyl$C_1$-$C_5$alkyl, $C_2$-$C_8$alkylideneaminoxy$C_1$-$C_5$alkyl, $C_1$-$C_5$alkylcarbonyl$C_1$-$C_5$alkyl, $C_1$-$C_5$alkoxycarbonyl$C_1$-$C_5$alkyl, aminocarbonyl$C_1$-$C_5$alkyl, $C_1$-$C_5$alkylaminocarbonyl$C_1$-$C_5$alkyl, $C_2$-$C_5$dialkylaminocarbonyl$C_1$-$C_5$alkyl, $C_1$-$C_5$alkylcarbonylamino$C_1$-$C_5$alkyl, N—$C_1$-$C_5$alkylcarbonyl-N—$C_1$-$C_5$alkylamino$C_1$-$C_5$alkyl, $C_3$-$C_6$-trialkylsilyl$C_1$-$C_5$alkyl, phenyl$C_1$-$C_5$alkyl (wherein the phenyl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$ alkylsulfonyl, halogen, cyano or by nitro), heteroaryl$C_1$-$C_5$alkyl (wherein the heteroaryl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$ alkylsulfonyl, halogen, cyano or by nitro), phenoxy$C_1$-$C_5$alkyl (wherein the phenyl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$ alkylsulfonyl, halogen, cyano or by nitro), heteroaryloxy$C_1$-$C_5$alkyl (wherein the heteroaryl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$ alkylsulfonyl, halogen, cyano or by nitro), $C_3$-$C_5$haloalkenyl, $C_3$-$C_8$cycloalkyl, phenyl or phenyl substituted by $C_1$-$C_3$alkyl, $C_1$-$C_3$haloalkyl, $C_1$-$C_3$alkoxy, $C_1$-$C_3$haloalkoxy, halogen or by nitro, or heteroaryl, or heteroaryl substituted by $C_1$-$C_3$alkyl, $C_1$-$C_3$haloalkyl, $C_1$-$C_3$alkoxy, $C_1$-$C_3$haloalkoxy, halogen, cyano or by nitro.

In particular, the latentiating group G is a group —$C(X^a)$—$R^a$ or —$C(X^b)$—$X^c$—$R^b$, and the meanings of $X^a$, $R^a$, $X^b$, $X^c$ and $R^b$ are as defined above.

In a preferred group of compounds of the formula I, $R^1$ is methyl, ethyl, vinyl, ethynyl, methoxy or halogen. More preferably, $R^1$ is methyl, ethyl, methoxy or halogen. Most preferably, $R^1$ is methyl or ethyl.

In a preferred group of compounds of the formula I, $R^2$ is hydrogen, halogen, methyl, ethyl, phenyl or phenyl substituted by $C_1$-$C_3$alkyl, $C_1$-$C_3$haloalkyl, $C_1$-$C_3$alkoxy, $C_1$-$C_3$haloalkoxy, cyano, nitro, halogen, $C_1$-$C_3$alkylthio, $C_1$-$C_3$alkylsulfinyl or $C_1$-$C_3$alkylsulfonyl.

Preferably, $R^2$ is methyl.

In a preferred group of compounds of the formula I, $R^3$ is hydrogen, halogen, methyl, ethyl, phenyl or phenyl substituted by $C_1$-$C_3$alkyl, $C_1$-$C_3$haloalkyl, $C_1$-$C_3$alkoxy, $C_1$-$C_3$haloalkoxy, cyano, nitro, halogen, $C_1$-$C_3$alkylthio, $C_1$-$C_3$alkylsulfinyl or $C_1$-$C_3$alkylsulfonyl Preferably, $R^2$ and $R^3$ are independently hydrogen, methyl, ethyl, halogen, optionally substituted phenyl or optionally substituted heteroaryl.

Preferably, $R^4$ is hydrogen, methyl, ethyl, vinyl or ethynyl and, more preferably, $R^4$ is hydrogen, methyl or ethyl.

Preferably, $R^6$ denotes hydrogen.

Another suitable group of compounds of the formula (I) is characterized by $R^6$ and $R^7$ each being hydrogen.

Preferably, $R^6$ and $R^7$ are methyl or ethyl, or $R^6$ is hydrogen and $R^7$ is methyl or ethyl.

In a preferred group of compounds of the formula (I), $R^8$, when X denotes S(O) or S(O)$_2$, is $C_1$-$C_{18}$alkyl, $C_3$-$C_7$cycloalkyl, $C_3$-$C_7$cycloalkyl substituted by methyl or ethyl, $C_1$-$C_8$alkoxy$C_1$-$C_{12}$alkyl, $C_1$-$C_8$alkylthio$C_1$-$C_{12}$alkyl, $C_3$-$C_{18}$ alkenyl, $C_3$-$C_{18}$alkynyl or $C_3$-$C_{18}$alkynyl substituted by halogen.

More preferably, $R^8$ is $C_1$-$C_8$alkyl or $C_3$-$C_7$cycloalkyl, and, in particular, $R^8$ is methyl, ethyl or propyl.

In another preferred group of compounds of the formula (I), $R^8$, when X denotes O or S, is methyl, ethyl, propyl, butyl, pentyl or hexyl, $C_3$-$C_7$cycloalkyl, $C_3$-$C_7$cycloalkyl substituted by methyl or ethyl, $C_1$-$C_8$alkoxy$C_1$-$C_{12}$alkyl, $C_1$-$C_8$alkylthio$C_1$-$C_{12}$alkyl, $C_3$-$C_{18}$ alkenyl, $C_3$-$C_{18}$alkynyl or $C_3$-$C_{18}$alkynyl substituted by halogen.

It is particularly preferred, that in the compounds of the formula (I), $R^8$, when X denotes O or S, is methyl, ethyl or propyl, and in particular ethyl or propyl.

Another group of preferred compounds of the formula (I) $R^8$, when X denotes S(O) or S(O)$_2$, is $C_1$-$C_{18}$alkyl, $C_3$-$C_7$cycloalkyl, $C_3$-$C_7$cycloalkyl substituted by methyl or ethyl, $C_1$-$C_6$alkoxy$C_1$-$C_{12}$alkyl, $C_1$-$C_6$alkylthio$C_1$-$C_{12}$alkyl, $C_3$-$C_{18}$ alkenyl, $C_3$-$C_{18}$alkynyl or $C_3$-$C_{18}$alkynyl substituted by halogen, and $R^6$ and $R^7$ are methyl or ethyl, or $R^6$ is hydrogen and $R^7$ is methyl or ethyl.

Preferably, in the compounds of formula (I), the substituent $R^8$—X—[$CR^6R^7$]$_1$— is different from $CH_3OCH_2$— and $CH_3SCH_2$—.

It is preferred that G is hydrogen, an alkali metal or alkaline earth metal, where hydrogen is especially preferred.

Preferably in the compounds of the formula (I), n is 1 or 2.

In the case that in the compounds of the formula (I) n denotes 2 or 3, the meanings of the 4 or 6 substituents $R^6$ and $R^7$ do not have to be the same. For example, the partial structure [$CR^6R^7$]$_2$ comprises also groups such as $CH(CH_3)CH_2$, $C(CH_3)_2CH_2$, $CH_2CH(CH_3)$ and $CH_2C(CH_3)_2$.

In another preferred group of compounds of the formula (I) $R^5$, when n denotes 1 or 2, and $R^8$ together form a $C_2$-$C_5$ alkylene chain.

In another preferred group of compounds of the formula (I), $R^5$, when n denotes 1, and $R^8$ together form a propylene chain and $R^6$ and $R^7$ are each hydrogen.

Preferably, $R^5$, when n denotes 1 or 2 and in particular 2, and $R^8$ together form an ethylene chain and $R^6$ and $R^7$ are each hydrogen. These meanings of $R^5$ apply especially when X is O or when X is S(O) or S(O)$_2$.

In another preferred group of compounds of the formula (I) $R^1$, $R^2$ and $R^4$ are independently of each other methyl or ethyl and $R^3$ is hydrogen.

In another preferred group of compounds of the formula (I) $R^1$ is methyl or ethyl, $R^2$ is hydrogen, $R^3$ is phenyl or phenyl substituted by $C_1$-$C_4$alkyl, $C_1$-$C_3$haloalkyl, $C_1$-$C_3$alkoxy, $C_1$-$C_3$haloalkoxy, cyano, nitro or halogen, or heteroaryl or heteroaryl substituted by $C_1$-$C_4$alkyl, $C_1$-$C_3$haloalkyl, $C_1$-$C_3$alkoxy, $C_1$-$C_3$ haloalkoxy, cyano, nitro or halogen.

In another preferred group of compounds of the formula (I) $R^1$ is methyl or ethyl, $R^2$ is phenyl or phenyl substituted by $C_1$-$C_4$alkyl, $C_1$-$C_3$haloalkyl, $C_1$-$C_3$alkoxy, $C_1$-$C_3$haloalkoxy, cyano, nitro or halogen, or heteroaryl or heteroaryl substituted by $C_1$-$C_4$alkyl, $C_1$-$C_3$haloalkyl, $C_1$-$C_3$alkoxy, $C_3$haloalkoxy, cyano, nitro or halogen, $R^3$ is hydrogen and $R^4$ is hydrogen, methyl or ethyl.

The invention relates also to the salts which the compounds of formula I are able to form with amines, alkali metal and alkaline earth metal bases or quaternary ammonium bases. Among the alkali metal and alkaline earth metal hydroxides as salt formers, special mention should be made of the hydroxides of lithium, sodium, potassium, magnesium and calcium, but especially the hydroxides of sodium and potassium. The compounds of formula I according to the invention also include hydrates which may be formed during the salt formation.

Examples of amines suitable for ammonium salt formation include ammonia as well as primary, secondary and tertiary $C_1$-$C_{10}$alkylamines, $C_1$-$C_4$hydroxyalkylamines and $C_2$-$C_4$-alkoxyalkylamines, for example methylamine, ethylamine, n-propylamine, isopropylamine, the four butylamine isomers, n-amylamine, isoamylamine, hexylamine, heptylamine, octylamine, nonylamine, decylamine, pentadecylamine, hexadecylamine, heptadecylamine, octadecylamine, methylethylamine, methylisopropylamine, methylhexylamine, methylnonylamine, methylpentadecylamine, methyloctadecylamine, ethylbutylamine, ethylheptylamine, ethyloctylamine, hexylheptylamine, hexyloctylamine, dimethylamine, diethylamine, di-n-propylamine, diisopropylamine, di-n-butylamine, di-n-amylamine, diisoamylamine, dihexylamine, diheptylamine, dioctylamine, ethanolamine, n-propanolamine, isopropanolamine, N,N-diethanolamine, N-ethylpropanolamine, N-butylethanolamine, allylamine, n-but-2-enylamine, n-pent-2-enylamine, 2,3-dimethylbut-2-enylamine, dibut-2-enylamine, n-hex-2-enylamine, propylenediamine, trimethylamine, triethylamine, tri-n-propylamine, triisopropylamine, tri-n-butylamine, triisobutylamine, tri-sec-butylamine, tri-n-amylamine, methoxyethylamine and ethoxyethylamine; heterocyclic amines, for example pyridine, quinoline, isoquinoline, morpholine, piperidine, pyrrolidine, indoline, quinuclidine and azepine; primary arylamines, for example anilines, methoxyanilines, ethoxyanilines, o-, m- and p-toluidines, phenylenediamines, benzidines, naphthylamines and o-, m- and p-chloroanilines; but especially triethylamine, isopropylamine and diisopropylamine.

Preferred quaternary ammonium bases suitable for salt formation correspond, for example, to the formula [N($R_a$ $R_b$ $R_c$ $R_d$)]OH wherein $R_a$, $R_b$, $R_c$ and $R_d$ are each independently of the others $C_1$-$C_4$alkyl. Further suitable tetraalkylammonium bases with other anions can be obtained, for example, by anion exchange reactions.

Depending on the nature of the substituents G, $R^2$, $R^3$, $R^6$, $R^7$ and $R^8$, compounds of Formula (I) may exist in different isomeric forms. When G is hydrogen, for example, compounds of Formula (I) may exist in different tautomeric forms. This invention covers all such isomers and tautomers and mixtures thereof in all proportions. Also, when substituents contain double bonds, cis- and trans-isomers can exist. These isomers, too, are within the scope of the claimed compounds of the Formula (I).

A compound of Formula (I) wherein G is $C_1$-$C_8$ alkyl, $C_2$-$C_8$ haloalkyl, phenyl$C_1$-$C_8$alkyl (wherein the phenyl may optionally be substituted by $C_1$-$C_3$alkyl, $C_1$-$C_3$haloalkyl, $C_1$-$C_3$alkoxy, $C_r$-$C_3$haloalkoxy, $C_1$-$C_3$alkylthio, $C_1$-$C_3$alkylsulfinyl, $C_1$-$C_3$ alkylsulfonyl, halogen, cyano or by nitro), heteroaryl$C_1$-$C_8$alkyl (wherein the heteroaryl may optionally be substituted by $C_1$-$C_3$alkyl, $C_r$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$ alkylsulfonyl, halogen, cyano or by nitro), $C_3$-$C_8$ alkenyl, $C_3$-$C_8$ haloalkenyl, $C_3$-$C_8$ alkynyl, C($X^a$)—$R^a$, C($X^b$)—$X^c$—$R^b$, C($X^d$)—N($R^c$)—$R^d$, —SO$_2$—$R^e$, —P($X^e$)($R^f$)—$R^g$ or CH$_2$—$X^f$—$R^h$ where $X^a$, $X^b$, $X^c$, $X^d$, $X^e$, $X^f$, $R^a$, $R^b$, $R^c$, $R^d$, $R^e$, $R^f$, $R^g$ and $R^h$ are as defined above may be prepared by treating a compound of Formula (A), which is a compound of Formula (I) wherein G is H, with a reagent G-Z, wherein G-Z is alkylating agent such as an alkyl halide (the definition of alkyl halides includes simple $C_1$-$C_8$ alkyl halides such as methyl iodide and ethyl iodide, substituted alkyl halides such as phenyl$C_1$-$C_8$alkyl halides, chloromethyl alkyl ethers, Cl—CH$_2$—$X^f$—$R^h$, wherein $X^f$ is oxygen, and chloromethyl alkyl sulfides Cl—CH$_2$—$X^f$—$R^h$, wherein $X^f$ is sulfur), a $C_1$-$C_8$ alkyl sulfonate, or a di-$C_1$-$C_8$-alkyl sulfate, or with a $C_3$-$C_8$ alkenyl halide, or with a $C_3$-$C_8$ alkynyl halide, or with an acylating agent such as a carboxylic acid, HO—C($X^a$)$R^a$, wherein $X^a$ is oxygen, an acid chloride, Cl—C($X^a$)$R^a$, wherein $X^a$ is oxygen, or acid anhydride, [$R^a$C($X^a$)]$_2$O, wherein $X^a$ is oxygen, or an isocyanate, $R^c$N=C=O, or a carbamoyl chloride, Cl—C($X^d$)—N($R^c$)—$R^d$ (wherein $X^d$ is oxygen and with the proviso that neither $R^c$ or $R^d$ is hydrogen), or a thiocarbamoyl chloride, Cl—C($X^d$)—N($R^c$)—$R^d$ (wherein $X^d$ is sulfur and with the proviso that neither $R^c$ or $R^d$ is hydrogen) or a chloroformate, Cl—C(X)—$X^c$—$R^b$, (wherein $X^b$ and $X^c$ are oxygen), or a chlorothioformate Cl—C($X^h$)—$X^c$—$R^h$ (wherein $X^b$ is oxygen and $X^c$ is sulfur), or a chlorodithioformate Cl—C($X^h$)—$X^c$—

$R^h$, (wherein $X^b$ and $X^c$ are sulfur), or an isothiocyanate, $R^cN=C=S$, or by sequential treatment with carbon disulfide and an alkylating agent, or with a phosphorylating agent such as a phosphoryl chloride, $Cl-P(X^e)(R^f)-R^g$ or with a sulfonylating agent such as a sulfonyl chloride $Cl-SO_2-R^e$, preferably in the presence of at least one equivalent of base.

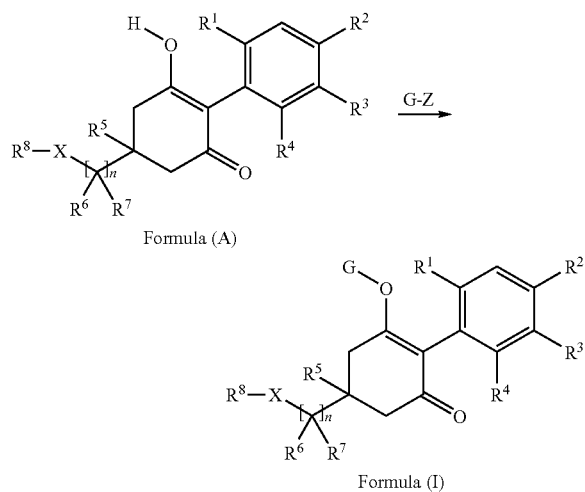

Formula (A)

Formula (I)

The O-alkylation of cyclic 1,3-diones is known; suitable methods are described, for example, by T. Wheeler, U.S. Pat. No. 4,436,666. Alternative procedures have been reported by M. Pizzorno and S. Albonico, Chem. Ind. (London), (1972), 425-426; H. Born et al., J. Chem. Soc., (1953), 1779-1782; M. G. Constantino et al., Synth. Commun., (1992), 22 (19), 2859-2864; Y. Tian et al., Synth. Commun., (1997), 27 (9), 1577-1582; S. Chandra Roy et al., Chem. Letters, (2006), 35 (1), 16-17; P. K. Zubaidha et al., Tetrahedron Lett., (2004), 45, 7187-7188.

The O-acylation of cyclic 1,3-diones may be effected by procedures similar to those described, for example, by R. Haines, U.S. Pat. No. 4,175,135, and by T. Wheeler, U.S. Pat. No. 4,422,870, U.S. Pat. No. 4,659,372 and U.S. Pat. No. 4,436,666. Typically diones of formula (A) may be treated with an acylating agent preferably in the presence of at least one equivalent of a suitable base, and optionally in the presence of a suitable solvent. The base may be inorganic, such as an alkali metal carbonate or hydroxide, or a metal hydride, or an organic base such as a tertiary amine or metal alkoxide. Examples of suitable inorganic bases include sodium carbonate, sodium or potassium hydroxide, sodium hydride, and suitable organic bases include trialkylamines, such as trimethylamine and triethylamine, pyridines or other amine bases such as 1,4-diazobicyclo[2.2.2]-octane and 1,8-diazabicyclo[5.4.0]undec-7-ene. Preferred bases include triethylamine and pyridine. Suitable solvents for this reaction are selected to be compatible with the reagents and include ethers such as tetrahydrofuran and 1,2-dimethoxyethane and halogenated solvents such as dichloromethane and chloroform. Certain bases, such as pyridine and triethylamine, may be employed successfully as both base and solvent. For cases where the acylating agent is a carboxylic acid, acylation is preferably effected in the presence of a known coupling agent such as 2-chloro-1-methylpyridinium iodide, N,N'-dicyclohexylcarbodiimide, 1-(3-dimethylaminopropyl)-3-ethylcarbodiimide and N,N'-carbodiimidazole, and optionally in the presence of a base such as triethylamine or pyridine in a suitable solvent such as tetrahydrofuran, dichloromethane or acetonitrile. Suitable procedures are described, for example, by W. Zhang and G. Pugh, Tetrahedron Lett., (1999), 40 (43), 7595-7598; T. Isobe and T. Ishikawa, J. Org. Chem., (1999), 64 (19), 6984-6988 and K. Nicolaou, T. Montagnon, G. Vassilikogiannakis, C. Mathison, J. Am. Chem. Soc., (2005), 127(24), 8872-8888.

Phosphorylation of cyclic 1,3-diones may be effected using a phosphoryl halide or thiophosphoryl halide and a base by procedures analogous to those described by L. Hodakowski, U.S. Pat. No. 4,409,153.

Sulfonylation of a compound of formula (A) may be achieved using an alkyl or aryl sulfonyl halide, preferably in the presence of at least one equivalent of base, for example by the procedure of C. Kowalski and K. Fields, J. Org. Chem., (1981), 46, 197-201. Compounds of formula (A), wherein Y is $S(O)_m$ and m is 1 or 2 may be prepared from compounds of formula (A) wherein Y is S by oxidation, according to a procedure analogous to that of E. Fehnel and A. Paul, J. Am. Chem. Soc., (1955), 77, 4241-4244.

A compound of Formula (A) may be prepared by the cyclisation of a compound of Formula (B), wherein R is hydrogen or an alkyl group, preferably in the presence of an acid or base, and optionally in the presence of a suitable solvent, by analogous methods to those described in U.S. Pat. No. 4,209,532. The compounds of Formula (B) have been particularly designed as intermediates in the synthesis of the compounds of the Formula (I). A compound of Formula (B) wherein R is hydrogen may be cyclised under acidic conditions, preferably in the presence of a strong acid such as sulfuric acid, polyphosphoric acid or Eaton's reagent, optionally in the presence of a suitable solvent such as acetic acid, toluene or dichloromethane.

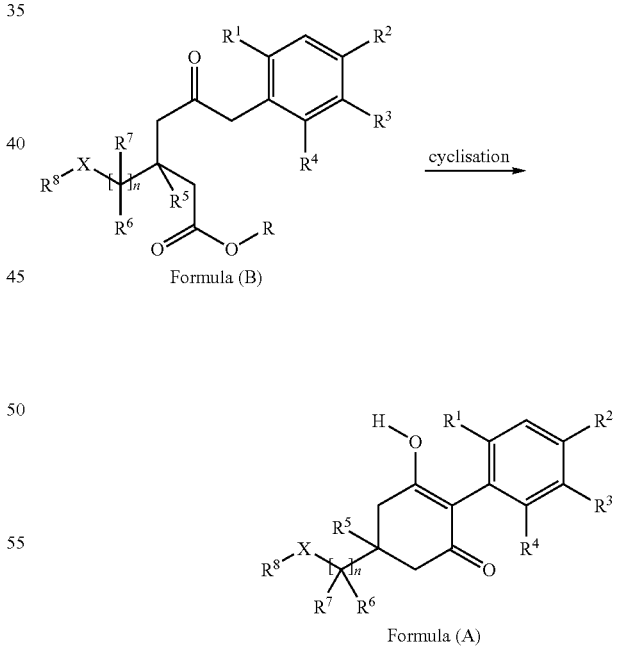

Formula (B)

Formula (A)

A compound of Formula (B) wherein R is alkyl (preferably methyl or ethyl), may be cyclised under acidic or basic conditions, preferably in the presence of at least one equivalent of a strong base such as potassium tert-butoxide, lithium diisopropylamide or sodium hydride and in a solvent such as tetrahydrofuran, dimethylsulfoxide or N,N-dimethylformamide.

A compound of Formula (B), wherein R is H, may be prepared by saponification of a compound of Formula (C) wherein R' is alkyl (preferably methyl or ethyl), under standard conditions, followed by acidification of the reaction mixture to effect decarboxylation, by similar processes to those described, for example, by T. Wheeler, U.S. Pat. No. 4,209,532.

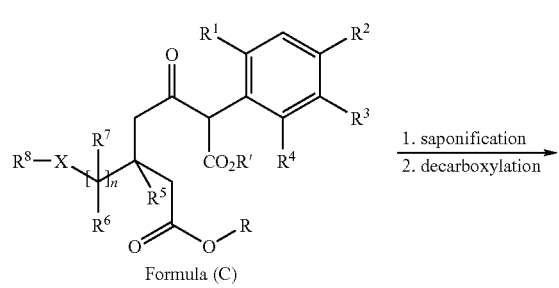

Formula (C)

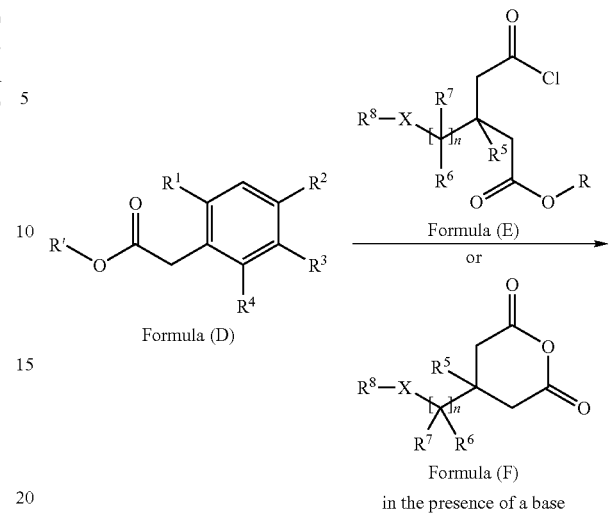

Formula (D)    Formula (E)
or

Formula (F)
in the presence of a base

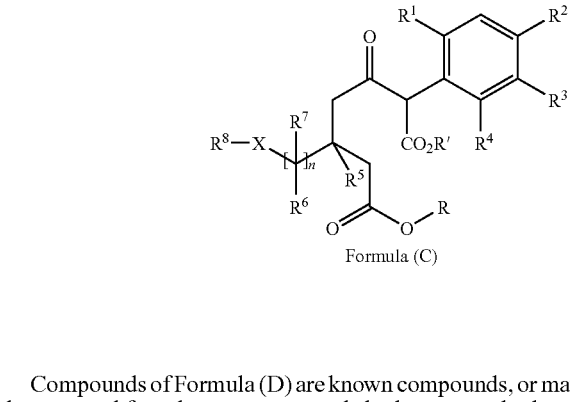

Formula (C)

A compound of Formula (B), wherein R is H, may be esterified to a compound of Formula (B), wherein R is alkyl, under known conditions, for example by heating with an alkyl alcohol, ROH, in the presence of an acid catalyst.

A compound of Formula (C), wherein R is alkyl, may be prepared by treating a compound of Formula (D) with a suitable carboxylic acid chloride of Formula (E) under acidic or basic conditions. Suitable acids include strong acids such as sulfuric acid. Suitable bases include potassium tert-butoxide, sodium bis(trimethylsilyl)amide and lithium diisopropylamide and the reaction is preferably conducted in a suitable solvent (such as tetrahydrofuran or toluene) at a temperature of between ±80° C. and 30° C. Alternatively, a compound of Formula (C), wherein R is H, may be prepared by treating a compound of Formula (D) with a suitable base (such as potassium tert-butoxide, sodium bis(trimethylsilyl)amide and lithium diisopropylamide) in a suitable solvent (such as tetrahydrofuran or toluene) at a suitable temperature (between ±80° C. and 30° C.) and reacting the resulting anion with a suitable anhydride of Formula (F):

Compounds of Formula (D) are known compounds, or may be prepared from known compounds by known methods.

A compound of Formula (E) may be prepared from a compound of Formula (F) by treatment with an alkyl alcohol, R—OH, followed by treatment of the resulting acid with a chlorinating reagent such as oxalyl chloride or thionyl chloride under known conditions (see, for example, C. Rouvier. Tetrahedron Lett., (1984), 25, (39), 4371; D. Walba and M. Wand, Tetrahedron Lett., (1982), 23, 4995; J. Cason, Org. Synth. Coll. Vol. III, (1955), 169).

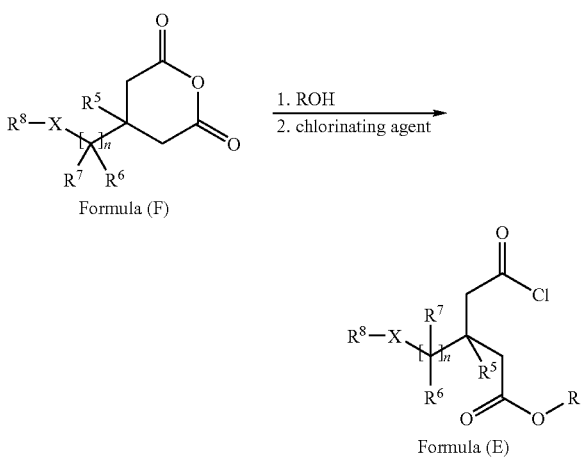

Formula (F)

1. ROH
2. chlorinating agent

Formula (E)

A compound of Formula (F) may be prepared by treating a compound of Formula (G) with a dehydrating agent such as an acid anhydride (as described, for example by J. Cason, Org. Synth. Coll. Vol. IV, (1963), 630). A preferred acid anhydride is acetic anhydride.

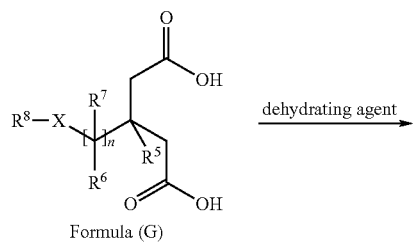

Formula (G)

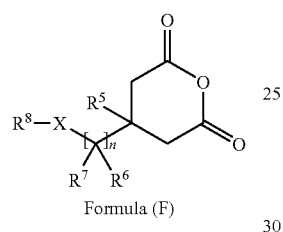

Formula (F)

A compound of Formula (G) may be prepared by saponification of an ester of Formula (H), wherein R'' and R''' are suitable alkyl groups followed by decarboxylation of resulting acid. Suitable alkyl groups are $C_1$-$C_6$ alkyl, especially methyl or ethyl. Suitable methods for effecting saponification are known, and include, for example, treating an ester of Formula (H) with an aqueous solution of a suitable base such as sodium hydroxide or potassium hydroxide, and acidifying the reaction mixture with an acid such as hydrochloric acid to promote decarboxylation.

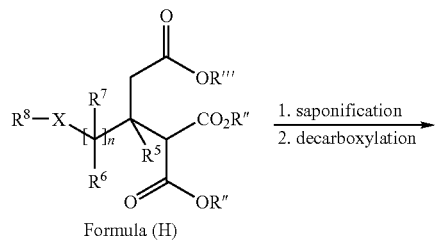

Formula (H)

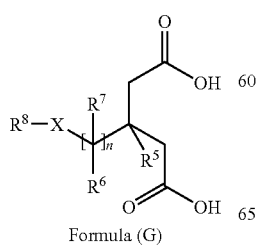

Formula (G)

A compound of Formula (H) may be prepared by reacting a compound of Formula (J) with a dialkyl malonate, such as dimethyl malonate or diethyl malonate, under basic conditions. Preferred bases include sodium alkoxide bases such as sodium methoxide and sodium ethoxide, and the reaction is preferably carried out in a solvent such as methanol, ethanol or toluene.

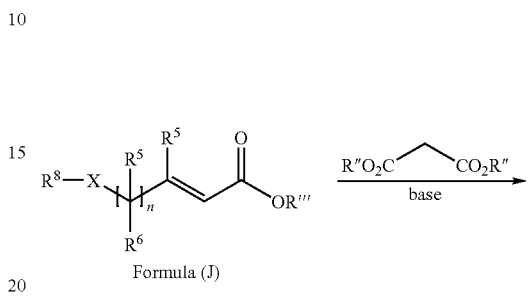

Formula (J)

Formula (H)

Compounds of Formula (J) are known compounds, or may be prepared from known compounds by known methods.

A compound of Formula (B) wherein R and $R^5$ are both H may also be prepared via the hydrolysis and decarboxylation of a compound of Formula (K), which in turn may be prepared by addition of a dialkyl malonate (preferably dimethyl malonate or diethyl malonate) to a compound of Formula (L) in the presence of a suitable base, such as sodium methoxide or sodium ethoxide in a suitable solvent such as methanol, ethanol or toluene. A compound of Formula (L) may be prepared by the Knoevenagel condensation of an aldehyde of Formula (M) with a β-ketoester of Formula (N), where R'''' is alkyl, according to known procedures (see, for example, J. March, Advanced Organic Chemistry, $3^{rd}$ Edition, pp 835-841, John Wiley and Sons Inc. 1985). A compound of Formula (N) may be prepared from a compound of Formula (D), wherein R is H, through conversion to the corresponding acid chloride and subsequent reaction to give the β-ketoester of Formula (N) according to procedures described in the literature (see, for example, J. Wemple et al., Synthesis, (1993), 290-292; J. Bowman, J. Chem. Soc., (1950), 322).

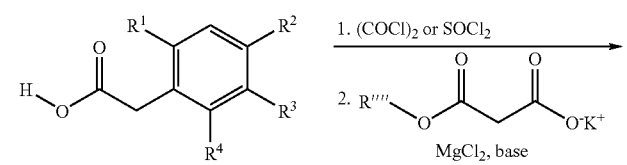

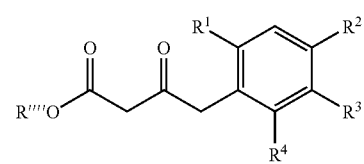

Formula (D)
wherein R' is H

Formula (N)

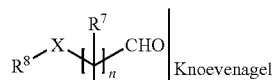

Formula (M)

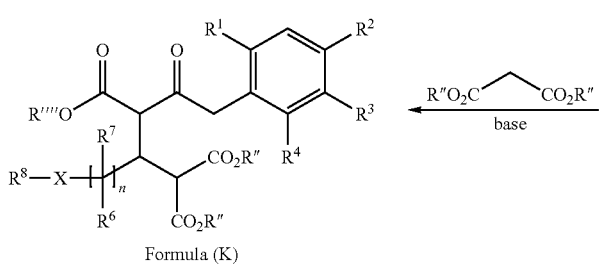

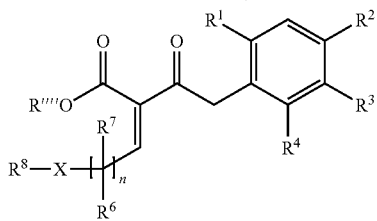

Formula (K)

Formula (L)

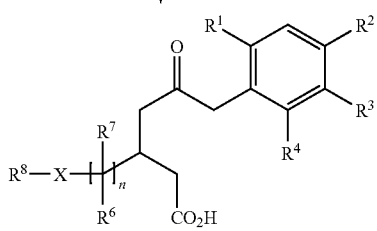

Formula (B)
wherein both R and $R^5$ are H

Compounds of Formula (M) are known compounds, or may be prepared from known compounds by known methods.

Additional compounds of Formula (A) may be prepared by reacting a 2-diazocyclohexane-1,3-dione of Formula (O) with a compound of Formula (P) under known conditions. Suitable procedures include the photosensitised decomposition of diazoketones (see, for example, T. Wheeler, J. Org. Chem., (1979), 44, 4906), or by using a suitable metal catalyst such as rhodium acetate, copper chloride or copper triflate in a suitable solvent under known conditions (see, for example, M. Oda et al., Chem. Lett. (1987), 1263). Where compounds of Formula (P) are liquids at room temperature, these reactions may be effected in the absence of any solvent. Compounds of Formula (P) are known, or may be prepared from known compounds by known methods.

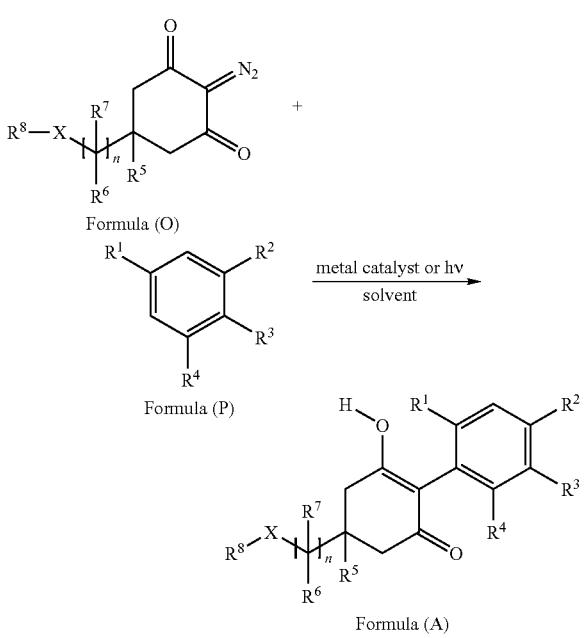

A compound of Formula (O) may be prepared through treatment of a compound of Formula (Q) with a diazo transfer reagent such as a tosyl azide or a mesyl azide and a base, as described, for example, by T. Ye and M. McKervey (Chem. Rev., (1994), 94, 1091-1160), by H. Stetter and K. Kiehs (Chem. Ber., (1965), 98, 1181) and by D. Taber et al. (J. Org. Chem., (1986), 51, 4077).

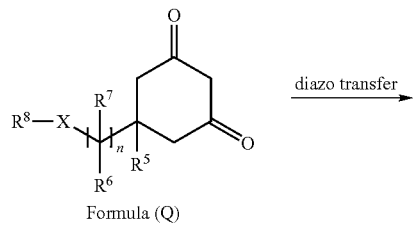

Formula (Q)

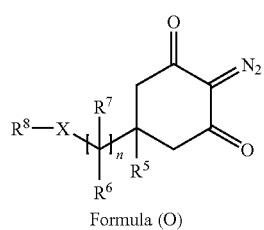

Formula (O)

A compound of Formula (Q) may be prepared via the hydrolysis and decarboxylation of a compound of Formula (R), under known conditions. Preferably R″ is methyl or ethyl.

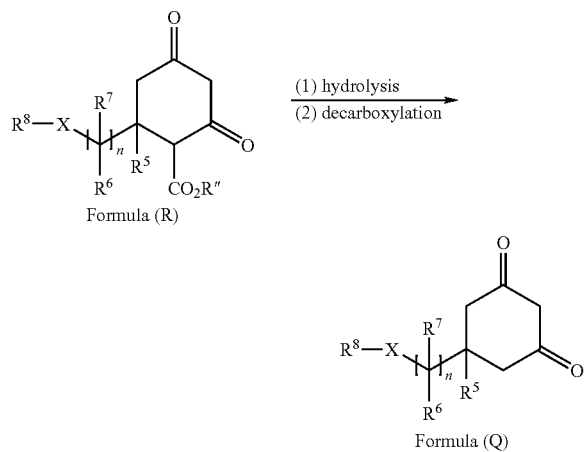

A compound of Formula (R) may be prepared by reacting a compound of Formula (S) with a dialkyl malonate under basic conditions. Preferably the dialkyl malonate is dimethyl malonate or diethyl malonate, the base is a metal alkoxide such as sodium methoxide or sodium ethoxide and the reaction is carried out in a suitable solvent such as methanol, ethanol or toluene.

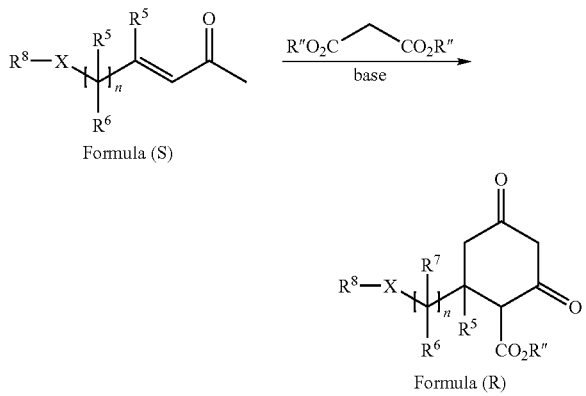

Compounds of Formula (S) are known, or may be prepared by known methods from known compounds.

Additional compounds of Formula (A) may be prepared by reacting an iodonium ylide of Formula (Y), wherein Ar is an optionally substituted phenyl group, and an aryl boronic acid of Formula (Z) in the presence of a suitable palladium catalyst, a base and in a suitable solvent.

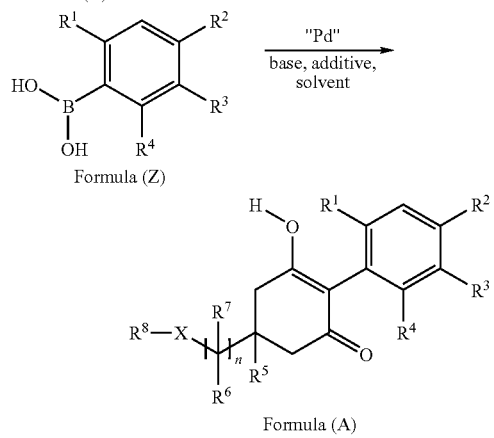

Suitable palladium catalysts are generally palladium(II) or palladium(0) complexes, for example palladium(II) dihalides, palladium(II) acetate, palladium(II) sulfate, bis(triphenylphosphine)palladium(II) dichloride, bis(tricyclopentylphosphine)palladium(II) dichloride, bis(tricyclohexylphosphine)palladium(II) dichloride, bis(dibenzylideneacetone)palladium(0) or tetrakis(triphenylphosphine)palladium(0). The palladium catalyst can also be prepared "in situ" from palladium(II) or palladium(0) compounds by complexing with the desired ligands, by, for example, combining the palladium(II) salt to be complexed, for example palladium(II) dichloride ($PdCl_2$) or palladium(II) acetate ($Pd(OAc)_2$), together with the desired ligand, for example triphenylphosphine ($PPh_3$), tricyclopentylphosphine, tricyclohexylphosphine, 2-dicyclohexyl-phosphino-2',6'-dimethoxybiphenyl or 2-dicyclohexylphosphino-2',4',6'-triisopropylbiphenyl and the selected solvent, with a compound of Formula (Y), the arylboronic acid of Formula (Z), and a base. Also suitable are bidendate ligands, for example 1, 1'-bis(diphenylphosphino)ferrocene or 1,2-bis (diphenylphosphino)ethane. By heating the reaction medium, the palladium(II) complex or palladium(0) complex desired for the C—C coupling reaction is thus formed "in situ", and then initiates the C—C coupling reaction.

The palladium catalysts are used in an amount of from 0.001 to 50 mol %, preferably in an amount of from 0.1 to 15 mol %, based on the compound of Formula (Y). The reaction may also be carried out in the presence of other additives, such as tetralkylammonium salts, for example, tetrabutylammonium bromide. Preferably the palladium catalyst is palladium acetate, the base is lithium hydroxide and the solvent is aqueous 1,2-dimethoxyethane.

A compound of Formula (Y) may be prepared from a compound of Formula (Q) by treatment with a hypervalent iodine reagent such as a (diacetoxy)iodobenzene or an iodosylbenzene and a base such as aqueous sodium carbonate, lithium hydroxide or sodium hydroxide in a solvent such as water or an aqueous alcohol such as aqueous ethanol according to the procedures of K. Schank and C. Lick, Synthesis (1983), 392; R. Moriarty et al, J. Am. Chem. Soc, (1985), 107, 1375, or of Z. Yang et al., Org. Lett., (2002), 4 (19), 3333:

An aryl boronic acid of Formula (Z) may be prepared from an aryl halide of Formula (AA), wherein Hal is bromine or iodine, by known methods (see, for example, W. Thompson and J. Gaudino, J. Org. Chem., (1984), 49, 5237 and R. Hawkins et al., J. Am. Chem. Soc., (1960), 82, 3053). For example, an aryl halide of Formula (AA) may be treated with an alkyl lithium or alkyl magnesium halide in a suitable solvent, preferably diethyl ether or tetrahydrofuran, at a temperature of between ±80° C. and 30° C., and the aryl magnesium or aryl lithium reagent obtained may then be reacted with a trialkyl borate (preferably trimethylborate) to give an aryl dialkylboronate which may be hydrolysed to the desired boronic acid of Formula (Z) under acidic conditions.

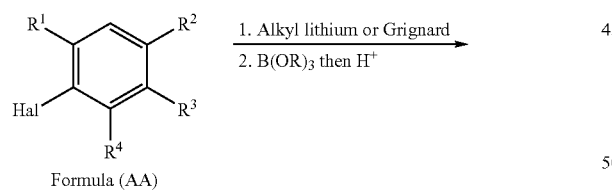

Alternatively a compound of Formula (AA) may be reacted with bis(pinacolato)diboron under known conditions (see, for example, N. Miyaura et al., J. Org. Chem., (1995), 60, 7508) and the resulting aryl boronate hydrolysed under acidic conditions to give a boronic acid of Formula (Z). Aryl halides of Formula (AA) may be prepared from anilines of Formula (BB) by known methods, for example the Sandmeyer reaction, via the corresponding diazonium salts.

Anilines of Formula (BB) are known compounds, or may be made from known compounds, by known methods.

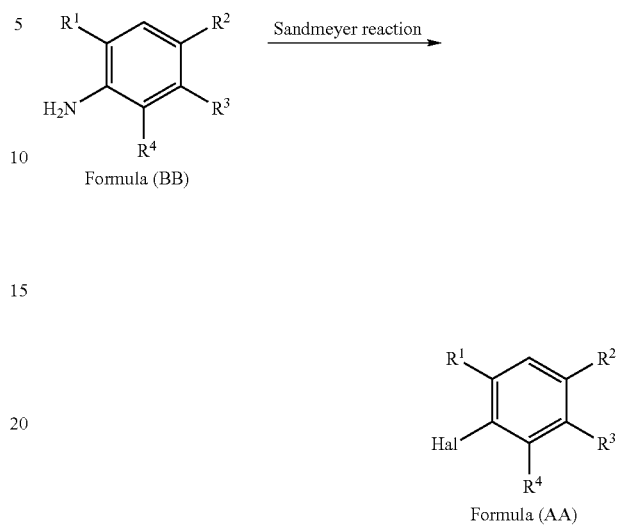

Additional compounds of Formula (A) wherein $R^2$ is optionally substituted aryl or heteroaryl may be prepared from compounds of Formula (CC) wherein X' is an atom or group suitable for cross-coupling with an aryl- or heteroarylboronic acid in the presence of a suitable palladium catalyst and a base under known conditions (see, for example F. Bellina, A. Carpita and R. Rossi, Synthesis, (2004), 15, 2419-2440 and A. Suzuki, Journal of Organometallic Chemistry, (2002), 653, 83). Suitable atoms and groups X' include triflates, and halogens, especially chlorine, bromine and iodine.

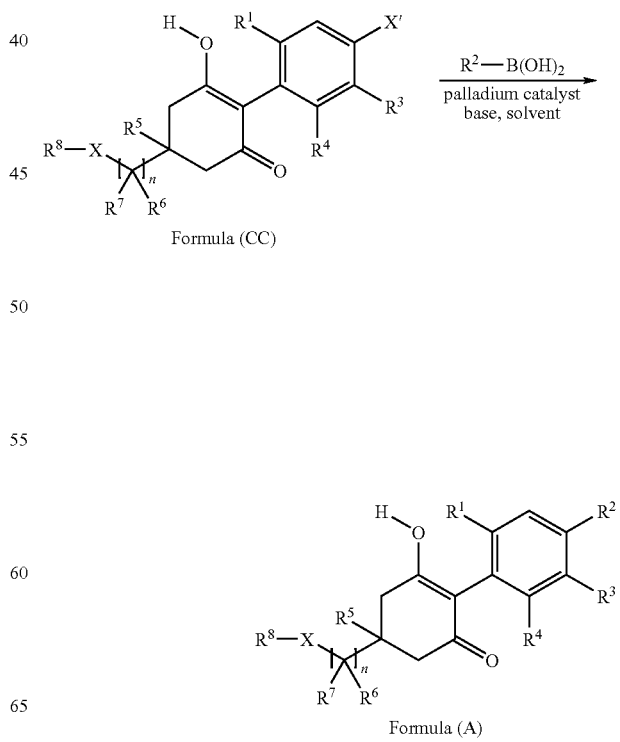

Similarly, a compound of Formula (A) wherein $R^3$ is optionally substituted aryl or heteroaryl may be prepared from a compound of Formula (DD) wherein X' is as defined previously and a suitable aryl- or heteroaryl-boronic acid under similar palladium catalysed conditions.

A compound of Formula (CC) may also be prepared by reacting a compound of Formula (O) with a compound of Formula (GG) under similar conditions to those described above for the conversion of a compound of Formula (O) to a compound of Formula (A).

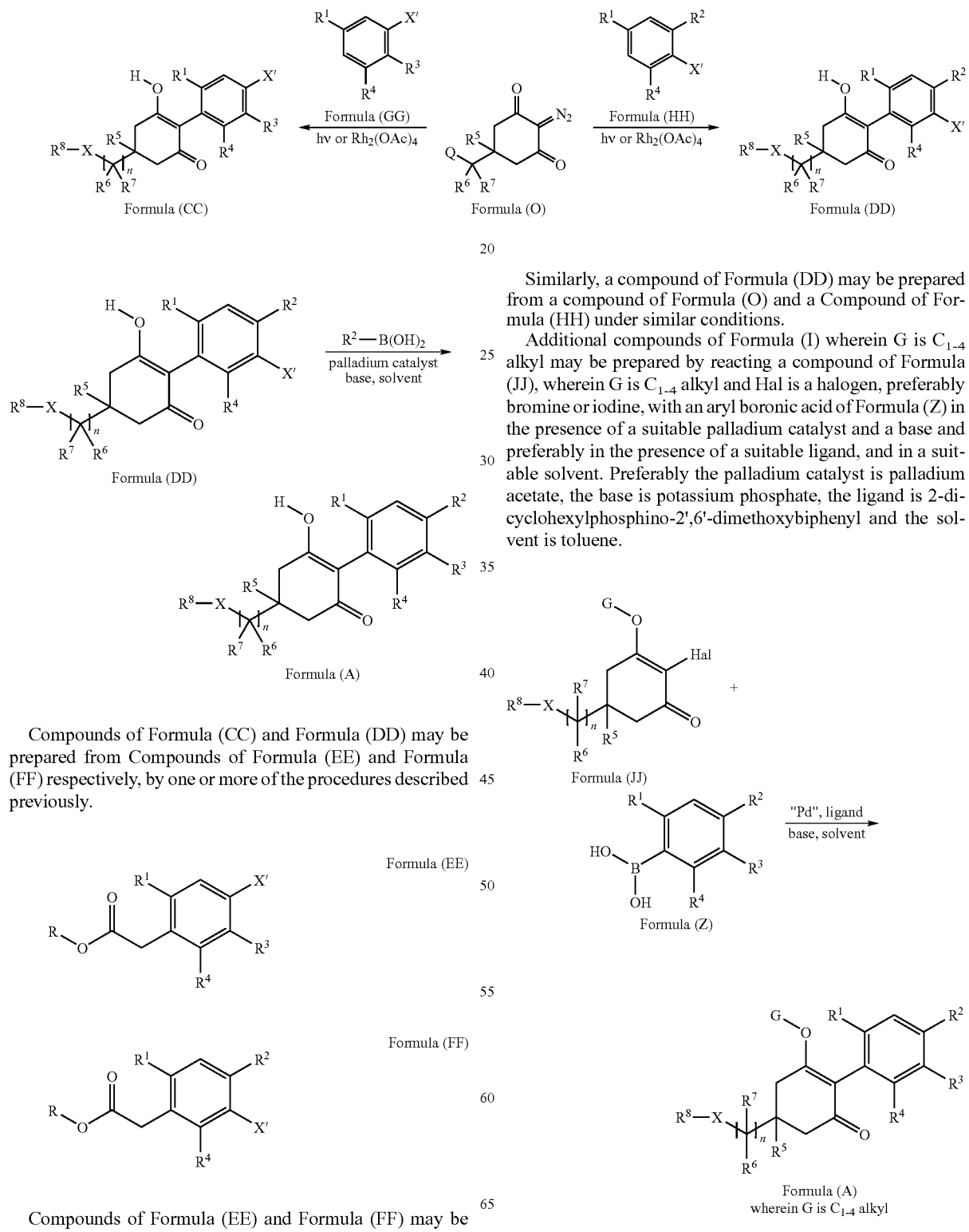

Similarly, a compound of Formula (DD) may be prepared from a compound of Formula (O) and a Compound of Formula (HH) under similar conditions.

Additional compounds of Formula (I) wherein G is $C_{1-4}$ alkyl may be prepared by reacting a compound of Formula (JJ), wherein G is $C_{1-4}$ alkyl and Hal is a halogen, preferably bromine or iodine, with an aryl boronic acid of Formula (Z) in the presence of a suitable palladium catalyst and a base and preferably in the presence of a suitable ligand, and in a suitable solvent. Preferably the palladium catalyst is palladium acetate, the base is potassium phosphate, the ligand is 2-dicyclohexylphosphino-2',6'-dimethoxybiphenyl and the solvent is toluene.

Compounds of Formula (CC) and Formula (DD) may be prepared from Compounds of Formula (EE) and Formula (FF) respectively, by one or more of the procedures described previously.

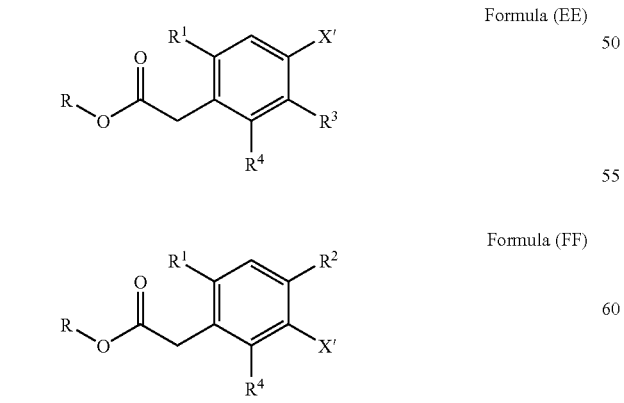

Compounds of Formula (EE) and Formula (FF) may be prepared from known compounds by known methods.

A compound of Formula (JJ) may be prepared by halogenating a compound of Formula (Q), followed by alkylation of the resulting halide of Formula (KK) with a $C_{1-4}$ alkyl halide or tri-$C_{1-4}$-alkylorthoformate under known conditions, for example by the procedures of R. Shepherd and A. White (J. Chem. Soc. Perkin Trans. 1 (1987), 2153) and Y.-L. Lin et al. (Bioorg. Med. Chem. (2002), 10, 685-690). Alternatively, a compound of Formula (JJ) may be prepared by alkylating a compound of Formula (Q) with a $C_{1-4}$ alkyl halide or a tri-$C_{1-4}$-alkylorthoformate, and halogenating the resulting enone of Formula (LL) under known conditions.

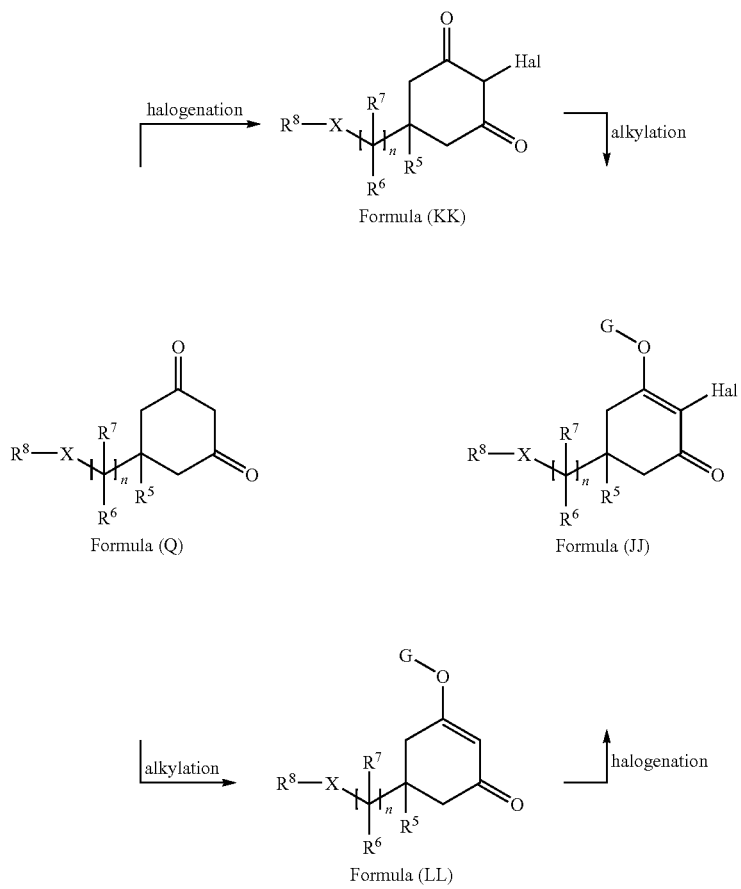

A compound of Formula (I) wherein G is H may be prepared from a compound of Formula (I) wherein G is $C_{1-4}$ alkyl by hydrolysis, preferably in the presence of an acid catalyst such as hydrochloric acid and optionally in the presence of a suitable solvent such as tetrahydrofuran. Additional compounds of formula (A) may be prepared by reacting a compound of formula (Q) with an organolead reagent of formula (MM) under conditions described, for example, by J. Pinhey, Pure and Appl. Chem., (1996), Vol. 68, No. 4, p 819-824 and by M. Moloney et al., Tetrahedron Lett., (2002), 43, 3407-3409. The organolead reagent of formula (MM) may be prepared from a boronic acid of formula (Z) a stannane of formula (NN), or by direct plumbation of a compound of formula (OO) with lead tetraacetate according to known procedures.

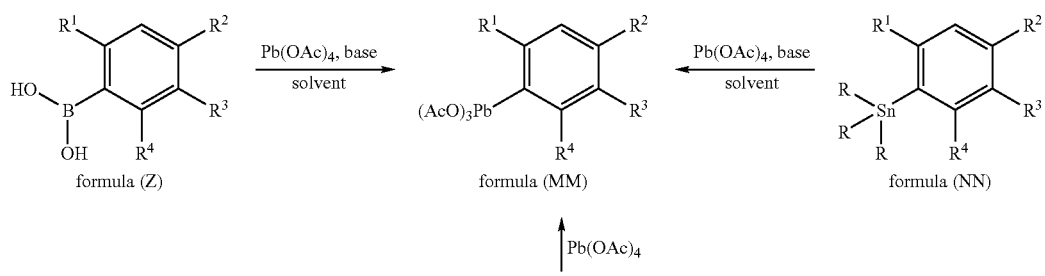

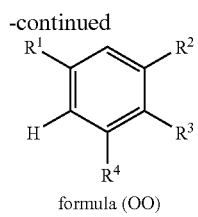

formula (OO)

Further compounds of formula (A) may be prepared by reacting a compound of formula (Q) with a suitable triarylbismuth compound under conditions described, for example, by A. Yu. Fedorov et al., Russ. Chem. Bull. Int. Ed., (2005), Vol. 54, No. 11, 2602-2611, and by P. Koech and M. Krische, J. Am. Chem. Soc., (2004), Vol. 126, No. 17, 5350-5351 (2004) and references therein.

The compounds of Formula (I) according to the invention can be used as herbicides in unmodified form, as obtained in the synthesis, but they are generally formulated into herbicidal compositions in a variety of ways using formulation adjuvants, such as carriers, solvents and surface-active substances. The formulations can be in various physical forms, for example in the form of dusting powders, gels, wettable powders, water-dispersible granules, water-dispersible tablets, effervescent compressed tablets, emulsifiable concentrates, microemulsifiable concentrates, oil-in-water emulsions, oil flowables, aqueous dispersions, oily dispersions, suspoemulsions, capsule suspensions, emulsifiable granules, soluble liquids, water-soluble concentrates (with water or a water-miscible organic solvent as carrier), impregnated polymer films or in other forms known, for example, from the Manual on Development and Use of FAO Specifications for Plant Protection Products, 5th Edition, 1999. Such formulations can either be used directly or are diluted prior to use. Diluted formulations can be prepared, for example, with water, liquid fertilisers, micronutrients, biological organisms, oil or solvents.

The formulations can be prepared, for example, by mixing the active ingredient with formulation adjuvants in order to obtain compositions in the form of finely divided solids, granules, solutions, dispersions or emulsions. The active ingredients can also be formulated with other adjuvants, for example finely divided solids, mineral oils, vegetable oils, modified vegetable oils, organic solvents, water, surface-active substances or combinations thereof. The active ingredients can also be contained in very fine microcapsules consisting of a polymer. Microcapsules contain the active ingredients in a porous carrier. This enables the active ingredients to be released into their surroundings in controlled amounts (e.g. slow release). Microcapsules usually have a diameter of from 0.1 to 500 microns. They contain active ingredients in an amount of about from 25 to 95% by weight of the capsule weight. The active ingredients can be present in the form of a monolithic solid, in the form of fine particles in solid or liquid dispersion or in the form of a suitable solution. The encapsulating membranes comprise, for example, natural and synthetic gums, cellulose, styrene-butadiene copolymers, polyacrylonitrile, polyacrylate, polyester, polyamides, polyureas, polyurethane or chemically modified polymers and starch xanthates or other polymers that are known to the person skilled in the art in this connection. Alternatively it is possible for very fine microcapsules to be formed wherein the active ingredient is present in the form of finely divided particles in a solid matrix of a base substance, but in that case the microcapsule is not encapsulated.

The formulation adjuvants suitable for the preparation of the compositions according to the invention are known per se. As liquid carriers there may be used: water, toluene, xylene, petroleum ether, vegetable oils, acetone, methyl ethyl ketone, cyclohexanone, acid anhydrides, acetonitrile, acetophenone, amyl acetate, 2-butanone, butylenes carbonate, chlorobenzene, cyclohexane, cyclohexanol, alkyl esters of acetic acid, diacetone alcohol, 1,2-dichloropropane, diethanolamine, p-diethylbenzene, diethylene glycol, diethylene glycol abietate, diethylene glycol butyl ether, diethylene glycol ethyl ether, diethylene glycol methyl ether, N,N-dimethylformamide, dimethyl sulfoxide, 1,4-dioxane, dipropylene glycol, dipropylene glycol methyl ether, dipropylene glycol dibenzoate, diproxitol, alkylpyrrolidone, ethyl acetate, 2-ethyl hexanol, ethylene carbonate, 1,1,1-trichloroethane, 2-heptanone, alpha-pinene, d-limonene, ethyl lactate, ethylene glycol, ethylene glycol butyl ether, ethylene glycol methyl ether, gamma-butyrolactone, glycerol, glycerol acetate, glycerol diacetate, glycerol triacetate, hexadecane, hexylene glycol, isoamyl acetate, isobornyl acetate, isooctane, isophorone, isopropylbenzene, isopropyl myristate, lactic acid, laurylamine, mesityl oxide, methoxypropanol, methyl isoamyl ketone, methyl isobutyl ketone, methyl laurate, methyl octanoate, methyl oleate, methylene chloride, m-xylene, n-hexane, n-octylamine, octadecanoic acid, octylamine acetate, oleic acid, oleylamine, o-xylene, phenol, polyethylene glycol (PEG 400), propionic acid, propyl lactate, propylene carbonate, propylene glycol, propylene glycol methyl ether, p-xylene, toluene, triethyl phosphate, triethylene glycol, xylenesulfonic acid, paraffin, mineral oil, trichloroethylene, perchloroethylene, ethyl acetate, amyl acetate, butyl acetate, propylene glycol methyl ether, diethylene glycol methyl ether, methanol, ethanol, isopropanol, and higher molecular weight alcohols, such as amyl alcohol, tetrahydrofurfuryl alcohol, hexanol, octanol, ethylene glycol, propylene glycol, glycerol, N-methyl-2-pyrrolidone and the like. Water is generally the carrier of choice for the dilution of the concentrates. Suitable solid carriers are, for example, talc, titanium dioxide, pyrophyllite clay, silica, attapulgite clay, kieselguhr, limestone, calcium carbonate, bentonite, calcium montmorillonite, cottonseed husks, wheatmeal, soybean flour, pumice, wood flour, ground walnut shells, lignin and similar materials, as described, for example, in CFR 180.1001. (c) & (d).

A large number of surface-active substances can advantageously be used both in solid and in liquid formulations, especially in those formulations which can be diluted with a carrier prior to use. Surface-active substances may be anionic, cationic, non-ionic or polymeric and they may be used as emulsifiying, wetting or suspending agents or for other purposes. Typical surface-active substances include, for example, salts of alkyl sulfates, such as diethanolammonium lauryl sulfate; salts of alkylarylsulfonates, such as calcium dodecylbenzenesulfonate; alkylphenol-alkylene oxide addition products, such as nonylphenol ethoxylate; alcohol-alkylene oxide addition products, such as tridecyl alcohol ethoxylate; soaps, such as sodium stearate; salts of alkylnaphthalenesulfonates, such as sodium dibutylnaphthalenesulfonate; dialkyl esters of sulfosuccinate salts, such as sodium di(2-ethylhexyl)sulfosuccinate; sorbitol esters, such as sorbitol oleate; quaternary amines, such as lauryl trimethylammonium chloride, polyethylene glycol esters of fatty acids, such as polyethylene glycol stearate; block copolymers of ethylene oxide and propylene oxide; and salts of mono- and di-alkyl phosphate esters; and also further substances described e.g. in "McCutcheon's Detergents and Emulsifiers Annual", MC Publishing Corp., Ridgewood, N.J., 1981.

Further adjuvants which can usually be used in pesticidal formulations include crystallisation inhibitors, viscosity-modifying substances, suspending agents, dyes, anti-oxidants, foaming agents, light absorbers, mixing aids, anti-foams, complexing agents, neutralising or pH-modifying substances and buffers, corrosion-inhibitors, fragrances, wetting agents, absorption improvers, micronutrients, plasticisers, glidants, lubricants, dispersants, thickeners, anti-freezes, microbiocides, and also liquid and solid fertilisers.

The formulations may also comprise additional active substances, for example further herbicides, herbicide safeners, plant growth regulators, fungicides or insecticides.

The compositions according to the invention can additionally include an additive comprising an oil of vegetable or animal origin, a mineral oil, alkyl esters of such oils or mixtures of such oils and oil derivatives. The amount of oil additive used in the composition according to the invention is generally from 0.01 to 10%, based on the spray mixture. For example, the oil additive can be added to the spray tank in the desired concentration after the spray mixture has been prepared. Preferred oil additives comprise mineral oils or an oil of vegetable origin, for example rapeseed oil, olive oil or sunflower oil, emulsified vegetable oil, such as AMIGO® (Rhône-Poulenc Canada Inc.), alkyl esters of oils of vegetable origin, for example the methyl derivatives, or an oil of animal origin, such as fish oil or beef tallow. A preferred additive contains, for example, as active components essentially 80% by weight alkyl esters of fish oils and 15% by weight methylated rapeseed oil, and also 5% by weight of customary emulsifiers and pH modifiers. Especially preferred oil additives comprise alkyl esters of $C_8$-$C_{22}$ fatty acids, especially the methyl derivatives of $C_{12}$-$C_{18}$ fatty acids, for example the methyl esters of lauric acid, palmitic acid and oleic acid, being important. Those esters are known as methyl laurate (CAS-111-82-0), methyl palmitate (CAS-112-39-0) and methyl oleate (CAS-112-62-9). A preferred fatty acid methyl ester derivative is Emery® 2230 and 2231 (Cognis GmbH). Those and other oil derivatives are also known from the Compendium of Herbicide Adjuvants, 5th Edition, Southern Illinois University, 2000.

The application and action of the oil additives can be further improved by combining them with surface-active substances, such as non-ionic, anionic or cationic surfactants. Examples of suitable anionic, non-ionic and cationic surfactants are listed on pages 7 and 8 of WO 97/34485. Preferred surface-active substances are anionic surfactants of the dodecylbenzylsulfonate type, especially the calcium salts thereof, and also non-ionic surfactants of the fatty alcohol ethoxylate type. Special preference is given to ethoxylated $C_{12}$-$C_{22}$ fatty alcohols having a degree of ethoxylation of from 5 to 40. Examples of commercially available surfactants are the Genapol types (Clariant AG). Also preferred are silicone surfactants, especially polyalkyl-oxide-modified heptamethyltrisiloxanes, which are commercially available e.g. as Silwet L-77®, and also perfluorinated surfactants. The concentration of surface-active substances in relation to the total additive is generally from 1 to 30% by weight. Examples of oil additives that consist of mixtures of oils or mineral oils or derivatives thereof with surfactants are Edenor ME SU®, Turbocharge® (Syngenta AG, CH) and Actipron® (BP Oil UK Limited, GB).

The said surface-active substances may also be used in the formulations alone, that is to say without oil additives.

Furthermore, the addition of an organic solvent to the oil additive/surfactant mixture can contribute to a further enhancement of action. Suitable solvents are, for example, Solvesso® (ESSO) and Aromatic Solvent® (Exxon Corporation). The concentration of such solvents can be from 10 to 80% by weight of the total weight. Such oil additives, which may be in admixture with solvents, are described, for example, in U.S. Pat. No. 4,834,908. A commercially available oil additive disclosed therein is known by the name MERGE® (BASF Corporation). A further oil additive that is preferred according to the invention is SCORE® (Syngenta Crop Protection Canada.)

In addition to the oil additives listed above, in order to enhance the activity of the compositions according to the invention it is also possible for formulations of alkylpyrrolidones, (e.g. Agrimax®) to be added to the spray mixture. Formulations of synthetic lattices, such as, for example, polyacrylamide, polyvinyl compounds or poly-1-p-menthene (e.g. Bond®, Courier® or Emerald®) can also be used. Solutions that contain propionic acid, for example Eurogkem Pene-trate®, can also be mixed into the spray mixture as activity-enhancing agents.

The herbicidal formulations generally contain from 0.1 to 99% by weight, especially from 0.1 to 95% by weight, of a compound of Formula (I) and from 1 to 99.9% by weight of a formulation adjuvant, which preferably includes from 0 to 25% by weight of a surface-active substance. Whereas commercial products will preferably be formulated as concentrates, the end user will normally employ dilute formulations.

The rate of application of the compounds of Formula (I) may vary within wide limits and depends upon the nature of the soil, the method of application (pre- or post-emergence; seed dressing; application to the seed furrow; no tillage application etc.), the crop plant, the weed or grass to be controlled, the prevailing climatic conditions, and other factors governed by the method of application, the time of application and the target crop. The compounds of formula I according to the invention are generally applied at a rate of 1 to 4000 g/ha, especially from 5 to 1000 g/ha. Preferred formulations have especially the following compositions:
(%=percent by weight):

| Emulsifiable concentrates: | |
|---|---|
| active ingredient: | 1 to 95%, preferably 60 to 90% |
| surface-active agent: | 1 to 30%, preferably 5 to 20% |
| liquid carrier: | 1 to 80%, preferably 1 to 35% |
| Dusts: | |
| active ingredient: | 0.1 to 10%, preferably 0.1 to 5% |
| solid carrier: | 99.9 to 90%, preferably 99.9 to 99% |
| Suspension concentrates: | |
| active ingredient: | 5 to 75%, preferably 10 to 50% |
| water: | 94 to 24%, preferably 88 to 30% |
| surface-active agent: | 1 to 40%, preferably 2 to 30% |
| Wettable powders: | |
| active ingredient: | 0.5 to 90%, preferably 1 to 80% |
| surface-active agent: | 0.5 to 20%, preferably 1 to 15% |
| solid carrier: | 5 to 95%, preferably 15 to 90% |

-continued

| Granules: | |
|---|---|
| active ingredient: | 0.1 to 30%, preferably 0.1 to 15% |
| solid carrier: | 99.5 to 70%, preferably 97 to 85% |

The following Examples further illustrate, but do not limit, the invention.

| F1. Emulsifiable concentrates | a) | b) | c) | d) |
|---|---|---|---|---|
| active ingredient | 5% | 10% | 25% | 50% |
| calcium dodecylbenzene-sulfonate | 6% | 8% | 6% | 8% |
| castor oil polyglycol ether (36 mol of ethylene oxide) | 4% | — | 4% | 4% |
| octylphenol polyglycol ether (7-8 mol of ethylene oxide) | — | 4% | — | 2% |
| NMP | — | — | 10% | 20% |
| arom. hydrocarbon mixture $C_9$-$C_{12}$ | 85% | 78% | 55% | 16% |

Emulsions of any desired concentration can be prepared from such concentrates by dilution with water.

| F2. Solutions | a) | b) | c) | d) |
|---|---|---|---|---|
| active ingredient | 5% | 10% | 50% | 90% |
| 1-methoxy-3-(3-methoxy-propoxy)-propane | — | 20% | 20% | — |
| polyethylene glycol MW 400 | 20% | 10% | — | — |
| NMP | — | — | 30% | 10% |
| arom. hydrocarbon mixture $C_9$-$C_{12}$ | 75% | 60% | — | — |

The solutions are suitable for application in the form of microdrops.

| F3. Wettable powders | a) | b) | c) | d) |
|---|---|---|---|---|
| active ingredient | 5% | 25% | 50% | 80% |
| sodium lignosulfonate | 4% | — | 3% | — |
| sodium lauryl sulfate | 2% | 3% | — | 4% |
| sodium diisobutylnaphthalene-sulfonate | — | 6% | 5% | 6% |
| octylphenol polyglycol ether (7-8 mol of ethylene oxide) | — | 1% | 2% | — |
| highly disperse silicic acid | 1% | 3% | 5% | 10% |
| kaolin | 88% | 62% | 35% | — |

The active ingredient is thoroughly mixed with the adjuvants and the mixture is thoroughly ground in a suitable mill, yielding wettable powders which can be diluted with water to give suspensions of any desired concentration.

| F4. Coated granules | a) | b) | c) |
|---|---|---|---|
| active ingredient | 0.1% | 5% | 15% |
| highly disperse silicic acid | 0.9% | 2% | 2% |
| inorg. carrier (diameter 0.1-1 mm) e.g. $CaCO_3$ or $SiO_2$ | 99.0% | 93% | 83% |

The active ingredient is dissolved in methylene chloride, the solution is sprayed onto the carrier and the solvent is subsequently evaporated off in vacuo.

| F5. Coated granules | a) | b) | c) |
|---|---|---|---|
| active ingredient | 0.1% | 5% | 15% |
| polyethylene glycol MW 200 | 1.0% | 2% | 3% |
| highly disperse silicic acid | 0.9% | 1% | 2% |
| inorg. carrier (diameter 0.1-1 mm) e.g. $CaCO_3$ or $SiO_2$ | 98.0% | 92% | 80% |

The finely ground active ingredient is applied uniformly, in a mixer, to the carrier moistened with polyethylene glycol. Non-dusty coated granules are obtained in this manner.

| F6. Extruder granules | a) | b) | c) | d) |
|---|---|---|---|---|
| active ingredient | 0.1% | 3% | 5% | 15% |
| sodium lignosulfonate | 1.5% | 2% | 3% | 4% |
| carboxymethylcellulose | 1.4% | 2% | 2% | 2% |
| kaolin | 97.0% | 93% | 90% | 79% |

The active ingredient is mixed and ground with the adjuvants and the mixture is moistened with water. The resulting mixture is extruded and then dried in a stream of air.

| F7. Dusts | a) | b) | c) |
|---|---|---|---|
| active ingredient | 0.1% | 1% | 5% |
| talcum | 39.9% | 49% | 35% |
| kaolin | 60.0% | 50% | 60% |

Ready-to-use dusts are obtained by mixing the active ingredient with the carriers and grinding the mixture in a suitable mill.

| F8. Suspension concentrates | a) | b) | c) | d) |
|---|---|---|---|---|
| active ingredient | 3% | 10% | 25% | 50% |
| ethylene glycol | 5% | 5% | 5% | 5% |
| nonylphenol polyglycol ether (15 mol of ethylene oxide) | — | 1% | 2% | — |
| sodium lignosulfonate | 3% | 3% | 4% | 5% |
| carboxymethylcellulose | 1% | 1% | 1% | 1% |
| 37% aqueous formaldehyde solution | 0.2% | 0.2% | 0.2% | 0.2% |
| silicone oil emulsion | 0.8% | 0.8% | 0.8% | 0.8% |
| water | 87% | 79% | 62% | 38% |

The finely ground active ingredient is intimately mixed with the adjuvants, yielding a suspension concentrate from which suspensions of any desired concentration can be prepared by dilution with water.

The invention relates also to a method for the selective control of grasses and weeds in crops of useful plants, which comprises treating the useful plants or the area under cultivation or the locus thereof with a compound of Formula (I).

Crops of useful plants in which the compositions according to the invention can be used include especially cereals, cotton, soybeans, sugar beet, sugar cane, plantation crops, rape, maize and rice, and for non-selective weed control. The term "crops" is to be understood as also including crops that have been rendered tolerant to herbicides or classes of herbicides (for example ALS, GS, EPSPS, PPO, ACCase and HPPD inhibitors) as a result of conventional methods of breeding or genetic engineering. An example of a crop that has been rendered tolerant e.g. to imidazolinones, such as imazamox, by conventional methods of breeding is Clearfield® summer rape (Canola). Examples of crops that have been rendered tolerant to herbicides by genetic engineering methods include e.g. glyphosate- and glufosinate-resistant maize varieties commercially available under the trade names RoundupReady® and LibertyLink®. The weeds to be controlled may be both monocotyledonous and dicotyledonous weeds, such as, for example, *Stellaria, Nasturtium, Agrostis, Digitaria, Avena, Setaria, Sinapis, Lolium, Solanum, Echinochloa, Scirpus, Monochoria, Sagittaria, Bromus, Alopecurus, Sorghum, Rottboellia, Cyperus, Abutilon, Sida, Xanthium, Amaranthus, Chenopodium, Ipomoea, Chrysanthemum, Galium, Viola* and *Veronica*.

Crops are also to be understood as being those which have been rendered resistant to harmful insects by genetic engineering methods, for example Bt maize (resistant to European corn borer), Bt cotton (resistant to cotton boll weevil) and also Bt potatoes (resistant to Colorado beetle). Examples of Bt maize are the Bt-176 maize hybrids of NK® (Syngenta Seeds). The Bt toxin is a protein that is formed naturally by *Bacillus thuringiensis* soil bacteria. Examples of toxins and transgenic plants able to synthesise such toxins are described in EP-A-451 878, EP-A-374 753, WO 93/07278, WO 95/34656, WO 03/052073 and EP-A-427 529. Examples of transgenic plants that contain one or more genes which code for an insecticidal resistance and express one or more toxins are KnockOut® (maize), Yield Gard® (maize), NuCOTIN33B® (cotton), Bollgard® (cotton), NewLeaf® (potatoes), NatureGard® and Protexcta®. Plant crops and their seed material can be resistant to herbicides and at the same time also to insect feeding ("stacked" transgenic events). Seed can, for example, have the ability to express an insecticidally active Cry3 protein and at the same time be glyphosate-tolerant. The term "crops" is to be understood as also including crops obtained as a result of conventional methods of breeding or genetic engineering which contain so-called output traits (e.g. improved flavour, storage stability, nutritional content).

Areas under cultivation are to be understood as including land where the crop plants are already growing as well as land intended for the cultivation of those crop plants.

The compounds of Formula (I) according to the invention can also be used in combination with other herbicides. The following mixtures of the compound of Formula (I) are especially important. Preferably, the compound of the Formula (I) is a compound listed in Tables 1 to 151 below:
compound of formula I+acetochlor, compound of formula I+acifluorfen, compound of formula I+acifluorfen-sodium, compound of formula I+aclonifen, compound of formula I+acrolein, compound of formula I+alachlor, compound of formula I+alloxydim, compound of formula I+allyl alcohol, compound of formula I+ametryn, compound of formula I+amicarbazone, compound of formula I+amidosulfuron, compound of formula I+aminopyralid, compound of formula I+amitrole, compound of formula I+ammonium sulfamate, compound of formula I+anilofos, compound of formula I+asulam, compound of formula I+atrazine, formula I+aviglycine, formula I+azafenidin, compound of formula I+azimsulfuron, compound of formula I+BCPC, compound of formula I+beflubutamid, compound of formula I+benazolin, formula I+bencarbazone, compound of formula I+benfluralin, compound of formula I+benfuresate, compound of formula I+bensulfuron, compound of formula I+bensulfuron-methyl, compound of formula I+bensulide, compound of formula I+bentazone, compound of formula I+benzfendizone, compound of formula I+benzobicyclon, compound of formula I+benzofenap, compound of formula I+bifenox, compound of formula I+bilanafos, compound of formula I+bispyribac, compound of formula I+bispyribac-sodium, compound of formula I+borax, compound of formula I+bromacil, compound of formula I+bromobutide, formula I+bromophenoxim, compound of formula I+bromoxynil, compound of formula I+butachlor, compound of formula I+butafenacil, compound of formula I+butamifos, compound of formula I+butralin, compound of formula I+butroxydim, compound of formula I+butylate, compound of formula I+cacodylic acid, compound of formula I+calcium chlorate, compound of formula I+cafenstrole, compound of formula I+carbetamide, compound of formula I+carfentrazone, compound of formula I+carfentrazone-ethyl, compound of formula I+CDEA, compound of formula I+CEPC, compound of formula I+chlorflurenol, compound of formula I+chlorflurenol-methyl, compound of formula I+chloridazon, compound of formula I+chlorimuron, compound of formula I+chlorimuron-ethyl, compound of formula I+chloroacetic acid, compound of formula I+chlorotoluron, compound of formula I+chlorpropham, compound of formula I+chlorsulfuron, compound of formula I+chlorthal, compound of formula I+chlorthal-dimethyl, compound of formula I+cinidon-ethyl, compound of formula I+cinmethylin, compound of formula I+cinosulfuron, compound of formula I+cisanilide, compound of formula I+clethodim, compound of formula I+clodinafop, compound of formula I+clodinafop-propargyl, compound of formula I+clomazone, compound of formula I+clomeprop, compound of formula I+clopyralid, compound of formula I+cloransulam, compound of formula I+cloransulam-methyl, compound of formula I+CMA, compound of formula I+4-CPB, compound of formula I+CPMF, compound of formula I+4-CPP, compound of formula I+CPPC, compound of formula I+cresol, compound of formula I+cumyluron, compound of formula I+cyanamide, compound of formula I+cyanazine, compound of formula I+cycloate, compound of formula I+cyclosulfamuron, compound of formula I+cycloxydim, compound of formula I+cyhalofop, compound of formula I+cyhalofop-butyl, compound of formula I+2,4-D, compound of formula I+3,4-DA, compound of formula I+daimuron, compound of formula I+dalapon, compound of formula I+dazomet, compound of formula I+2,4-DB, compound of formula I+3,4-DB, compound of formula I+2,4-DEB, compound of formula I+desmedipham, formula I+desmetryn, compound of formula I+dicamba, compound of formula I+dichlobenil, compound of formula I+ortho-dichlorobenzene, compound of formula I+para-dichlorobenzene, compound of formula I+dichiorprop, compound of formula I+dichlorprop-P, compound of formula I+diclofop, compound of formula I+diclofop-methyl, compound of formula I+diclosulam, compound of formula I+difenzoquat, compound of formula I+difenzoquat metilsulfate, compound of formula I+diflufenican, compound of formula I+diflufenzopyr, compound of formula I+dimefuron, compound of formula I+dimepiperate, compound of formula I+dimethachlor, compound of formula I+dimethametryn, compound of formula I+dimethenamid, compound of formula I+dimethenamid-P, compound of formula I+dimethipin, compound of formula I+dimethylarsinic acid, compound of formula I+dinitramine, compound of formula I+dinoterb, compound of formula I+diphenamid, formula I+dipropetryn, compound of formula I+diquat, compound of formula I+diquat dibromide, compound of formula I+dithiopyr, compound of formula I+diuron, compound of formula I+DNOC, compound of formula I+3,4-DP, compound of formula I+DSMA, compound of formula I+EBEP, compound of formula I+endothal, compound of formula I+EPTC, compound of formula I+esprocarb, compound of formula I+ethalfluralin, compound of formula I+ethametsulfuron, compound of formula I+ethametsulfuron-methyl, formula I+ethephon, compound of formula I+ethofumesate, compound of formula I+ethoxyfen, compound of formula I+ethoxysulfuron, compound of formula I+etobenzanid, compound of formula I+fenoxaprop-P, compound of formula I+fenoxaprop-P-ethyl, compound of formula I+fentrazamide, compound of formula I+ferrous sulfate, compound of formula I+flamprop-M, compound of formula I+flazasulfuron, compound of formula I+florasulam, compound of formula I+fluazifop, compound of formula I+fluazifop-butyl, compound of formula I+fluazifop-P, compound of formula I+fluazifop-P-butyl, formula I+fluazolate, compound of formula I+flucarbazone, compound of formula I+flucarbazone-sodium, compound of formula I+flucetosulfuron, compound of formula I+fluchloralin, compound of formula I+flufenacet, compound of formula I+flufenpyr, compound of formula I+flufenpyr-ethyl, formula I+flumetralin, compound of formula I+flumetsulam, compound of formula I+flumiclorac, compound of formula I+flumiclorac-pentyl, compound of formula I+flumioxazin, formula I+flumipropin, compound of formula I+fluometuron, compound of formula I+fluoroglycofen, compound of formula I+fluoroglycofen-ethyl, formula I+fluoxaprop, formula I+flupoxam, formula I+flupropacil, compound of formula I+flupropanate, compound of formula I+flupyrsulfuron, compound of formula I+flupyrsulfuron-methyl-sodium, compound of formula I+flurenol, compound of formula I+fluridone, compound of formula I+fluorochloridone, compound of formula I+fluoroxypyr, compound of formula I+flurtamone, compound of formula I+fluthiacet, compound of formula I+fluthiacet-methyl, compound of formula I+fomesafen, compound of formula I+foramsulfuron, compound of formula I+fosamine, compound of formula I+glufosinate, compound of formula I+glufosinate-ammonium, compound of formula I+glyphosate, compound of formula I+halosulfuron, compound of formula I+halosulfuron-methyl, compound of formula I+haloxyfop, compound of formula I+haloxyfop-P, compound of formula I+HC-252, compound of formula I+hexazinone, compound of formula I+imazamethabenz, compound of formula I+imazamethabenz-methyl, compound of formula I+imazamox, compound of formula I+imazapic, compound of formula I+imazapyr, compound of formula I+imazaquin, compound of formula I+imazethapyr, compound of formula I+imazosulfuron, compound of formula I+indanofan, compound of formula I+iodomethane, compound of formula I+iodosulfuron, compound of formula I+iodosulfuron-methyl-sodium, compound of formula I+ioxynil, compound of formula I+isoproturon, compound of formula I+isouron, compound of formula I+isoxaben, compound of formula I+isoxachlortole, compound of formula I+isoxaflutole, formula I+isoxapyrifop, compound of formula I+karbutilate, compound of formula I+lactofen, compound of formula I+lenacil, compound of formula I+linuron, compound of formula I+MAA, compound of formula I+MAMA, compound of formula I+MCPA, compound of formula I+MCPA-thioethyl, compound of formula I+MCPB, compound of formula I+mecoprop, compound of formula I+mecoprop-P, compound of formula I+mefenacet, compound of formula I+mefluidide, compound of formula I+mesosulfuron, compound of formula I+mesosulfuron-methyl, compound of formula I+mesotrione, compound of formula I+metam, compound of formula I+metamifop, compound of formula I+metamitron, compound of formula I+metazachlor, compound of formula I+methabenzthiazuron, formula I+methazole, compound of formula I+methylarsonic acid, compound of formula I+methyldymron, compound of formula I+methyl isothiocyanate, compound of formula I+metobenzuron, formula I+metobromuron, compound of formula I+metolachlor, compound of formula I+S-metolachlor, compound of formula I+metosulam, compound of formula I+metoxuron, compound of formula I+metribuzin, compound of formula I+metsulfuron, compound of formula I+metsulfuron-methyl, compound of formula I+MK-616, compound of formula I+molinate, compound of formula I+monolinuron, compound of formula I+MSMA, compound of formula I+naproanilide, compound of formula I+napropamide, compound of formula I+naptalam, formula I+NDA-402989, compound of formula I+neburon, compound of formula I+nicosulfuron, formula I+nipyraclofen, formula I+n-methyl glyphosate, compound of formula I+nonanoic acid, compound of formula I+norflurazon, compound of formula I+oleic acid (fatty acids), compound of formula I+orbencarb, compound of formula I+orthosulfamuron, compound of formula I+oryzalin, compound of formula I+oxadiargyl, compound of formula I+oxadiazon, compound of formula I+oxasulfuron, compound of formula I+oxaziclomefone, compound of formula I+oxyfluorfen, compound of formula I+paraquat, compound of formula I+paraquat dichloride, compound of formula I+pebulate, compound of formula I+pendimethalin, compound of formula I+penoxsulam, compound of formula I+pentachlorophenol, compound of formula I+pentanochlor, compound of formula I+pentoxazone, compound of formula I+pethoxamid, compound of formula I+petrolium oils, compound of formula I+phenmedipham, compound of formula I+phenmedipham-ethyl, compound of formula I+picloram, compound of formula I+picolinafen, compound of formula I+pinoxaden, compound of formula I+piperophos, compound of formula I+potassium arsenite, compound of formula I+potassium azide, compound of formula I+pretilachlor, compound of formula I+primisulfuron, compound of formula I+primisulfuron-methyl, compound of formula I+prodiamine, compound of formula I+profluazol, compound of formula I+profoxydim, formula I+prohexadione-calcium, compound of formula I+prometon, compound of formula I+prometryn, compound of formula I+propachlor, compound of formula I+propanil, compound of formula I+propaquizafop, compound of formula I+propazine, compound of formula I+propham, compound of formula I+propisochlor, compound of formula I+propoxycarbazone, compound of formula I+propoxycarbazone-sodium, compound of formula I+propyzamide, compound of formula I+prosulfocarb, compound of formula I+prosulfuron, compound of formula I+pyraclonil, compound of formula I+pyraflufen, compound of formula I+pyraflufen-ethyl, formula I+pyrasulfotole, compound of formula I+pyrazolynate, compound of formula I+pyrazosulfuron, compound of formula I+pyrazosulfuron-ethyl, compound of formula I+pyrazoxyfen, compound of formula I+pyribenzoxim, compound of formula I+pyributicarb, compound of formula I+pyridafol, compound of formula I+pyridate, compound of formula I+pyriftalid, compound of formula I+pyriminobac, compound of formula I+pyriminobac-methyl, compound of formula I+pyrimisulfan, compound of formula I+pyrithiobac, compound of formula I+pyrithiobac-sodium, formula I+pyroxasulfone (KIH-485), formula I+pyroxulam, compound of formula I+quinclorac, compound of formula I+quinmerac, compound of formula I+quinoclamine, compound of formula I+quizalofop, compound of formula I+quizalofop-P, compound of formula I+rimsulfuron, compound of formula I+sethoxydim, compound of formula I+siduron, compound of formula I+simazine, compound of formula I+simetryn, compound of formula I+SMA, compound of formula I+sodium arsenite, compound of formula I+sodium azide, compound of formula I+sodium chlorate, compound of formula I+sulcotrione, compound of formula I+sulfentrazone, compound of formula I+sulfometuron, compound of formula I+sulfometuron-methyl, compound of formula I+sulfosate, compound of formula I+sulfosulfuron, compound of formula I+sulfuric acid, compound of formula I+tar oils, compound of formula I+2,3,6-TBA, compound of formula I+TCA, compound of formula I+TCA-sodium, formula I+tebutam, compound of formula I+tebuthiuron, formula I+tefuryltrione, compound of formula I+tembotrione, compound of formula I+tepraloxydim, compound of formula I+terbacil, compound of formula I+terbumeton, compound of formula I+terbuthylazine, compound of formula I+terbutryn, compound of formula I+thenylchlor, compound of formula I+thiazafluoron, compound of formula I+thiazopyr, compound of formula I+thifensulfuron, compound of formula I+thiencarbazone, compound of formula I+thifensulfuron-methyl, compound of formula I+thiobencarb, compound of formula I+tiocarbazil, compound of formula I+topramezone, compound of formula I+tralkoxydim, compound of formula I+tri-allate, compound of formula I+triasulfuron, compound of formula I+triaziflam, compound of formula I+tribenuron, compound of formula I+tribenuron-methyl, compound of formula I+tricamba, compound of formula I+triclopyr, compound of formula I+trietazine, compound of formula I+trifloxysulfuron, compound of formula I+trifloxysulfuron-sodium, compound of formula I+trifluralin, compound of formula I+triflusulfuron, compound of formula I+triflusulfuron-methyl, compound of formula I+trihydroxytriazine, compound of formula I+trinexapac-ethyl, compound of formula I+tritosulfuron, compound of formula I+[3-[2-chloro-4-fluoro-5-(1-methyl-6-trifluoromethyl-2,4-dioxo-1,2,3,4-tetrahydropyrimidin-3-yl)phenoxy]-2-pyridyloxy]acetic acid ethyl ester (CAS RN 353292-31-6), compound of formula I+4-hydroxy-3-[[2-[(2-methoxyethoxy) methyl]-6-(trifluoromethyl)-3-pyridinyl]carbonyl]-bicyclo [3.2.1]oct-3-en-2-one (CAS RN 352010-68-5), compound of formula I+2-chloro-5-[3,6-dihydro-3-methyl-2,6-dioxo-4-(trifluoromethyl)-1(2H)-pyrimidinyl]-4-fluoro-N-[[methyl (1-methylethyl)amino]sulfonyl]benzamide (CAS RN 372137-35-4), and compound of formula I+4-hydroxy-3-[[2-(3-methoxypropyl)-6-(difluoromethyl)-3-pyridinyl]carbonyl]bicyclo[3.2.1]oct-3-en-2-one.

The mixing partners of the compound of Formula (I) may also be in the form of esters or salts, as mentioned e.g. in The Pesticide Manual, 12th Edition (BCPC), 2000.

The mixing ratio of the compound of Formula (I) to the mixing partner is preferably from 1:100 to 1000:1. The mixtures can advantageously be used in the above-mentioned formulations (in which case "active ingredient" relates to the respective mixture of compound of Formula (I) with the mixing partner).

The compounds of Formula (I) according to the invention can also be used in combination with safeners. Preferably, in these mixtures, the compound of the Formula (I) is one of those compounds listed in Tables 1 to 151 below. The following mixtures with safeners, especially, come into consideration: compound of formula (I)+cloquintocet-mexyl, compound of formula (I)+cloquintocet acid and salts thereof, compound of formula (I)+fenchlorazole-ethyl, compound of formula (I)+fenchlorazole acid and salts thereof, compound of formula (I)+mefenpyr-diethyl, compound of formula (I)+mefenpyr diacid, compound of formula (I)+isoxadifen-ethyl, compound of formula (I)+isoxadifen acid, compound of formula (I)+furilazole, compound of formula (I)+furilazole R isomer, compound of formula (I)+benoxacor, compound of formula (I)+dichlormid, compound of formula (I)+AD-67, compound of formula (I)+oxabetrinil, compound of formula (I)+cyometrinil, compound of formula (I)+cyometrinil Z-isomer, compound of formula (I)+fenclorim, compound of formula (I)+cyprosulfamide, compound of formula (I)+naphthalic anhydride, compound of formula (I)+flurazole, compound of formula (I)+N-(2-methoxybenzoyl)-4-[(methylaminocarbonyl)amino]benzenesulfonamide, compound of formula (I)+ CL 304,415, compound of formula (I)+dicyclonon, compound of formula (I)+fluxofenim, compound of formula (I)+ DKA-24, compound of formula (I)+R-29148 and compound of formula (I)+PPG-1292. A safening effect can also be observed for the mixtures compound of the formula (I)+ dymron, compound of the formula (I)+MCPA, compound of the formula (I)+mecopropand compound of the formula (I)+ mecoprop-P.

The above-mentioned safeners and herbicides are described, for example, in the Pesticide Manual, Twelfth Edition, British Crop Protection Council, 2000. R-29148 is described, for example by P. B. Goldsbrough et al., Plant Physiology, (2002), Vol. 130 pp. 1497-1505 and references therein, PPG-1292 is known from WO09211761 and N-(2-methoxybenzoyl)-4-[(methylaminocarbonyl)amino]benzenesulfonamide is known from EP365484.

The compounds of Formula (I) according to the invention can also be used in combination with the co-herbicides and safeners mentioned above to form a three-way mixture containing a compound of the Formula (I), a co-herbicide and a safener.

EXAMPLE 1

Preparation of 2-(2,6-diethyl-4-methylphenyl)-5-[2-(ethylthio)propyl]cyclohexane-1,3-dione (Compound number T7 in Table T1)

Step 1

Ethanethiol (1.48 ml, 20.0 mmol) is added dropwise to a mixture of 1.66 ml crotonaldehyde (1.66 ml, 20.0 mmol) and 0.02 ml triethylamine (0.02 ml, 0.1 mmol) and the mixture is stirred at room temperature for 4 hours, then concentrated under reduced pressure to give 3-(ethylthio)butyraldehyde (2.66 g) as a yellow liquid which is used without further purification in the next step.

Step 2

1-Triphenylphosphoranylidene-2-propanone (12.77 g, 40.0 mmol) is added to a solution of 3-(ethylthio)butyraldehyde (5.30 g, 40.0 mmol) in dichloromethane (100 ml) and the mixture is heated under reflux for 24 hours. The reaction mixture is cooled to room temperature, and the solvent evaporated in vacuo to give a beige solid. The crude product is taken up in a 1:1 mixture of hexane:ether (the insoluble material is discarded), and then concentrated under reduced pressure to give an orange oil which is further purified by column chromatography on silica gel to give 6-(ethylthio)hept-3-en-2-one as a yellow oil.

Step 3

Hexane washed sodium (0.73 g, 32.0 mmol) is added to ethanol (40 ml), stirred at 0° C. under nitrogen. After 2 hours of stirring, a solution of diethyl malonate (4.64 g, 29.0 mmol) in ethanol (20 ml) is added dropwise over 5 minutes, and once the addition is complete, the cooling bath is removed and reaction mixture is allowed to warm to room temperature. The reaction mixture is stirred at room temperature for 1 hour, then cooled again to 0° C.

A solution of 6-(ethylthio)hept-3-en-2-one (4.2 g, 24.0 mmol) in ethanol (20 ml) is added dropwise over 10 minutes.

Once addition is complete, the cooling bath is removed and reaction mixture is allowed to warm to room temperature. The reaction mixture is stirred for 24 hours at room temperature, then poured into 2M aqueous hydrochloric acid (200 ml). The reaction mixture extracted with dichloromethane, and the combined organic extracts are dried over anhydrous magnesium sulfate, filtered, and the filtrate evaporated in vacuo to give a yellow gum, which is dissolved in a mixture of 2M aqueous sodium hydroxide solution (75 ml) and propan-2-ol (25 ml) and then stirred at room temperature for 44 hours. Some of the solvent (by roughly one quarter to one half) is removed under reduced pressure, and the reaction mixture is acidified carefully to pH 2 by the addition of concentrated hydrochloric acid. The reaction mixture is heated to 70° C., held at 70° C. for 30 minutes, and then the heat removed and reaction allowed to cool to room temperature. The reaction mixture is extracted with ethyl acetate, and the combined organic extracts are dried over anhydrous magnesium sulfate, filtered, and the filtrate is evaporated in vacuo to give a yellow gum. Further purification by column chromatography on silica gel affords 5-[(2-ethylthio)propyl)cyclo-hexane-1,3-dione as a yellow gum.

Step 4

A solution of 5-(2-ethylthio)propyl)cyclohexane-1,3-dione (2.50 g, 11.7 mmol) and sodium carbonate (1.24 g, 11.7 mmol) in a mixture of water (35 ml) and ethanol (5 ml) is prepared, and then add dropwise over 5 minutes to a mixture of (diacetoxyiodo)benzene (3.76 g, 11.7 mmol) and sodium carbonate (1.24 g, 11.7 mmol) in water (40 ml) at room temperature. The reaction mixture is stirred for 2 hours at room temperature, then extracted with dichloromethane. The organic extracts are combined, dried over anhydrous magnesium sulfate, filtered, and the filtrate is evaporated in vacuo to give the iodonium ylide, used without further purification in the next step.

Step 5

The iodonium ylide (1.90 g, 4.56 mmol), prepared in Step 4,2,6-diethyl-4-methyl-phenylboronic acid (1.05 g, 5.48 mmol), palladium (II) acetate (0.082 g, 0.36 mmol), lithium hydroxide monohydrate (0.766 g, 18.24 mmol) are stirred together a mixture of 1,2-dimethoxyethane (40 ml) and water (10 ml) under an atmosphere of nitrogen and then heated to 50° C. for 4.75 hours. The mixture is cooled to room temperature, filtered through celite, and the celite washed with 2M aqueous hydrochloric acid (80 ml) and 40 ml ethyl acetate (40 ml). The mixture is poured into a separating funnel, the organic layer is separated, and the aqueous layer is extracted with ethyl acetate. The organic extracts are combined, dried over anhydrous magnesium sulfate, filtered, and the filtrate is evaporated in vacuo to give a brown gum. Purification by column chromatography on silica gel gives 2-(2,6-diethyl-4-methylphenyl)-5-[2-(ethylthio)propyl]-cyclohexane-1,3-dione as a pale yellow gum.

$\delta_H$ (CDCl$_3$) 6.98 (d, 2H), 5.52 (d, 1H), 2.93-2.83 (m, 1H), 2.21-2.76 (m, 11H), 2.33 (s, 3H), 1.78-1.59 (m, 2H), 1.34 (dd, 3H), 1.27 (m, 3H), 1.08 (m, 6H)

EXAMPLE 2

Preparation of 9-(2,6-diethyl-4-methylphenyl)-3-oxaspiro[5.5]undecane-8,10-dione (Compound Number T22 in Table T1)

Step 1

To a solution at 5° C. of potassium hydroxide (12.85 g, 0.229 mol) in a mixture of water (50 ml) and ethanol (200 ml) is added dimethyl 2-oxopropylphosphonate (38.0 g, 0.229 mol), followed by the dropwise addition of tetrahydropyran-4-one (15 ml, 16.4 g, 0.163 mol). The clear solution is stirred for 5 hours at room temperature.

Most of the solvent is removed from the reaction mixture under reduced pressure, and the residue is diluted with tent-butyl methyl ether and water. The organic layer is separated, the aqueous layer is extracted twice with tert-butyl methylether, the combined organic phases dried over anhydrous sodium sulfate, filtered and the filtrate concentrated in vacuo.

The crude product is purified by distillation under reduced pressure to give 18.8 g (82%) of product with a boiling point of 102-104° C./12 mbar. $^1$H-NMR reveals the product to be a 4:1-mixture of the desired 1-(tetrahydropyran-4-ylidene)propan-2-one and an isomer, 1-(3,6-dihydro-2H-pyran-4-yl)propan-2-one which is used without further purification in the next step.

Step 2

To a solution at room temperature of the product of Step 1 (13.18 g, 94.0 mmol) in 100 ml of ethanol (100 ml) is added diethyl malonate (14.3 ml, 15.09 g; 94.2 mmol), followed by the dropwise addition of a ~2.72 M solution of sodium ethoxide in ethanol (36.6 ML~94.1 mmol). The solution is stirred for 3 hours at room temperature, then for 1 hour at reflux.

The solvent is removed from the reaction mixture under reduced pressure and the solid residue is taken up in 12N aqueous sodium hydroxide (150 ml) and stirred at room temperature over night. The alkaline aqueous mixture is washed once with tert-butylmethyl ether, then acidified to pH 2-3 using concentrated hydrochloric acid and warmed to 70° C. for 2 hours. The aqueous mixture is extracted with ethyl acetate and dichloromethane, and the organic phases are combined, dried over anhydrous sodium sulfate, filtered and the filtrate concentrated in vacuo. The solid residue is taken up in tert-butyl methyl ether, the mixture stirred, and the off-white solid collected by filtration to give 3-oxaspiro[5.5]undecane-8,10-dione (12.3 g), m.p. 162-164° C.

Step 3

3-Oxaspiro[5.5]undecane-8,10-dione (5.47 g, 30.0 mmol) is stirred in a mixture of water (50 ml) and ethanol (16 ml) at 0° C. and lithium hydroxide monohydrate (2.52 g, 60.0 mmol) is added. When the solution becomes clear, (diacetoxyiodo)benzene (9.65 g, 30.0 mmol) is added at once and the mixture is stirred for 45 min at 0° C., followed by 3 hours at room temperature.

The reaction mixture is diluted with 1,2-dimethoxyethane (200 ml) and 2,6-diethyl-4-methylphenylboronic acid (6.50 g, 33.8 mmol), palladium(II) acetate (0.5 g, 2.23 mmol), and lithium hydroxide monohydrate (5.05 g, 120.0 mmol) are added at 0° C. The mixture is warmed to 50° C. and as it thickens after ca. 1-2 hours, it is further diluted with a mixture of water and 1,2-dimethoxyethane (50+50 ml). After addition of a further catalytic amount of palladium(II) acetate, stirring at 50° C. is continued for about 16 hours.

The reaction mixture is diluted with ethyl acetate and water, and the alkaline water layer is extracted twice with ethyl acetate. The combined organic layer is discarded and the aqueous phase further diluted with ethyl acetate and acidified at 0° C. to pH 2-3 using 4N aqueous hydrochloric acid. The organic layer is separated, the water layer is extracted twice with ethyl acetate, the combined organic phases dried over anhydrous sodium sulfate, filtered and the filtrate concentrated in vacuo.

The crude product is purified by flash filtration first (ethyl acetate/hexane 3:1), followed by flash chromatography (ethyl acetate/hexane 3:2→2:1). The yellowish oil obtained after concentration is taken up in a 4:1 mixture of hexane:tert-butyl methyl-ether, the mixture stirred, and the white solid is collected by filtration to give 9-(2,6-diethyl-4-methylphenyl)-3-oxaspiro[5.5]undecane-8,10-dione, m.p. 139-141° C.

$\delta_H$ (CDCl$_3$) 6.97 (s, 2H), 5.83 (br s, 1H), 3.72 (t, 4H), 2.59 (br s, 4H), 2.39-2.27 (m, 4H), 2.32 (s, 3H), 1.69 (t, 4H), 1.06 (t, 6H)

EXAMPLE 3

Preparation of 2-(2,6-diethyl-4-methylphenyl)-5-[2-(ethylsulfonyl)propyl]cyclohexane-1,3-dione (Compound number 28 in Table T1)

35% peracetic acid in acetic acid (0.3 ml, 1.55 mmol) is added dropwise to a solution of 2-(2,6-diethyl-4-methylphenyl)-5-[2-(ethylthio)propyl]cyclohexane-1,3-dione (0.17 g, 0.47 mmol) in dichloromethane (5 ml) and the reaction mixture is stirred for 2 hours at room temperature and then allowed to stand overnight. The reaction mixture is diluted with dichloromethane, washed with 15% aqueous sodium metabisulfite solution and brine, dried over anhydrous magnesium sulfate, filtered and the filtrate evaporated in vacuo. The residue is purified by column chromatography on silica gel to give 2-(2,6-diethyl-4-methylphenyl)-5-[2-(ethylsulfonyl)propyl]-cyclohexane-1,3-dione, m.p. 62-65° C.

$\delta_H$ (CDCl$_3$) 6.99 (s, 2H), 5.67 (d, 1H), 3.16-3.05 (m, 1H), 3.01 (q, 2H), 2.80-2.61 (m, 2H), 2.55-2.13 (m, 7H), 2.33 (s, 3H), 1.82-1.60 (m, 2H), 1.48-1.38 (m, 6H), 1.08 (q, 6H)

EXAMPLE 4

Preparation of 2-(2,6-diethyl-4-methylphenyl)-5-[2-(ethylsulfinyl)propyl]-1'-cyclohexane-1,3-dione (Compound Number T29 in Table T1)

A solution of 70% 3-chloroperoxybenzoic acid (0.104 g, 0.42 mmol) in dichloromethane (2 ml) is added dropwise to a solution of 2-(2,6-diethyl-4-methylphenyl)-5-[2-(ethylthio) propyl]cyclo-hexane-1,3-dione (0.17 g, 0.47 mmol) in dichloromethane (3 ml) at 0° C. and the reaction mixture is stirred for 1 hour at 0° C. and then left to stand at room temperature overnight. The reaction mixture is diluted with dichloromethane, washed with 15% aqueous sodium metabisulfite solution and brine, dried over anhydrous magnesium sulfate, filtered and the filtrate evaporated in vacuo. The residue is purified by column chromatography on silica gel to give 2-(2,6-diethyl-4-methylphenyl)-5-[2-(ethylsulfinyl) propyl]cyclohexane-1,3-dione, m.p. 58-61° C.

$\delta_H$ (CDCl$_3$) 6.98 (s, 2H), 6.00 (br s, 1H), 2.87-2.18 (m, 12H), 2.33 (s, 3H), 1.81-1.52 (m, 2H), 1.44-1.23 (m, 6H), 1.08 (q, 6H)

EXAMPLE 5

Preparation of 9-(5-(4'-chlorophenyl)-2-ethylphenyl)-3-oxaspiro[5.5]undecane-8,10-dione (Compound Number T4 in Table T1)
Step 1
3-oxaspiro[5.5]undecane-8,10-dione (14.0 g, 77.0 mol) prepared according to the procedure given in Example 2, is added to a solution of sodium carbonate (16.32 g, 0.154 mol) in a mixture of water (200 ml) and ethanol (50 ml) and the mixture stirred at room temperature for 5 minutes, and then cooled to 5° C. in an ice bath. (Diacetoxyiodo)benzene (24.77 g, 77.0 mmol) is added portionwise over 5 minutes, and once the addition is complete the reaction mixture is stirred at 5° C. for 15 minutes and then the cooling bath is removed and the mixture stirred at room temperature for 4 hours. The precipitate is collected by filtration, washed with water and dried to give the desired iodonium ylide (28.2 g) as a cream solid.
Step 2
A mixture of the iodonium ylide prepared in step 1 (1.0 g, 2.6 mmol), 5-(4-chlorophenyl)-2-ethylphenylboronic acid (0.745 g, 2.86 mmol), palladium (II) acetate (0.047 g, 0.21 mmol) and lithium hydroxide monohydrate (0.437 g, 10.4 mmol) are stirred together in a mixture of 1,2-dimethoxyethane (24 ml) and water (6 ml)) under an atmosphere of nitrogen and the mixture stirred and heated to 50° C. for 5½ hours. The reaction mixture is cooled to room temperature and filtered through celite, washing with 100 ml water and 40 ml ethyl acetate, and the filtrate is poured into a separating funnel. The organic phase is separated and aqueous layer extracted with ethyl acetate. The organic extracts are discarded.

The aqueous phase is acidified to pH2 by addition of concentrated hydrochloric acid, and then extracted with ethyl acetate. The organic extracts are dried over anhydrous magnesium sulphate, filtered, and the filtrate is evaporated in vacuo to give a brown gum. Further purification by column chromatography on silica gel gives 9-(5-(4'-chlorophenyl)-2-ethylphenyl)-3-oxaspiro[5.5]undecane-8,10-dione as a colourless solid, m.p. 94.5-97.5° C.

$\delta_H$ (CDCl$_3$) 7.53 (dd, 1H), 7.50-7.45 (m, 2H), 7.43-7.36 (m, 3H), 7.20 (d, 1H), 5.79 (s, 1H), 3.75 (m, 4H), 2.65 (s, 2H), 2.59 (q, 2H), 2.45 (m, 2H), 1.72 (t, 4H) 1.13 (t, 3H)

EXAMPLE 6

Preparation of 9-(3,5-dimethylbiphen-4-yl)-3-oxaspiro[5,5]undecane-8,10-dione (Compound Number T73 in Table T1)

To a mixture of 3-oxaspiro[5.5]undecane-8,10-dione (0.182 g, 1 mmol) and 4-dimethylamino-pyridine (0.61 g; 5 mmol) is added dry chloroform (4 ml), and the mixture is stirred under an atmosphere of nitrogen at room temperature until the solid dissolves. To this solution is then added dry toluene (2 ml), and then a solution of 3,5-dimethylbiphen-4-yllead triacetate (1.2 mmol) in chloroform is added. The reaction mixture is heated under reflux for 1 hour, then cooled to room temperature, acidified to pH=1 with 2N aqueous hydrochloric acid, filtered and the filtrate is extracted with dichloromethane (2×40 ml). The organic extracts are combined, dried over anhydrous magnesium sulfate, filtered and the filtrate is evaporated in vacuo. The residue is purified by column chromatography over silica gel to give 9-(3,5-dimethylbiphenyl-4-yl)-3-oxa-spiro[5.5]undecane-8,10-dione.

$\delta_H$ (CDCl$_3$) 7.57 (d, 2H), 7.42 (dd, 2H), 7.35 (d, 1H), 7.33 (s, 2H), 5.91 (bs, 1H), 3.73 (dd, 4H), 2.64 (s, 2H), 2.58 (s, 2H), 2.14 (s, 6H); 1.72 (dd, 4H)

Compounds in Table T1 below were prepared by similar methods using appropriate starting materials.

TABLE T1

| Compound Number | Structure | $^1$H NMR-CDCl$_3$ unless stated |
|---|---|---|
| T1 | 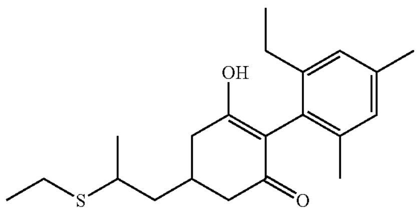 | δ 6.96 (d, 2H), 5.54 (br s, 1H), 2.88 (m, 1H), 2.19-2.76 (m, 9H), 2.30 (s, 3H), 2.06, 2.02 (2 × S, 3H), 1.58-1.78 (m, 2H), 1.34 (d, 3H), 1.27 (t, 3H), 1.08 (q, 3H) |
| T2 | 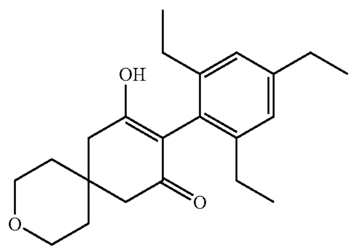 | δ 7.00 (s, 2H), 5.55 (s, 1H), 3.75 (t, 4H), 2.56-2.69 (m, 6H), 2.34 (m, 4H), 1.71 (t, 4H), 1.25 (t, 3H), 1.07 (t, 6H) |
| T3 | 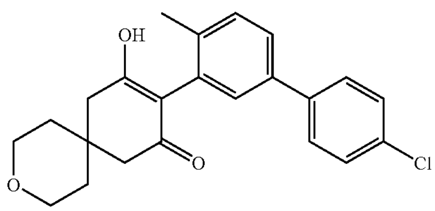 | δ 7.51-7.44 (m, 3H), 7.40-7.35 (m, 3H), 7.22 (d, 1H), 5.83 (s, 1H), 3.74 (m, 4H), 2.65 (s, 2H), 2.58 (q, 2H), 2.15 (s, 3H), 1.72 (m, 4H) |
| T4 | 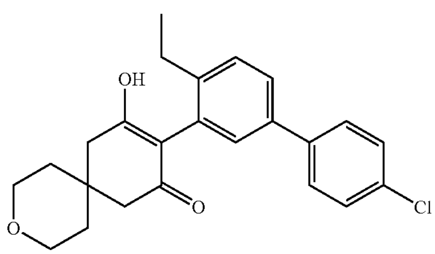 | δ 7.53 (dd, 1H), 7.50-7.45 (m, 2H), 7.43-7.36 (m, 3H), 7.20 (d, 1H), 5.79 (s, 1H), 3.75 (m, 4H), 2.65 (s, 2H), 2.59 (q, 2H), 2.45 (m, 2H), 1.72 (t, 4H) 1.13 (t, 3H) |
| T5 | 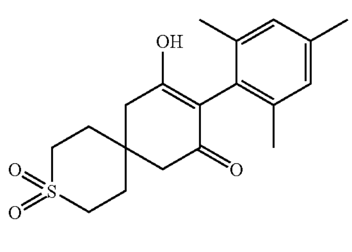 | δ 6.95 (s, 2H), 5.59 (br s, 1H), 3.07 (m, 4H), 2.67 (d, 4H), 2.29 (s, 3H), 2.24 (m, 4H), 2.04 (s, 6H), |
| T6 | 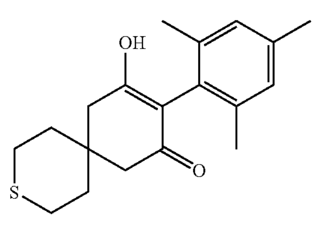 | δ 6.94 (s, 2H), 5.56 (br s, 1H), 2.70 (m, 4H), 2.56 (s, 2H), 2.42 (s, 2H), 2.28 (s, 3H), 2.04 (s, 6H), 1.95 (m, 4H) |

TABLE T1-continued

| Compound Number | Structure | ¹H NMR-CDCl₃ unless stated |
|---|---|---|
| T7 | 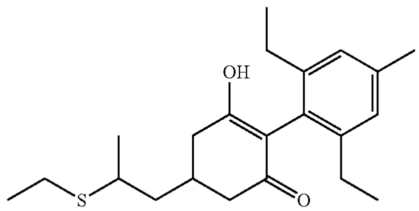 | δ 6.98 (d, 2H), 5.52 (d, 1H), 2.93-2.83 (m, 1H), 2.21-2.76 (m, 11H), 2.33 (s, 3H), 1.78-1.59 (m, 2H), 1.34 (dd, 3H), 1.27 (m, 3H), 1.08 (m, 6H) |
| T8 | 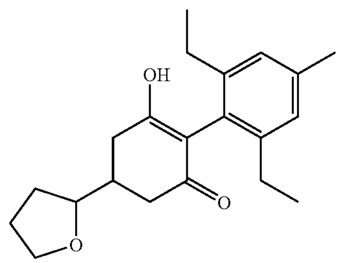 | δ 6.98 (s, 2H), 5.54 (br s, 1H), 3.89-3.77 (br m, 3H), 2.8-2.70 (m, 1H), 2.62-2.55 (m, 2H), 2.38-2.30 (m, 9H), 2.07-1.90 (m, 3H), 1.7-1.55 (m, 1H), 1.09-1.05 (m, 6H) |
| T9 | 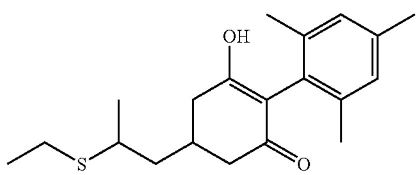 | δ 6.94 (d, 2H), 5.56 (br d, 1H), 2.88 (m, 1H), 2.75-2.19- (m, 7H), 2.28 (s, 3H), 2.07 (s, 3H), 2.03 (s, 3H), 1.77-1.57 (m, 2H), 1.34 (dd, 3H), 1.27 (m, 3H) |
| T10 | 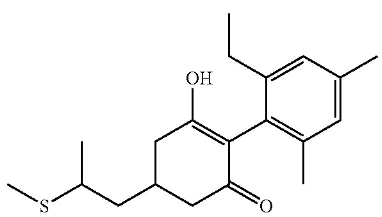 | δ 6.96 (m, 2H), 5.53 (d, 1H), 2.82-2.19 (m, 8H), 2.30 (s, 3H), 2.09 (dd, 3H), 2.06, 2.02 (2 × S, 3H), 1.78-1.57 (m, 2H), 1.34 (dd, 3H), 1.07 (m, 3H) |
| T11 | 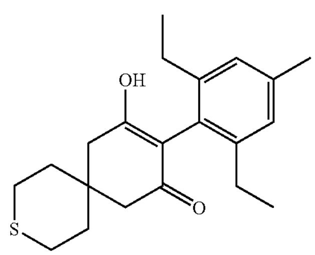 | δ 6.98 (s, 2H), 5.26 (bs, 1H), 2.71 (s, 4H), 2.54 (br s, 4H), 2.33 (m, 7H), 1.92 (br s, 4H), 1.06 (t, 6H) |
| T12 | 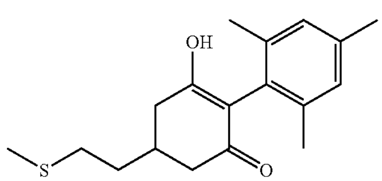 | δ 6.94 (s, 2H), 5.60 (br s, 1H), 2.68 (m, 2H), 2.60 (t, 2H), 2.50-2.25 (m, 3H), 2.28 (s, 3H), 2.13 (s, 3H), 2.06 (s, 3H), 2.03 (s, 3H), 1.79 (q, 2H) |
| T13 | 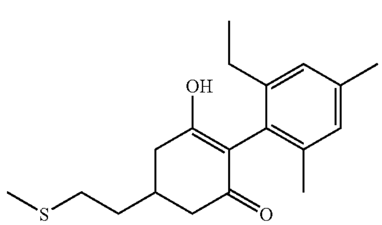 | δ 6.96 (s, 1H), 6.95 (s, 1H), 5.60 (br s, 1H), 2.68 (m, 2H), 2.60 (t, 2H), 2.50-2.25 (m, 5H), 2.30 (s, 3H), 2.13 (s, 3H), 2.06, 2.02 (2 × s, 3H), 1.79 (q, 2H), 1.08 (m, 3H) |

TABLE T1-continued

| Compound Number | Structure | $^1$H NMR-CDCl$_3$ unless stated |
|---|---|---|
| T14 | 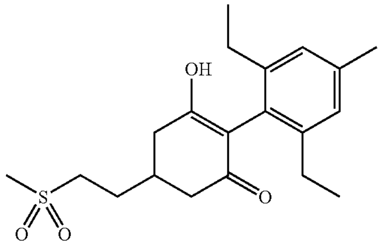 | δ 7.00 (s, 2H), 5.61 (br s, 1H), 3.12 (m, 2H), 2.96 (s, 3H), 2.72 (m, 2H), 2.53-2.41 (m, 2H), 2.40-2.25 (m, 5H), 2.33 (s, 3H), 2.16-2.01 (m, 2H), 1.08 (t, 6H) |
| T15 | 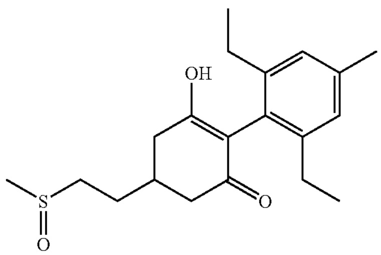 | δ 6.98 (s, 2H), 2.78 (t, 2H), 2.72 (m, 2H), 2.61 (s, 3H), 2.48-2.27 (m, 10H), 2.03-1.95 (m, 2H), 1.08 (m, 6H) |
| T16 | 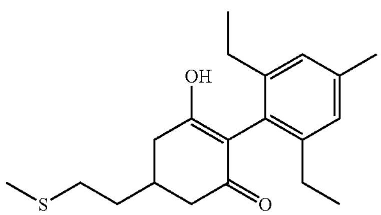 | δ 6.99 (s, 2H), 5.62 (br s, 1H), 2.69 (m, 2H), 2.60 (m, 2H), 2.46-2.46 (m, 7H), 2.33 (s, 3H), 2.14 (s, 3H), 1.80 (q, 2H), 1.08 (m, 6H) |
| T17 | 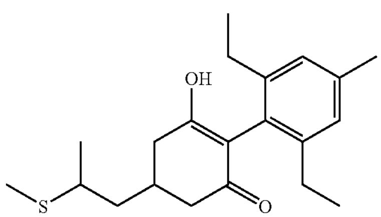 | δ 7.00 (d, 2H), 5.58 (d, 1H), 2.85-2.22 (m, 10H), 2.33 (s, 3H), 2.10 (d, 3H), 1.78-1.57 (m, 2H), 1.34 (d, 3H), 1.08 (q, 6H) |
| T18 | 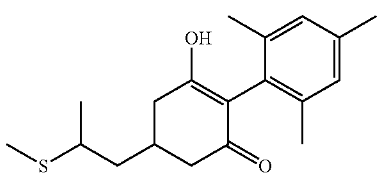 | δ 6.95 (s, 2H), 5.61 (s, 1H), 2.83-2.17 (m, 6H), 2.28 (s, 3H), 2.10 (d, 3H), 2.07 (s, 3H), 2.03 (s, 3H), 1.78-1.59 (m, 2H), 1.34 (d, 3H) |
| T19 | 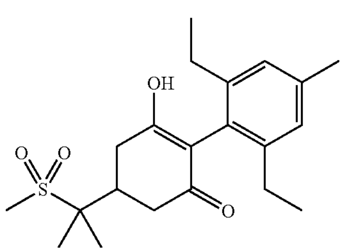 | δ 6.99 (s, 2H), 5.59 (br s, 1H), 3.09-3.00 (m, 1H), 2.90 (s, 3H), 2.87-2.76 (m, 3H), 2.55-2.25 (m, 5H), 2.33 (s, 3H), 1.51 (s, 6H), 1.16-1.02 (m, 6H) |

TABLE T1-continued

| Compound Number | Structure | $^1$H NMR-CDCl$_3$ unless stated |
|---|---|---|
| T20 | 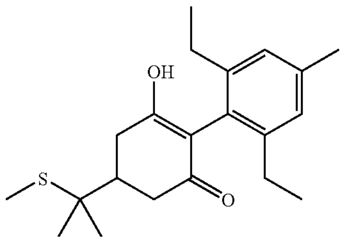 | δ 6.98 (s, 2H), 5.66 (s, 1H), 2.83-2.59 (m, 3H), 2.49-2.22 (m, 6H), 2.33 (s, 3H), 2.07 (s, 3H), 1.37 (s, 3H), 1.35 (s, 3H), 1.15-1.02 (m, 6H) |
| T21 | 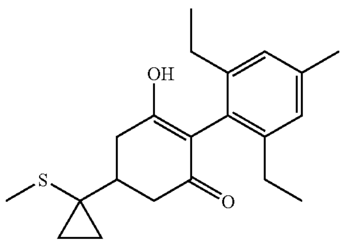 | δ 6.98 (s, 2H), 5.70 (s, 1H), 2.99-2.87 (dd, 1H), 2.75-2.50 (m, 3H), 2.42-2.25 (m, 4H), 2.32 (s, 3H), 2.16 (s, 3H), 1.80-1.67 (m, 1H), 1.15-1.01 (m, 6H), 0.99 (m, 2H), 0.82 (m, 2H) |
| T22 | 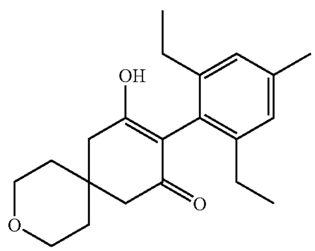 | δ 6.97 (s, 2H), 5.83 (br s, 1H), 3.72 (t, 4H), 2.59 (br s, 4H), 2.39-2.27 (m, 4H), 2.32 (s, 3H), 1.69 (t, 4H), 1.06 (t, 6H) |
| T23 | 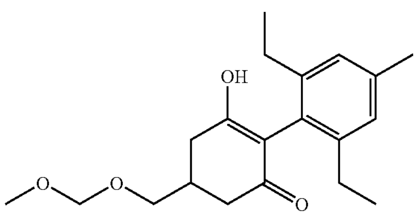 | δ 6.98 (s, 2H), 5.61 (br s, 1H), 4.67 (s, 2H), 3.63-3.53 (m, 2H), 3.39 (s, 3H), 2.75-2.52 (m, 4H), 2.49-2.24 (m, 5H), 2.32 (s, 3H), 1.08 (t, 6H) |
| T24 | 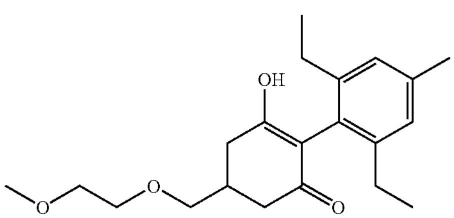 | δ 6.98 (s, 2H), 5.62 (br s, 1H), 3.69-3.45 (m, 6H), 3.39 (s, 3H), 2.80-2.48 (m, 4H), 2.48-2.22 (m, 5H), 2.32 (s, 3H), 1.08 (t, 6H) |
| T25 | 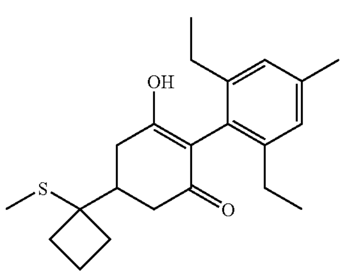 | δ 6.98 (s, 2H), 5.60 (br s, 1H), 2.75-2.27 (m, 10H), 2.32 (s, 3H), 2.27-2.10 (m, 4H), 2.12 (s, 3H), 1.98-1.85 (m, 1H), 1.18-1.02 (m, 6H) |

TABLE T1-continued

| Compound Number | Structure | $^1$H NMR-CDCl$_3$ unless stated |
| --- | --- | --- |
| T26 | 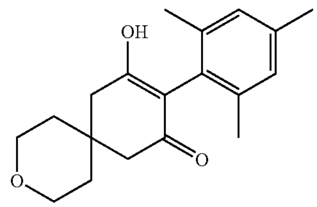 | δ 6.94 (s, 2H), 5.50 (br s, 1H), 3.75 (t, 4H), 2.61 (d, 4H), 2.28 (s, 3H), 2.05 (s, 6H), 1.72 (t, 4H) |
| T27 | 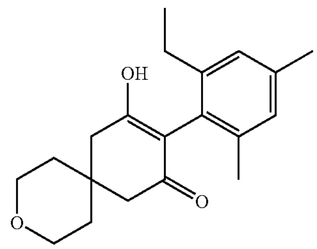 | δ 6.96 (s, 2H), 5.55 (br s, 1H), 3.75 (t, 4H), 2.63 (br s, 2H), 2.58 (br s, 2H), 2.30 (s, 3H), 2.41-2.24 (m, 2H), 2.04 (s, 3H), 1.71 (t, 4H), 1.06 (t, 3H) |
| T28 | 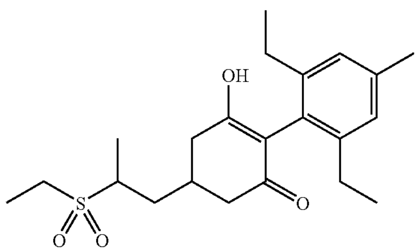 | δ 6.99 (s, 2H), 5.67 (d, 1H), 3.16-3.05 (m, 1H), 3.01 (q, 2H), 2.80-2.61 (m, 2H), 2.55-2.13 (m, 7H), 2.33 (s, 3H), 1.82-1.60 (m, 2H), 1.48-1.38 (m, 6H), 1.08 (q, 6H) |
| T29 | 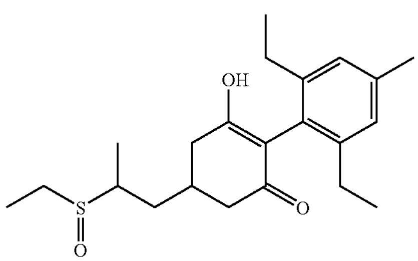 | δ 6.98 (s, 2H), 6.00 (br s, 1H), 2.87-2.18 (m, 12H), 2.33 (s, 3H), 1.81-1.52 (m, 2H), 1.44-1.23 (m, 6H), 1.08 (q, 6H) |
| T30 | 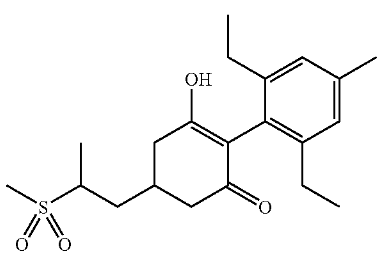 | δ 6.99 (s, 2H), 5.59 (d, 1H), 3.12-3.02 (m, 1H), 2.88 (d, 3H), 2.81-2.62 (m, 2H), 2.55-2.16 (m, 10H), 1.80-1.53 (m, 2H), 1.47 (dd, 3H), 1.08 (m 6H) |
| T31 | 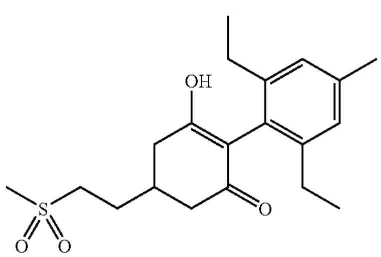 | δ 6.97 (d, 2H), 5.59 (s, 1H), 3.11 (m, 2H), 2.95 (s, 3H), 2.71 (m, 2H), 2.52-2.24 (m, 5H), 2.30 (s, 3H), 2.16-1.97 (m, 2H), 2.03 (d, 3H), 1.07 (t, 3H) |

TABLE T1-continued

| Compound Number | Structure | ¹H NMR-CDCl₃ unless stated |
|---|---|---|
| T32 | 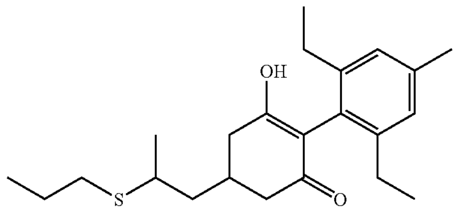 | δ 6.98 (s, 2H), 5.52 (s, 1H), 2.84 (m, 1H), 2.68 (m, 2H), 2.53 (m, 3H), 2.43-2.20 (m, 6H), 2.32 (s, 3H), 1.78-1.56 (m, 4H), 1.34 (dd, 3H), 1.08 (q, 6H), 1.01 (t, 3H) |
| T33 | 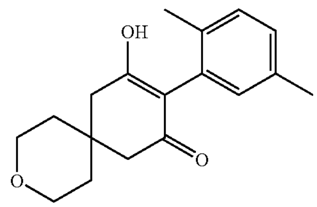 | δ 7.18 (d, 1H), 7.09 (d, 1H), 6.85 (s, 1H), 5.70 (br s, 1H), 3.74 (t, 4H), 2.63 (s, 2H), 2.57 (s, 1H), 2.55 (s, 1H), 2.30 (s, 3H), 2.07 (s, 3H), 1.75-1.68 (m, 4H) |
| T34 | 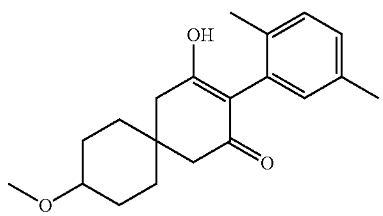 | δ 7.17 (d, 1H), 7.08 (d, 1H), 6.86 (s, 1H), 5.81 (br s, 1H), 3.35 (s, 3H), 3.26 (m, 1H), 2.58 (s, 1H), 2.51 (br s, 2H), 2.42 (s, 1H), 2.30 (s, 3H), 2.07 (s, 3H), 1.91-1.73 (m, 4H), 1.65-1.50 (m, 2H), 1.50-1.34 (m, 2H |
| T35 | 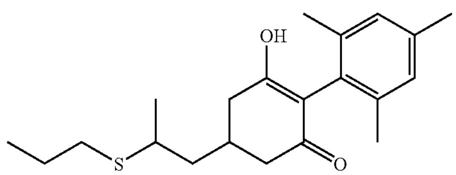 | δ 6.94 (s, 2H), 5.53 (br d, 1H), 2.84 (m, 1H), 2.75-2.60 (m, 2H), 2.59-2.46 (m, 3H), 2.37 (dd, 1H), 2.28 (s, 3H), 2.24 (dd, 1H), 2.07 (s, 3H), 2.03 (s, 3H), 1.77-1.55 (m, 4H), 1.33 (dd, 3H), 1.00 (t, 3H) |
| T36 | 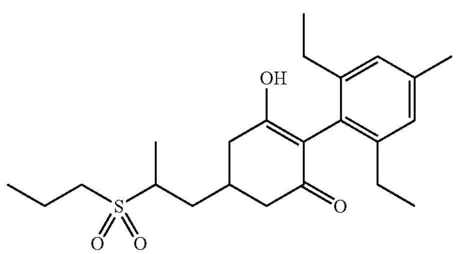 | δ 6.99 (s, 2H), 5.57 (d, 1H), 3.11-3.01 (m, 1H), 2.94 (m, 2H), 2.78-2.61 (m, 2H), 2.55-2.13 (m, 7H), 2.33 (s, 3H), 1.99-1.84 (m, 2H), 1.81-1.52 (m, 2H), 1.44 (t, 3H), 1.16-1.03 (m, 9H) |
| T37 | 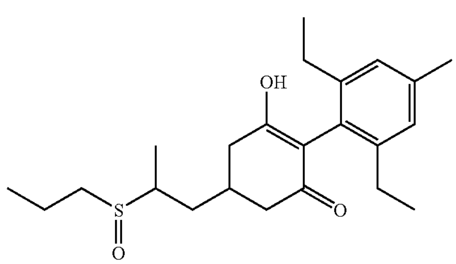 | δ 6.98 (s, 2H), 5.86-5.72 (m, 1H), 2.85-1.52 (m, 16H), 2.33 (s, 3H), 1.30 (t, 3H), 1.16-1.04 (m, 9H) |
| T38 | 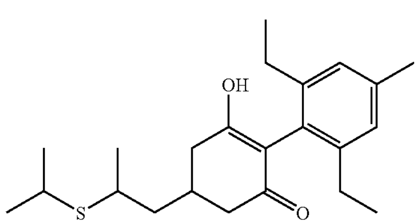 | δ 6.98 (s, 2H), 5.51 (br d, 1H), 3.02 (m, 1H), 2.93 (m, 1H), 2.69 (m, 2H), 2.53 (m, 1H), 2.44-2.21 (m, 6H), 2.33 (s, 3H), 1.78-1.59 (m, 2H), 1.34 (dd, 3H), 1.29 (dd, 6H), 1.08 (q, 6H) |

TABLE T1-continued

| Compound Number | Structure | ¹H NMR-CDCl₃ unless stated |
|---|---|---|
| T39 | 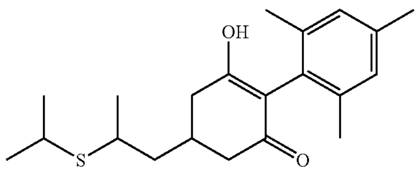 | δ 6.93 (s, 2H), 5.62 (br s, 1H), 3.02 (m, 1H), 2.92 (m, 1H), 2.74-2.60 (m, 2H), 2.59-2.45 (m, 1H), 2.37 (m, 1H), 2.28 (s, 3H), 2.23 (m, 1H), 2.07 (s, 3H), 2.03 (s, 3H), 1.77-1.58 (m, 2H), 1.33 (dd, 3H), 1.28 (dd, 6H) |
| T40 | 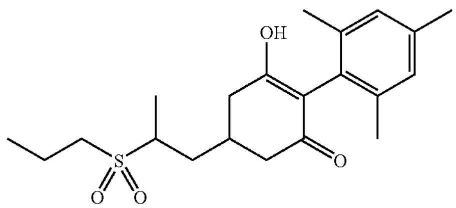 | δ 6.94 (s, 2H), 5.61 (d, 1H), 3.11-3.01 (m, 1H), 2.94 (m, 2H), 2.78-2.59 (m, 2H), 2.54-2.11 (m, 3H), 2.28 (s, 3H), 2.06 (s, 3H), 2.03 (s, 3H), 1.91 (m, 2H), 1.80-1.54 (m, 2H), 1.44 (dd, 3H), 1.12 (m, 3H) |
| T41 | 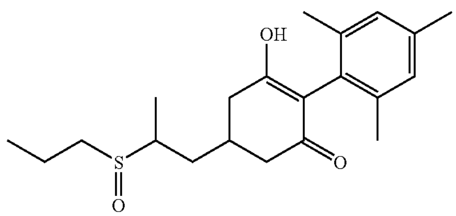 | δ 6.94 (s, 2H), 6.19-5.86 (m, 1H), 2.84-1.41 (m, 12H), 2.28 (s, 3H), 2.06 (s, 3H), 2.03 (s, 3H), 1.30 (t, 3H), 1.10 (m, 3H) |
| T42 | 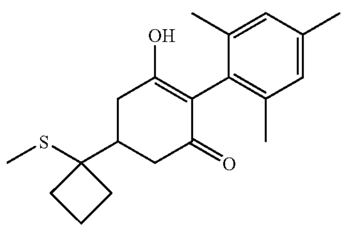 | MS (electrospray ES+): 331 (M + H)⁺<br>HPLC retention time 1.64 min |
| T43 | 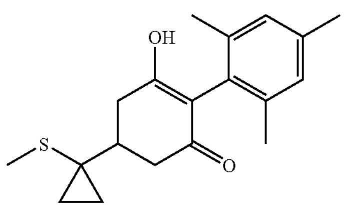 | MS (electrospray ES+): 317 (M + H)⁺<br>HPLC retention time 1.57 min |
| T44 | 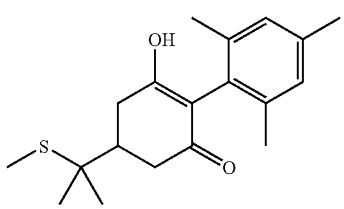 | MS (electrospray ES+): 319 (M + H)⁺<br>HPLC retention time 1.50 min |
| T45 | 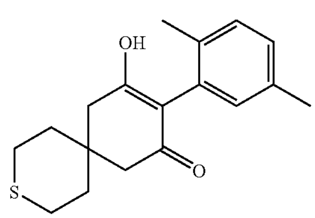 | MS (electrospray ES+): 303 (M + H)⁺<br>HPLC retention time 1.30 min |

TABLE T1-continued

| Compound Number | Structure | $^1$H NMR-CDCl$_3$ unless stated |
|---|---|---|
| T46 | 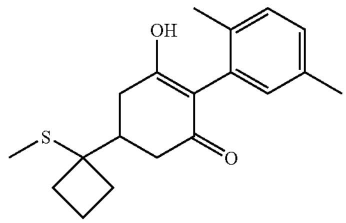 | MS (electrospray ES+): 317 (M + H)$^+$<br>HPLC retention time 1.55 min |
| T47 | 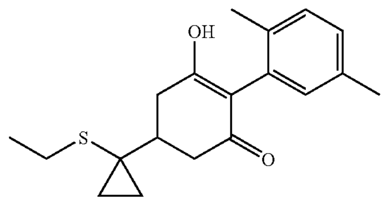 | MS (electrospray ES+): 317 (M + H)$^+$<br>HPLC retention time 1.60 min |
| T48 | 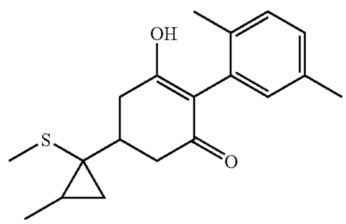 | MS (electrospray ES+): 317 (M + H)$^+$<br>HPLC retention time 1.64 min |
| T49 | 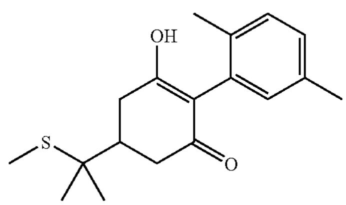 | MS (electrospray ES+): 305 (M + H)$^+$<br>HPLC retention time 1.40 min |
| T50 | 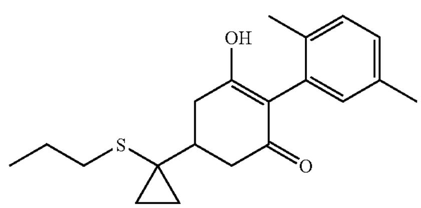 | MS (electrospray ES+): 331 (M + H)$^+$<br>HPLC retention time 1.80 min |
| T51 | 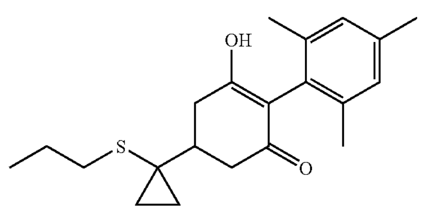 | MS (electrospray ES+): 345 (M + H)$^+$<br>HPLC retention time 1.84 min |
| T52 | 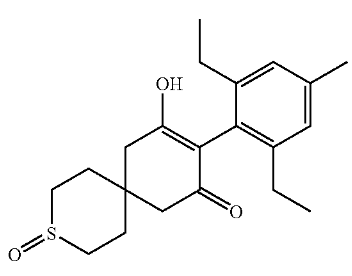 | δ 6.99 (s, 2H), 5.84 (s, 1H), 2.93 (m, 2H), 2.77 (m, 2), 2.64 (s, 2H); 2.58 (s, 2H); 2.45 (m, 2H), 2.33 (m, 7H), 1.85 (m, 2H), 1.07 (t, 6H) |

TABLE T1-continued

| Compound Number | Structure | $^1$H NMR-CDCl$_3$ unless stated |
|---|---|---|
| T53 | 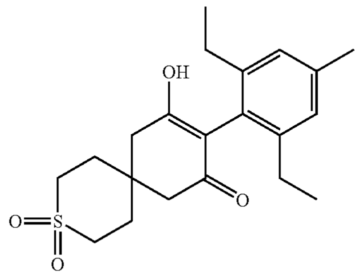 | δ 6.99 (s, 2H), 5.84 (bs, 1H), 3.06 (m, 4H) 2.66 (s, 2H), 2.60 (s, 2H), 2.37-2.28 (m, 7H), 2.25-2.22 (m, 4H), 1.06 (2 × t, 6H) |
| T54 | 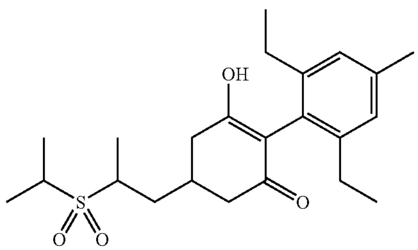 | δ 6.99 (s, 2H), 5.64, 5.60 (2 × s, 1H), 3.15-3.36 (m, 2H), 2.70 (m, 2H), 2.08-2.56 (m, 7H), 2.33 (s, 3H), 1.65-1.84 (m, 2H), 1.35-1.46 (m, 9H), 1.08 (q, 4H) |
| T55 | 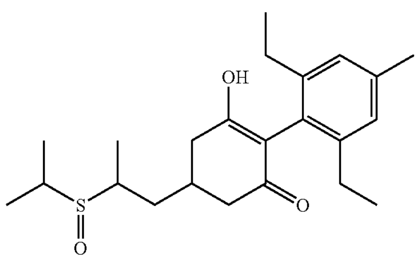 | δ 6.98 (s, 2H), 6.11, 6.04, 6.00, 5.88 (4 × S, 1H), 1.57-2.92 (m, 13H), 2.33 (s, 3H), 1.17-1.42 (m, 9H), 1.08 (q, 6H) |
| T56 | 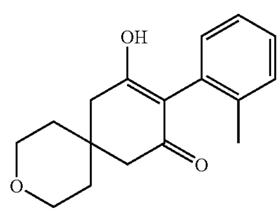 | d$_3$-MeCN δ 7.26 (m, 1H), 7.22 (m, 2H), 7.00 (d, 1H), 3.69 (m, 4H), 2.65 (m, 2H), 2.48 (m, 2H), 2.10 (s, 3H), 1.67 (m, 4H) |
| T57 | 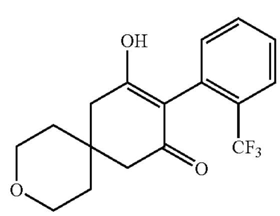 | d$_3$-MeCN δ 7.78 (d, 1H), 7.65 (t, 1H), 7.54 (t, 1H), 7.20 (d, 1H), 3.69 (m, 4H), 2.56 (m, 4H), 1.66 (m, 4H) |
| T58 | 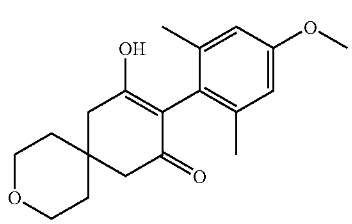 | d$_3$-MeCN δ 6.69 (s, 2H), 3.79 (s, 3H), 3.69 (m, 4H), 2.65 (m, 2H), 2.49 (m, 2H), 2.02 (s, 6H), 1.68 (m, 4H) |

TABLE T1-continued

| Compound Number | Structure | ¹H NMR-CDCl₃ unless stated |
|---|---|---|
| T59 | 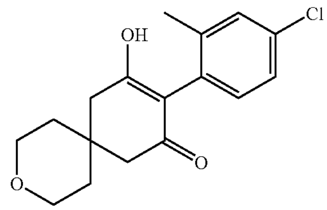 | δ 7.29 (d, 1H), 7.22 (dd, 1H), 6.97 (d, 1H), 5.97 (br. s, 1H), 3.72 (t, 4H), 2.62 (s, 2H), 2.54 (q, 2H), 2.09 (s, 3H), 1.69 (q, 4H) |
| T60 | 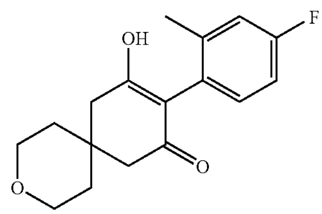 | d₃-MeCN δ 7.06-6.93 (m, 3H), 3.69 (m, 4H), 2.7-2.4 (br, 4H), 2.10 (s, 3H), 1.67 (m, 4H) |
| T61 | 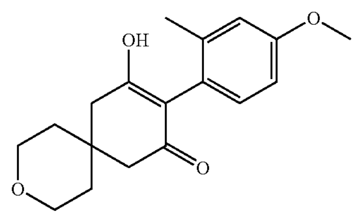 | d₃-MeCN δ 6.90 (d, 1H), 6.86, (d, 1H), 6.78 (dd, 1H), 3.81 (s, 3H), 3.49 (m, 4H), 2.7-2.4 (br, 4H), 2.06 (s, 3H), 1.67 (m, 4H) |
| T62 | 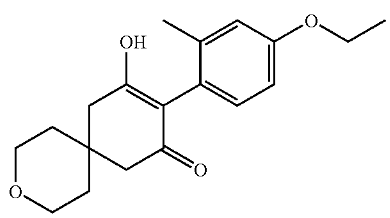 | δ 6.93 (s, 1H), 6.84 (d, 1H), 6.77 (dd, 1H), 5.81 (br. s, 1H), 4.03 (q, 2H), 3.73 (m, 4H), 2.62 (s, 2H), 2.55 (q, 2H), 2.08 (s, 3H), 1.70 (q, 4H), 1.41 (t, 3H) |
| T63 | 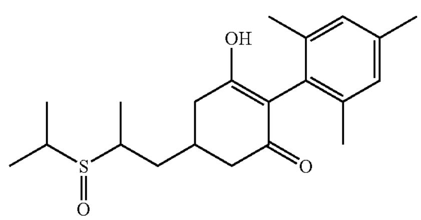 | δ 6.93 (s, 2H), 5.92-6.38 (m, 1H), 2.19-2.91 (m, 7H), 2.28 (s, 3H), 2.07 (s, 3H), 2.03 (s, 3H), 1.57-1.94 (m, 2H), 1.16-1.41 (m, 9H) |
| T64 | 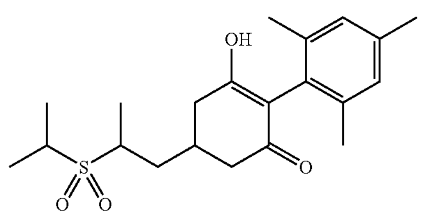 | δ 6.94 (s, 2H), 5.68 (d, 1H), 3.16-3.34 (m, 2H), 2.69 (m, 2H), 2.12-2.53 (m, 3H), 2.28 (s, 3H), 2.06 (s, 3H), 2.03 (s, 3H), 1.62-1.84 (m, 2H), 1.40 (m, 9H) |
| T65 | 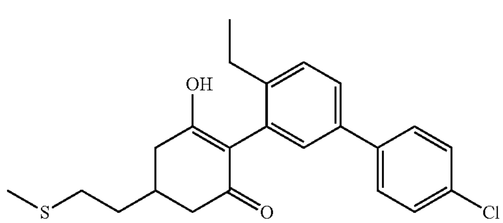 | δ 7.20-7.55 (m, 7H), 5.77 (d, 1H), 2.56-2.78 (m, 4H), 2.36-2.53 (m, 4H), 2.27 (m, 1H), 2.14 (d, 3H), 1.79 (q, 2H), 1.15 (m, 3H) |

TABLE T1-continued

| Compound Number | Structure | ¹H NMR-CDCl₃ unless stated |
|---|---|---|
| T66 | 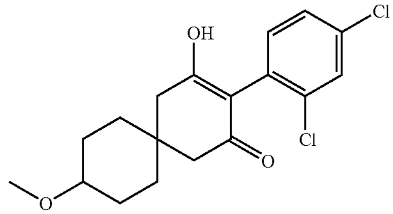 | MS (electrospray ES+): 355 (M + H)⁺<br>HPLC retention time 1.32 min |
| T67 | 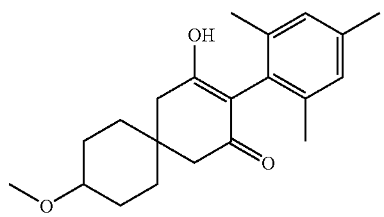 | δ 6.94 (s, 2H), 5.46 (bs, 1H), 3.37 (s, 3H), 3.10 (m, 1H), 2.64-2.61 (m, 2H), 2,48 (m, 1H), 2.28 (s, 3H), 2.25 (m, 1H), 2.13 (m, 2H), 2.06 (m, 7H), 1.91 (m, 2H), 1.33 (m, 1H), 1.19 (m, 2H), 1.07 (m, 2H) |
| T68 | 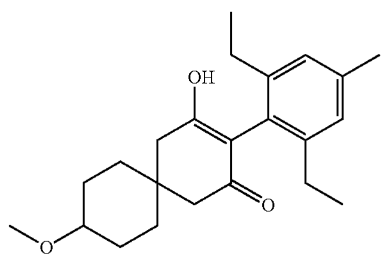 | δ 6.97 (s, 2H), 5.60 (bs, 1H), 3.35 (s, 3H), 3.27 (m, 1H), 2.60 (m, 4H), 2.32 (m, 7H), 1.84 (m, 4H), 1.58 (bs, 2H), 1.44 (m, 2H), 1.06 (t, 6H) |
| T69 | 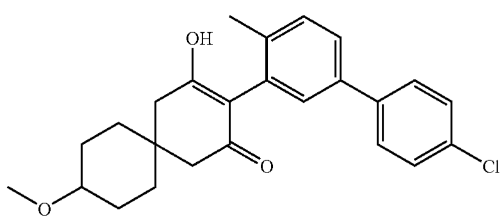 | δ 6.97 7.49 (m, 3H), 7.39 (m, 3H), 7.24 (m, 1H), 5.68 (bs, 1H), 3.35 (s, 3H), 3.30 (m, 1H), 2.55 (m, 4H), 2.16 (s, 3H), 1.84 (m, 4H), 1.58 (m, 1H), 1.44, m, 2H), 1.25 (m, 1H) |
| T70 | 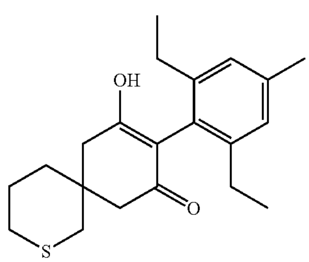 | δ 6.98 (s, 2H), 5.52 (s, 1H), 3.03 (d, 1H), 2.72 (m, 2H), 2.57 (m, 4H) 2.32 (m, 7H), 1.91 (m, 2H), 1.73 (m, 1H), 1.55 (m, 2H), 1.06 (2 × t, 6H) |
| T71 | 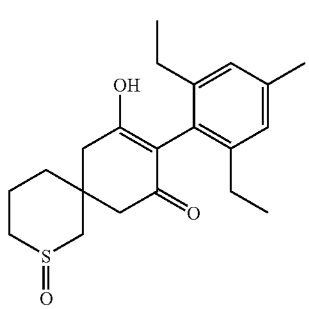 | δ 6.99 (s, 2H), 5.63 (s, 1H), 3.20 (m, 2H), 3.10 (m, 1H), 3.00 (m, 2H), 2.86 (m, 1H), 2.63 (q, 2H), 2.33 (m, 8H), 2.33 (m, 1H), 1.99 (m, 1H), 1.67 (m, 1H), 1.09 (2 × t, 6H), |

TABLE T1-continued

| Compound Number | Structure | $^1$H NMR-CDCl$_3$ unless stated |
|---|---|---|
| T72 | 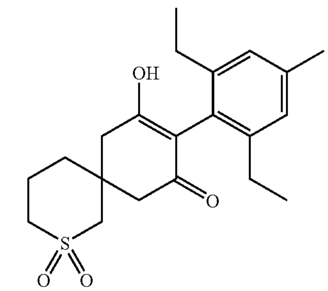 | δ 6.99 (s, 2H), 5.92 (2s, 1H), 3.39 (m, 1H), 3.12 (m, 1H), 2.94 (m, 2H), 2.79 (m, 2H), 2.62 (m, 2H), 2.33 (m, 8H), 2.17 (m, 1H), 1.67 (m, 2H), 1.09 (m, 6H) |
| T73 | 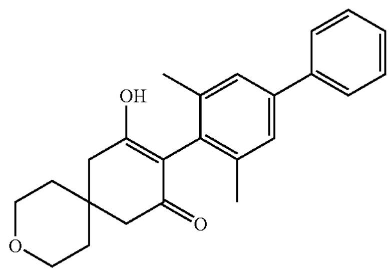 | δ 7.57 (d, 2H), 7.42 (dd, 2H), 7.35 (d, 1H), 7.33 (s, 2H), 5.91 (bs, 1H), 3.73 (dd, 4H), 2.64 (s, 2H), 2.58 (s, 2H), 2.14 (s, 6H), 1.72 (dd, 4H) |

Note:
Compounds characterised by HPLC-MS were analysed using an Agilent 1100 Series HPLC equipped with a Waters Atlantis dC18 column (column length 20 mm, internal diameter of column 3 mm, particle size 3 micron, temperature 40° C.), Waters photodiode array and Micromass ZQ2000. The analysis was conducted using a three minute run time, according to the following gradient table:

| Time (mins) | Solvent A (%) | Solvent B (%) | Flow (ml/mn) | Pressure (bar) |
|---|---|---|---|---|
| 0.00 | 90.0 | 10.0 | 1.700 | 400 |
| 2.50 | 0.0 | 100 | 1.700 | 400 |
| 2.80 | 0.00 | 100 | 1.700 | 400 |
| 2.90 | 90.0 | 10.0 | 1.700 | 400 |

Solvent A: H$_2$O/CH$_3$CN 90/10 with 0.1% HCOOH
Solvent B: 0.1% HCOOH in CH$_3$CN The characteristic values obtained for each compound were the retention time (recorded in minutes) and the molecular ion, typically the cation M+H$^+$ as listed in Table T1.

The compounds of the following Tables 1 to 84 can be obtained in an analogous manner. The spelling C.C used in the following tables indicates the presence of a triple bond between these 2 carbon atoms. For example, CH$_2$C.CH denotes a propargyl group.

TABLE 1

This Table contains 646 compounds of the following type, where X, R$^2$, R$^3$ and R$^4$ are as defined below:

| Compound number | R$^6$ | R$^7$ | X | R$^8$ |
|---|---|---|---|---|
| 1.1 | H | H | O | CH$_2$CH$_3$ |
| 1.2 | H | H | O | CH$_2$CH$_2$CH$_3$ |
| 1.3 | H | H | O | CH(CH$_3$)$_2$ |
| 1.4 | H | H | O | CH$_2$CH$_2$CH$_2$CH$_3$ |
| 1.5 | H | H | O | CH$_2$CH(CH$_3$)$_2$ |
| 1.6 | H | H | O | CH(CH$_3$)CH$_2$CH$_3$ |
| 1.7 | H | H | O | C(CH$_3$)$_3$ |
| 1.8 | H | H | O | CH$_2$CH$_2$CH$_2$CH$_2$CH$_3$ |
| 1.9 | H | H | O | CH$_2$CH$_2$CH(CH$_3$)$_2$ |
| 1.10 | H | H | O | CH$_2$C(CH$_3$)$_3$ |
| 1.11 | H | H | O | CH$_2$CH(CH$_3$)CH$_2$CH$_3$ |
| 1.12 | H | H | O | CH(CH$_3$)CH$_2$CH$_2$CH$_3$ |
| 1.13 | H | H | O | C(CH$_3$)$_2$CH$_2$CH$_3$ |
| 1.14 | H | H | O | CH$_2$CH=CH$_2$ |
| 1.15 | H | H | O | CH$_2$CH=CHCH$_3$ |
| 1.16 | H | H | O | CH$_2$CH=C(CH$_3$)$_2$ |
| 1.17 | H | H | O | CH$_2$C(CH$_3$)=CH$_2$ |
| 1.18 | H | H | O | CH$_2$C(CH$_3$)=CHCH$_3$ |
| 1.19 | H | H | O | CH$_2$C(CH$_3$)=C(CH$_3$)$_2$ |
| 1.20 | H | H | O | CH(CH$_3$)CH=CH$_2$ |
| 1.21 | H | H | O | CH(CH$_3$)CH=CHCH$_3$ |
| 1.22 | H | H | O | CH(CH$_3$)CH=C(CH$_3$)$_2$ |

TABLE 1-continued

This Table contains 646 compounds of the following type,

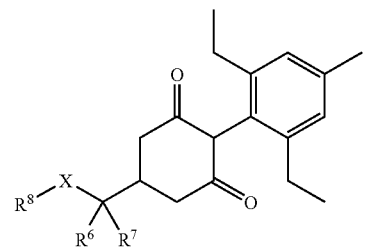

where X, R², R³ and R⁴ are as defined below:

| Compound number | R⁶ | R⁷ | X | R⁸ |
|---|---|---|---|---|
| 1.23 | H | H | O | C(CH₃)₂CH=CH₂ |
| 1.24 | H | H | O | C(CH₃)₂CH=CHCH₃ |
| 1.25 | H | H | O | C(CH₃)₂CH=C(CH₃)₂ |
| 1.26 | H | H | O | CH₂CH=CHCl |
| 1.27 | H | H | O | CH₂CH=CCl₂ |
| 1.28 | H | H | O | CH₂CCl=CHCl |
| 1.29 | H | H | O | CH₂CCl=CCl₂ |
| 1.30 | H | H | O | CH₂CH=CF₂ |
| 1.31 | H | H | O | CH₂CF=CF₂ |
| 1.32 | H | H | O | CH₂C•CH |
| 1.33 | H | H | O | CH₂C•CCH₃ |
| 1.34 | H | H | O | CH₂C•CCH₂CH₃ |
| 1.35 | H | H | O | CH(CH₃)C•CH |
| 1.36 | H | H | O | CH(CH₃)C•CCH₃ |
| 1.37 | H | H | O | CH(CH₃)C•CCH₂CH₃ |
| 1.38 | H | H | O | C(CH₃)₂C•CH |
| 1.39 | H | H | O | C(CH₃)₂C•CCH₃ |
| 1.40 | H | H | O | C(CH₃)₂C•CCH₂CH₃ |
| 1.41 | H | H | O | Cyclopropyl |
| 1.42 | H | H | O | Cyclobutyl |
| 1.43 | H | H | O | Cyclopentyl |
| 1.44 | H | H | O | Cyclohexyl |
| 1.45 | H | H | O | CH₂CF₃ |
| 1.46 | H | H | O | CH₂CH₂CF₃ |
| 1.47 | H | H | O | CH₂-cyclopropyl |
| 1.48 | H | H | O | CH₂-cyclobutyl |
| 1.49 | H | H | O | CH₂-cyclopentyl |
| 1.50 | H | H | O | CH₂-cyclohexyl |
| 1.51 | H | H | O | CH₂OCH₃ |
| 1.52 | H | H | O | CH₂OCH₂CH₃ |
| 1.53 | H | H | O | CH₂CH₂OCH₃ |
| 1.54 | H | H | O | CH₂CH₂OCH₂CH₃ |
| 1.55 | CH₃ | H | O | CH₃ |
| 1.56 | CH₃ | H | O | CH₂CH₃ |
| 1.57 | CH₃ | H | O | CH₂CH₂CH₃ |
| 1.58 | CH₃ | H | O | CH(CH₃)₂ |
| 1.59 | CH₃ | H | O | CH₂CH₂CH₂CH₃ |
| 1.60 | CH₃ | H | O | CH₂CH(CH₃)₂ |
| 1.61 | CH₃ | H | O | CH(CH₃)CH₂CH₃ |
| 1.62 | CH₃ | H | O | C(CH₃)₃ |
| 1.63 | CH₃ | H | O | CH₂CH₂CH₂CH₂CH₃ |
| 1.64 | CH₃ | H | O | CH₂CH₂CH(CH₃)₂ |
| 1.65 | CH₃ | H | O | CH₂C(CH₃)₃ |
| 1.66 | CH₃ | H | O | CH₂CH(CH₃)CH₂CH₃ |
| 1.67 | CH₃ | H | O | CH(CH₃)CH₂CH₂CH₃ |
| 1.68 | CH₃ | H | O | C(CH₃)₂CH₂CH₃ |
| 1.69 | CH₃ | H | O | CH₂CH=CH₂ |
| 1.70 | CH₃ | H | O | CH₂CH=CHCH₃ |
| 1.71 | CH₃ | H | O | CH₂CH=C(CH₃)₂ |
| 1.72 | CH₃ | H | O | CH₂C(CH₃)=CH₂ |
| 1.73 | CH₃ | H | O | CH₂C(CH₃)=CHCH₃ |
| 1.74 | CH₃ | H | O | CH₂C(CH₃)=C(CH₃)₂ |
| 1.75 | CH₃ | H | O | CH(CH₃)CH=CH₂ |
| 1.76 | CH₃ | H | O | CH(CH₃)CH=CHCH₃ |
| 1.77 | CH₃ | H | O | CH(CH₃)CH=C(CH₃)₂ |
| 1.78 | CH₃ | H | O | C(CH₃)₂CH=CH₂ |
| 1.79 | CH₃ | H | O | C(CH₃)₂CH=CHCH₃ |
| 1.80 | CH₃ | H | O | C(CH₃)₂CH=C(CH₃)₂ |
| 1.81 | CH₃ | H | O | CH₂CH=CHCl |
| 1.82 | CH₃ | H | O | CH₂CH=CCl₂ |
| 1.83 | CH₃ | H | O | CH₂CCl=CHCl |

TABLE 1-continued

This Table contains 646 compounds of the following type,

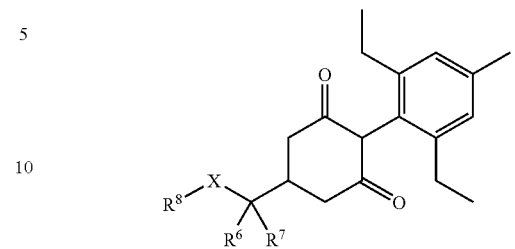

where X, R², R³ and R⁴ are as defined below:

| Compound number | R⁶ | R⁷ | X | R⁸ |
|---|---|---|---|---|
| 1.84 | CH₃ | H | O | CH₂CCl=CCl₂ |
| 1.85 | CH₃ | H | O | CH₂CH=CF₂ |
| 1.86 | CH₃ | H | O | CH₂CF=CF₂ |
| 1.87 | CH₃ | H | O | CH₂C•CH |
| 1.88 | CH₃ | H | O | CH₂C•CCH₃ |
| 1.89 | CH₃ | H | O | CH₂C•CCH₂CH₃ |
| 1.90 | CH₃ | H | O | CH(CH₃)C•CH |
| 1.91 | CH₃ | H | O | CH(CH₃)C•CCH₃ |
| 1.92 | CH₃ | H | O | CH(CH₃)C•CCH₂CH₃ |
| 1.93 | CH₃ | H | O | C(CH₃)₂C•CH |
| 1.94 | CH₃ | H | O | C(CH₃)₂C•CCH₃ |
| 1.95 | CH₃ | H | O | C(CH₃)₂C•CCH₂CH₃ |
| 1.96 | CH₃ | H | O | Cyclopropyl |
| 1.97 | CH₃ | H | O | Cyclobutyl |
| 1.98 | CH₃ | H | O | Cyclopentyl |
| 1.99 | CH₃ | H | O | Cyclohexyl |
| 1.100 | CH₃ | H | O | CH₂CF₃ |
| 1.101 | CH₃ | H | O | CH₂CH₂CF₃ |
| 1.102 | CH₃ | H | O | CH₂-cyclopropyl |
| 1.103 | CH₃ | H | O | CH₂-cyclobutyl |
| 1.104 | CH₃ | H | O | CH₂-cyclopentyl |
| 1.105 | CH₃ | H | O | CH₂-cyclohexyl |
| 1.106 | CH₃ | H | O | CH₂OCH₃ |
| 1.107 | CH₃ | H | O | CH₂OCH₂CH₃ |
| 1.108 | CH₃ | H | O | CH₂CH₂OCH₃ |
| 1.109 | CH₃ | H | O | CH₂CH₂OCH₂CH₃ |
| 1.110 | CH₃ | CH₃ | O | CH₃ |
| 1.111 | CH₃ | CH₃ | O | CH₂CH₃ |
| 1.112 | CH₃ | CH₃ | O | CH₂CH₂CH₃ |
| 1.113 | CH₃ | CH₃ | O | CH(CH₃)₂ |
| 1.114 | CH₃ | CH₃ | O | CH₂CH₂CH₂CH₃ |
| 1.115 | CH₃ | CH₃ | O | CH₂CH(CH₃)₂ |
| 1.116 | CH₃ | CH₃ | O | CH(CH₃)CH₂CH₃ |
| 1.117 | CH₃ | CH₃ | O | C(CH₃)₃ |
| 1.118 | CH₃ | CH₃ | O | CH₂CH₂CH₂CH₂CH₃ |
| 1.119 | CH₃ | CH₃ | O | CH₂CH₂CH(CH₃)₂ |
| 1.120 | CH₃ | CH₃ | O | CH₂C(CH₃)₃ |
| 1.121 | CH₃ | CH₃ | O | CH₂CH(CH₃)CH₂CH₃ |
| 1.122 | CH₃ | CH₃ | O | CH(CH₃)CH₂CH₂CH₃ |
| 1.123 | CH₃ | CH₃ | O | C(CH₃)₂CH₂CH₃ |
| 1.124 | CH₃ | CH₃ | O | CH₂CH=CH₂ |
| 1.125 | CH₃ | CH₃ | O | CH₂CH=CHCH₃ |
| 1.126 | CH₃ | CH₃ | O | CH₂CH=C(CH₃)₂ |
| 1.127 | CH₃ | CH₃ | O | CH₂C(CH₃)=CH₂ |
| 1.128 | CH₃ | CH₃ | O | CH₂C(CH₃)=CHCH₃ |
| 1.129 | CH₃ | CH₃ | O | CH₂C(CH₃)=C(CH₃)₂ |
| 1.130 | CH₃ | CH₃ | O | CH(CH₃)CH=CH₂ |
| 1.131 | CH₃ | CH₃ | O | CH(CH₃)CH=CHCH₃ |
| 1.132 | CH₃ | CH₃ | O | CH(CH₃)CH=C(CH₃)₂ |
| 1.133 | CH₃ | CH₃ | O | C(CH₃)₂CH=CH₂ |
| 1.134 | CH₃ | CH₃ | O | C(CH₃)₂CH=CHCH₃ |
| 1.135 | CH₃ | CH₃ | O | C(CH₃)₂CH=C(CH₃)₂ |
| 1.136 | CH₃ | CH₃ | O | CH₂CH=CHCl |
| 1.137 | CH₃ | CH₃ | O | CH₂CH=CCl₂ |
| 1.138 | CH₃ | CH₃ | O | CH₂CCl=CHCl |
| 1.139 | CH₃ | CH₃ | O | CH₂CCl=CCl₂ |
| 1.140 | CH₃ | CH₃ | O | CH₂CH=CF₂ |
| 1.141 | CH₃ | CH₃ | O | CH₂CF=CF₂ |
| 1.142 | CH₃ | CH₃ | O | CH₂C•CH |
| 1.143 | CH₃ | CH₃ | O | CH₂C•CCH₃ |
| 1.144 | CH₃ | CH₃ | O | CH₂C•CCH₂CH₃ |

TABLE 1-continued

This Table contains 646 compounds of the following type,

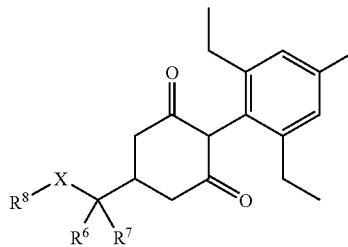

where X, R², R³ and R⁴ are as defined below:

| Compound number | R⁶ | R⁷ | X | R⁸ |
|---|---|---|---|---|
| 1.145 | CH₃ | CH₃ | O | CH(CH₃)C•CH |
| 1.146 | CH₃ | CH₃ | O | CH(CH₃)C•CCH₃ |
| 1.147 | CH₃ | CH₃ | O | CH(CH₃)C•CCH₂CH₃ |
| 1.148 | CH₃ | CH₃ | O | C(CH₃)₂C•CH |
| 1.149 | CH₃ | CH₃ | O | C(CH₃)₂C•CCH₃ |
| 1.150 | CH₃ | CH₃ | O | C(CH₃)₂C•CCH₂CH₃ |
| 1.151 | CH₃ | CH₃ | O | Cyclopropyl |
| 1.152 | CH₃ | CH₃ | O | Cyclobutyl |
| 1.153 | CH₃ | CH₃ | O | Cyclopentyl |
| 1.154 | CH₃ | CH₃ | O | Cyclohexyl |
| 1.155 | CH₃ | CH₃ | O | CH₂CF₃ |
| 1.156 | CH₃ | CH₃ | O | CH₂CH₂CF₃ |
| 1.157 | CH₃ | CH₃ | O | CH₂-cyclopropyl |
| 1.158 | CH₃ | CH₃ | O | CH₂-cyclobutyl |
| 1.159 | CH₃ | CH₃ | O | CH₂-cyclopentyl |
| 1.160 | CH₃ | CH₃ | O | CH₂-cyclohexyl |
| 1.161 | CH₃ | CH₃ | O | CH₂OCH₃ |
| 1.162 | CH₃ | CH₃ | O | CH₂OCH₂CH₃ |
| 1.163 | CH₃ | CH₃ | O | CH₂CH₂OCH₃ |
| 1.164 | CH₃ | CH₃ | O | CH₂CH₂OCH₂CH₃ |
| 1.165 | H | H | S | CH₂CH₃ |
| 1.166 | H | H | S | CH₂CH₂CH₃ |
| 1.167 | H | H | S | CH(CH₃)₂ |
| 1.168 | H | H | S | CH₂CH₂CH₂CH₃ |
| 1.169 | H | H | S | CH₂CH(CH₃)₂ |
| 1.170 | H | H | S | CH(CH₃)CH₂CH₃ |
| 1.171 | H | H | S | C(CH₃)₃ |
| 1.172 | H | H | S | CH₂CH₂CH₂CH₂CH₃ |
| 1.173 | H | H | S | CH₂CH₂CH(CH₃)₂ |
| 1.174 | H | H | S | CH₂C(CH₃)₃ |
| 1.175 | H | H | S | CH₂CH(CH₃)CH₂CH₃ |
| 1.176 | H | H | S | CH(CH₃)CH₂CH₂CH₃ |
| 1.177 | H | H | S | C(CH₃)₂CH₂CH₃ |
| 1.178 | H | H | S | CH₂CH=CH₂ |
| 1.179 | H | H | S | CH₂CH=CHCH₃ |
| 1.180 | H | H | S | CH₂CH=C(CH₃)₂ |
| 1.181 | H | H | S | CH₂C(CH₃)=CH₂ |
| 1.182 | H | H | S | CH₂C(CH₃)=CHCH₃ |
| 1.183 | H | H | S | CH₂C(CH₃)=C(CH₃)₂ |
| 1.184 | H | H | S | CH(CH₃)CH=CH₂ |
| 1.185 | H | H | S | CH(CH₃)CH=CHCH₃ |
| 1.186 | H | H | S | CH(CH₃)CH=C(CH₃)₂ |
| 1.187 | H | H | S | C(CH₃)₂CH=CH₂ |
| 1.188 | H | H | S | C(CH₃)₂CH=CHCH₃ |
| 1.189 | H | H | S | C(CH₃)₂CH=C(CH₃)₂ |
| 1.190 | H | H | S | CH₂CH=CHCl |
| 1.191 | H | H | S | CH₂CH=CCl₂ |
| 1.192 | H | H | S | CH₂CCl=CHCl |
| 1.193 | H | H | S | CH₂CCl=CCl₂ |
| 1.194 | H | H | S | CH₂CH=CF₂ |
| 1.195 | H | H | S | CH₂CF=CF₂ |
| 1.196 | H | H | S | CH₂C•CH |
| 1.197 | H | H | S | CH₂C•CCH₃ |
| 1.198 | H | H | S | CH₂C•CCH₂CH₃ |
| 1.199 | H | H | S | CH(CH₃)C•CH |
| 1.200 | H | H | S | CH(CH₃)C•CCH₃ |
| 1.201 | H | H | S | CH(CH₃)C•CCH₂CH₃ |
| 1.202 | H | H | S | C(CH₃)₂C•CH |
| 1.203 | H | H | S | C(CH₃)₂C•CCH₃ |
| 1.204 | H | H | S | C(CH₃)₂C•CCH₂CH₃ |
| 1.205 | H | H | S | Cyclopropyl |

TABLE 1-continued

This Table contains 646 compounds of the following type,

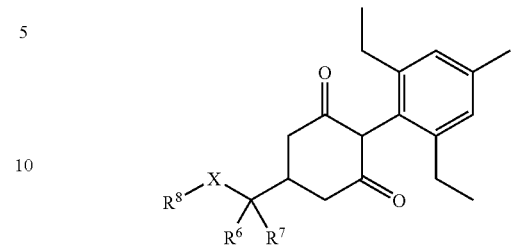

where X, R², R³ and R⁴ are as defined below:

| Compound number | R⁶ | R⁷ | X | R⁸ |
|---|---|---|---|---|
| 1.206 | H | H | S | Cyclobutyl |
| 1.207 | H | H | S | Cyclopentyl |
| 1.208 | H | H | S | Cyclohexyl |
| 1.209 | H | H | S | CH₂CF₃ |
| 1.210 | H | H | S | CH₂CH₂CF₃ |
| 1.211 | H | H | S | CH₂-cyclopropyl |
| 1.212 | H | H | S | CH₂-cyclobutyl |
| 1.213 | H | H | S | CH₂-cyclopentyl |
| 1.214 | H | H | S | CH₂-cyclohexyl |
| 1.215 | CH₃ | H | S | CH₃ |
| 1.216 | CH₃ | H | S | CH₂CH₃ |
| 1.217 | CH₃ | H | S | CH₂CH₂CH₃ |
| 1.218 | CH₃ | H | S | CH(CH₃)₂ |
| 1.219 | CH₃ | H | S | CH₂CH₂CH₂CH₃ |
| 1.220 | CH₃ | H | S | CH₂CH(CH₃)₂ |
| 1.221 | CH₃ | H | S | CH(CH₃)CH₂CH₃ |
| 1.222 | CH₃ | H | S | C(CH₃)₃ |
| 1.223 | CH₃ | H | S | CH₂CH₂CH₂CH₂CH₃ |
| 1.224 | CH₃ | H | S | CH₂CH₂CH(CH₃)₂ |
| 1.225 | CH₃ | H | S | CH₂C(CH₃)₃ |
| 1.226 | CH₃ | H | S | CH₂CH(CH₃)CH₂CH₃ |
| 1.227 | CH₃ | H | S | CH(CH₃)CH₂CH₂CH₃ |
| 1.228 | CH₃ | H | S | C(CH₃)₂CH₂CH₃ |
| 1.229 | CH₃ | H | S | CH₂CH=CH₂ |
| 1.230 | CH₃ | H | S | CH₂CH=CHCH₃ |
| 1.231 | CH₃ | H | S | CH₂CH=C(CH₃)₂ |
| 1.232 | CH₃ | H | S | CH₂C(CH₃)=CH₂ |
| 1.233 | CH₃ | H | S | CH₂C(CH₃)=CHCH₃ |
| 1.234 | CH₃ | H | S | CH₂C(CH₃)=C(CH₃)₂ |
| 1.235 | CH₃ | H | S | CH(CH₃)CH=CH₂ |
| 1.236 | CH₃ | H | S | CH(CH₃)CH=CHCH₃ |
| 1.237 | CH₃ | H | S | CH(CH₃)CH=C(CH₃)₂ |
| 1.238 | CH₃ | H | S | C(CH₃)₂CH=CH₂ |
| 1.239 | CH₃ | H | S | C(CH₃)₂CH=CHCH₃ |
| 1.240 | CH₃ | H | S | C(CH₃)₂CH=C(CH₃)₂ |
| 1.241 | CH₃ | H | S | CH₂CH=CHCl |
| 1.242 | CH₃ | H | S | CH₂CH=CCl₂ |
| 1.243 | CH₃ | H | S | CH₂CCl=CHCl |
| 1.244 | CH₃ | H | S | CH₂CCl=CCl₂ |
| 1.245 | CH₃ | H | S | CH₂CH=CF₂ |
| 1.246 | CH₃ | H | S | CH₂CF=CF₂ |
| 1.247 | CH₃ | H | S | CH₂C•CH |
| 1.248 | CH₃ | H | S | CH₂C•CCH₃ |
| 1.249 | CH₃ | H | S | CH₂C•CCH₂CH₃ |
| 1.250 | CH₃ | H | S | CH(CH₃)C•CH |
| 1.251 | CH₃ | H | S | CH(CH₃)C•CCH₃ |
| 1.252 | CH₃ | H | S | CH(CH₃)C•CCH₂CH₃ |
| 1.253 | CH₃ | H | S | C(CH₃)₂C•CH |
| 1.254 | CH₃ | H | S | C(CH₃)₂C•CCH₃ |
| 1.255 | CH₃ | H | S | C(CH₃)₂C•CCH₂CH₃ |
| 1.256 | CH₃ | H | S | Cyclopropyl |
| 1.257 | CH₃ | H | S | Cyclobutyl |
| 1.258 | CH₃ | H | S | Cyclopentyl |
| 1.259 | CH₃ | H | S | Cyclohexyl |
| 1.260 | CH₃ | H | S | CH₂CF₃ |
| 1.261 | CH₃ | H | S | CH₂CH₂CF₃ |
| 1.262 | CH₃ | H | S | CH₂-cyclopropyl |
| 1.263 | CH₃ | H | S | CH₂-cyclobutyl |
| 1.264 | CH₃ | H | S | CH₂-cyclopentyl |
| 1.265 | CH₃ | H | S | CH₂-cyclohexyl |
| 1.266 | CH₃ | CH₃ | S | CH₃ |

TABLE 1-continued

This Table contains 646 compounds of the following type,

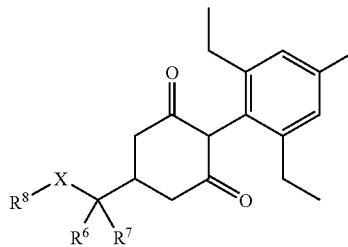

where X, $R^2$, $R^3$ and $R^4$ are as defined below:

| Compound number | $R^6$ | $R^7$ | X | $R^8$ |
|---|---|---|---|---|
| 1.267 | $CH_3$ | $CH_3$ | S | $CH_2CH_3$ |
| 1.268 | $CH_3$ | $CH_3$ | S | $CH_2CH_2CH_3$ |
| 1.269 | $CH_3$ | $CH_3$ | S | $CH(CH_3)_2$ |
| 1.270 | $CH_3$ | $CH_3$ | S | $CH_2CH_2CH_2CH_3$ |
| 1.271 | $CH_3$ | $CH_3$ | S | $CH_2CH(CH_3)_2$ |
| 1.272 | $CH_3$ | $CH_3$ | S | $CH(CH_3)CH_2CH_3$ |
| 1.273 | $CH_3$ | $CH_3$ | S | $C(CH_3)_3$ |
| 1.274 | $CH_3$ | $CH_3$ | S | $CH_2CH_2CH_2CH_2CH_3$ |
| 1.275 | $CH_3$ | $CH_3$ | S | $CH_2CH_2CH(CH_3)_2$ |
| 1.276 | $CH_3$ | $CH_3$ | S | $CH_2C(CH_3)_3$ |
| 1.277 | $CH_3$ | $CH_3$ | S | $CH_2CH(CH_3)CH_2CH_3$ |
| 1.278 | $CH_3$ | $CH_3$ | S | $CH(CH_3)CH_2CH_2CH_3$ |
| 1.279 | $CH_3$ | $CH_3$ | S | $C(CH_3)_2CH_2CH_3$ |
| 1.280 | $CH_3$ | $CH_3$ | S | $CH_2CH=CH_2$ |
| 1.281 | $CH_3$ | $CH_3$ | S | $CH_2CH=CHCH_3$ |
| 1.282 | $CH_3$ | $CH_3$ | S | $CH_2CH=C(CH_3)_2$ |
| 1.283 | $CH_3$ | $CH_3$ | S | $CH_2C(CH_3)=CH_2$ |
| 1.284 | $CH_3$ | $CH_3$ | S | $CH_2C(CH_3)=CHCH_3$ |
| 1.285 | $CH_3$ | $CH_3$ | S | $CH_2C(CH_3)=C(CH_3)_2$ |
| 1.286 | $CH_3$ | $CH_3$ | S | $CH(CH_3)CH=CH_2$ |
| 1.287 | $CH_3$ | $CH_3$ | S | $CH(CH_3)CH=CHCH_3$ |
| 1.288 | $CH_3$ | $CH_3$ | S | $CH(CH_3)CH=C(CH_3)_2$ |
| 1.289 | $CH_3$ | $CH_3$ | S | $C(CH_3)_2CH=CH_2$ |
| 1.290 | $CH_3$ | $CH_3$ | S | $C(CH_3)_2CH=CHCH_3$ |
| 1.291 | $CH_3$ | $CH_3$ | S | $C(CH_3)_2CH=C(CH_3)_2$ |
| 1.292 | $CH_3$ | $CH_3$ | S | $CH_2CH=CHCl$ |
| 1.293 | $CH_3$ | $CH_3$ | S | $CH_2CH=CCl_2$ |
| 1.294 | $CH_3$ | $CH_3$ | S | $CH_2CCl=CHCl$ |
| 1.295 | $CH_3$ | $CH_3$ | S | $CH_2CCl=CCl_2$ |
| 1.296 | $CH_3$ | $CH_3$ | S | $CH_2CH=CF_2$ |
| 1.297 | $CH_3$ | $CH_3$ | S | $CH_2CF=CF_2$ |
| 1.298 | $CH_3$ | $CH_3$ | S | $CH_2C\bullet CH$ |
| 1.299 | $CH_3$ | $CH_3$ | S | $CH_2C\bullet CCH_3$ |
| 1.300 | $CH_3$ | $CH_3$ | S | $CH_2C\bullet CCH_2CH_3$ |
| 1.301 | $CH_3$ | $CH_3$ | S | $CH(CH_3)C\bullet CH$ |
| 1.302 | $CH_3$ | $CH_3$ | S | $CH(CH_3)C\bullet CCH_3$ |
| 1.303 | $CH_3$ | $CH_3$ | S | $CH(CH_3)C\bullet CCH_2CH_3$ |
| 1.304 | $CH_3$ | $CH_3$ | S | $C(CH_3)_2C\bullet CH$ |
| 1.305 | $CH_3$ | $CH_3$ | S | $C(CH_3)_2C\bullet CCH_3$ |
| 1.306 | $CH_3$ | $CH_3$ | S | $C(CH_3)_2C\bullet CCH_2CH_3$ |
| 1.307 | $CH_3$ | $CH_3$ | S | Cyclopropyl |
| 1.308 | $CH_3$ | $CH_3$ | S | Cyclobutyl |
| 1.309 | $CH_3$ | $CH_3$ | S | Cyclopentyl |
| 1.310 | $CH_3$ | $CH_3$ | S | Cyclohexyl |
| 1.311 | $CH_3$ | $CH_3$ | S | $CH_2CF_3$ |
| 1.312 | $CH_3$ | $CH_3$ | S | $CH_2CH_2CF_3$ |
| 1.313 | $CH_3$ | $CH_3$ | S | $CH_2$-cyclopropyl |
| 1.314 | $CH_3$ | $CH_3$ | S | $CH_2$-cyclobutyl |
| 1.315 | $CH_3$ | $CH_3$ | S | $CH_2$-cyclopentyl |
| 1.316 | $CH_3$ | $CH_3$ | S | $CH_2$-cyclohexyl |
| 1.317 | H | H | S(O) | $CH_3$ |
| 1.318 | H | H | S(O) | $CH_2CH_3$ |
| 1.319 | H | H | S(O) | $CH_2CH_2CH_3$ |
| 1.320 | H | H | S(O) | $CH(CH_3)_2$ |
| 1.321 | H | H | S(O) | $CH_2CH_2CH_2CH_3$ |
| 1.322 | H | H | S(O) | $CH_2CH(CH_3)_2$ |
| 1.323 | H | H | S(O) | $CH(CH_3)CH_2CH_3$ |
| 1.324 | H | H | S(O) | $C(CH_3)_3$ |
| 1.325 | H | H | S(O) | $CH_2CH_2CH_2CH_2CH_3$ |
| 1.326 | H | H | S(O) | $CH_2CH_2CH(CH_3)_2$ |
| 1.327 | H | H | S(O) | $CH_2C(CH_3)_3$ |

TABLE 1-continued

This Table contains 646 compounds of the following type,

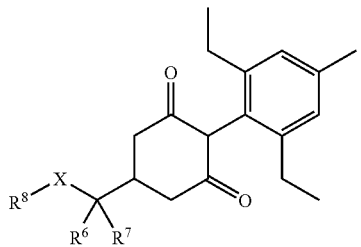

where X, $R^2$, $R^3$ and $R^4$ are as defined below:

| Compound number | $R^6$ | $R^7$ | X | $R^8$ |
|---|---|---|---|---|
| 1.328 | H | H | S(O) | $CH_2CH(CH_3)CH_2CH_3$ |
| 1.329 | H | H | S(O) | $CH(CH_3)CH_2CH_2CH_3$ |
| 1.330 | H | H | S(O) | $C(CH_3)_2CH_2CH_3$ |
| 1.331 | H | H | S(O) | $CH_2CH=CH_2$ |
| 1.332 | H | H | S(O) | $CH_2CH=CHCH_3$ |
| 1.333 | H | H | S(O) | $CH_2CH=C(CH_3)_2$ |
| 1.334 | H | H | S(O) | $CH_2C(CH_3)=CH_2$ |
| 1.335 | H | H | S(O) | $CH_2C(CH_3)=CHCH_3$ |
| 1.336 | H | H | S(O) | $CH_2C(CH_3)=C(CH_3)_2$ |
| 1.337 | H | H | S(O) | $CH(CH_3)CH=CH_2$ |
| 1.338 | H | H | S(O) | $CH(CH_3)CH=CHCH_3$ |
| 1.339 | H | H | S(O) | $CH(CH_3)CH=C(CH_3)_2$ |
| 1.340 | H | H | S(O) | $C(CH_3)_2CH=CH_2$ |
| 1.341 | H | H | S(O) | $C(CH_3)_2CH=CHCH_3$ |
| 1.342 | H | H | S(O) | $C(CH_3)_2CH=C(CH_3)_2$ |
| 1.343 | H | H | S(O) | $CH_2CH=CHCl$ |
| 1.344 | H | H | S(O) | $CH_2CH=CCl_2$ |
| 1.345 | H | H | S(O) | $CH_2CCl=CHCl$ |
| 1.346 | H | H | S(O) | $CH_2CCl=CCl_2$ |
| 1.347 | H | H | S(O) | $CH_2CH=CF_2$ |
| 1.348 | H | H | S(O) | $CH_2CF=CF_2$ |
| 1.349 | H | H | S(O) | $CH_2C\bullet CH$ |
| 1.350 | H | H | S(O) | $CH_2C\bullet CCH_3$ |
| 1.351 | H | H | S(O) | $CH_2C\bullet CCH_2CH_3$ |
| 1.352 | H | H | S(O) | $CH(CH_3)C\bullet CH$ |
| 1.353 | H | H | S(O) | $CH(CH_3)C\bullet CCH_3$ |
| 1.354 | H | H | S(O) | $CH(CH_3)C\bullet CCH_2CH_3$ |
| 1.355 | H | H | S(O) | $C(CH_3)_2C\bullet CH$ |
| 1.356 | H | H | S(O) | $C(CH_3)_2C\bullet CCH_3$ |
| 1.357 | H | H | S(O) | $C(CH_3)_2C\bullet CCH_2CH_3$ |
| 1.358 | H | H | S(O) | Cyclopropyl |
| 1.359 | H | H | S(O) | Cyclobutyl |
| 1.360 | H | H | S(O) | Cyclopentyl |
| 1.361 | H | H | S(O) | Cyclohexyl |
| 1.362 | H | H | S(O) | $CH_2CF_3$ |
| 1.363 | H | H | S(O) | $CH_2CH_2CF_3$ |
| 1.364 | H | H | S(O) | $CH_2$-cyclopropyl |
| 1.365 | H | H | S(O) | $CH_2$-cyclobutyl |
| 1.366 | H | H | S(O) | $CH_2$-cyclopentyl |
| 1.367 | H | H | S(O) | $CH_2$-cyclohexyl |
| 1.368 | H | H | S(O) | $CH_2OCH_3$ |
| 1.369 | H | H | S(O) | $CH_2OCH_2CH_3$ |
| 1.370 | H | H | S(O) | $CH_2CH_2OCH_3$ |
| 1.371 | H | H | S(O) | $CH_2CH_2OCH_2CH_3$ |
| 1.372 | $CH_3$ | H | S(O) | $CH_3$ |
| 1.373 | $CH_3$ | H | S(O) | $CH_2CH_3$ |
| 1.374 | $CH_3$ | H | S(O) | $CH_2CH_2CH_3$ |
| 1.375 | $CH_3$ | H | S(O) | $CH(CH_3)_2$ |
| 1.376 | $CH_3$ | H | S(O) | $CH_2CH_2CH_2CH_3$ |
| 1.377 | $CH_3$ | H | S(O) | $CH_2CH(CH_3)_2$ |
| 1.378 | $CH_3$ | H | S(O) | $CH(CH_3)CH_2CH_3$ |
| 1.379 | $CH_3$ | H | S(O) | $C(CH_3)_3$ |
| 1.380 | $CH_3$ | H | S(O) | $CH_2CH_2CH_2CH_2CH_3$ |
| 1.381 | $CH_3$ | H | S(O) | $CH_2CH_2CH(CH_3)_2$ |
| 1.382 | $CH_3$ | H | S(O) | $CH_2C(CH_3)_3$ |
| 1.383 | $CH_3$ | H | S(O) | $CH_2CH(CH_3)CH_2CH_3$ |
| 1.384 | $CH_3$ | H | S(O) | $CH(CH_3)CH_2CH_2CH_3$ |
| 1.385 | $CH_3$ | H | S(O) | $C(CH_3)_2CH_2CH_3$ |
| 1.386 | $CH_3$ | H | S(O) | $CH_2CH=CH_2$ |
| 1.387 | $CH_3$ | H | S(O) | $CH_2CH=CHCH_3$ |
| 1.388 | $CH_3$ | H | S(O) | $CH_2CH=C(CH_3)_2$ |

TABLE 1-continued

This Table contains 646 compounds of the following type,

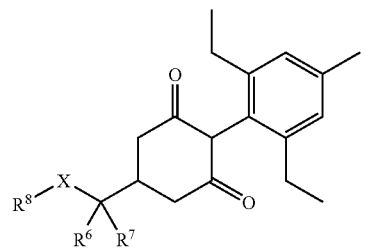

where X, $R^2$, $R^3$ and $R^4$ are as defined below:

| Compound number | $R^6$ | $R^7$ | X | $R^8$ |
|---|---|---|---|---|
| 1.389 | $CH_3$ | H | S(O) | $CH_2C(CH_3)=CH_2$ |
| 1.390 | $CH_3$ | H | S(O) | $CH_2C(CH_3)=CHCH_3$ |
| 1.391 | $CH_3$ | H | S(O) | $CH_2C(CH_3)=C(CH_3)_2$ |
| 1.392 | $CH_3$ | H | S(O) | $CH(CH_3)CH=CH_2$ |
| 1.393 | $CH_3$ | H | S(O) | $CH(CH_3)CH=CHCH_3$ |
| 1.394 | $CH_3$ | H | S(O) | $CH(CH_3)CH=C(CH_3)_2$ |
| 1.395 | $CH_3$ | H | S(O) | $C(CH_3)_2CH=CH_2$ |
| 1.396 | $CH_3$ | H | S(O) | $C(CH_3)_2CH=CHCH_3$ |
| 1.397 | $CH_3$ | H | S(O) | $C(CH_3)_2CH=C(CH_3)_2$ |
| 1.398 | $CH_3$ | H | S(O) | $CH_2CH=CHCl$ |
| 1.399 | $CH_3$ | H | S(O) | $CH_2CH=CCl_2$ |
| 1.400 | $CH_3$ | H | S(O) | $CH_2CCl=CHCl$ |
| 1.401 | $CH_3$ | H | S(O) | $CH_2CCl=CCl_2$ |
| 1.402 | $CH_3$ | H | S(O) | $CH_2CH=CF_2$ |
| 1.403 | $CH_3$ | H | S(O) | $CH_2CF=CF_2$ |
| 1.404 | $CH_3$ | H | S(O) | $CH_2C•CH$ |
| 1.405 | $CH_3$ | H | S(O) | $CH_2C•CCH_3$ |
| 1.406 | $CH_3$ | H | S(O) | $CH_2C•CCH_2CH_3$ |
| 1.407 | $CH_3$ | H | S(O) | $CH(CH_3)C•CH$ |
| 1.408 | $CH_3$ | H | S(O) | $CH(CH_3)C•CCH_3$ |
| 1.409 | $CH_3$ | H | S(O) | $CH(CH_3)C•CCH_2CH_3$ |
| 1.410 | $CH_3$ | H | S(O) | $C(CH_3)_2C•CH$ |
| 1.411 | $CH_3$ | H | S(O) | $C(CH_3)_2C•CCH_3$ |
| 1.412 | $CH_3$ | H | S(O) | $C(CH_3)_2C•CCH_2CH_3$ |
| 1.413 | $CH_3$ | H | S(O) | Cyclopropyl |
| 1.414 | $CH_3$ | H | S(O) | Cyclobutyl |
| 1.415 | $CH_3$ | H | S(O) | Cyclopentyl |
| 1.416 | $CH_3$ | H | S(O) | Cyclohexyl |
| 1.417 | $CH_3$ | H | S(O) | $CH_2CF_3$ |
| 1.418 | $CH_3$ | H | S(O) | $CH_2CH_2CF_3$ |
| 1.419 | $CH_3$ | H | S(O) | $CH_2$-cyclopropyl |
| 1.420 | $CH_3$ | H | S(O) | $CH_2$-cyclobutyl |
| 1.421 | $CH_3$ | H | S(O) | $CH_2$-cyclopentyl |
| 1.422 | $CH_3$ | H | S(O) | $CH_2$-cyclohexyl |
| 1.423 | $CH_3$ | H | S(O) | $CH_2OCH_3$ |
| 1.424 | $CH_3$ | H | S(O) | $CH_2OCH_2CH_3$ |
| 1.425 | $CH_3$ | H | S(O) | $CH_2CH_2OCH_3$ |
| 1.426 | $CH_3$ | H | S(O) | $CH_2CH_2OCH_2CH_3$ |
| 1.427 | $CH_3$ | $CH_3$ | S(O) | $CH_3$ |
| 1.428 | $CH_3$ | $CH_3$ | S(O) | $CH_2CH_3$ |
| 1.429 | $CH_3$ | $CH_3$ | S(O) | $CH_2CH_2CH_3$ |
| 1.430 | $CH_3$ | $CH_3$ | S(O) | $CH(CH_3)_2$ |
| 1.431 | $CH_3$ | $CH_3$ | S(O) | $CH_2CH_2CH_2CH_3$ |
| 1.432 | $CH_3$ | $CH_3$ | S(O) | $CH_2CH(CH_3)_2$ |
| 1.433 | $CH_3$ | $CH_3$ | S(O) | $CH(CH_3)CH_2CH_3$ |
| 1.434 | $CH_3$ | $CH_3$ | S(O) | $C(CH_3)_3$ |
| 1.435 | $CH_3$ | $CH_3$ | S(O) | $CH_2CH_2CH_2CH_2CH_3$ |
| 1.436 | $CH_3$ | $CH_3$ | S(O) | $CH_2CH_2CH(CH_3)_2$ |
| 1.437 | $CH_3$ | $CH_3$ | S(O) | $CH_2C(CH_3)_3$ |
| 1.438 | $CH_3$ | $CH_3$ | S(O) | $CH_2CH(CH_3)CH_2CH_3$ |
| 1.439 | $CH_3$ | $CH_3$ | S(O) | $CH(CH_3)CH_2CH_2CH_3$ |
| 1.440 | $CH_3$ | $CH_3$ | S(O) | $C(CH_3)_2CH_2CH_3$ |
| 1.441 | $CH_3$ | $CH_3$ | S(O) | $CH_2CH=CH_2$ |
| 1.442 | $CH_3$ | $CH_3$ | S(O) | $CH_2CH=CHCH_3$ |
| 1.443 | $CH_3$ | $CH_3$ | S(O) | $CH_2CH=C(CH_3)_2$ |
| 1.444 | $CH_3$ | $CH_3$ | S(O) | $CH_2C(CH_3)=CH_2$ |
| 1.445 | $CH_3$ | $CH_3$ | S(O) | $CH_2C(CH_3)=CHCH_3$ |
| 1.446 | $CH_3$ | $CH_3$ | S(O) | $CH_2C(CH_3)=C(CH_3)_2$ |
| 1.447 | $CH_3$ | $CH_3$ | S(O) | $CH(CH_3)CH=CH_2$ |
| 1.448 | $CH_3$ | $CH_3$ | S(O) | $CH(CH_3)CH=CHCH_3$ |
| 1.449 | $CH_3$ | $CH_3$ | S(O) | $CH(CH_3)CH=C(CH_3)_2$ |

TABLE 1-continued

This Table contains 646 compounds of the following type,

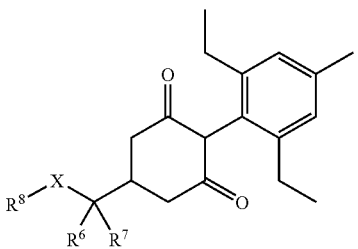

where X, $R^2$, $R^3$ and $R^4$ are as defined below:

| Compound number | $R^6$ | $R^7$ | X | $R^8$ |
|---|---|---|---|---|
| 1.450 | $CH_3$ | $CH_3$ | S(O) | $C(CH_3)_2CH=CH_2$ |
| 1.451 | $CH_3$ | $CH_3$ | S(O) | $C(CH_3)_2CH=CHCH_3$ |
| 1.452 | $CH_3$ | $CH_3$ | S(O) | $C(CH_3)_2CH=C(CH_3)_2$ |
| 1.453 | $CH_3$ | $CH_3$ | S(O) | $CH_2CH=CHCl$ |
| 1.454 | $CH_3$ | $CH_3$ | S(O) | $CH_2CH=CCl_2$ |
| 1.455 | $CH_3$ | $CH_3$ | S(O) | $CH_2CCl=CHCl$ |
| 1.456 | $CH_3$ | $CH_3$ | S(O) | $CH_2CCl=CCl_2$ |
| 1.457 | $CH_3$ | $CH_3$ | S(O) | $CH_2CH=CF_2$ |
| 1.458 | $CH_3$ | $CH_3$ | S(O) | $CH_2CF=CF_2$ |
| 1.459 | $CH_3$ | $CH_3$ | S(O) | $CH_2C•CH$ |
| 1.460 | $CH_3$ | $CH_3$ | S(O) | $CH_2C•CCH_3$ |
| 1.461 | $CH_3$ | $CH_3$ | S(O) | $CH_2C•CCH_2CH_3$ |
| 1.462 | $CH_3$ | $CH_3$ | S(O) | $CH(CH_3)C•CH$ |
| 1.463 | $CH_3$ | $CH_3$ | S(O) | $CH(CH_3)C•CCH_3$ |
| 1.464 | $CH_3$ | $CH_3$ | S(O) | $CH(CH_3)C•CCH_2CH_3$ |
| 1.465 | $CH_3$ | $CH_3$ | S(O) | $C(CH_3)_2C•CH$ |
| 1.466 | $CH_3$ | $CH_3$ | S(O) | $C(CH_3)_2C•CCH_3$ |
| 1.467 | $CH_3$ | $CH_3$ | S(O) | $C(CH_3)_2C•CCH_2CH_3$ |
| 1.468 | $CH_3$ | $CH_3$ | S(O) | Cyclopropyl |
| 1.469 | $CH_3$ | $CH_3$ | S(O) | Cyclobutyl |
| 1.470 | $CH_3$ | $CH_3$ | S(O) | Cyclopentyl |
| 1.471 | $CH_3$ | $CH_3$ | S(O) | Cyclohexyl |
| 1.472 | $CH_3$ | $CH_3$ | S(O) | $CH_2CF_3$ |
| 1.473 | $CH_3$ | $CH_3$ | S(O) | $CH_2CH_2CF_3$ |
| 1.474 | $CH_3$ | $CH_3$ | S(O) | $CH_2$-cyclopropyl |
| 1.475 | $CH_3$ | $CH_3$ | S(O) | $CH_2$-cyclobutyl |
| 1.476 | $CH_3$ | $CH_3$ | S(O) | $CH_2$-cyclopentyl |
| 1.477 | $CH_3$ | $CH_3$ | S(O) | $CH_2$-cyclohexyl |
| 1.478 | $CH_3$ | $CH_3$ | S(O) | $CH_2OCH_3$ |
| 1.479 | $CH_3$ | $CH_3$ | S(O) | $CH_2OCH_2CH_3$ |
| 1.480 | $CH_3$ | $CH_3$ | S(O) | $CH_2CH_2OCH_3$ |
| 1.481 | $CH_3$ | $CH_3$ | S(O) | $CH_2CH_2OCH_2CH_3$ |
| 1.482 | H | H | $SO_2$ | $CH_3$ |
| 1.483 | H | H | $SO_2$ | $CH_2CH_3$ |
| 1.484 | H | H | $SO_2$ | $CH_2CH_2CH_3$ |
| 1.485 | H | H | $SO_2$ | $CH(CH_3)_2$ |
| 1.486 | H | H | $SO_2$ | $CH_2CH_2CH_2CH_3$ |
| 1.487 | H | H | $SO_2$ | $CH_2CH(CH_3)_2$ |
| 1.488 | H | H | $SO_2$ | $CH(CH_3)CH_2CH_3$ |
| 1.489 | H | H | $SO_2$ | $C(CH_3)_3$ |
| 1.490 | H | H | $SO_2$ | $CH_2CH_2CH_2CH_2CH_3$ |
| 1.491 | H | H | $SO_2$ | $CH_2CH_2CH(CH_3)_2$ |
| 1.492 | H | H | $SO_2$ | $CH_2C(CH_3)_3$ |
| 1.493 | H | H | $SO_2$ | $CH_2CH(CH_3)CH_2CH_3$ |
| 1.494 | H | H | $SO_2$ | $CH(CH_3)CH_2CH_2CH_3$ |
| 1.495 | H | H | $SO_2$ | $C(CH_3)_2CH_2CH_3$ |
| 1.496 | H | H | $SO_2$ | $CH_2CH=CH_2$ |
| 1.497 | H | H | $SO_2$ | $CH_2CH=CHCH_3$ |
| 1.498 | H | H | $SO_2$ | $CH_2CH=C(CH_3)_2$ |
| 1.499 | H | H | $SO_2$ | $CH_2C(CH_3)=CH_2$ |
| 1.500 | H | H | $SO_2$ | $CH_2C(CH_3)=CHCH_3$ |
| 1.501 | H | H | $SO_2$ | $CH_2C(CH_3)=C(CH_3)_2$ |
| 1.502 | H | H | $SO_2$ | $CH(CH_3)CH=CH_2$ |
| 1.503 | H | H | $SO_2$ | $CH(CH_3)CH=CHCH_3$ |
| 1.504 | H | H | $SO_2$ | $CH(CH_3)CH=C(CH_3)_2$ |
| 1.505 | H | H | $SO_2$ | $C(CH_3)_2CH=CH_2$ |
| 1.506 | H | H | $SO_2$ | $C(CH_3)_2CH=CHCH_3$ |
| 1.507 | H | H | $SO_2$ | $C(CH_3)_2CH=C(CH_3)_2$ |
| 1.508 | H | H | $SO_2$ | $CH_2CH=CHCl$ |
| 1.509 | H | H | $SO_2$ | $CH_2CH=CCl_2$ |
| 1.510 | H | H | $SO_2$ | $CH_2CCl=CHCl$ |

TABLE 1-continued

This Table contains 646 compounds of the following type,

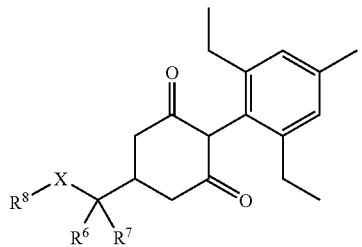

where X, R², R³ and R⁴ are as defined below:

| Compound number | R⁶ | R⁷ | X | R⁸ |
|---|---|---|---|---|
| 1.511 | H | H | SO₂ | CH₂CCl=CCl₂ |
| 1.512 | H | H | SO₂ | CH₂CH=CF₂ |
| 1.513 | H | H | SO₂ | CH₂CF=CF₂ |
| 1.514 | H | H | SO₂ | CH₂C•CH |
| 1.515 | H | H | SO₂ | CH₂C•CCH₃ |
| 1.516 | H | H | SO₂ | CH₂C•CCH₂CH₃ |
| 1.517 | H | H | SO₂ | CH(CH₃)C•CH |
| 1.518 | H | H | SO₂ | CH(CH₃)C•CCH₃ |
| 1.519 | H | H | SO₂ | CH(CH₃)C•CCH₂CH₃ |
| 1.520 | H | H | SO₂ | C(CH₃)₂C•CH |
| 1.521 | H | H | SO₂ | C(CH₃)₂C•CCH₃ |
| 1.522 | H | H | SO₂ | C(CH₃)₂C•CCH₂CH₃ |
| 1.523 | H | H | SO₂ | Cyclopropyl |
| 1.524 | H | H | SO₂ | Cyclobutyl |
| 1.525 | H | H | SO₂ | Cyclopentyl |
| 1.526 | H | H | SO₂ | Cyclohexyl |
| 1.527 | H | H | SO₂ | CH₂CF₃ |
| 1.528 | H | H | SO₂ | CH₂CH₂CF₃ |
| 1.529 | H | H | SO₂ | CH₂-cyclopropyl |
| 1.530 | H | H | SO₂ | CH₂-cyclobutyl |
| 1.531 | H | H | SO₂ | CH₂-cyclopentyl |
| 1.532 | H | H | SO₂ | CH₂-cyclohexyl |
| 1.533 | H | H | SO₂ | CH₂OCH₃ |
| 1.534 | H | H | SO₂ | CH₂OCH₂CH₃ |
| 1.535 | H | H | SO₂ | CH₂CH₂OCH₃ |
| 1.536 | H | H | SO₂ | CH₂CH₂OCH₂CH₃ |
| 1.537 | CH₃ | H | SO₂ | CH₃ |
| 1.538 | CH₃ | H | SO₂ | CH₂CH₃ |
| 1.539 | CH₃ | H | SO₂ | CH₂CH₂CH₃ |
| 1.540 | CH₃ | H | SO₂ | CH(CH₃)₂ |
| 1.541 | CH₃ | H | SO₂ | CH₂CH₂CH₂CH₃ |
| 1.542 | CH₃ | H | SO₂ | CH₂CH(CH₃)₂ |
| 1.543 | CH₃ | H | SO₂ | CH(CH₃)CH₂CH₃ |
| 1.544 | CH₃ | H | SO₂ | C(CH₃)₃ |
| 1.545 | CH₃ | H | SO₂ | CH₂CH₂CH₂CH₂CH₃ |
| 1.546 | CH₃ | H | SO₂ | CH₂CH₂CH(CH₃)₂ |
| 1.547 | CH₃ | H | SO₂ | CH₂C(CH₃)₃ |
| 1.548 | CH₃ | H | SO₂ | CH₂CH(CH₃)CH₂CH₃ |
| 1.549 | CH₃ | H | SO₂ | CH(CH₃)CH₂CH₂CH₃ |
| 1.550 | CH₃ | H | SO₂ | C(CH₃)₂CH₂CH₃ |
| 1.551 | CH₃ | H | SO₂ | CH₂CH=CH₂ |
| 1.552 | CH₃ | H | SO₂ | CH₂CH=CHCH₃ |
| 1.553 | CH₃ | H | SO₂ | CH₂CH=C(CH₃)₂ |
| 1.554 | CH₃ | H | SO₂ | CH₂C(CH₃)=CH₂ |
| 1.555 | CH₃ | H | SO₂ | CH₂C(CH₃)=CHCH₃ |
| 1.556 | CH₃ | H | SO₂ | CH₂C(CH₃)=C(CH₃)₂ |
| 1.557 | CH₃ | H | SO₂ | CH(CH₃)CH=CH₂ |
| 1.558 | CH₃ | H | SO₂ | CH(CH₃)CH=CHCH₃ |
| 1.559 | CH₃ | H | SO₂ | CH(CH₃)CH=C(CH₃)₂ |
| 1.560 | CH₃ | H | SO₂ | C(CH₃)₂CH=CH₂ |
| 1.561 | CH₃ | H | SO₂ | C(CH₃)₂CH=CHCH₃ |
| 1.562 | CH₃ | H | SO₂ | C(CH₃)₂CH=C(CH₃)₂ |
| 1.563 | CH₃ | H | SO₂ | CH₂CH=CHCl |
| 1.564 | CH₃ | H | SO₂ | CH₂CH=CCl₂ |
| 1.565 | CH₃ | H | SO₂ | CH₂CCl=CHCl |
| 1.566 | CH₃ | H | SO₂ | CH₂CCl=CCl₂ |
| 1.567 | CH₃ | H | SO₂ | CH₂CH=CF₂ |
| 1.568 | CH₃ | H | SO₂ | CH₂CF=CF₂ |
| 1.569 | CH₃ | H | SO₂ | CH₂C•CH |
| 1.570 | CH₃ | H | SO₂ | CH₂C•CCH₃ |
| 1.571 | CH₃ | H | SO₂ | CH₂C•CCH₂CH₃ |
| 1.572 | CH₃ | H | SO₂ | CH(CH₃)C•CH |
| 1.573 | CH₃ | H | SO₂ | CH(CH₃)C•CCH₃ |
| 1.574 | CH₃ | H | SO₂ | CH(CH₃)C•CCH₂CH₃ |
| 1.575 | CH₃ | H | SO₂ | C(CH₃)₂C•CH |
| 1.576 | CH₃ | H | SO₂ | C(CH₃)₂C•CCH₃ |
| 1.577 | CH₃ | H | SO₂ | C(CH₃)₂C•CCH₂CH₃ |
| 1.578 | CH₃ | H | SO₂ | Cyclopropyl |
| 1.579 | CH₃ | H | SO₂ | Cyclobutyl |
| 1.580 | CH₃ | H | SO₂ | Cyclopentyl |
| 1.581 | CH₃ | H | SO₂ | Cyclohexyl |
| 1.582 | CH₃ | H | SO₂ | CH₂CF₃ |
| 1.583 | CH₃ | H | SO₂ | CH₂CH₂CF₃ |
| 1.584 | CH₃ | H | SO₂ | CH₂-cyclopropyl |
| 1.585 | CH₃ | H | SO₂ | CH₂-cyclobutyl |
| 1.586 | CH₃ | H | SO₂ | CH₂-cyclopentyl |
| 1.587 | CH₃ | H | SO₂ | CH₂-cyclohexyl |
| 1.588 | CH₃ | H | SO₂ | CH₂OCH₃ |
| 1.589 | CH₃ | H | SO₂ | CH₂OCH₂CH₃ |
| 1.590 | CH₃ | H | SO₂ | CH₂CH₂OCH₃ |
| 1.591 | CH₃ | H | SO₂ | CH₂CH₂OCH₂CH₃ |
| 1.592 | CH₃ | CH₃ | SO₂ | CH₃ |
| 1.593 | CH₃ | CH₃ | SO₂ | CH₂CH₃ |
| 1.594 | CH₃ | CH₃ | SO₂ | CH₂CH₂CH₃ |
| 1.595 | CH₃ | CH₃ | SO₂ | CH(CH₃)₂ |
| 1.596 | CH₃ | CH₃ | SO₂ | CH₂CH₂CH₂CH₃ |
| 1.597 | CH₃ | CH₃ | SO₂ | CH₂CH(CH₃)₂ |
| 1.598 | CH₃ | CH₃ | SO₂ | CH(CH₃)CH₂CH₃ |
| 1.599 | CH₃ | CH₃ | SO₂ | C(CH₃)₃ |
| 1.600 | CH₃ | CH₃ | SO₂ | CH₂CH₂CH₂CH₂CH₃ |
| 1.601 | CH₃ | CH₃ | SO₂ | CH₂CH₂CH(CH₃)₂ |
| 1.602 | CH₃ | CH₃ | SO₂ | CH₂C(CH₃)₃ |
| 1.603 | CH₃ | CH₃ | SO₂ | CH₂CH(CH₃)CH₂CH₃ |
| 1.604 | CH₃ | CH₃ | SO₂ | CH(CH₃)CH₂CH₂CH₃ |
| 1.605 | CH₃ | CH₃ | SO₂ | C(CH₃)₂CH₂CH₃ |
| 1.606 | CH₃ | CH₃ | SO₂ | CH₂CH=CH₂ |
| 1.607 | CH₃ | CH₃ | SO₂ | CH₂CH=CHCH₃ |
| 1.608 | CH₃ | CH₃ | SO₂ | CH₂CH=C(CH₃)₂ |
| 1.609 | CH₃ | CH₃ | SO₂ | CH₂C(CH₃)=CH₂ |
| 1.610 | CH₃ | CH₃ | SO₂ | CH₂C(CH₃)=CHCH₃ |
| 1.611 | CH₃ | CH₃ | SO₂ | CH₂C(CH₃)=C(CH₃)₂ |
| 1.612 | CH₃ | CH₃ | SO₂ | CH(CH₃)CH=CH₂ |
| 1.613 | CH₃ | CH₃ | SO₂ | CH(CH₃)CH=CHCH₃ |
| 1.614 | CH₃ | CH₃ | SO₂ | CH(CH₃)CH=C(CH₃)₂ |
| 1.615 | CH₃ | CH₃ | SO₂ | C(CH₃)₂CH=CH₂ |
| 1.616 | CH₃ | CH₃ | SO₂ | C(CH₃)₂CH=CHCH₃ |
| 1.617 | CH₃ | CH₃ | SO₂ | C(CH₃)₂CH=C(CH₃)₂ |
| 1.618 | CH₃ | CH₃ | SO₂ | CH₂CH=CHCl |
| 1.619 | CH₃ | CH₃ | SO₂ | CH₂CH=CCl₂ |
| 1.620 | CH₃ | CH₃ | SO₂ | CH₂CCl=CHCl |
| 1.621 | CH₃ | CH₃ | SO₂ | CH₂CCl=CCl₂ |
| 1.622 | CH₃ | CH₃ | SO₂ | CH₂CH=CF₂ |
| 1.623 | CH₃ | CH₃ | SO₂ | CH₂CF=CF₂ |
| 1.624 | CH₃ | CH₃ | SO₂ | CH₂C•CH |
| 1.625 | CH₃ | CH₃ | SO₂ | CH₂C•CCH₃ |
| 1.626 | CH₃ | CH₃ | SO₂ | CH₂C•CCH₂CH₃ |
| 1.627 | CH₃ | CH₃ | SO₂ | CH(CH₃)C•CH |
| 1.628 | CH₃ | CH₃ | SO₂ | CH(CH₃)C•CCH₃ |
| 1.629 | CH₃ | CH₃ | SO₂ | CH(CH₃)C•CCH₂CH₃ |
| 1.630 | CH₃ | CH₃ | SO₂ | C(CH₃)₂C•CH |
| 1.631 | CH₃ | CH₃ | SO₂ | C(CH₃)₂C•CCH₃ |
| 1.632 | CH₃ | CH₃ | SO₂ | C(CH₃)₂C•CCH₂CH₃ |

TABLE 1-continued

This Table contains 646 compounds of the following type,

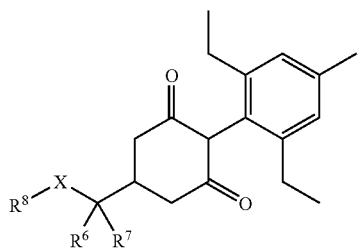

where X, R², R³ and R⁴ are as defined below:

| Compound number | $R^6$ | $R^7$ | X | $R^8$ |
|---|---|---|---|---|
| 1.633 | $CH_3$ | $CH_3$ | $SO_2$ | Cyclopropyl |
| 1.634 | $CH_3$ | $CH_3$ | $SO_2$ | Cyclobutyl |
| 1.635 | $CH_3$ | $CH_3$ | $SO_2$ | Cyclopentyl |
| 1.636 | $CH_3$ | $CH_3$ | $SO_2$ | Cyclohexyl |
| 1.637 | $CH_3$ | $CH_3$ | $SO_2$ | $CH_2CF_3$ |
| 1.638 | $CH_3$ | $CH_3$ | $SO_2$ | $CH_2CH_2CF_3$ |
| 1.639 | $CH_3$ | $CH_3$ | $SO_2$ | $CH_2$-cyclopropyl |
| 1.640 | $CH_3$ | $CH_3$ | $SO_2$ | $CH_2$-cyclobutyl |
| 1.641 | $CH_3$ | $CH_3$ | $SO_2$ | $CH_2$-cyclopentyl |
| 1.642 | $CH_3$ | $CH_3$ | $SO_2$ | $CH_2$-cyclohexyl |
| 1.643 | $CH_3$ | $CH_3$ | $SO_2$ | $CH_2OCH_3$ |
| 1.644 | $CH_3$ | $CH_3$ | $SO_2$ | $CH_2OCH_2CH_3$ |
| 1.645 | $CH_3$ | $CH_3$ | $SO_2$ | $CH_2CH_2OCH_3$ |
| 1.646 | $CH_3$ | $CH_3$ | $SO_2$ | $CH_2CH_2OCH_2CH_3$ |

TABLE 2

This table contains 646 compounds of the following type,

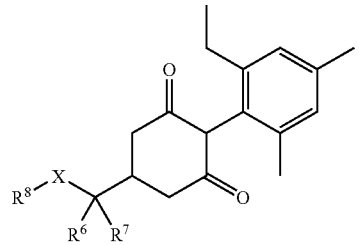

where X, $R^6$, $R^7$ and $R^8$ are as defined in Table 1.

TABLE 3

This table contains 646 compounds of the following type,

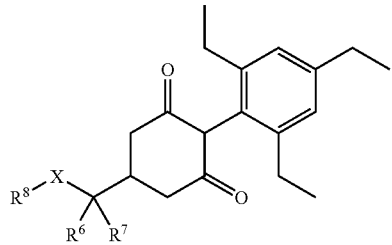

where X, $R^6$, $R^7$ and $R^8$ are as defined in Table 1

TABLE 4

Table 4 contains 646 compounds of the following type,

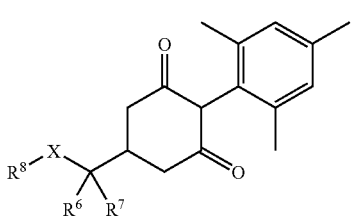

where X, $R^6$, $R^7$ and $R^8$ are as defined in Table 1.

TABLE 5

This table contains 646 compounds of the following type,

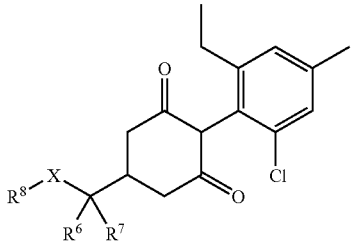

where X, $R^6$, $R^7$ and $R^8$ are as defined in Table 1.

TABLE 6

This table contains 646 compounds of the following type,

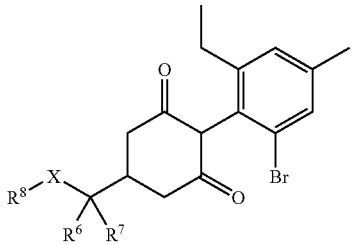

where X, $R^6$, $R^7$ and $R^8$ are as defined in Table 1.

TABLE 7

This table contains 646 compounds of the following type,

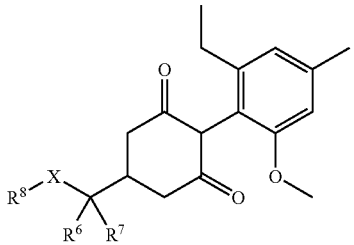

where X, $R^6$, $R^7$ and $R^8$ are as defined in Table 1.

TABLE 8

This table contains 646 compounds of the following type,

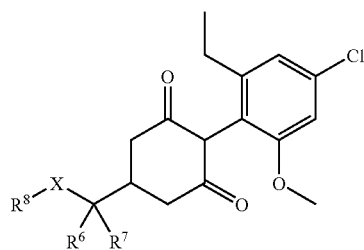

where X, $R^6$, $R^7$ and $R^8$ are as defined in Table 1.

TABLE 9

This table contains 646 compounds of the following type,

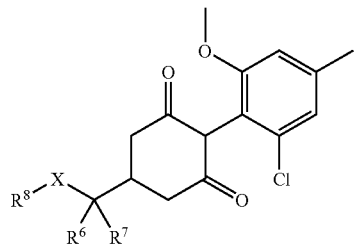

where X, $R^6$, $R^7$ and $R^8$ are as defined in Table 1.

TABLE 10

This table contains 646 compounds of the following type,

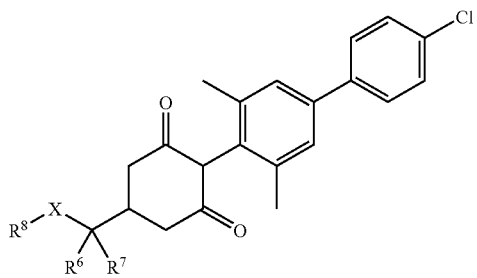

where X, $R^6$, $R^7$ and $R^8$ are as defined in Table 1.

TABLE 11

This table contains 646 compounds of the following type,

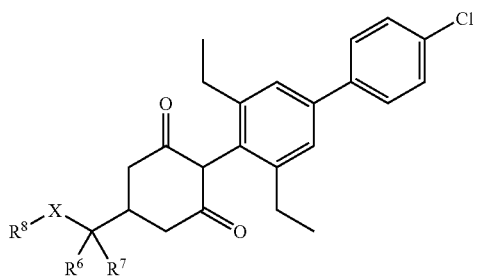

where X, $R^6$, $R^7$ and $R^8$ are as defined in Table 1.

TABLE 12

This table contains 646 compounds of the following type,

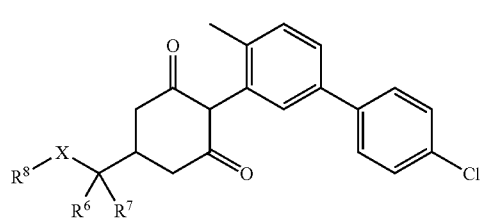

where X, $R^6$, $R^7$ and $R^8$ are as defined in Table 1.

TABLE 13

This table contains 646 compounds of the following type,

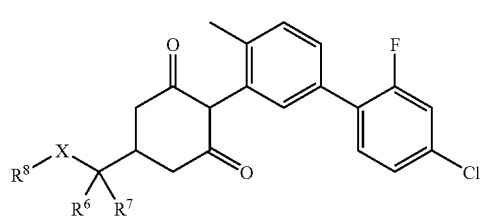

where X, $R^6$, $R^7$ and $R^8$ are as defined in Table 1.

TABLE 14

This table contains 646 compounds of the following type,

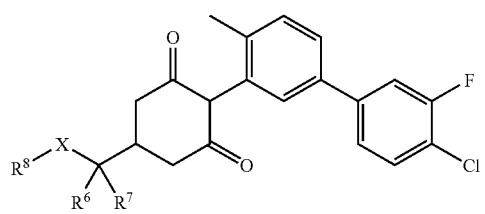

where X, $R^6$, $R^7$ and $R^8$ are as defined in Table 1.

TABLE 15

This table contains 646 compounds of the following type,

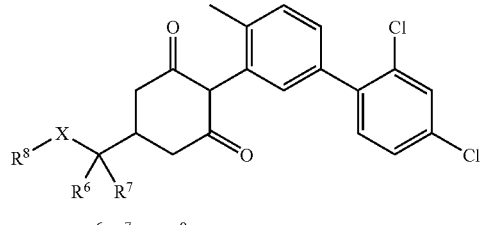

where X, $R^6$, $R^7$ and $R^8$ are as defined in Table 1.

TABLE 16

This table 12 contains 646 compounds of the following type,

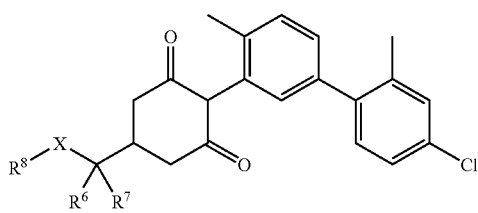

where X, $R^6$, $R^7$ and $R^8$ are as defined in Table 1.

TABLE 17

This table contains 646 compounds of the following type,

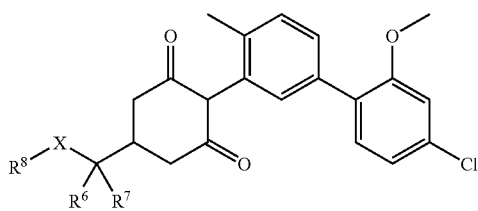

where X, $R^6$, $R^7$ and $R^8$ are as defined in Table 1.

TABLE 18

This table contains 646 compounds of the following type,

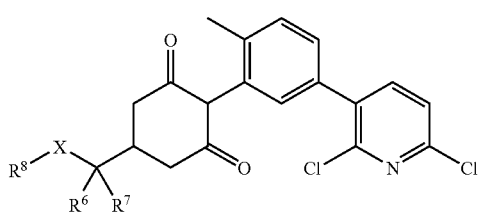

where X, $R^6$, $R^7$ and $R^8$ are as defined in Table 1.

TABLE 19

This table contains 646 compounds of the following type,

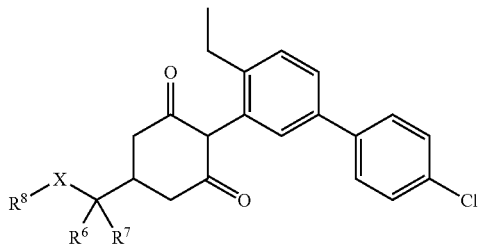

where X, $R^6$, $R^7$ and $R^8$ are as defined in Table 1.

TABLE 20

This table contains 646 compounds of the following type,

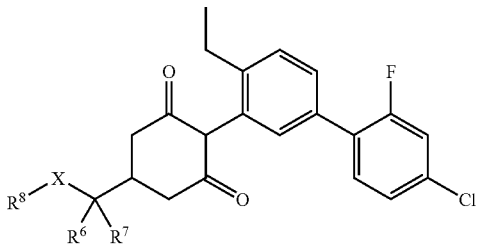

where X, $R^6$, $R^7$ and $R^8$ are as defined in Table 1.

TABLE 21

This table contains 646 compounds of the following type,

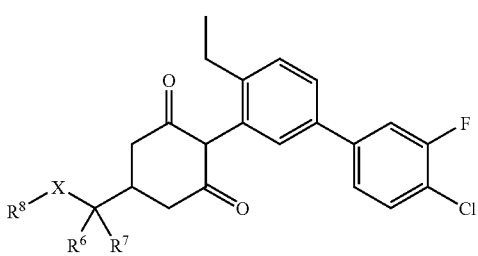

where X, $R^6$, $R^7$ and $R^8$ are as defined in Table 1.

TABLE 22

This table contains 646 compounds of the following type,

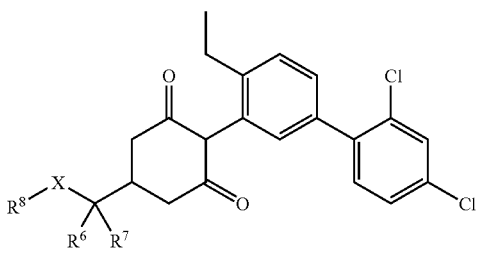

where X, $R^6$, $R^7$ and $R^8$ are as defined in Table 1.

TABLE 23

This table 12 contains 646 compounds of the following type,

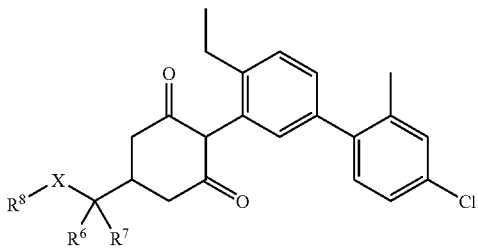

where X, $R^6$, $R^7$ and $R^8$ are as defined in Table 1.

TABLE 24

This table contains 646 compounds of the following type,

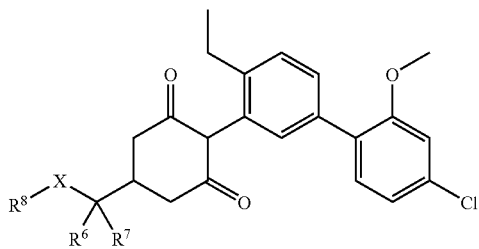

where X, R$^6$, R$^7$ and R$^8$ are as defined in Table 1.

TABLE 25

This table contains 646 compounds of the following type,

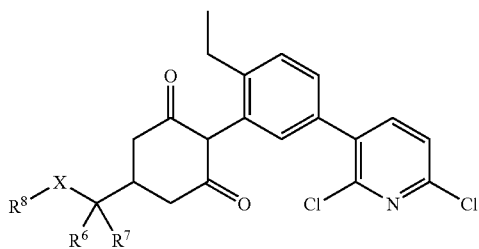

where X, R$^6$, R$^7$ and R$^8$ are as defined in Table 1.

TABLE 26

This table contains 618 compounds of the following type,

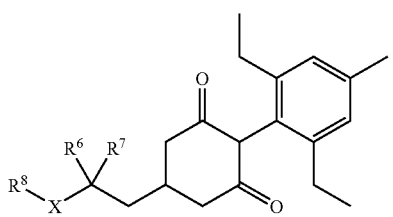

where X, R$^6$, R$^7$ and R$^8$ are as defined below:

| Compound number | R$^6$ | R$^7$ | X | R$^8$ |
|---|---|---|---|---|
| 26.1 | H | H | O | CH$_3$ |
| 26.2 | H | H | O | CH$_2$CH$_3$ |
| 26.3 | H | H | O | CH$_2$CH$_2$CH$_3$ |
| 26.4 | H | H | O | CH(CH$_3$)$_2$ |
| 26.5 | H | H | O | CH$_2$CH$_2$CH$_2$CH$_3$ |
| 26.6 | H | H | O | CH$_2$CH(CH$_3$)$_2$ |
| 26.7 | H | H | O | CH(CH$_3$)CH$_2$CH$_3$ |
| 26.8 | H | H | O | C(CH$_3$)$_3$ |
| 26.9 | H | H | O | CH$_2$CH$_2$CH$_2$CH$_2$CH$_3$ |
| 26.10 | H | H | O | CH$_2$CH$_2$CH(CH$_3$)$_2$ |
| 26.11 | H | H | O | CH$_2$C(CH$_3$)$_3$ |
| 26.12 | H | H | O | CH$_2$CH(CH$_3$)CH$_2$CH$_3$ |
| 26.13 | H | H | O | CH(CH$_3$)CH$_2$CH$_2$CH$_3$ |
| 26.14 | H | H | O | C(CH$_3$)$_2$CH$_2$CH$_3$ |
| 26.15 | H | H | O | CH$_2$CH=CH$_2$ |
| 26.16 | H | H | O | CH$_2$CH=CHCH$_3$ |
| 26.17 | H | H | O | CH$_2$CH=C(CH$_3$)$_2$ |
| 26.18 | H | H | O | CH$_2$C(CH$_3$)=CH$_2$ |
| 26.19 | H | H | O | CH$_2$C(CH$_3$)=CHCH$_3$ |
| 26.20 | H | H | O | CH$_2$C(CH$_3$)=C(CH$_3$)$_2$ |
| 26.21 | H | H | O | CH(CH$_3$)CH=CH$_2$ |
| 26.22 | H | H | O | CH(CH$_3$)CH=CHCH$_3$ |
| 26.23 | H | H | O | CH(CH$_3$)CH=C(CH$_3$)$_2$ |
| 26.24 | H | H | O | C(CH$_3$)$_2$CH=CH$_2$ |
| 26.25 | H | H | O | C(CH$_3$)$_2$CH=CHCH$_3$ |
| 26.26 | H | H | O | C(CH$_3$)$_2$CH=C(CH$_3$)$_2$ |
| 26.27 | H | H | O | CH$_2$CH=CHCl |
| 26.28 | H | H | O | CH$_2$CH=CCl$_2$ |
| 26.29 | H | H | O | CH$_2$CCl=CHCl |
| 26.30 | H | H | O | CH$_2$CCl=CCl$_2$ |
| 26.31 | H | H | O | CH$_2$CH=CF$_2$ |
| 26.32 | H | H | O | CH$_2$CF=CF$_2$ |
| 26.33 | H | H | O | CH$_2$C•CH |
| 26.34 | H | H | O | CH$_2$C•CCH$_3$ |
| 26.35 | H | H | O | CH$_2$C•CCH$_2$CH$_3$ |
| 26.36 | H | H | O | CH(CH$_3$)C•CH |
| 26.37 | H | H | O | CH(CH$_3$)C•CCH$_3$ |
| 26.38 | H | H | O | CH(CH$_3$)C•CCH$_2$CH$_3$ |
| 26.39 | H | H | O | C(CH$_3$)$_2$C•CH |
| 26.40 | H | H | O | C(CH$_3$)$_2$C•CCH$_3$ |
| 26.41 | H | H | O | C(CH$_3$)$_2$C•CCH$_2$CH$_3$ |
| 26.42 | H | H | O | Cyclopropyl |
| 26.43 | H | H | O | Cyclobutyl |
| 26.44 | H | H | O | Cyclopentyl |
| 26.45 | H | H | O | Cyclohexyl |
| 26.46 | H | H | O | CH$_2$CF$_3$ |
| 26.47 | H | H | O | CH$_2$CH$_2$CF$_3$ |
| 26.48 | H | H | O | CH$_2$-cyclopropyl |
| 26.49 | H | H | O | CH$_2$-cyclobutyl |
| 26.50 | H | H | O | CH$_2$-cyclopentyl |
| 26.51 | H | H | O | CH$_2$-cyclohexyl |
| 26.52 | H | H | O | CH$_2$OCH$_3$ |
| 26.53 | H | H | O | CH$_2$OCH$_2$CH$_3$ |
| 26.54 | H | H | O | CH$_2$CH$_2$OCH$_3$ |
| 26.55 | H | H | O | CH$_2$CH$_2$OCH$_2$CH$_3$ |
| 26.56 | CH$_3$ | H | O | CH$_3$ |
| 26.57 | CH$_3$ | H | O | CH$_2$CH$_3$ |
| 26.58 | CH$_3$ | H | O | CH$_2$CH$_2$CH$_3$ |
| 26.59 | CH$_3$ | H | O | CH(CH$_3$)$_2$ |
| 26.60 | CH$_3$ | H | O | CH$_2$CH$_2$CH$_2$CH$_3$ |
| 26.61 | CH$_3$ | H | O | CH$_2$CH(CH$_3$)$_2$ |
| 26.62 | CH$_3$ | H | O | CH(CH$_3$)CH$_2$CH$_3$ |
| 26.63 | CH$_3$ | H | O | C(CH$_3$)$_3$ |
| 26.64 | CH$_3$ | H | O | CH$_2$CH$_2$CH$_2$CH$_2$CH$_3$ |
| 26.65 | CH$_3$ | H | O | CH$_2$CH$_2$CH(CH$_3$)$_2$ |
| 26.66 | CH$_3$ | H | O | CH$_2$C(CH$_3$)$_3$ |
| 26.67 | CH$_3$ | H | O | CH$_2$CH(CH$_3$)CH$_2$CH$_3$ |
| 26.68 | CH$_3$ | H | O | CH(CH$_3$)CH$_2$CH$_2$CH$_3$ |
| 26.69 | CH$_3$ | H | O | C(CH$_3$)$_2$CH$_2$CH$_3$ |
| 26.70 | CH$_3$ | H | O | CH$_2$CH=CH$_2$ |
| 26.71 | CH$_3$ | H | O | CH$_2$CH=CHCH$_3$ |
| 26.72 | CH$_3$ | H | O | CH$_2$CH=C(CH$_3$)$_2$ |
| 26.73 | CH$_3$ | H | O | CH$_2$C(CH$_3$)=CH$_2$ |
| 26.74 | CH$_3$ | H | O | CH$_2$C(CH$_3$)=CHCH$_3$ |
| 26.75 | CH$_3$ | H | O | CH$_2$C(CH$_3$)=C(CH$_3$)$_2$ |
| 26.76 | CH$_3$ | H | O | CH(CH$_3$)CH=CH$_2$ |
| 26.77 | CH$_3$ | H | O | CH(CH$_3$)CH=CHCH$_3$ |
| 26.78 | CH$_3$ | H | O | CH(CH$_3$)CH=C(CH$_3$)$_2$ |
| 26.79 | CH$_3$ | H | O | C(CH$_3$)$_2$CH=CH$_2$ |
| 26.80 | CH$_3$ | H | O | C(CH$_3$)$_2$CH=CHCH$_3$ |
| 26.81 | CH$_3$ | H | O | C(CH$_3$)$_2$CH=C(CH$_3$)$_2$ |
| 26.82 | CH$_3$ | H | O | CH$_2$CH=CHCl |
| 26.83 | CH$_3$ | H | O | CH$_2$CH=CCl$_2$ |
| 26.84 | CH$_3$ | H | O | CH$_2$CCl=CHCl |
| 26.85 | CH$_3$ | H | O | CH$_2$CCl=CCl$_2$ |
| 26.86 | CH$_3$ | H | O | CH$_2$CH=CF$_2$ |
| 26.87 | CH$_3$ | H | O | CH$_2$CF=CF$_2$ |
| 26.88 | CH$_3$ | H | O | CH$_2$C•CH |
| 26.89 | CH$_3$ | H | O | CH$_2$C•CCH$_3$ |
| 26.90 | CH$_3$ | H | O | CH$_2$C•CCH$_2$CH$_3$ |
| 26.91 | CH$_3$ | H | O | CH(CH$_3$)C•CH |
| 26.92 | CH$_3$ | H | O | CH(CH$_3$)C•CCH$_3$ |
| 26.93 | CH$_3$ | H | O | CH(CH$_3$)C•CCH$_2$CH$_3$ |
| 26.94 | CH$_3$ | H | O | C(CH$_3$)$_2$C•CH |
| 26.95 | CH$_3$ | H | O | C(CH$_3$)$_2$C•CCH$_3$ |
| 26.96 | CH$_3$ | H | O | C(CH$_3$)$_2$C•CCH$_2$CH$_3$ |
| 26.97 | CH$_3$ | H | O | Cyclopropyl |
| 26.98 | CH$_3$ | H | O | Cyclobutyl |
| 26.99 | CH$_3$ | H | O | Cyclopentyl |
| 26.100 | CH$_3$ | H | O | Cyclohexyl |
| 26.101 | CH$_3$ | H | O | CH$_2$CF$_3$ |

TABLE 26-continued

| | | | | |
|---|---|---|---|---|
| 26.102 | CH$_3$ | H | O | CH$_2$CH$_2$CF$_3$ |
| 26.103 | CH$_3$ | H | O | CH$_2$-cyclopropyl |
| 26.104 | CH$_3$ | H | O | CH$_2$-cyclobutyl |
| 26.105 | CH$_3$ | H | O | CH$_2$-cyclopentyl |
| 26.106 | CH$_3$ | H | O | CH$_2$-cyclohexyl |
| 26.107 | CH$_3$ | H | O | CH$_2$OCH$_3$ |
| 26.108 | CH$_3$ | H | O | CH$_2$OCH$_2$CH$_3$ |
| 26.109 | CH$_3$ | H | O | CH$_2$CH$_2$OCH$_3$ |
| 26.110 | CH$_3$ | H | O | CH$_2$CH$_2$OCH$_2$CH$_3$ |
| 26.111 | CH$_3$ | CH$_3$ | O | CH$_3$ |
| 26.112 | CH$_3$ | CH$_3$ | O | CH$_2$CH$_3$ |
| 26.113 | CH$_3$ | CH$_3$ | O | CH$_2$CH$_2$CH$_3$ |
| 26.114 | CH$_3$ | CH$_3$ | O | CH(CH$_3$)$_2$ |
| 26.115 | CH$_3$ | CH$_3$ | O | CH$_2$CH$_2$CH$_2$CH$_3$ |
| 26.116 | CH$_3$ | CH$_3$ | O | CH$_2$CH(CH$_3$)$_2$ |
| 26.117 | CH$_3$ | CH$_3$ | O | CH(CH$_3$)CH$_2$CH$_3$ |
| 26.118 | CH$_3$ | CH$_3$ | O | C(CH$_3$)$_3$ |
| 26.119 | CH$_3$ | CH$_3$ | O | CH$_2$CH$_2$CH$_2$CH$_2$CH$_3$ |
| 26.120 | CH$_3$ | CH$_3$ | O | CH$_2$CH$_2$CH(CH$_3$)$_2$ |
| 26.121 | CH$_3$ | CH$_3$ | O | CH$_2$C(CH$_3$)$_3$ |
| 26.122 | CH$_3$ | CH$_3$ | O | CH$_2$CH(CH$_3$)CH$_2$CH$_3$ |
| 26.123 | CH$_3$ | CH$_3$ | O | CH(CH$_3$)CH$_2$CH$_2$CH$_3$ |
| 26.124 | CH$_3$ | CH$_3$ | O | C(CH$_3$)$_2$CH$_2$CH$_3$ |
| 26.125 | CH$_3$ | CH$_3$ | O | CH$_2$CH=CH$_2$ |
| 26.126 | CH$_3$ | CH$_3$ | O | CH$_2$CH=CHCH$_3$ |
| 26.127 | CH$_3$ | CH$_3$ | O | CH$_2$CH=C(CH$_3$)$_2$ |
| 26.128 | CH$_3$ | CH$_3$ | O | CH$_2$C(CH$_3$)=CH$_2$ |
| 26.129 | CH$_3$ | CH$_3$ | O | CH$_2$C(CH$_3$)=CHCH$_3$ |
| 26.130 | CH$_3$ | CH$_3$ | O | CH$_2$C(CH$_3$)=C(CH$_3$)$_2$ |
| 26.131 | CH$_3$ | CH$_3$ | O | CH(CH$_3$)CH=CH$_2$ |
| 26.132 | CH$_3$ | CH$_3$ | O | CH(CH$_3$)CH=CHCH$_3$ |
| 26.133 | CH$_3$ | CH$_3$ | O | CH(CH$_3$)CH=C(CH$_3$)$_2$ |
| 26.134 | CH$_3$ | CH$_3$ | O | C(CH$_3$)$_2$CH=CH$_2$ |
| 26.135 | CH$_3$ | CH$_3$ | O | C(CH$_3$)$_2$CH=CHCH$_3$ |
| 26.136 | CH$_3$ | CH$_3$ | O | C(CH$_3$)$_2$CH=C(CH$_3$)$_2$ |
| 26.137 | CH$_3$ | CH$_3$ | O | CH$_2$CH=CHCl |
| 26.138 | CH$_3$ | CH$_3$ | O | CH$_2$CH=CCl$_2$ |
| 26.139 | CH$_3$ | CH$_3$ | O | CH$_2$CCl=CHCl |
| 26.140 | CH$_3$ | CH$_3$ | O | CH$_2$CCl=CCl$_2$ |
| 26.141 | CH$_3$ | CH$_3$ | O | CH$_2$CH=CF$_2$ |
| 26.142 | CH$_3$ | CH$_3$ | O | CH$_2$CF=CF$_2$ |
| 26.143 | CH$_3$ | CH$_3$ | O | CH$_2$C•CH |
| 26.144 | CH$_3$ | CH$_3$ | O | CH$_2$C•CCH$_3$ |
| 26.145 | CH$_3$ | CH$_3$ | O | CH$_2$C•CCH$_2$CH$_3$ |
| 26.146 | CH$_3$ | CH$_3$ | O | CH(CH$_3$)C•CH |
| 26.147 | CH$_3$ | CH$_3$ | O | CH(CH$_3$)C•CCH$_3$ |
| 26.148 | CH$_3$ | CH$_3$ | O | CH(CH$_3$)C•CCH$_2$CH$_3$ |
| 26.149 | CH$_3$ | CH$_3$ | O | C(CH$_3$)$_2$C•CH |
| 26.150 | CH$_3$ | CH$_3$ | O | C(CH$_3$)$_2$C•CCH$_3$ |
| 26.151 | CH$_3$ | CH$_3$ | O | C(CH$_3$)$_2$C•CCH$_2$CH$_3$ |
| 26.152 | CH$_3$ | CH$_3$ | O | Cyclopropyl |
| 26.153 | CH$_3$ | CH$_3$ | O | Cyclobutyl |
| 26.154 | CH$_3$ | CH$_3$ | O | Cyclopentyl |
| 26.155 | CH$_3$ | CH$_3$ | O | Cyclohexyl |
| 26.156 | CH$_3$ | CH$_3$ | O | CH$_2$CF$_3$ |
| 26.157 | CH$_3$ | CH$_3$ | O | CH$_2$CH$_2$CF$_3$ |
| 26.158 | CH$_3$ | CH$_3$ | O | CH$_2$-cyclopropyl |
| 26.159 | CH$_3$ | CH$_3$ | O | CH$_2$-cyclobutyl |
| 26.160 | CH$_3$ | CH$_3$ | O | CH$_2$-cyclopentyl |
| 26.161 | CH$_3$ | CH$_3$ | O | CH$_2$-cyclohexyl |
| 26.162 | CH$_3$ | CH$_3$ | O | CH$_2$OCH$_3$ |
| 26.163 | CH$_3$ | CH$_3$ | O | CH$_2$OCH$_2$CH$_3$ |
| 26.164 | CH$_3$ | CH$_3$ | O | CH$_2$CH$_2$OCH$_3$ |
| 26.165 | CH$_3$ | CH$_3$ | O | CH$_2$CH$_2$OCH$_2$CH$_3$ |
| 26.166 | H | H | S | CH$_3$ |
| 26.167 | H | H | S | CH$_2$CH$_3$ |
| 26.168 | H | H | S | CH$_2$CH$_2$CH$_3$ |
| 26.169 | H | H | S | CH(CH$_3$)$_2$ |
| 26.170 | H | H | S | CH$_2$CH$_2$CH$_2$CH$_3$ |
| 26.171 | H | H | S | CH$_2$CH(CH$_3$)$_2$ |
| 26.172 | H | H | S | CH(CH$_3$)CH$_2$CH$_3$ |
| 26.173 | H | H | S | C(CH$_3$)$_3$ |
| 26.174 | H | H | S | CH$_2$CH$_2$CH$_2$CH$_2$CH$_3$ |
| 26.175 | H | H | S | CH$_2$CH$_2$CH(CH$_3$)$_2$ |
| 26.176 | H | H | S | CH$_2$C(CH$_3$)$_3$ |
| 26.177 | H | H | S | CH$_2$CH(CH$_3$)CH$_2$CH$_3$ |
| 26.178 | H | H | S | CH(CH$_3$)CH$_2$CH$_2$CH$_3$ |
| 26.179 | H | H | S | C(CH$_3$)$_2$CH$_2$CH$_3$ |
| 26.180 | H | H | S | CH$_2$CH=CH$_2$ |
| 26.181 | H | H | S | CH$_2$CH=CHCH$_3$ |
| 26.182 | H | H | S | CH$_2$CH=C(CH$_3$)$_2$ |
| 26.183 | H | H | S | CH$_2$C(CH$_3$)=CH$_2$ |
| 26.184 | H | H | S | CH$_2$C(CH$_3$)=CHCH$_3$ |
| 26.185 | H | H | S | CH$_2$C(CH$_3$)=C(CH$_3$)$_2$ |
| 26.186 | H | H | S | CH(CH$_3$)CH=CH$_2$ |
| 26.187 | H | H | S | CH(CH$_3$)CH=CHCH$_3$ |
| 26.188 | H | H | S | CH(CH$_3$)CH=C(CH$_3$)$_2$ |
| 26.189 | H | H | S | C(CH$_3$)$_2$CH=CH$_2$ |
| 26.190 | H | H | S | C(CH$_3$)$_2$CH=CHCH$_3$ |
| 26.191 | H | H | S | C(CH$_3$)$_2$CH=C(CH$_3$)$_2$ |
| 26.192 | H | H | S | CH$_2$CH=CHCl |
| 26.193 | H | H | S | CH$_2$CH=CCl$_2$ |
| 26.194 | H | H | S | CH$_2$CCl=CHCl |
| 26.195 | H | H | S | CH$_2$CCl=CCl$_2$ |
| 26.196 | H | H | S | CH$_2$CH=CF$_2$ |
| 26.197 | H | H | S | CH$_2$CF=CF$_2$ |
| 26.198 | H | H | S | CH$_2$C•CH |
| 26.199 | H | H | S | CH$_2$C•CCH$_3$ |
| 26.200 | H | H | S | CH$_2$C•CCH$_2$CH$_3$ |
| 26.201 | H | H | S | CH(CH$_3$)C•CH |
| 26.202 | H | H | S | CH(CH$_3$)C•CCH$_3$ |
| 26.203 | H | H | S | CH(CH$_3$)C•CCH$_2$CH$_3$ |
| 26.204 | H | H | S | C(CH$_3$)$_2$C•CH |
| 26.205 | H | H | S | C(CH$_3$)$_2$C•CCH$_3$ |
| 26.206 | H | H | S | C(CH$_3$)$_2$C•CCH$_2$CH$_3$ |
| 26.207 | H | H | S | Cyclopropyl |
| 26.208 | H | H | S | Cyclobutyl |
| 26.209 | H | H | S | Cyclopentyl |
| 26.210 | H | H | S | Cyclohexyl |
| 26.211 | H | H | S | CH$_2$CF$_3$ |
| 26.212 | H | H | S | CH$_2$CH$_2$CF$_3$ |
| 26.213 | H | H | S | CH$_2$-cyclopropyl |
| 26.214 | H | H | S | CH$_2$-cyclobutyl |
| 26.215 | H | H | S | CH$_2$-cyclopentyl |
| 26.216 | H | H | S | CH$_2$-cyclohexyl |
| 26.217 | CH$_3$ | H | S | CH$_3$ |
| 26.218 | CH$_3$ | H | S | CH$_2$CH$_3$ |
| 26.219 | CH$_3$ | H | S | CH$_2$CH$_2$CH$_3$ |
| 26.220 | CH$_3$ | H | S | CH(CH$_3$)$_2$ |
| 26.221 | CH$_3$ | H | S | CH$_2$CH$_2$CH$_2$CH$_3$ |
| 26.222 | CH$_3$ | H | S | CH$_2$CH(CH$_3$)$_2$ |
| 26.223 | CH$_3$ | H | S | CH(CH$_3$)CH$_2$CH$_3$ |
| 26.224 | CH$_3$ | H | S | C(CH$_3$)$_3$ |
| 26.225 | CH$_3$ | H | S | CH$_2$CH$_2$CH$_2$CH$_2$CH$_3$ |
| 26.226 | CH$_3$ | H | S | CH$_2$CH$_2$CH(CH$_3$)$_2$ |
| 26.227 | CH$_3$ | H | S | CH$_2$C(CH$_3$)$_3$ |
| 26.228 | CH$_3$ | H | S | CH$_2$CH(CH$_3$)CH$_2$CH$_3$ |
| 26.229 | CH$_3$ | H | S | CH(CH$_3$)CH$_2$CH$_2$CH$_3$ |
| 26.230 | CH$_3$ | H | S | C(CH$_3$)$_2$CH$_2$CH$_3$ |
| 26.231 | CH$_3$ | H | S | CH$_2$CH=CH$_2$ |
| 26.232 | CH$_3$ | H | S | CH$_2$CH=CHCH$_3$ |
| 26.233 | CH$_3$ | H | S | CH$_2$CH=C(CH$_3$)$_2$ |
| 26.234 | CH$_3$ | H | S | CH$_2$C(CH$_3$)=CH$_2$ |
| 26.235 | CH$_3$ | H | S | CH$_2$C(CH$_3$)=CHCH$_3$ |
| 26.236 | CH$_3$ | H | S | CH$_2$C(CH$_3$)=C(CH$_3$)$_2$ |
| 26.237 | CH$_3$ | H | S | CH(CH$_3$)CH=CH$_2$ |
| 26.238 | CH$_3$ | H | S | CH(CH$_3$)CH=CHCH$_3$ |
| 26.239 | CH$_3$ | H | S | CH(CH$_3$)CH=C(CH$_3$)$_2$ |
| 26.240 | CH$_3$ | H | S | C(CH$_3$)$_2$CH=CH$_2$ |
| 26.241 | CH$_3$ | H | S | C(CH$_3$)$_2$CH=CHCH$_3$ |
| 26.242 | CH$_3$ | H | S | C(CH$_3$)$_2$CH=C(CH$_3$)$_2$ |
| 26.243 | CH$_3$ | H | S | CH$_2$CH=CHCl |
| 26.244 | CH$_3$ | H | S | CH$_2$CH=CCl$_2$ |
| 26.245 | CH$_3$ | H | S | CH$_2$CCl=CHCl |
| 26.246 | CH$_3$ | H | S | CH$_2$CCl=CCl$_2$ |
| 26.247 | CH$_3$ | H | S | CH$_2$CH=CF$_2$ |
| 26.248 | CH$_3$ | H | S | CH$_2$CF=CF$_2$ |
| 26.249 | CH$_3$ | H | S | CH$_2$C•CH |
| 26.250 | CH$_3$ | H | S | CH$_2$C•CCH$_3$ |
| 26.251 | CH$_3$ | H | S | CH$_2$C•CCH$_2$CH$_3$ |
| 26.252 | CH$_3$ | H | S | CH(CH$_3$)C•CH |
| 26.253 | CH$_3$ | H | S | CH(CH$_3$)C•CCH$_3$ |
| 26.254 | CH$_3$ | H | S | CH(CH$_3$)C•CCH$_2$CH$_3$ |
| 26.255 | CH$_3$ | H | S | C(CH$_3$)$_2$C•CH |
| 26.256 | CH$_3$ | H | S | C(CH$_3$)$_2$C•CCH$_3$ |
| 26.257 | CH$_3$ | H | S | C(CH$_3$)$_2$C•CCH$_2$CH$_3$ |
| 26.258 | CH$_3$ | H | S | Cyclopropyl |
| 26.259 | CH$_3$ | H | S | Cyclobutyl |
| 26.260 | CH$_3$ | H | S | Cyclopentyl |
| 26.261 | CH$_3$ | H | S | Cyclohexyl |

TABLE 26-continued

| | | | | |
|---|---|---|---|---|
| 26.262 | CH₃ | H | S | CH₂CF₃ |
| 26.263 | CH₃ | H | S | CH₂CH₂CF₃ |
| 26.264 | CH₃ | H | S | CH₂-cyclopropyl |
| 26.265 | CH₃ | H | S | CH₂-cyclobutyl |
| 26.266 | CH₃ | H | S | CH₂-cyclopentyl |
| 26.267 | CH₃ | H | S | CH₂-cyclohexyl |
| 26.268 | CH₃ | CH₃ | S | CH₃ |
| 26.269 | CH₃ | CH₃ | S | CH₂CH₃ |
| 26.270 | CH₃ | CH₃ | S | CH₂CH₂CH₃ |
| 26.271 | CH₃ | CH₃ | S | CH(CH₃)₂ |
| 26.272 | CH₃ | CH₃ | S | CH₂CH₂CH₂CH₃ |
| 26.273 | CH₃ | CH₃ | S | CH₂CH(CH₃)₂ |
| 26.274 | CH₃ | CH₃ | S | CH(CH₃)CH₂CH₃ |
| 26.275 | CH₃ | CH₃ | S | C(CH₃)₃ |
| 26.276 | CH₃ | CH₃ | S | CH₂CH₂CH₂CH₂CH₃ |
| 26.277 | CH₃ | CH₃ | S | CH₂CH₂CH(CH₃)₂ |
| 26.278 | CH₃ | CH₃ | S | CH₂C(CH₃)₃ |
| 26.279 | CH₃ | CH₃ | S | CH₂CH(CH₃)CH₂CH₃ |
| 26.280 | CH₃ | CH₃ | S | CH(CH₃)CH₂CH₂CH₃ |
| 26.281 | CH₃ | CH₃ | S | C(CH₃)₂CH₂CH₃ |
| 26.282 | CH₃ | CH₃ | S | CH₂CH=CH₂ |
| 26.283 | CH₃ | CH₃ | S | CH₂CH=CHCH₃ |
| 26.284 | CH₃ | CH₃ | S | CH₂CH=C(CH₃)₂ |
| 26.285 | CH₃ | CH₃ | S | CH₂C(CH₃)=CH₂ |
| 26.286 | CH₃ | CH₃ | S | CH₂C(CH₃)=CHCH₃ |
| 26.287 | CH₃ | CH₃ | S | CH₂C(CH₃)=C(CH₃)₂ |
| 26.288 | CH₃ | CH₃ | S | CH(CH₃)CH=CH₂ |
| 26.289 | CH₃ | CH₃ | S | CH(CH₃)CH=CHCH₃ |
| 26.290 | CH₃ | CH₃ | S | CH(CH₃)CH=C(CH₃)₂ |
| 26.291 | CH₃ | CH₃ | S | C(CH₃)₂CH=CH₂ |
| 26.292 | CH₃ | CH₃ | S | C(CH₃)₂CH=CHCH₃ |
| 26.293 | CH₃ | CH₃ | S | C(CH₃)₂CH=C(CH₃)₂ |
| 26.294 | CH₃ | CH₃ | S | CH₂CH=CHCl |
| 26.295 | CH₃ | CH₃ | S | CH₂CH=CCl₂ |
| 26.296 | CH₃ | CH₃ | S | CH₂CCl=CHCl |
| 26.297 | CH₃ | CH₃ | S | CH₂CCl=CCl₂ |
| 26.298 | CH₃ | CH₃ | S | CH₂CH=CF₂ |
| 26.299 | CH₃ | CH₃ | S | CH₂CF=CF₂ |
| 26.300 | CH₃ | CH₃ | S | CH₂C•CH |
| 26.301 | CH₃ | CH₃ | S | CH₂C•CCH₃ |
| 26.302 | CH₃ | CH₃ | S | CH₂C•CCH₂CH₃ |
| 26.303 | CH₃ | CH₃ | S | CH(CH₃)C•CH |
| 26.304 | CH₃ | CH₃ | S | CH(CH₃)C•CCH₃ |
| 26.305 | CH₃ | CH₃ | S | CH(CH₃)C•CCH₂CH₃ |
| 26.306 | CH₃ | CH₃ | S | C(CH₃)₂C•CH |
| 26.307 | CH₃ | CH₃ | S | C(CH₃)₂C•CCH₃ |
| 26.308 | CH₃ | CH₃ | S | C(CH₃)₂C•CCH₂CH₃ |
| 26.309 | CH₃ | CH₃ | S | Cyclopropyl |
| 26.310 | CH₃ | CH₃ | S | Cyclobutyl |
| 26.311 | CH₃ | CH₃ | S | Cyclopentyl |
| 26.312 | CH₃ | CH₃ | S | Cyclohexyl |
| 26.313 | CH₃ | CH₃ | S | CH₂CF₃ |
| 26.314 | CH₃ | CH₃ | S | CH₂CH₂CF₃ |
| 26.315 | CH₃ | CH₃ | S | CH₂-cyclopropyl |
| 26.316 | CH₃ | CH₃ | S | CH₂-cyclobutyl |
| 26.317 | CH₃ | CH₃ | S | CH₂-cyclopentyl |
| 26.318 | CH₃ | CH₃ | S | CH₂-cyclohexyl |
| 26.319 | H | H | S(O) | CH₃ |
| 26.320 | H | H | S(O) | CH₂CH₃ |
| 26.321 | H | H | S(O) | CH₂CH₂CH₃ |
| 26.322 | H | H | S(O) | CH(CH₃)₂ |
| 26.323 | H | H | S(O) | CH₂CH₂CH₂CH₃ |
| 26.324 | H | H | S(O) | CH₂CH(CH₃)₂ |
| 26.325 | H | H | S(O) | CH(CH₃)CH₂CH₃ |
| 26.326 | H | H | S(O) | C(CH₃)₃ |
| 26.327 | H | H | S(O) | CH₂CH₂CH₂CH₂CH₃ |
| 26.328 | H | H | S(O) | CH₂CH₂CH(CH₃)₂ |
| 26.329 | H | H | S(O) | CH₂C(CH₃)₃ |
| 26.330 | H | H | S(O) | CH₂CH(CH₃)CH₂CH₃ |
| 26.331 | H | H | S(O) | CH(CH₃)CH₂CH₂CH₃ |
| 26.332 | H | H | S(O) | C(CH₃)₂CH₂CH₃ |
| 26.333 | H | H | S(O) | CH₂CH=CH₂ |
| 26.334 | H | H | S(O) | CH₂CH=CHCH₃ |
| 26.335 | H | H | S(O) | CH₂CH=C(CH₃)₂ |
| 26.336 | H | H | S(O) | CH₂C(CH₃)=CH₂ |
| 26.337 | H | H | S(O) | CH₂C(CH₃)=CHCH₃ |
| 26.338 | H | H | S(O) | CH₂C(CH₃)=C(CH₃)₂ |
| 26.339 | H | H | S(O) | CH(CH₃)CH=CH₂ |
| 26.340 | H | H | S(O) | CH(CH₃)CH=CHCH₃ |
| 26.341 | H | H | S(O) | CH(CH₃)CH=C(CH₃)₂ |
| 26.342 | H | H | S(O) | C(CH₃)₂CH=CH₂ |
| 26.343 | H | H | S(O) | C(CH₃)₂CH=CHCH₃ |
| 26.344 | H | H | S(O) | C(CH₃)₂CH=C(CH₃)₂ |
| 26.345 | H | H | S(O) | CH₂CH=CHCl |
| 26.346 | H | H | S(O) | CH₂CH=CCl₂ |
| 26.347 | H | H | S(O) | CH₂CCl=CHCl |
| 26.348 | H | H | S(O) | CH₂CCl=CCl₂ |
| 26.349 | H | H | S(O) | CH₂CH=CF₂ |
| 26.350 | H | H | S(O) | CH₂CF=CF₂ |
| 26.351 | H | H | S(O) | CH₂C•CH |
| 26.352 | H | H | S(O) | CH₂C•CCH₃ |
| 26.353 | H | H | S(O) | CH₂C•CCH₂CH₃ |
| 26.354 | H | H | S(O) | CH(CH₃)C•CH |
| 26.355 | H | H | S(O) | CH(CH₃)C•CCH₃ |
| 26.356 | H | H | S(O) | CH(CH₃)C•CCH₂CH₃ |
| 26.357 | H | H | S(O) | C(CH₃)₂C•CH |
| 26.358 | H | H | S(O) | C(CH₃)₂C•CCH₃ |
| 26.359 | H | H | S(O) | C(CH₃)₂C•CCH₂CH₃ |
| 26.360 | H | H | S(O) | Cyclopropyl |
| 26.361 | H | H | S(O) | Cyclobutyl |
| 26.362 | H | H | S(O) | Cyclopentyl |
| 26.363 | H | H | S(O) | Cyclohexyl |
| 26.364 | H | H | S(O) | CH₂CF₃ |
| 26.365 | H | H | S(O) | CH₂CH₂CF₃ |
| 26.366 | H | H | S(O) | CH₂-cyclopropyl |
| 26.357 | H | H | S(O) | CH₂-cyclobutyl |
| 26.358 | H | H | S(O) | CH₂-cyclopentyl |
| 26.359 | H | H | S(O) | CH₂-cyclohexyl |
| 26.360 | H | H | S(O) | CH₂OCH₃ |
| 26.361 | H | H | S(O) | CH₂OCH₂CH₃ |
| 26.362 | H | H | S(O) | CH₂CH₂OCH₃ |
| 26.363 | H | H | S(O) | CH₂CH₂OCH₂CH₃ |
| 26.364 | CH₃ | H | S(O) | CH₃ |
| 26.365 | CH₃ | H | S(O) | CH₂CH₃ |
| 26.366 | CH₃ | H | S(O) | CH₂CH₂CH₃ |
| 26.367 | CH₃ | H | S(O) | CH(CH₃)₂ |
| 26.368 | CH₃ | H | S(O) | CH₂CH₂CH₂CH₃ |
| 26.369 | CH₃ | H | S(O) | CH₂CH(CH₃)₂ |
| 26.370 | CH₃ | H | S(O) | CH(CH₃)CH₂CH₃ |
| 26.371 | CH₃ | H | S(O) | C(CH₃)₃ |
| 26.372 | CH₃ | H | S(O) | CH₂CH₂CH₂CH₂CH₃ |
| 26.373 | CH₃ | H | S(O) | CH₂CH₂CH(CH₃)₂ |
| 26.374 | CH₃ | H | S(O) | CH₂C(CH₃)₃ |
| 26.375 | CH₃ | H | S(O) | CH₂CH(CH₃)CH₂CH₃ |
| 26.376 | CH₃ | H | S(O) | CH(CH₃)CH₂CH₂CH₃ |
| 26.377 | CH₃ | H | S(O) | C(CH₃)₂CH₂CH₃ |
| 26.378 | CH₃ | H | S(O) | CH₂CH=CH₂ |
| 26.379 | CH₃ | H | S(O) | CH₂CH=CHCH₃ |
| 26.380 | CH₃ | H | S(O) | CH₂CH=C(CH₃)₂ |
| 26.381 | CH₃ | H | S(O) | CH₂C(CH₃)=CH₂ |
| 26.382 | CH₃ | H | S(O) | CH₂C(CH₃)=CHCH₃ |
| 26.383 | CH₃ | H | S(O) | CH₂C(CH₃)=C(CH₃)₂ |
| 26.384 | CH₃ | H | S(O) | CH(CH₃)CH=CH₂ |
| 26.385 | CH₃ | H | S(O) | CH(CH₃)CH=CHCH₃ |
| 26.386 | CH₃ | H | S(O) | CH(CH₃)CH=C(CH₃)₂ |
| 26.387 | CH₃ | H | S(O) | C(CH₃)₂CH=CH₂ |
| 26.388 | CH₃ | H | S(O) | C(CH₃)₂CH=CHCH₃ |
| 26.389 | CH₃ | H | S(O) | C(CH₃)₂CH=C(CH₃)₂ |
| 26.390 | CH₃ | H | S(O) | CH₂CH=CHCl |
| 26.391 | CH₃ | H | S(O) | CH₂CH=CCl₂ |
| 26.392 | CH₃ | H | S(O) | CH₂CCl=CHCl |
| 26.393 | CH₃ | H | S(O) | CH₂CCl=CCl₂ |
| 26.394 | CH₃ | H | S(O) | CH₂CH=CF₂ |
| 26.395 | CH₃ | H | S(O) | CH₂CF=CF₂ |
| 26.396 | CH₃ | H | S(O) | CH₂C•CH |
| 26.397 | CH₃ | H | S(O) | CH₂C•CCH₃ |
| 26.398 | CH₃ | H | S(O) | CH₂C•CCH₂CH₃ |
| 26.399 | CH₃ | H | S(O) | CH(CH₃)C•CH |
| 26.400 | CH₃ | H | S(O) | CH(CH₃)C•CCH₃ |
| 26.401 | CH₃ | H | S(O) | CH(CH₃)C•CCH₂CH₃ |
| 26.402 | CH₃ | H | S(O) | C(CH₃)₂C•CH |
| 26.403 | CH₃ | H | S(O) | C(CH₃)₂C•CCH₃ |
| 26.404 | CH₃ | H | S(O) | C(CH₃)₂C•CCH₂CH₃ |
| 26.405 | CH₃ | H | S(O) | Cyclopropyl |
| 26.406 | CH₃ | H | S(O) | Cyclobutyl |
| 26.407 | CH₃ | H | S(O) | Cyclopentyl |
| 26.408 | CH₃ | H | S(O) | Cyclohexyl |
| 26.409 | CH₃ | H | S(O) | CH₂CF₃ |
| 26.410 | CH₃ | H | S(O) | CH₂CH₂CF₃ |
| 26.411 | CH₃ | H | S(O) | CH₂-cyclopropyl |

TABLE 26-continued

| | | | | |
|---|---|---|---|---|
| 26.412 | $CH_3$ | H | S(O) | $CH_2$-cyclobutyl |
| 26.413 | $CH_3$ | H | S(O) | $CH_2$-cyclopentyl |
| 26.414 | $CH_3$ | H | S(O) | $CH_2$-cyclohexyl |
| 26.415 | $CH_3$ | $CH_3$ | S(O) | $CH_3$ |
| 26.416 | $CH_3$ | $CH_3$ | S(O) | $CH_2CH_3$ |
| 26.417 | $CH_3$ | $CH_3$ | S(O) | $CH_2CH_2CH_3$ |
| 26.418 | $CH_3$ | $CH_3$ | S(O) | $CH(CH_3)_2$ |
| 26.419 | $CH_3$ | $CH_3$ | S(O) | $CH_2CH_2CH_2CH_3$ |
| 26.420 | $CH_3$ | $CH_3$ | S(O) | $CH_2CH(CH_3)_2$ |
| 26.421 | $CH_3$ | $CH_3$ | S(O) | $CH(CH_3)CH_2CH_3$ |
| 26.422 | $CH_3$ | $CH_3$ | S(O) | $C(CH_3)_3$ |
| 26.423 | $CH_3$ | $CH_3$ | S(O) | $CH_2CH_2CH_2CH_2CH_3$ |
| 26.424 | $CH_3$ | $CH_3$ | S(O) | $CH_2CH_2CH(CH_3)_2$ |
| 26.425 | $CH_3$ | $CH_3$ | S(O) | $CH_2C(CH_3)_3$ |
| 26.426 | $CH_3$ | $CH_3$ | S(O) | $CH_2CH(CH_3)CH_2CH_3$ |
| 26.427 | $CH_3$ | $CH_3$ | S(O) | $CH(CH_3)CH_2CH_2CH_3$ |
| 26.428 | $CH_3$ | $CH_3$ | S(O) | $C(CH_3)_2CH_2CH_3$ |
| 26.429 | $CH_3$ | $CH_3$ | S(O) | $CH_2CH=CH_2$ |
| 26.430 | $CH_3$ | $CH_3$ | S(O) | $CH_2CH=CHCH_3$ |
| 26.431 | $CH_3$ | $CH_3$ | S(O) | $CH_2CH=C(CH_3)_2$ |
| 26.432 | $CH_3$ | $CH_3$ | S(O) | $CH_2C(CH_3)=CH_2$ |
| 26.433 | $CH_3$ | $CH_3$ | S(O) | $CH_2C(CH_3)=CHCH_3$ |
| 26.434 | $CH_3$ | $CH_3$ | S(O) | $CH_2C(CH_3)=C(CH_3)_2$ |
| 26.435 | $CH_3$ | $CH_3$ | S(O) | $CH(CH_3)CH=CH_2$ |
| 26.436 | $CH_3$ | $CH_3$ | S(O) | $CH(CH_3)CH=CHCH_3$ |
| 26.437 | $CH_3$ | $CH_3$ | S(O) | $CH(CH_3)CH=C(CH_3)_2$ |
| 26.438 | $CH_3$ | $CH_3$ | S(O) | $C(CH_3)_2CH=CH_2$ |
| 26.439 | $CH_3$ | $CH_3$ | S(O) | $C(CH_3)_2CH=CHCH_3$ |
| 26.440 | $CH_3$ | $CH_3$ | S(O) | $C(CH_3)_2CH=C(CH_3)_2$ |
| 26.441 | $CH_3$ | $CH_3$ | S(O) | $CH_2CH=CHCl$ |
| 26.442 | $CH_3$ | $CH_3$ | S(O) | $CH_2CH=CCl_2$ |
| 26.443 | $CH_3$ | $CH_3$ | S(O) | $CH_2CCl=CHCl$ |
| 26.444 | $CH_3$ | $CH_3$ | S(O) | $CH_2CCl=CCl_2$ |
| 26.445 | $CH_3$ | $CH_3$ | S(O) | $CH_2CH=CF_2$ |
| 26.446 | $CH_3$ | $CH_3$ | S(O) | $CH_2CF=CF_2$ |
| 26.447 | $CH_3$ | $CH_3$ | S(O) | $CH_2C•CH$ |
| 26.448 | $CH_3$ | $CH_3$ | S(O) | $CH_2C•CCH_3$ |
| 26.449 | $CH_3$ | $CH_3$ | S(O) | $CH_2C•CCH_2CH_3$ |
| 26.450 | $CH_3$ | $CH_3$ | S(O) | $CH(CH_3)C•CH$ |
| 26.451 | $CH_3$ | $CH_3$ | S(O) | $CH(CH_3)C•CCH_3$ |
| 26.452 | $CH_3$ | $CH_3$ | S(O) | $CH(CH_3)C•CCH_2CH_3$ |
| 26.453 | $CH_3$ | $CH_3$ | S(O) | $C(CH_3)_2C•CH$ |
| 26.454 | $CH_3$ | $CH_3$ | S(O) | $C(CH_3)_2C•CCH_3$ |
| 26.455 | $CH_3$ | $CH_3$ | S(O) | $C(CH_3)_2C•CCH_2CH_3$ |
| 26.456 | $CH_3$ | $CH_3$ | S(O) | Cyclopropyl |
| 26.457 | $CH_3$ | $CH_3$ | S(O) | Cyclobutyl |
| 26.458 | $CH_3$ | $CH_3$ | S(O) | Cyclopentyl |
| 26.459 | $CH_3$ | $CH_3$ | S(O) | Cyclohexyl |
| 26.460 | $CH_3$ | $CH_3$ | S(O) | $CH_2CF_3$ |
| 26.461 | $CH_3$ | $CH_3$ | S(O) | $CH_2CH_2CF_3$ |
| 26.462 | $CH_3$ | $CH_3$ | S(O) | $CH_2$-cyclopropyl |
| 26.463 | $CH_3$ | $CH_3$ | S(O) | $CH_2$-cyclobutyl |
| 26.464 | $CH_3$ | $CH_3$ | S(O) | $CH_2$-cyclopentyl |
| 26.465 | $CH_3$ | $CH_3$ | S(O) | $CH_2$-cyclohexyl |
| 26.466 | H | H | $SO_2$ | $CH_3$ |
| 26.467 | H | H | $SO_2$ | $CH_2CH_3$ |
| 26.468 | H | H | $SO_2$ | $CH_2CH_2CH_3$ |
| 26.469 | H | H | $SO_2$ | $CH(CH_3)_2$ |
| 26.470 | H | H | $SO_2$ | $CH_2CH_2CH_2CH_3$ |
| 26.471 | H | H | $SO_2$ | $CH_2CH(CH_3)_2$ |
| 26.472 | H | H | $SO_2$ | $CH(CH_3)CH_2CH_3$ |
| 26.473 | H | H | $SO_2$ | $C(CH_3)_3$ |
| 26.474 | H | H | $SO_2$ | $CH_2CH_2CH_2CH_2CH_3$ |
| 26.475 | H | H | $SO_2$ | $CH_2CH_2CH(CH_3)_2$ |
| 26.476 | H | H | $SO_2$ | $CH_2C(CH_3)_3$ |
| 26.477 | H | H | $SO_2$ | $CH_2CH(CH_3)CH_2CH_3$ |
| 26.478 | H | H | $SO_2$ | $CH(CH_3)CH_2CH_2CH_3$ |
| 26.479 | H | H | $SO_2$ | $C(CH_3)_2CH_2CH_3$ |
| 26.480 | H | H | $SO_2$ | $CH_2CH=CH_2$ |
| 26.481 | H | H | $SO_2$ | $CH_2CH=CHCH_3$ |
| 26.482 | H | H | $SO_2$ | $CH_2CH=C(CH_3)_2$ |
| 26.483 | H | H | $SO_2$ | $CH_2C(CH_3)=CH_2$ |
| 26.484 | H | H | $SO_2$ | $CH_2C(CH_3)=CHCH_3$ |
| 26.485 | H | H | $SO_2$ | $CH_2C(CH_3)=C(CH_3)_2$ |
| 26.486 | H | H | $SO_2$ | $CH(CH_3)CH=CH_2$ |
| 26.487 | H | H | $SO_2$ | $CH(CH_3)CH=CHCH_3$ |
| 26.488 | H | H | $SO_2$ | $CH(CH_3)CH=C(CH_3)_2$ |
| 26.489 | H | H | $SO_2$ | $C(CH_3)_2CH=CH_2$ |
| 26.490 | H | H | $SO_2$ | $C(CH_3)_2CH=CHCH_3$ |
| 26.491 | H | H | $SO_2$ | $C(CH_3)_2CH=C(CH_3)_2$ |
| 26.492 | H | H | $SO_2$ | $CH_2CH=CHCl$ |
| 26.493 | H | H | $SO_2$ | $CH_2CH=CCl_2$ |
| 26.494 | H | H | $SO_2$ | $CH_2CCl=CHCl$ |
| 26.495 | H | H | $SO_2$ | $CH_2CCl=CCl_2$ |
| 26.496 | H | H | $SO_2$ | $CH_2CH=CF_2$ |
| 26.497 | H | H | $SO_2$ | $CH_2CF=CF_2$ |
| 26.498 | H | H | $SO_2$ | $CH_2C•CH$ |
| 26.499 | H | H | $SO_2$ | $CH_2C•CCH_3$ |
| 26.500 | H | H | $SO_2$ | $CH_2C•CCH_2CH_3$ |
| 26.501 | H | H | $SO_2$ | $CH(CH_3)C•CH$ |
| 26.502 | H | H | $SO_2$ | $CH(CH_3)C•CCH_3$ |
| 26.503 | H | H | $SO_2$ | $CH(CH_3)C•CCH_2CH_3$ |
| 26.504 | H | H | $SO_2$ | $C(CH_3)_2C•CH$ |
| 26.505 | H | H | $SO_2$ | $C(CH_3)_2C•CCH_3$ |
| 26.506 | H | H | $SO_2$ | $C(CH_3)_2C•CCH_2CH_3$ |
| 26.507 | H | H | $SO_2$ | Cyclopropyl |
| 26.508 | H | H | $SO_2$ | Cyclobutyl |
| 26.509 | H | H | $SO_2$ | Cyclopentyl |
| 26.510 | H | H | $SO_2$ | Cyclohexyl |
| 26.511 | H | H | $SO_2$ | $CH_2CF_3$ |
| 26.512 | H | H | $SO_2$ | $CH_2CH_2CF_3$ |
| 26.513 | H | H | $SO_2$ | $CH_2$-cyclopropyl |
| 26.514 | H | H | $SO_2$ | $CH_2$-cyclobutyl |
| 26.515 | H | H | $SO_2$ | $CH_2$-cyclopentyl |
| 26.516 | H | H | $SO_2$ | $CH_2$-cyclohexyl |
| 26.517 | $CH_3$ | H | $SO_2$ | $CH_3$ |
| 26.518 | $CH_3$ | H | $SO_2$ | $CH_2CH_3$ |
| 26.519 | $CH_3$ | H | $SO_2$ | $CH_2CH_2CH_3$ |
| 26.520 | $CH_3$ | H | $SO_2$ | $CH(CH_3)_2$ |
| 26.521 | $CH_3$ | H | $SO_2$ | $CH_2CH_2CH_2CH_3$ |
| 26.522 | $CH_3$ | H | $SO_2$ | $CH_2CH(CH_3)_2$ |
| 26.523 | $CH_3$ | H | $SO_2$ | $CH(CH_3)CH_2CH_3$ |
| 26.524 | $CH_3$ | H | $SO_2$ | $C(CH_3)_3$ |
| 26.525 | $CH_3$ | H | $SO_2$ | $CH_2CH_2CH_2CH_2CH_3$ |
| 26.526 | $CH_3$ | H | $SO_2$ | $CH_2CH_2CH(CH_3)_2$ |
| 26.527 | $CH_3$ | H | $SO_2$ | $CH_2C(CH_3)_3$ |
| 26.528 | $CH_3$ | H | $SO_2$ | $CH_2CH(CH_3)CH_2CH_3$ |
| 26.529 | $CH_3$ | H | $SO_2$ | $CH(CH_3)CH_2CH_2CH_3$ |
| 26.530 | $CH_3$ | H | $SO_2$ | $C(CH_3)_2CH_2CH_3$ |
| 26.531 | $CH_3$ | H | $SO_2$ | $CH_2CH=CH_2$ |
| 26.532 | $CH_3$ | H | $SO_2$ | $CH_2CH=CHCH_3$ |
| 26.533 | $CH_3$ | H | $SO_2$ | $CH_2CH=C(CH_3)_2$ |
| 26.534 | $CH_3$ | H | $SO_2$ | $CH_2C(CH_3)=CH_2$ |
| 26.535 | $CH_3$ | H | $SO_2$ | $CH_2C(CH_3)=CHCH_3$ |
| 26.536 | $CH_3$ | H | $SO_2$ | $CH_2C(CH_3)=C(CH_3)_2$ |
| 26.537 | $CH_3$ | H | $SO_2$ | $CH(CH_3)CH=CH_2$ |
| 26.538 | $CH_3$ | H | $SO_2$ | $CH(CH_3)CH=CHCH_3$ |
| 26.539 | $CH_3$ | H | $SO_2$ | $CH(CH_3)CH=C(CH_3)_2$ |
| 26.540 | $CH_3$ | H | $SO_2$ | $C(CH_3)_2CH=CH_2$ |
| 26.541 | $CH_3$ | H | $SO_2$ | $C(CH_3)_2CH=CHCH_3$ |
| 26.542 | $CH_3$ | H | $SO_2$ | $C(CH_3)_2CH=C(CH_3)_2$ |
| 26.543 | $CH_3$ | H | $SO_2$ | $CH_2CH=CHCl$ |
| 26.544 | $CH_3$ | H | $SO_2$ | $CH_2CH=CCl_2$ |
| 26.545 | $CH_3$ | H | $SO_2$ | $CH_2CCl=CHCl$ |
| 26.546 | $CH_3$ | H | $SO_2$ | $CH_2CCl=CCl_2$ |
| 26.547 | $CH_3$ | H | $SO_2$ | $CH_2CH=CF_2$ |
| 26.548 | $CH_3$ | H | $SO_2$ | $CH_2CF=CF_2$ |
| 26.549 | $CH_3$ | H | $SO_2$ | $CH_2C•CH$ |
| 26.550 | $CH_3$ | H | $SO_2$ | $CH_2C•CCH_3$ |
| 26.551 | $CH_3$ | H | $SO_2$ | $CH_2C•CCH_2CH_3$ |
| 26.552 | $CH_3$ | H | $SO_2$ | $CH(CH_3)C•CH$ |
| 26.553 | $CH_3$ | H | $SO_2$ | $CH(CH_3)C•CCH_3$ |
| 26.554 | $CH_3$ | H | $SO_2$ | $CH(CH_3)C•CCH_2CH_3$ |
| 26.555 | $CH_3$ | H | $SO_2$ | $C(CH_3)_2C•CH$ |
| 26.556 | $CH_3$ | H | $SO_2$ | $C(CH_3)_2C•CCH_3$ |
| 26.557 | $CH_3$ | H | $SO_2$ | $C(CH_3)_2C•CCH_2CH_3$ |
| 26.558 | $CH_3$ | H | $SO_2$ | Cyclopropyl |
| 26.559 | $CH_3$ | H | $SO_2$ | Cyclobutyl |
| 26.560 | $CH_3$ | H | $SO_2$ | Cyclopentyl |
| 26.561 | $CH_3$ | H | $SO_2$ | Cyclohexyl |
| 26.562 | $CH_3$ | H | $SO_2$ | $CH_2CF_3$ |
| 26.563 | $CH_3$ | H | $SO_2$ | $CH_2CH_2CF_3$ |
| 26.564 | $CH_3$ | H | $SO_2$ | $CH_2$-cyclopropyl |
| 26.565 | $CH_3$ | H | $SO_2$ | $CH_2$-cyclobutyl |
| 26.566 | $CH_3$ | H | $SO_2$ | $CH_2$-cyclopentyl |
| 26.567 | $CH_3$ | H | $SO_2$ | $CH_2$-cyclohexyl |
| 26.568 | $CH_3$ | $CH_3$ | $SO_2$ | $CH_3$ |
| 26.569 | $CH_3$ | $CH_3$ | $SO_2$ | $CH_2CH_3$ |
| 26.570 | $CH_3$ | $CH_3$ | $SO_2$ | $CH_2CH_2CH_3$ |
| 26.571 | $CH_3$ | $CH_3$ | $SO_2$ | $CH(CH_3)_2$ |

TABLE 26-continued

| | | | | |
|---|---|---|---|---|
| 26.572 | CH₃ | CH₃ | SO₂ | CH₂CH₂CH₂CH₃ |
| 26.573 | CH₃ | CH₃ | SO₂ | CH₂CH(CH₃)₂ |
| 26.574 | CH₃ | CH₃ | SO₂ | CH(CH₃)CH₂CH₃ |
| 26.575 | CH₃ | CH₃ | SO₂ | C(CH₃)₃ |
| 26.576 | CH₃ | CH₃ | SO₂ | CH₂CH₂CH₂CH₂CH₃ |
| 26.577 | CH₃ | CH₃ | SO₂ | CH₂CH₂CH(CH₃)₂ |
| 26.578 | CH₃ | CH₃ | SO₂ | CH₂C(CH₃)₃ |
| 26.579 | CH₃ | CH₃ | SO₂ | CH₂CH(CH₃)CH₂CH₃ |
| 26.580 | CH₃ | CH₃ | SO₂ | CH(CH₃)CH₂CH₂CH₃ |
| 26.581 | CH₃ | CH₃ | SO₂ | C(CH₃)₂CH₂CH₃ |
| 26.582 | CH₃ | CH₃ | SO₂ | CH₂CH=CH₂ |
| 26.583 | CH₃ | CH₃ | SO₂ | CH₂CH=CHCH₃ |
| 26.584 | CH₃ | CH₃ | SO₂ | CH₂CH=C(CH₃)₂ |
| 26.585 | CH₃ | CH₃ | SO₂ | CH₂C(CH₃)=CH₂ |
| 26.586 | CH₃ | CH₃ | SO₂ | CH₂C(CH₃)=CHCH₃ |
| 26.587 | CH₃ | CH₃ | SO₂ | CH₂C(CH₃)=C(CH₃)₂ |
| 26.588 | CH₃ | CH₃ | SO₂ | CH(CH₃)CH=CH₂ |
| 26.589 | CH₃ | CH₃ | SO₂ | CH(CH₃)CH=CHCH₃ |
| 26.590 | CH₃ | CH₃ | SO₂ | CH(CH₃)CH=C(CH₃)₂ |
| 26.591 | CH₃ | CH₃ | SO₂ | C(CH₃)₂CH=CH₂ |
| 26.592 | CH₃ | CH₃ | SO₂ | C(CH₃)₂CH=CHCH₃ |
| 26.593 | CH₃ | CH₃ | SO₂ | C(CH₃)₂CH=C(CH₃)₂ |
| 26.594 | CH₃ | CH₃ | SO₂ | CH₂CH=CHCl |
| 26.595 | CH₃ | CH₃ | SO₂ | CH₂CH=CCl₂ |
| 26.596 | CH₃ | CH₃ | SO₂ | CH₂CCl=CHCl |
| 26.597 | CH₃ | CH₃ | SO₂ | CH₂CCl=CCl₂ |
| 26.598 | CH₃ | CH₃ | SO₂ | CH₂CH=CF₂ |
| 26.599 | CH₃ | CH₃ | SO₂ | CH₂CF=CF₂ |
| 26.600 | CH₃ | CH₃ | SO₂ | CH₂C•CH |
| 26.601 | CH₃ | CH₃ | SO₂ | CH₂C•CCH₃ |
| 26.602 | CH₃ | CH₃ | SO₂ | CH₂C•CCH₂CH₃ |
| 26.603 | CH₃ | CH₃ | SO₂ | CH(CH₃)C•CH |
| 26.604 | CH₃ | CH₃ | SO₂ | CH(CH₃)C•CCH₃ |
| 26.605 | CH₃ | CH₃ | SO₂ | CH(CH₃)C•CCH₂CH₃ |
| 26.606 | CH₃ | CH₃ | SO₂ | C(CH₃)₂C•CH |
| 26.607 | CH₃ | CH₃ | SO₂ | C(CH₃)₂C•CCH₃ |
| 26.608 | CH₃ | CH₃ | SO₂ | C(CH₃)₂C•CCH₂CH₃ |
| 26.609 | CH₃ | CH₃ | SO₂ | Cyclopropyl |
| 26.610 | CH₃ | CH₃ | SO₂ | Cyclobutyl |
| 26.611 | CH₃ | CH₃ | SO₂ | Cyclopentyl |
| 26.612 | CH₃ | CH₃ | SO₂ | Cyclohexyl |
| 26.613 | CH₃ | CH₃ | SO₂ | CH₂CF₃ |
| 26.614 | CH₃ | CH₃ | SO₂ | CH₂CH₂CF₃ |
| 26.615 | CH₃ | CH₃ | SO₂ | CH₂-cyclopropyl |
| 26.616 | CH₃ | CH₃ | SO₂ | CH₂-cyclobutyl |
| 26.617 | CH₃ | CH₃ | SO₂ | CH₂-cyclopentyl |
| 26.618 | CH₃ | CH₃ | SO₂ | CH₂-cyclohexyl |

TABLE 27

This table contains 618 compounds of the following type,

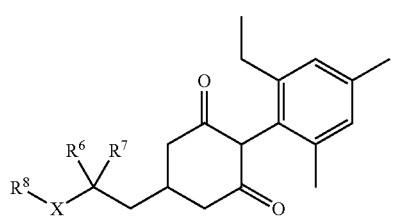

where X, R⁶, R⁷ and R⁸ are as defined in Table 26.

TABLE 28

This table contains 618 compounds of the following type,

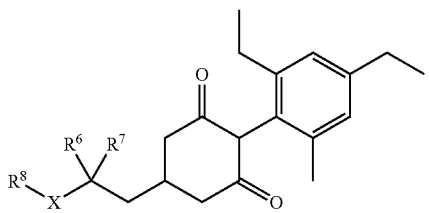

where X, R⁶, R⁷ and R⁸ are as defined in Table 26.

TABLE 29

This table contains 618 compounds of the following type,

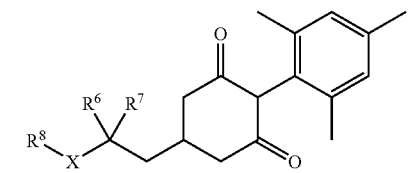

where X, R⁶, R⁷ and R⁸ are as defined in Table 26.

TABLE 30

This table contains 618 compounds of the following type,

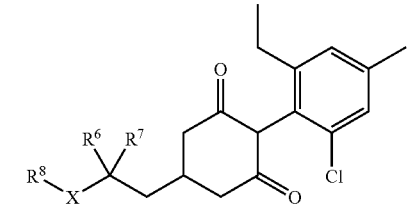

where X, R⁶, R⁷ and R⁸ are as defined in Table 26.

TABLE 31

This table contains 618 compounds of the following type,

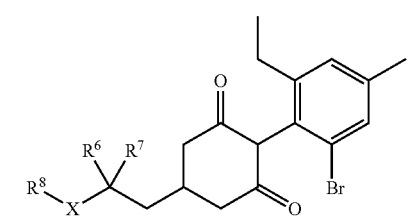

where X, R⁶, R⁷ and R⁸ are as defined in Table 26.

TABLE 32

This table contains 618 compounds of the following type,

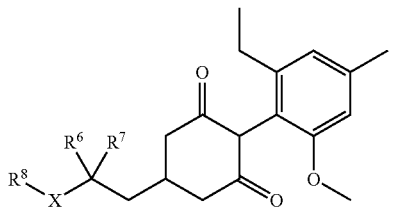

where X, $R^6$, $R^7$ and $R^8$ are as defined in Table 26.

TABLE 33

This table contains 618 compounds of the following type,

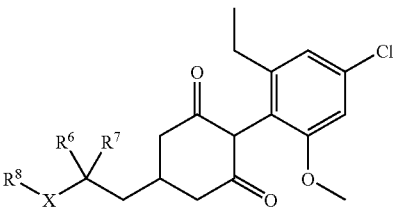

where X, $R^6$, $R^7$ and $R^8$ are as defined in Table 26.

TABLE 34

This table contains 618 compounds of the following type,

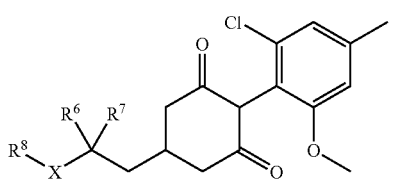

where X, $R^6$, $R^7$ and $R^8$ are as defined in Table 26.

TABLE 35

This table contains 618 compounds of the following type,

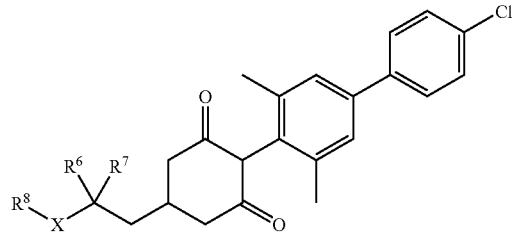

where X, $R^6$, $R^7$ and $R^8$ are as defined in Table 26.

TABLE 36

This table contains 618 compounds of the following type,

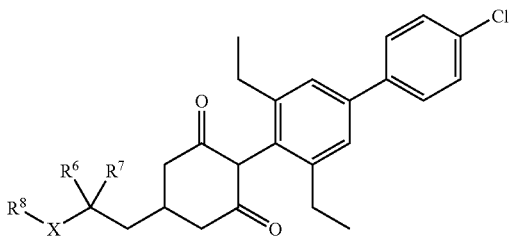

where X, $R^6$, $R^7$ and $R^8$ are as defined in Table 26.

TABLE 37

This table contains 618 compounds of the following type,

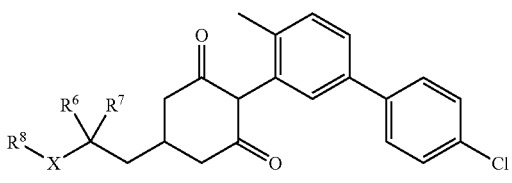

where X, $R^6$, $R^7$ and $R^8$ are as defined in Table 26.

TABLE 38

This table contains 618 compounds of the following type,

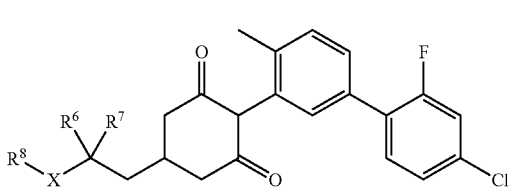

where X, $R^6$, $R^7$ and $R^8$ are as defined in Table 26.

TABLE 39

This table contains 618 compounds of the following type,

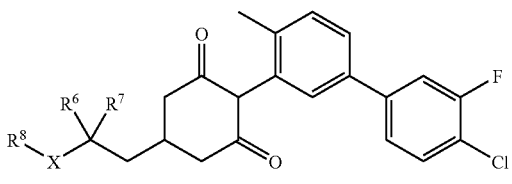

where X, $R^6$, $R^7$ and $R^8$ are as defined in Table 26.

TABLE 40

This table contains 618 compounds of the following type,

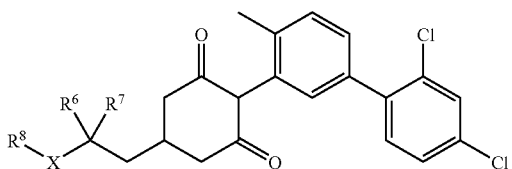

where X, $R^6$, $R^7$ and $R^8$ are as defined in Table 26.

TABLE 41

This table contains 618 compounds of the following type,

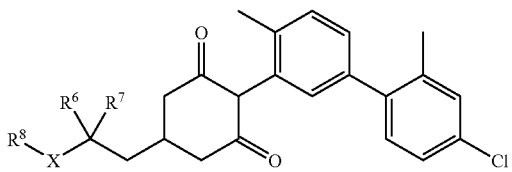

where X, $R^6$, $R^7$ and $R^8$ are as defined in Table 26.

TABLE 42

This table contains 618 compounds of the following type,

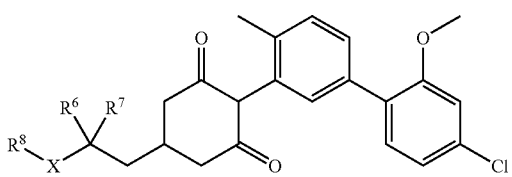

where X, $R^6$, $R^7$ and $R^8$ are as defined in Table 26.

TABLE 43

This table contains 618 compounds of the following type,

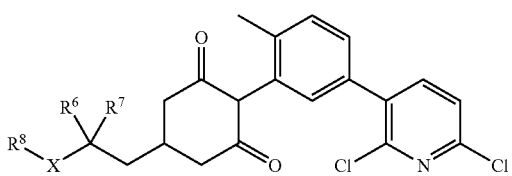

where X, $R^6$, $R^7$ and $R^8$ are as defined in Table 26.

TABLE 44

This table contains 618 compounds of the following type,

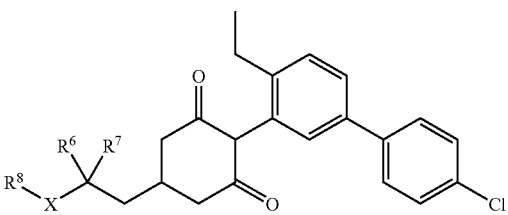

where X, $R^6$, $R^7$ and $R^8$ are as defined in Table 26.

TABLE 45

This table contains 618 compounds of the following type,

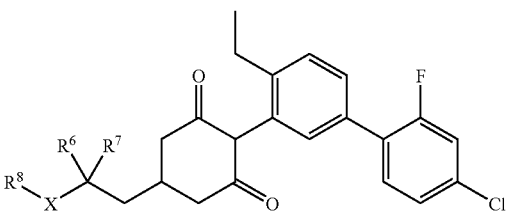

where X, $R^6$, $R^7$ and $R^8$ are as defined in Table 26.

TABLE 46

This table contains 618 compounds of the following type,

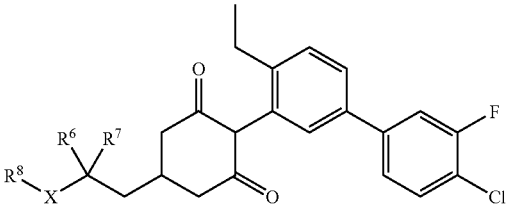

where X, $R^6$, $R^7$ and $R^8$ are as defined in Table 26.

TABLE 47

This table contains 618 compounds of the following type,

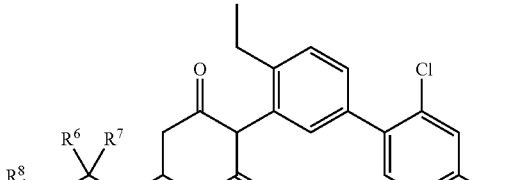

where X, $R^6$, $R^7$ and $R^8$ are as defined in Table 26.

TABLE 48

This table contains 618 compounds of the following type,

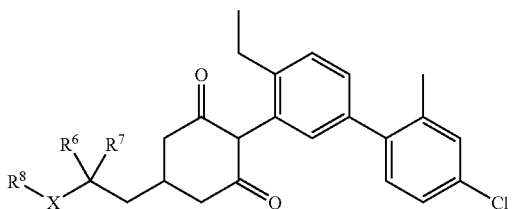

where X, R⁶, R⁷ and R⁸ are as defined in Table 26.

TABLE 49

This table contains 618 compounds of the following type,

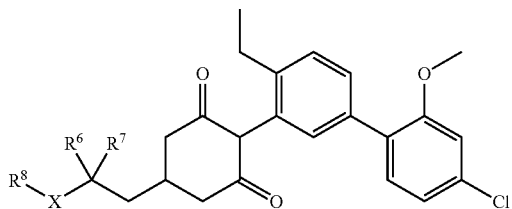

where X, R⁶, R⁷ and R⁸ are as defined in Table 26.

TABLE 50

This table contains 618 compounds of the following type,

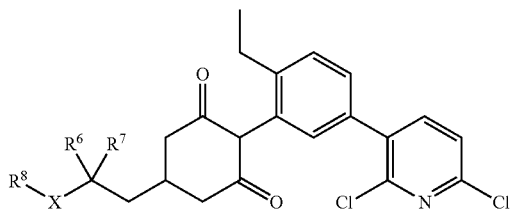

where X, R⁶, R⁷ and R⁸ are as defined in Table 26.

TABLE 51

This table contains 220 compounds of the following type,

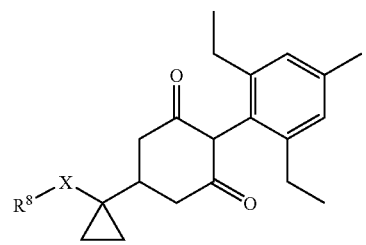

where X and R⁴ are as defined below:

| Compound number | X | R⁸ |
|---|---|---|
| 51.1 | O | $CH_3$ |
| 51.2 | O | $CH_2CH_3$ |
| 51.3 | O | $CH_2CH_2CH_3$ |
| 51.4 | O | $CH(CH_3)_2$ |

TABLE 51-continued

| | | |
|---|---|---|
| 51.5 | O | $CH_2CH_2CH_2CH_3$ |
| 51.6 | O | $CH_2CH(CH_3)_2$ |
| 51.7 | O | $CH(CH_3)CH_2CH_3$ |
| 51.8 | O | $C(CH_3)_3$ |
| 51.9 | O | $CH_2CH_2CH_2CH_2CH_3$ |
| 51.10 | O | $CH_2CH_2CH(CH_3)_2$ |
| 51.11 | O | $CH_2C(CH_3)_3$ |
| 51.12 | O | $CH_2CH(CH_3)CH_2CH_3$ |
| 51.13 | O | $CH(CH_3)CH_2CH_2CH_3$ |
| 51.14 | O | $C(CH_3)_2CH_2CH_3$ |
| 51.15 | O | $CH_2CH=CH_2$ |
| 51.16 | O | $CH_2CH=CHCH_3$ |
| 51.17 | O | $CH_2CH=C(CH_3)_2$ |
| 51.18 | O | $CH_2C(CH_3)=CH_2$ |
| 51.19 | O | $CH_2C(CH_3)=CHCH_3$ |
| 51.20 | O | $CH_2C(CH_3)=C(CH_3)_2$ |
| 51.21 | O | $CH(CH_3)CH=CH_2$ |
| 51.22 | O | $CH(CH_3)CH=CHCH_3$ |
| 51.23 | O | $CH(CH_3)CH=C(CH_3)_2$ |
| 51.24 | O | $C(CH_3)_2CH=CH_2$ |
| 51.25 | O | $C(CH_3)_2CH=CHCH_3$ |
| 51.26 | O | $C(CH_3)_2CH=C(CH_3)_2$ |
| 51.27 | O | $CH_2CH=CHCl$ |
| 51.28 | O | $CH_2CH=CCl_2$ |
| 51.29 | O | $CH_2CCl=CHCl$ |
| 51.30 | O | $CH_2CCl=CCl_2$ |
| 51.31 | O | $CH_2CH=CF_2$ |
| 51.32 | O | $CH_2CF=CF_2$ |
| 51.33 | O | $CH_2C \cdot CH$ |
| 51.34 | O | $CH_2C \cdot CCH_3$ |
| 51.35 | O | $CH_2C \cdot CCH_2CH_3$ |
| 51.36 | O | $CH(CH_3)C \cdot CH$ |
| 51.37 | O | $CH(CH_3)C \cdot CCH_3$ |
| 51.38 | O | $CH(CH_3)C \cdot CCH_2CH_3$ |
| 51.39 | O | $C(CH_3)_2C \cdot CH$ |
| 51.40 | O | $C(CH_3)_2C \cdot CCH_3$ |
| 51.41 | O | $C(CH_3)_2C \cdot CCH_2CH_3$ |
| 51.42 | O | Cyclopropyl |
| 51.43 | O | Cyclobutyl |
| 51.44 | O | Cyclopentyl |
| 51.45 | O | Cyclohexyl |
| 51.46 | O | $CH_2CF_3$ |
| 51.47 | O | $CH_2CH_2CF_3$ |
| 51.48 | O | $CH_2$-cyclopropyl |
| 51.49 | O | $CH_2$-cyclobutyl |
| 51.50 | O | $CH_2$-cyclopentyl |
| 51.51 | O | $CH_2$-cyclohexyl |
| 51.52 | O | $CH_2OCH_3$ |
| 51.53 | O | $CH_2OCH_2CH_3$ |
| 51.54 | O | $CH_2CH_2OCH_3$ |
| 51.55 | O | $CH_2CH_2OCH_2CH_3$ |
| 51.56 | S | $CH_3$ |
| 51.57 | S | $CH_2CH_3$ |
| 51.58 | S | $CH_2CH_2CH_3$ |
| 51.59 | S | $CH(CH_3)_2$ |
| 51.60 | S | $CH_2CH_2CH_2CH_3$ |
| 51.61 | S | $CH_2CH(CH_3)_2$ |
| 51.62 | S | $CH(CH_3)CH_2CH_3$ |
| 51.63 | S | $C(CH_3)_3$ |
| 51.64 | S | $CH_2CH_2CH_2CH_2CH_3$ |
| 51.65 | S | $CH_2CH_2CH(CH_3)_2$ |
| 51.66 | S | $CH_2C(CH_3)_3$ |
| 51.67 | S | $CH_2CH(CH_3)CH_2CH_3$ |
| 51.68 | S | $CH(CH_3)CH_2CH_2CH_3$ |
| 51.69 | S | $C(CH_3)_2CH_2CH_3$ |
| 51.70 | S | $CH_2CH=CH_2$ |
| 51.71 | S | $CH_2CH=CHCH_3$ |
| 51.72 | S | $CH_2CH=C(CH_3)_2$ |
| 51.73 | S | $CH_2C(CH_3)=CH_2$ |
| 51.74 | S | $CH_2C(CH_3)=CHCH_3$ |
| 51.75 | S | $CH_2C(CH_3)=C(CH_3)_2$ |
| 51.76 | S | $CH(CH_3)CH=CH_2$ |

TABLE 51-continued

| | | |
|---|---|---|
| 51.77 | S | CH(CH₃)CH=CHCH₃ |
| 51.78 | S | CH(CH₃)CH=C(CH₃)₂ |
| 51.79 | S | C(CH₃)₂CH=CH₂ |
| 51.80 | S | C(CH₃)₂CH=CHCH₃ |
| 51.81 | S | C(CH₃)₂CH=C(CH₃)₂ |
| 51.82 | S | CH₂CH=CHCl |
| 51.83 | S | CH₂CH=CCl₂ |
| 51.84 | S | CH₂CCl=CHCl |
| 51.85 | S | CH₂CCl=CCl₂ |
| 51.86 | S | CH₂CH=CF₂ |
| 51.87 | S | CH₂CF=CF₂ |
| 51.88 | S | CH₂C•CH |
| 51.89 | S | CH₂C•CCH₃ |
| 51.90 | S | CH₂C•CCH₂CH₃ |
| 51.91 | S | CH(CH₃)C•CH |
| 51.92 | S | CH(CH₃)C•CCH₃ |
| 51.93 | S | CH(CH₃)C•CCH₂CH₃ |
| 51.94 | S | C(CH₃)₂C•CH |
| 51.95 | S | C(CH₃)₂C•CCH₃ |
| 51.96 | S | C(CH₃)₂C•CCH₂CH₃ |
| 51.97 | S | Cyclopropyl |
| 51.98 | S | Cyclobutyl |
| 51.99 | S | Cyclopentyl |
| 51.100 | S | Cyclohexyl |
| 51.101 | S | CH₂CF₃ |
| 51.102 | S | CH₂CH₂CF₃ |
| 51.103 | S | CH₂-cyclopropyl |
| 51.104 | S | CH₂-cyclobutyl |
| 51.105 | S | CH₂-cyclopentyl |
| 51.106 | S | CH₂-cyclohexyl |
| 51.107 | S | CH₂OCH₃ |
| 51.108 | S | CH₂OCH₂CH₃ |
| 51.109 | S | CH₂CH₂OCH₃ |
| 51.110 | S | CH₂CH₂OCH₂CH₃ |
| 51.111 | S(O) | CH₃ |
| 51.112 | S(O) | CH₂CH₃ |
| 51.113 | S(O) | CH₂CH₂CH₃ |
| 51.114 | S(O) | CH(CH₃)₂ |
| 51.115 | S(O) | CH₂CH₂CH₂CH₃ |
| 51.116 | S(O) | CH₂CH(CH₃)₂ |
| 51.117 | S(O) | CH(CH₃)CH₂CH₃ |
| 51.118 | S(O) | C(CH₃)₃ |
| 51.119 | S(O) | CH₂CH₂CH₂CH₂CH₃ |
| 51.120 | S(O) | CH₂CH₂CH(CH₃)₂ |
| 51.121 | S(O) | CH₂C(CH₃)₃ |
| 51.122 | S(O) | CH₂CH(CH₃)CH₂CH₃ |
| 51.123 | S(O) | CH(CH₃)CH₂CH₂CH₃ |
| 51.124 | S(O) | C(CH₃)₂CH₂CH₃ |
| 51.125 | S(O) | CH₂CH=CH₂ |
| 51.126 | S(O) | CH₂CH=CHCH₃ |
| 51.127 | S(O) | CH₂CH=C(CH₃)₂ |
| 51.128 | S(O) | CH₂C(CH₃)=CH₂ |
| 51.129 | S(O) | CH₂C(CH₃)=CHCH₃ |
| 51.130 | S(O) | CH₂C(CH₃)=C(CH₃)₂ |
| 51.131 | S(O) | CH(CH₃)CH=CH₂ |
| 51.132 | S(O) | CH(CH₃)CH=CHCH₃ |
| 51.133 | S(O) | CH(CH₃)CH=C(CH₃)₂ |
| 51.134 | S(O) | C(CH₃)₂CH=CH₂ |
| 51.135 | S(O) | C(CH₃)₂CH=CHCH₃ |
| 51.136 | S(O) | C(CH₃)₂CH=C(CH₃)₂ |
| 51.137 | S(O) | CH₂CH=CHCl |
| 51.138 | S(O) | CH₂CH=CCl₂ |
| 51.139 | S(O) | CH₂CCl=CHCl |
| 51.140 | S(O) | CH₂CCl=CCl₂ |
| 51.141 | S(O) | CH₂CH=CF₂ |
| 51.142 | S(O) | CH₂CF=CF₂ |
| 51.143 | S(O) | CH₂C•CH |
| 51.144 | S(O) | CH₂C•CCH₃ |
| 51.145 | S(O) | CH₂C•CCH₂CH₃ |
| 51.146 | S(O) | CH(CH₃)C•CH |
| 51.147 | S(O) | CH(CH₃)C•CCH₃ |
| 51.148 | S(O) | CH(CH₃)C•CCH₂CH₃ |
| 51.149 | S(O) | C(CH₃)₂C•CH |
| 51.150 | S(O) | C(CH₃)₂C•CCH₃ |
| 51.151 | S(O) | C(CH₃)₂C•CCH₂CH₃ |
| 51.152 | S(O) | Cyclopropyl |
| 51.153 | S(O) | Cyclobutyl |
| 51.154 | S(O) | Cyclopentyl |
| 51.155 | S(O) | Cyclohexyl |
| 51.156 | S(O) | CH₂CF₃ |
| 51.157 | S(O) | CH₂CH₂CF₃ |
| 51.158 | S(O) | CH₂-cyclopropyl |
| 51.159 | S(O) | CH₂-cyclobutyl |
| 51.160 | S(O) | CH₂-cyclopentyl |
| 51.161 | S(O) | CH₂-cyclohexyl |
| 51.162 | S(O) | CH₂OCH₃ |
| 51.163 | S(O) | CH₂OCH₂CH₃ |
| 51.164 | S(O) | CH₂CH₂OCH₃ |
| 51.165 | S(O) | CH₂CH₂OCH₂CH₃ |
| 51.166 | SO₂ | CH₃ |
| 51.167 | SO₂ | CH₂CH₃ |
| 51.168 | SO₂ | CH₂CH₂CH₃ |
| 51.169 | SO₂ | CH(CH₃)₂ |
| 51.170 | SO₂ | CH₂CH₂CH₂CH₃ |
| 51.171 | SO₂ | CH₂CH(CH₃)₂ |
| 51.172 | SO₂ | CH(CH₃)CH₂CH₃ |
| 51.173 | SO₂ | C(CH₃)₃ |
| 51.174 | SO₂ | CH₂CH₂CH₂CH₂CH₃ |
| 51.175 | SO₂ | CH₂CH₂CH(CH₃)₂ |
| 51.176 | SO₂ | CH₂C(CH₃)₃ |
| 51.177 | SO₂ | CH₂CH(CH₃)CH₂CH₃ |
| 51.178 | SO₂ | CH(CH₃)CH₂CH₂CH₃ |
| 51.179 | SO₂ | C(CH₃)₂CH₂CH₃ |
| 51.180 | SO₂ | CH₂CH=CH₂ |
| 51.181 | SO₂ | CH₂CH=CHCH₃ |
| 51.182 | SO₂ | CH₂CH=C(CH₃)₂ |
| 51.183 | SO₂ | CH₂C(CH₃)=CH₂ |
| 51.184 | SO₂ | CH₂C(CH₃)=CHCH₃ |
| 51.185 | SO₂ | CH₂C(CH₃)=C(CH₃)₂ |
| 51.186 | SO₂ | CH(CH₃)CH=CH₂ |
| 51.187 | SO₂ | CH(CH₃)CH=CHCH₃ |
| 51.188 | SO₂ | CH(CH₃)CH=C(CH₃)₂ |
| 51.189 | SO₂ | C(CH₃)₂CH=CH₂ |
| 51.190 | SO₂ | C(CH₃)₂CH=CHCH₃ |
| 51.191 | SO₂ | C(CH₃)₂CH=C(CH₃)₂ |
| 51.192 | SO₂ | CH₂CH=CHCl |
| 51.193 | SO₂ | CH₂CH=CCl₂ |
| 51.194 | SO₂ | CH₂CCl=CHCl |
| 51.195 | SO₂ | CH₂CCl=CCl₂ |
| 51.196 | SO₂ | CH₂CH=CF₂ |
| 51.197 | SO₂ | CH₂CF=CF₂ |
| 51.198 | SO₂ | CH₂C•CH |
| 51.199 | SO₂ | CH₂C•CCH₃ |
| 51.200 | SO₂ | CH₂C•CCH₂CH₃ |
| 51.201 | SO₂ | CH(CH₃)C•CH |
| 51.202 | SO₂ | CH(CH₃)C•CCH₃ |
| 51.203 | SO₂ | CH(CH₃)C•CCH₂CH₃ |
| 51.204 | SO₂ | C(CH₃)₂C•CH |
| 51.205 | SO₂ | C(CH₃)₂C•CCH₃ |
| 51.206 | SO₂ | C(CH₃)₂C•CCH₂CH₃ |
| 51.207 | SO₂ | Cyclopropyl |
| 51.208 | SO₂ | Cyclobutyl |
| 51.209 | SO₂ | Cyclopentyl |
| 51.210 | SO₂ | Cyclohexyl |
| 51.211 | SO₂ | CH₂CF₃ |
| 51.212 | SO₂ | CH₂CH₂CF₃ |
| 51.213 | SO₂ | CH₂-cyclopropyl |
| 51.214 | SO₂ | CH₂-cyclobutyl |
| 51.215 | SO₂ | CH₂-cyclopentyl |
| 51.216 | SO₂ | CH₂-cyclohexyl |
| 51.217 | SO₂ | CH₂OCH₃ |
| 51.218 | SO₂ | CH₂OCH₂CH₃ |
| 51.219 | SO₂ | CH₂CH₂OCH₃ |
| 51.220 | SO₂ | CH₂CH₂OCH₂CH₃ |

TABLE 52

This table contains 220 compounds of the following type,

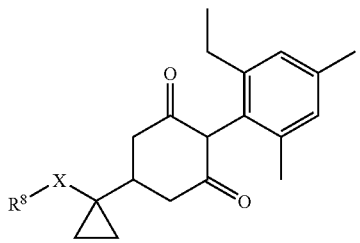

where X and R⁸ are as defined in Table 51.

TABLE 53

This table contains 220 compounds of the following type,

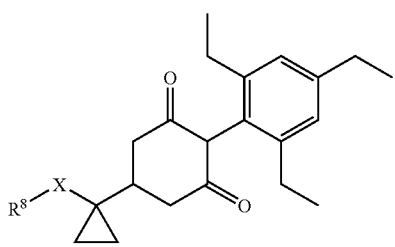

where X and R⁸ are as defined in Table 51.

TABLE 54

This table contains 220 compounds of the following type,

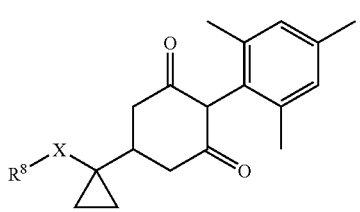

where X and R⁸ are as defined in Table 51.

TABLE 55

This table contains 220 compounds of the following type,

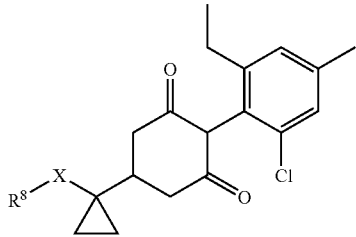

where X and R⁸ are as defined in Table 51.

TABLE 56

This table contains 220 compounds of the following type,

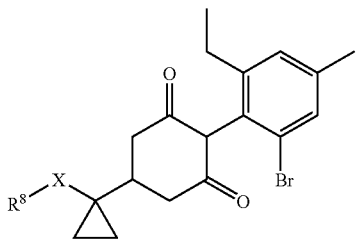

where X and R⁸ are as defined in Table 51.

TABLE 57

This table contains 220 compounds of the following type,

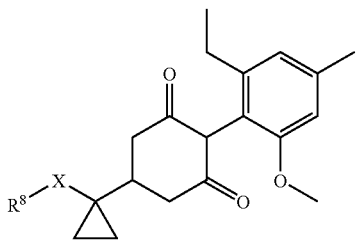

where X and R⁸ are as defined in Table 51.

TABLE 58

This table contains 220 compounds of the following type,

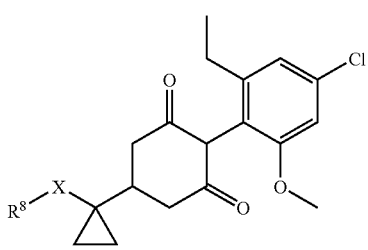

where X and R⁸ are as defined in Table 51.

TABLE 59

This table contains 220 compounds of the following type,

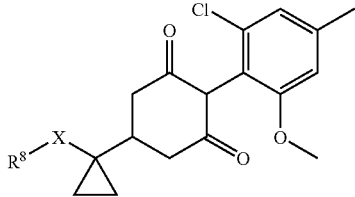

where X and R⁸ are as defined in Table 51.

TABLE 60

This table contains 220 compounds of the following type,

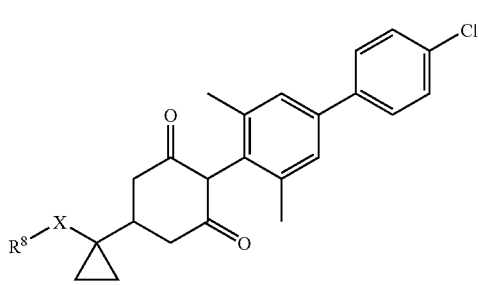

where X and R⁸ are as defined in Table 51.

TABLE 61

This table contains 220 compounds of the following type,

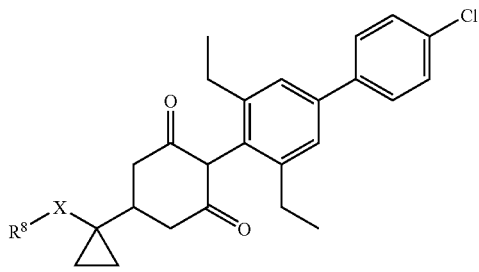

where X and R⁸ are as defined in Table 51.

TABLE 62

This table contains 220 compounds of the following type,

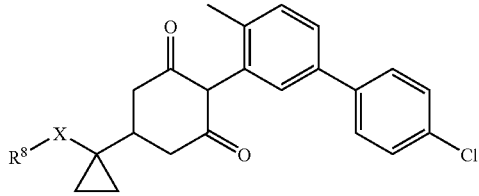

where X and R⁸ are as defined in Table 51.

TABLE 63

This table contains 220 compounds of the following type,

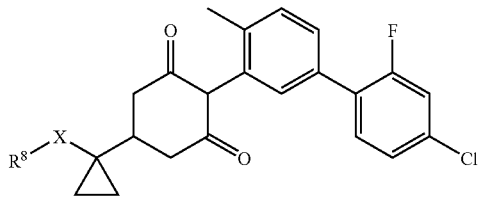

where X and R⁸ are as defined in Table 51.

TABLE 64

This table contains 220 compounds of the following type,

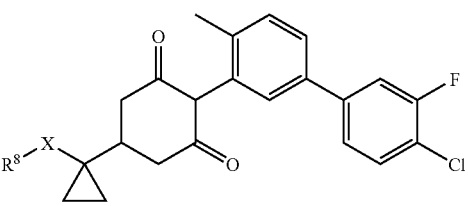

where X and R⁸ are as defined in Table 51.

TABLE 65

This table contains 220 compounds of the following type,

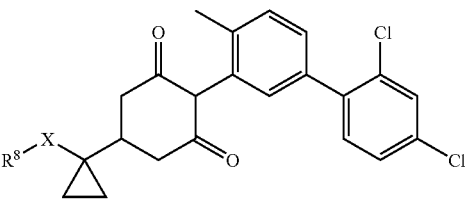

where X and R⁸ are as defined in Table 51.

TABLE 66

This table contains 220 compounds of the following type,

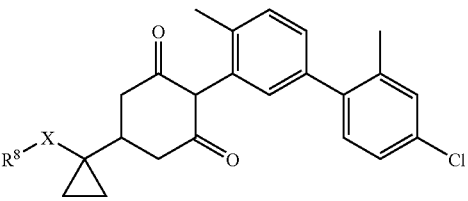

where X and R⁸ are as defined in Table 51.

TABLE 67

This table contains 220 compounds of the following type,

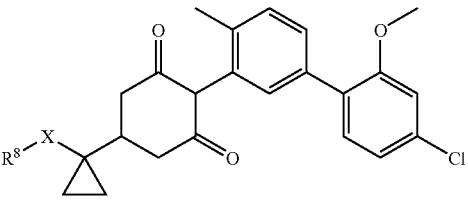

where X and R⁸ are as defined in Table 51.

TABLE 68

This table contains 220 compounds of the following type,

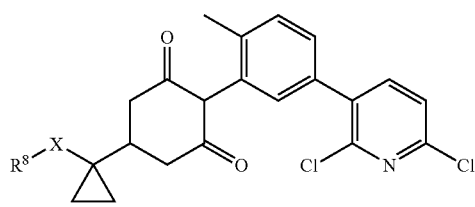

where X and R$^8$ are as defined in Table 51.

TABLE 69

This table contains 220 compounds of the following type,

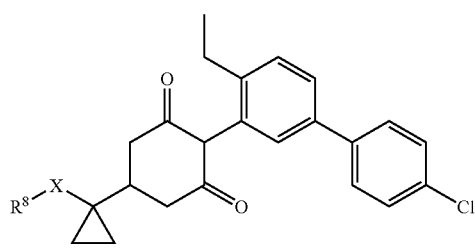

where X and R$^8$ are as defined in Table 51.

TABLE 70

This table contains 220 compounds of the following type,

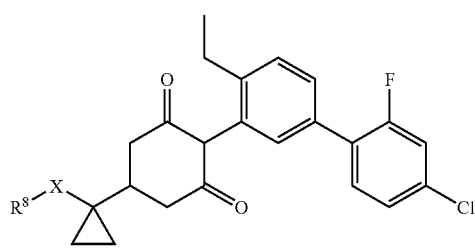

where X and R$^8$ are as defined in Table 51.

TABLE 71

This table contains 220 compounds of the following type,

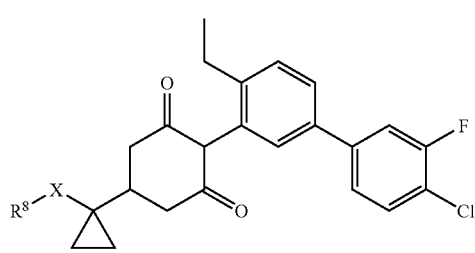

where X and R$^8$ are as defined in Table 51.

TABLE 72

This table contains 220 compounds of the following type,

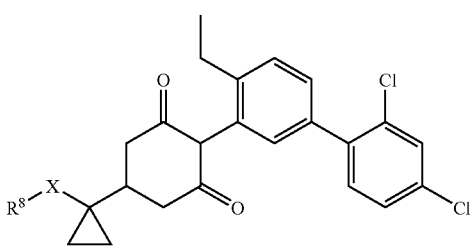

where X and R$^8$ are as defined in Table 51.

TABLE 73

This table contains 220 compounds of the following type,

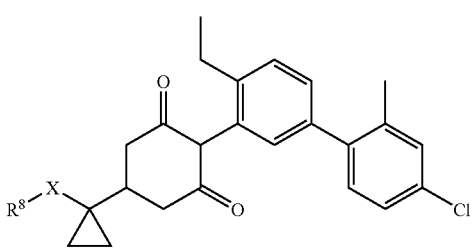

where X and R$^8$ are as defined in Table 51.

TABLE 74

This table contains 220 compounds of the following type,

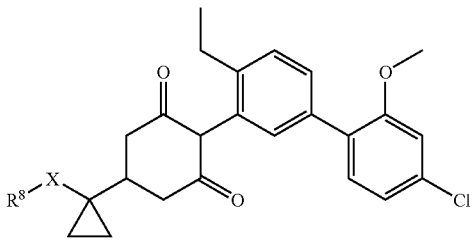

where X and R$^8$ are as defined in Table 51.

TABLE 75

This table contains 220 compounds of the following type,

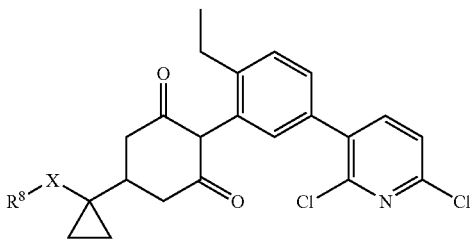

where X and R$^8$ are as defined in Table 51.

TABLE 76

This table contains 12 compounds of the following type

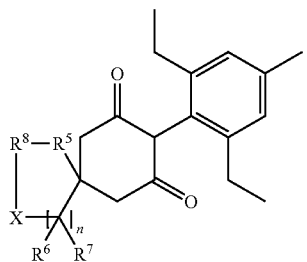

where n, X, $R^5$, $R^6$, $R^7$ and $R^8$ are as defined below:

| Compound No | n | X | $R^5$ | $R^6$ | $R^7$ | $R^8$ |
|---|---|---|---|---|---|---|
| 76.1 | 1 | O | $CH_2$ | H | H | $CH_2$ |
| 76.2 | 1 | O | $CH_2CH_2$ | H | H | $CH_2$ |
| 76.3 | 2 | O | $CH_2$ | H | H | $CH_2$ |
| 76.4 | 1 | S | $CH_2$ | H | H | $CH_2$ |
| 76.5 | 1 | S | $CH_2CH_2$ | H | H | $CH_2$ |
| 76.6 | 2 | S | $CH_2$ | H | H | $CH_2$ |
| 76.7 | 1 | S(O) | $CH_2$ | H | H | $CH_2$ |
| 76.8 | 1 | S(O) | $CH_2CH_2$ | H | H | $CH_2$ |
| 76.9 | 2 | S(O) | $CH_2$ | H | H | $CH_2$ |
| 76.10 | 1 | $SO_2$ | $CH_2$ | H | H | $CH_2$ |
| 76.11 | 1 | $SO_2$ | $CH_2CH_2$ | H | H | $CH_2$ |
| 76.12 | 2 | $SO_2$ | $CH_2$ | H | H | $CH_2$ |

TABLE 77

This table contains 12 compounds of the following type

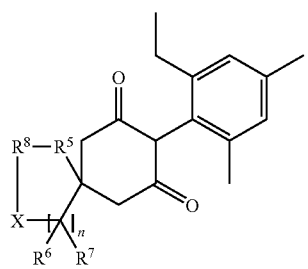

where n, X, $R^5$, $R^6$, $R^7$ and $R^8$ are as defined in Table 76.

TABLE 78

This table contains 12 compounds of the following type

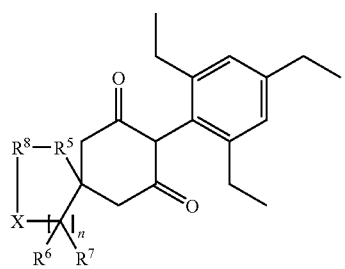

where n, X, $R^5$, $R^6$, $R^7$ and $R^8$ are as defined in Table 76.

TABLE 79

This table contains 12 compounds of the following type

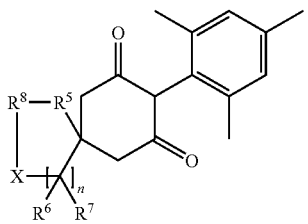

where n, X, $R^5$, $R^6$, $R^7$ and $R^8$ are as defined in Table 76.

TABLE 80

This table contains 12 compounds of the following type

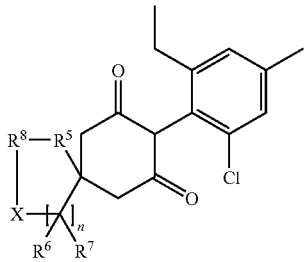

where n, X, $R^5$, $R^6$, $R^7$ and $R^8$ are as defined in Table 76.

TABLE 81

This table contains 12 compounds of the following type

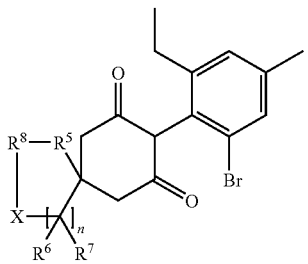

where n, X, $R^5$, $R^6$, $R^7$ and $R^8$ are as defined in Table 76.

TABLE 82

This table contains 12 compounds of the following type

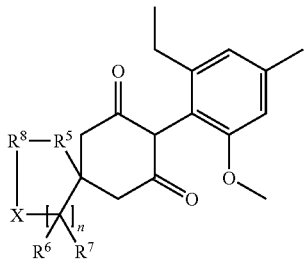

where n, X, $R^5$, $R^6$, $R^7$ and $R^8$ are as defined in Table 76.

TABLE 83

This table contains 12 compounds of the following type

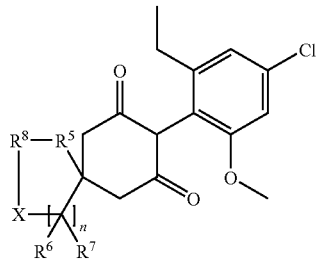

where n, X, $R^5$, $R^6$, $R^7$ and $R^8$ are as defined in Table 76.

TABLE 84

This table contains 12 compounds of the following type

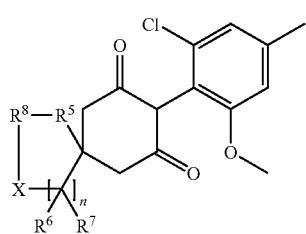

where n, X, $R^5$, $R^6$, $R^7$ and $R^8$ are as defined in Table 76.

TABLE 85

This table contains 12 compounds of the following type

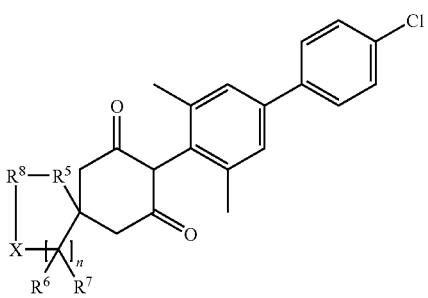

where n, X, $R^5$, $R^6$, $R^7$ and $R^8$ are as defined in Table 76.

TABLE 86

This table contains 12 compounds of the following type

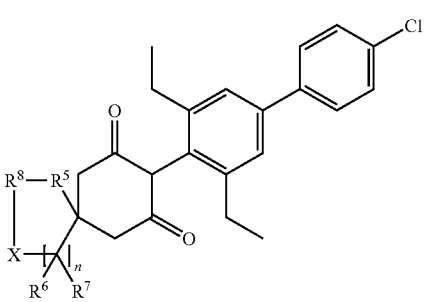

where n, X, $R^5$, $R^6$, $R^7$ and $R^8$ are as defined in Table 76.

TABLE 87

This table contains 12 compounds of the following type

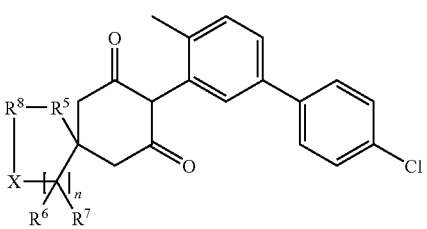

where n, X, $R^5$, $R^6$, $R^7$ and $R^8$ are as defined in Table 76.

TABLE 88

This table contains 12 compounds of the following type

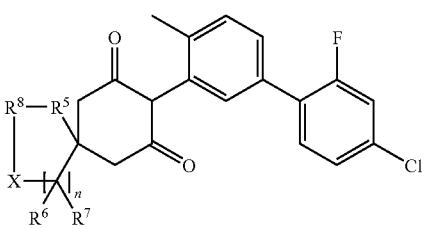

where n, X, $R^5$, $R^6$, $R^7$ and $R^8$ are as defined in Table 76.

TABLE 89

This table contains 12 compounds of the following type

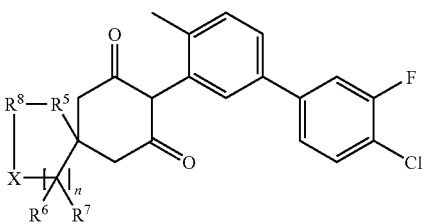

where n, X, $R^5$, $R^6$, $R^7$ and $R^8$ are as defined in Table 76.

TABLE 90

This table contains 12 compounds of the following type

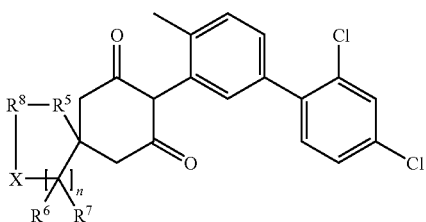

where n, X, $R^5$, $R^6$, $R^7$ and $R^8$ are as defined in Table 76.

TABLE 91

This table contains 12 compounds of the following type

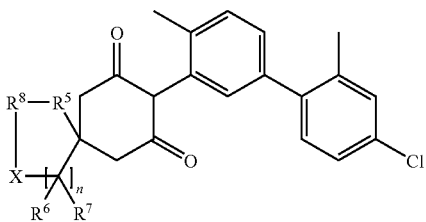

where n, X, $R^5$, $R^6$, $R^7$ and $R^8$ are as defined in Table 76.

TABLE 92

This table contains 12 compounds of the following type

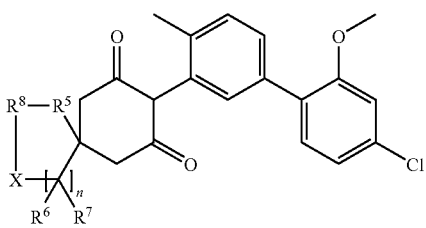

where n, X, $R^5$, $R^6$, $R^7$ and $R^8$ are as defined in Table 76.

TABLE 93

This table contains 12 compounds of the following type

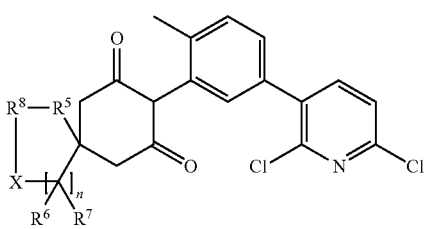

where n, X, $R^5$, $R^6$, $R^7$ and $R^8$ are as defined in Table 76.

TABLE 94

This table contains 12 compounds of the following type

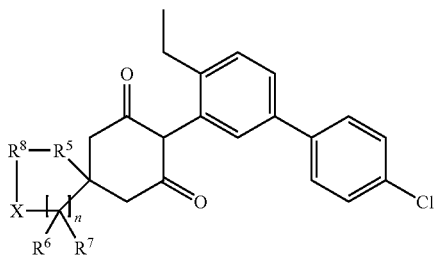

where n, X, $R^5$, $R^6$, $R^7$ and $R^8$ are as defined in Table 76.

TABLE 95

This table contains 12 compounds of the following type

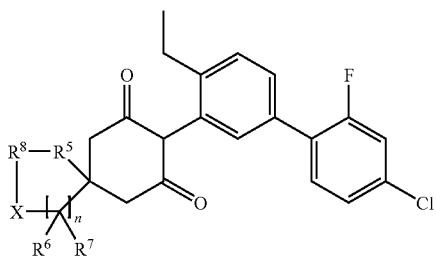

where n, X, $R^5$, $R^6$, $R^7$ and $R^8$ are as defined in Table 76.

TABLE 96

This table contains 12 compounds of the following type

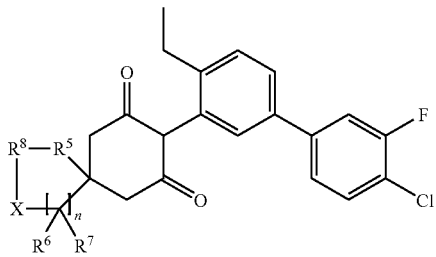

where n, X, $R^5$, $R^6$, $R^7$ and $R^8$ are as defined in Table 76.

TABLE 97

This table contains 12 compounds of the following type

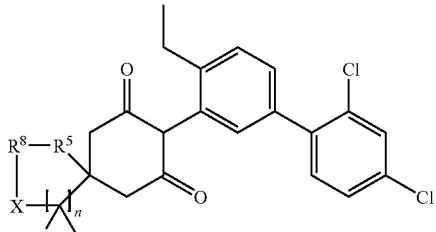

where n, X, $R^5$, $R^6$, $R^7$ and $R^8$ are as defined in Table 76.

TABLE 98

This table contains 12 compounds of the following type

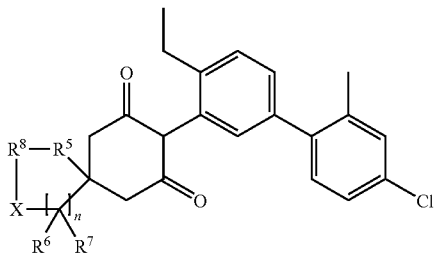

where n, X, $R^5$, $R^6$, $R^7$ and $R^8$ are as defined in Table 76.

TABLE 99

This table contains 12 compounds of the following type

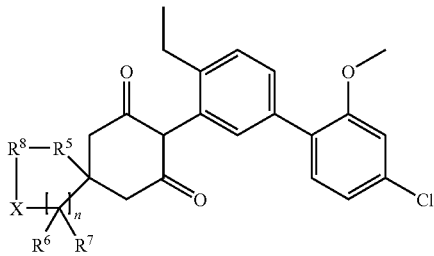

where n, X, $R^5$, $R^6$, $R^7$ and $R^8$ are as defined in Table 76.

TABLE 100

This table contains 12 compounds of the following type

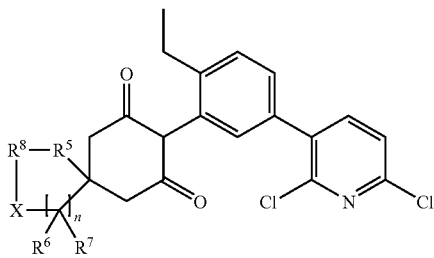

where n, X, $R^5$, $R^6$, $R^7$ and $R^8$ are as defined in Table 76.

TABLE 101

This table contains 12 compounds of the following type

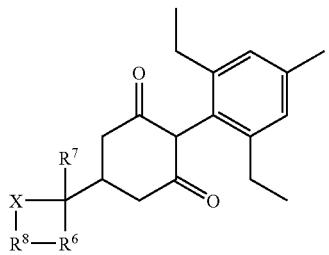

where X, $R^6$, $R^7$ and $R^8$ are as defined below:

| Compound Number | X | $R^6$ | $R^7$ | $R^8$ |
|---|---|---|---|---|
| 101.1 | O | $CH_2$ | H | $CH_2$ |
| 101.2 | O | $CH_2CH_2$ | H | $CH_2$ |
| 101.3 | O | $CH_2CH_2$ | H | $CH_2CH_2$ |
| 101.4 | S | $CH_2$ | H | $CH_2$ |
| 101.5 | S | $CH_2CH_2$ | H | $CH_2$ |
| 101.6 | S | $CH_2CH_2$ | H | $CH_2CH_2$ |
| 101.7 | S(O) | $CH_2$ | H | $CH_2$ |
| 101.8 | S(O) | $CH_2CH_2$ | H | $CH_2$ |
| 101.9 | S(O) | $CH_2CH_2$ | H | $CH_2CH_2$ |
| 101.10 | $SO_2$ | $CH_2$ | H | $CH_2$ |
| 101.11 | $SO_2$ | $CH_2CH_2$ | H | $CH_2$ |
| 101.12 | $SO_2$ | $CH_2CH_2$ | H | $CH_2CH_2$ |

TABLE 102

This table contains 12 compounds of the following type

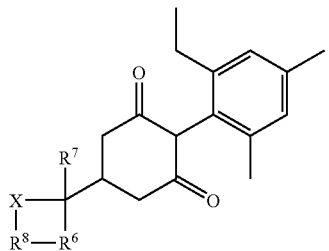

where X, $R^6$, $R^7$ and $R^8$ are as defined in Table 101.

TABLE 103

This table contains 12 compounds of the following type

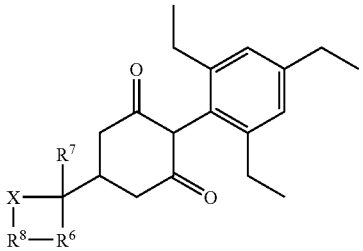

where X, $R^6$, $R^7$ and $R^8$ are as defined in Table 101.

TABLE 104

This table contains 12 compounds of the following type

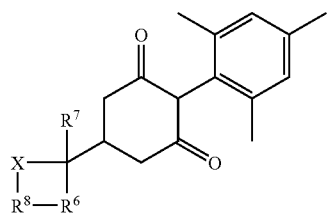

where X, $R^6$, $R^7$ and $R^8$ are as defined in Table 101.

TABLE 105

This table contains 12 compounds of the following type

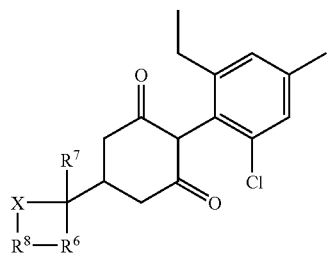

where X, $R^6$, $R^7$ and $R^8$ are as defined in Table 101.

TABLE 106

This table contains 12 compounds of the following type

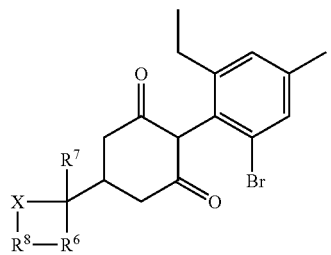

where X, $R^6$, $R^7$ and $R^8$ are as defined in Table 101.

TABLE 107

This table contains 12 compounds of the following type

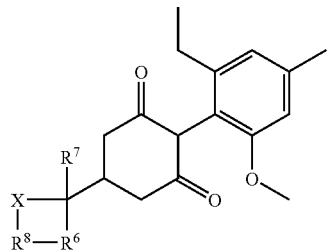

where X, $R^6$, $R^7$ and $R^8$ are as defined in Table 101.

TABLE 108

This table contains 12 compounds of the following type

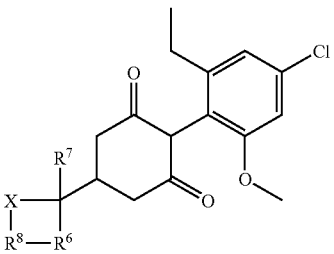

where X, $R^6$, $R^7$ and $R^8$ are as defined in Table 101.

TABLE 109

This table contains 12 compounds of the following type

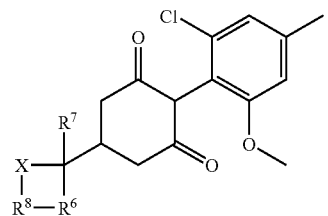

where X, $R^6$, $R^7$ and $R^8$ are as defined in Table 101.

TABLE 110

This table contains 12 compounds of the following type

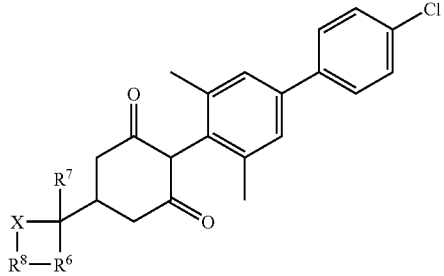

where X, $R^6$, $R^7$ and $R^8$ are as defined in Table 101.

TABLE 111

This table contains 12 compounds of the following type

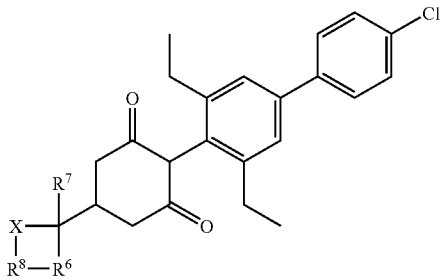

where X, $R^6$, $R^7$ and $R^8$ are as defined in Table 101.

TABLE 112

This table contains 12 compounds of the following type

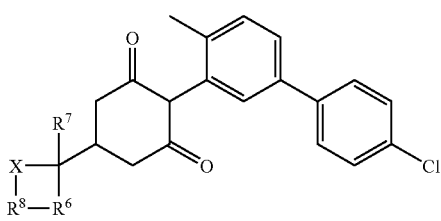

where X, $R^6$, $R^7$ and $R^8$ are as defined in Table 101.

TABLE 113

This table contains 12 compounds of the following type

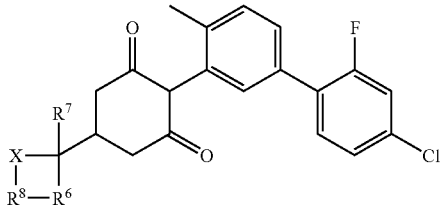

where X, $R^6$, $R^7$ and $R^8$ are as defined in Table 101.

TABLE 114

This table contains 12 compounds of the following type

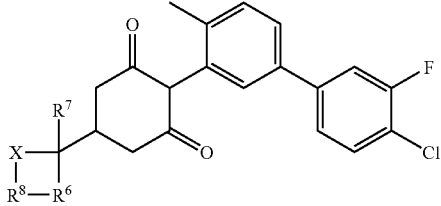

where X, $R^6$, $R^7$ and $R^8$ are as defined in Table 101.

TABLE 115

This table contains 12 compounds of the following type

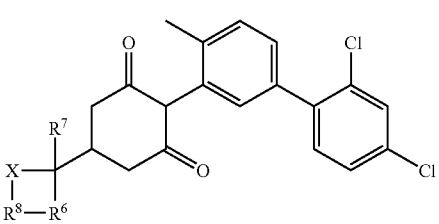

where X, $R^6$, $R^7$ and $R^8$ are as defined in Table 101.

TABLE 116

This table contains 12 compounds of the following type

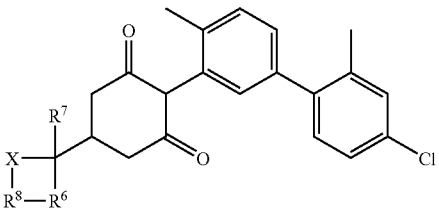

where X, $R^6$, $R^7$ and $R^8$ are as defined in Table 101.

TABLE 117

This table contains 12 compounds of the following type

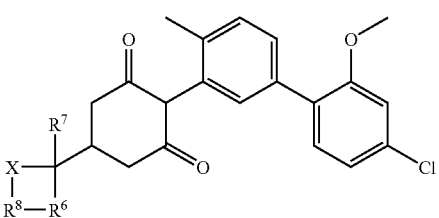

where X, $R^6$, $R^7$ and $R^8$ are as defined in Table 101.

TABLE 118

This table contains 12 compounds of the following type

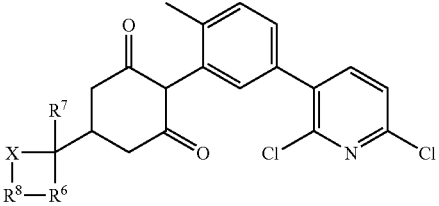

where X, $R^6$, $R^7$ and $R^8$ are as defined in Table 101.

TABLE 119

This table contains 12 compounds of the following type

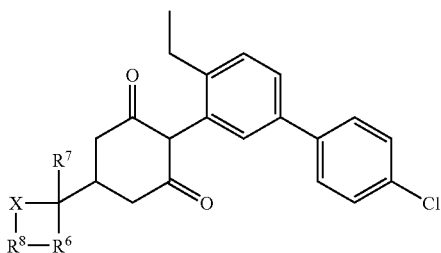

where X, $R^6$, $R^7$ and $R^8$ are as defined in Table 101.

TABLE 120

This table contains 12 compounds of the following type

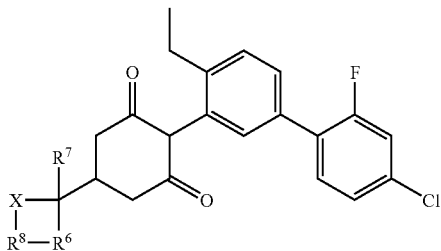

where X, $R^6$, $R^7$ and $R^8$ are as defined in Table 101.

TABLE 121

This table contains 12 compounds of the following type

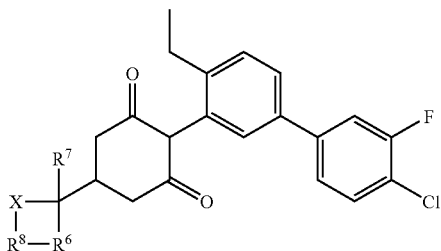

where X, $R^6$, $R^7$ and $R^8$ are as defined in Table 101.

TABLE 122

This table contains 12 compounds of the following type

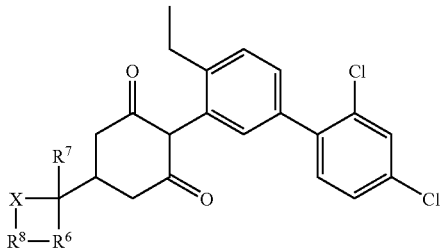

where X, $R^6$, $R^7$ and $R^8$ are as defined in Table 101.

TABLE 123

This table contains 12 compounds of the following type

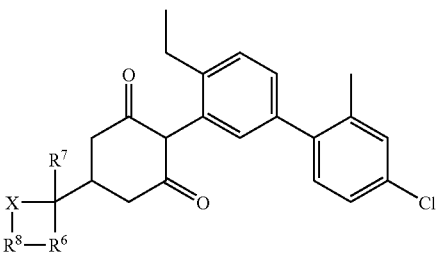

where X, $R^6$, $R^7$ and $R^8$ are as defined in Table 101.

TABLE 124

This table contains 12 compounds of the following type

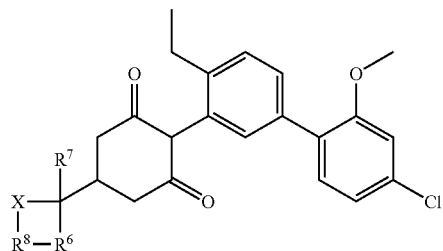

where X, $R^6$, $R^7$ and $R^8$ are as defined in Table 101q.

TABLE 125

This table contains 12 compounds of the following type

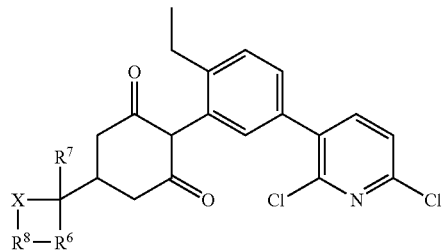

where X, $R^6$, $R^7$ and $R^8$ are as defined in Table 101.

TABLE 126

This table contains 16 compounds of the following type

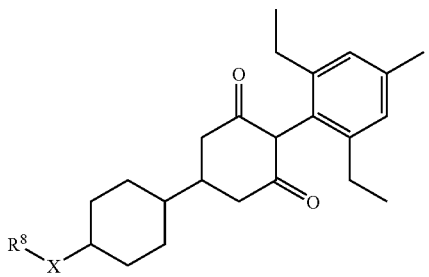

where X and R⁸ as defined below:

| Compound number | X | R⁸ |
|---|---|---|
| 126.1 | O | $CH_3$ |
| 126.2 | O | $CH_2CH_3$ |
| 126.3 | O | $CH(CH_3)_2$ |
| 126.4 | O | $CF_3$ |
| 126.5 | S | $CH_3$ |
| 126.6 | S | $CH_2CH_3$ |
| 126.7 | S | $CH(CH_3)_2$ |
| 126.8 | S | $CF_3$ |
| 126.9 | S(O) | $CH_3$ |
| 126.10 | S(O) | $CH_2CH_3$ |
| 126.11 | S(O) | $CH(CH_3)_2$ |
| 126.12 | S(O) | $CF_3$ |
| 126.13 | $SO_2$ | $CH_3$ |
| 126.14 | $SO_2$ | $CH_2CH_3$ |
| 126.15 | $SO_2$ | $CH(CH_3)_2$ |
| 126.16 | $SO_2$ | $CF_3$ |

TABLE 127

This table contains 16 compounds of the following type

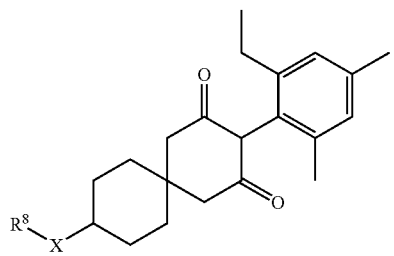

where n and R⁸ are as defined in Table 126.

TABLE 128

This table contains 16 compounds of the following type

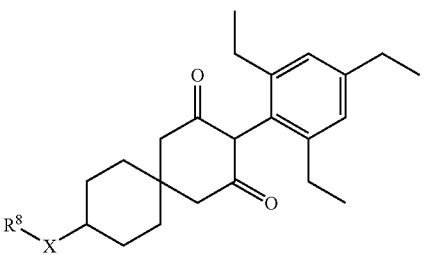

where n and R⁸ are as defined in Table 126.

TABLE 129

This table contains 16 compounds of the following type

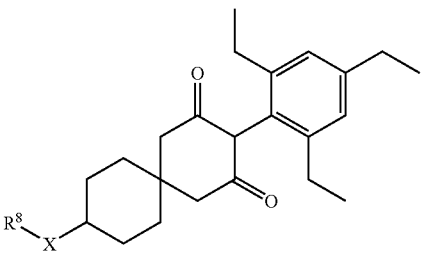

where n and R⁸ are as defined in Table 126.

TABLE 130

This table contains 16 compounds of the following type

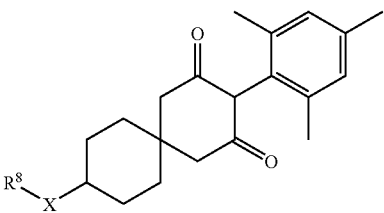

where n and R⁸ are as defined in Table 126.

TABLE 131

This table contains 16 compounds of the following type

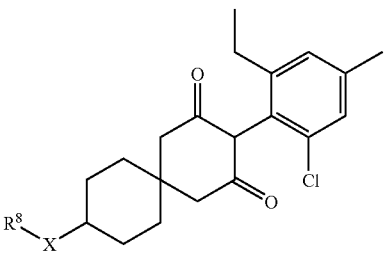

where n and R⁸ are as defined in Table 126.

TABLE 132

This table contains 16 compounds of the following type

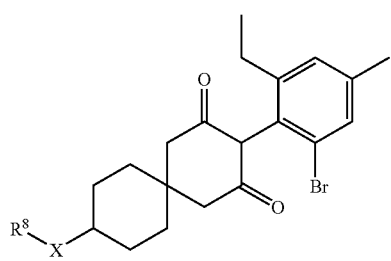

where n and R⁸ are as defined in Table 126.

TABLE 133

This table contains 16 compounds of the following type

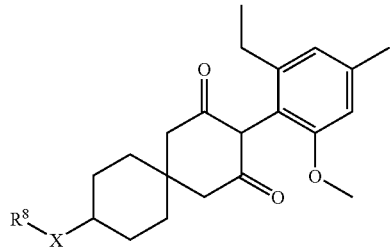

where n and R⁸ are as defined in Table 126.

TABLE 134

This table contains 16 compounds of the following type

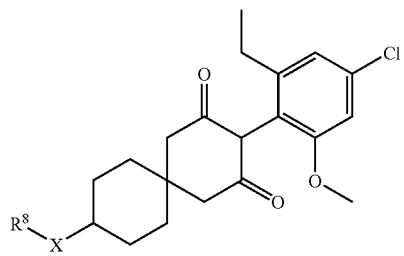

where n and R⁸ are as defined in Table 126.

TABLE 135

This table contains 16 compounds of the following type

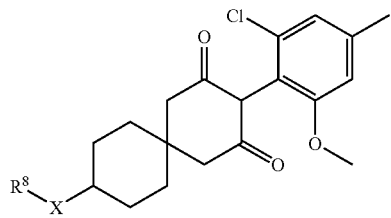

where n and R⁸ are as defined in Table 126.

TABLE 136

This table contains 16 compounds of the following type

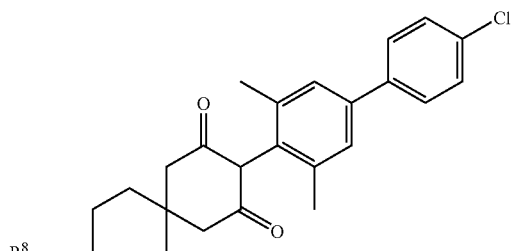

where n and R⁸ are as defined in Table 126.

TABLE 137

This table contains 16 compounds of the following type

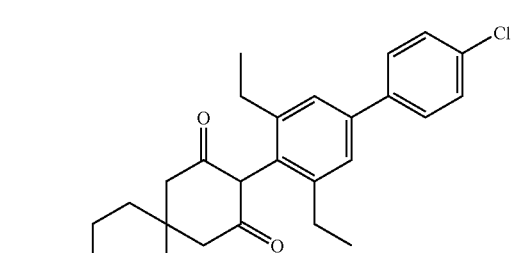

where n and R⁸ are as defined in Table 126.

TABLE 138

This table contains 16 compounds of the following type

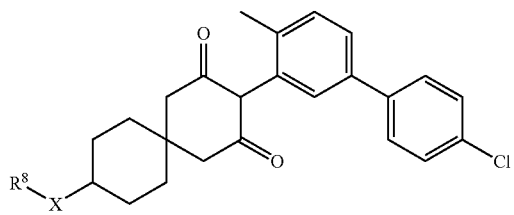

where n and R⁸ are as defined in Table 126.

TABLE 139

This table contains 16 compounds of the following type

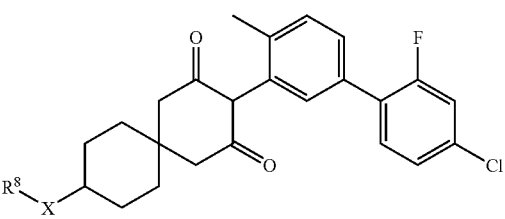

where n and R⁸ are as defined in Table 126.

TABLE 140

This table contains 16 compounds of the following type

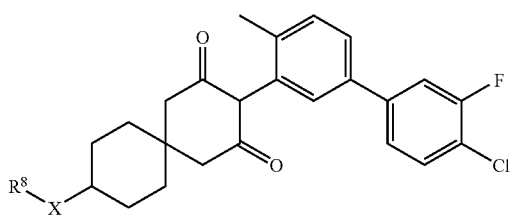

where n and R⁸ are as defined in Table 126.

TABLE 141

This table contains 16 compounds of the following type

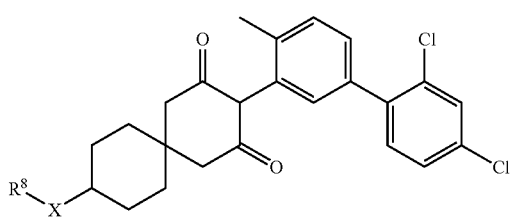

where n and R⁸ are as defined in Table 126.

TABLE 142

This table contains 16 compounds of the following type

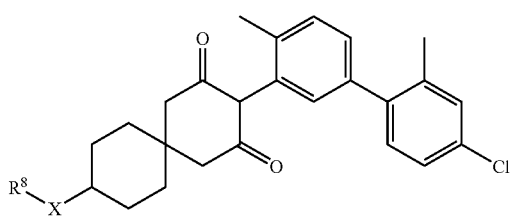

where n and R⁸ are as defined in Table 126.

TABLE 143

This table contains 16 compounds of the following type

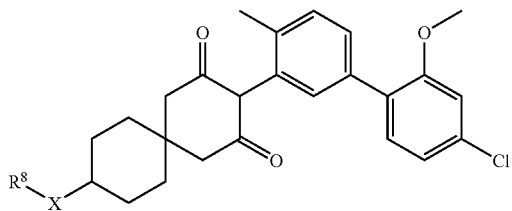

where n and R⁸ are as defined in Table 126.

TABLE 144

This table contains 16 compounds of the following type

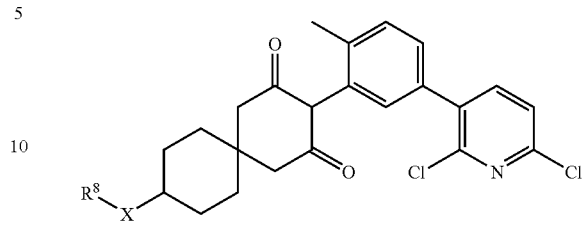

where n and R⁸ are as defined in Table 126.

TABLE 145

This table contains 16 compounds of the following type

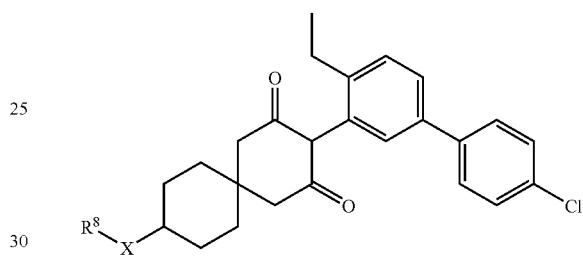

where n and R⁸ are as defined in Table 126.

TABLE 146

This table contains 16 compounds of the following type

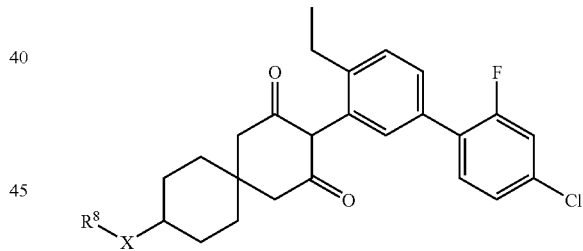

where n and R⁸ are as defined in Table 126.

TABLE 147

This table contains 16 compounds of the following type

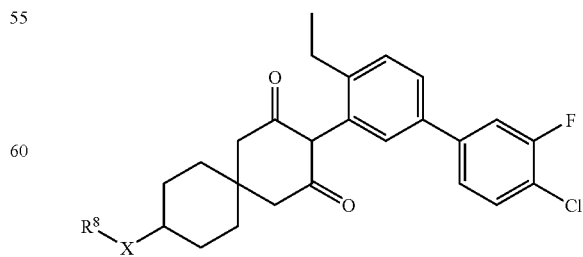

where n and R⁸ are as defined in Table 126.

TABLE 148

This table contains 16 compounds of the following type

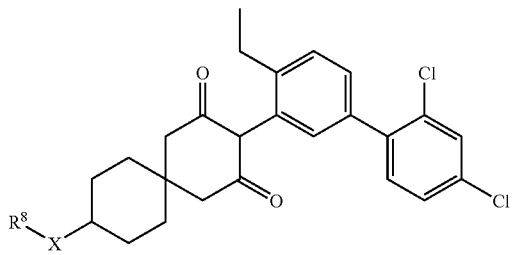

where n and R⁸ are as defined in Table 126.

TABLE 149

This table contains 16 compounds of the following type

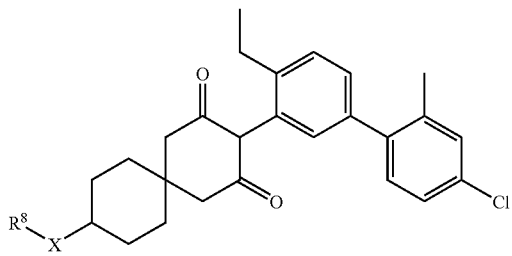

where n and R⁸ are as defined in Table 126.

TABLE 150

This table contains 16 compounds of the following type

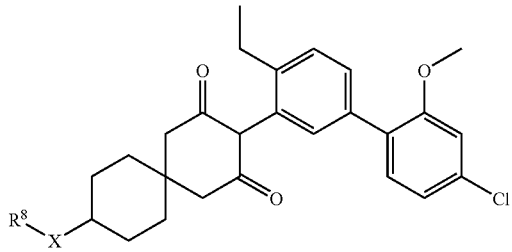

where n and R⁸ are as defined in Table 126.

TABLE 151

This table contains 16 compounds of the following type

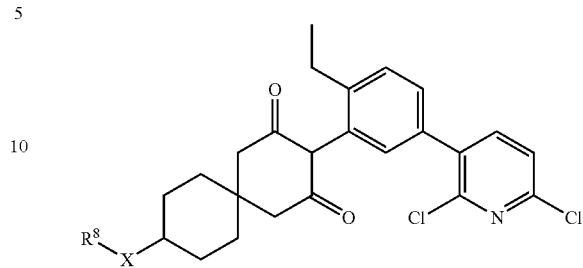

where n and R⁸ are as defined in Table 126.

EXAMPLE 7

Preparation of 9-(2,6-diethyl-4-methylphenyl)-10-oxo-3-oxaspiro[5.5]undec-8-enyl 3,3-dimethylbutyrate (Compound Number P6 in Table T2)

A solution of tert-butylacetyl chloride (0.049 g, 0.36 mmol) in dichloromethane (2 ml) is added dropwise to a solution of 9-(2,6-diethyl-4-methylphenyl)-3-oxaspiro[5.5]undecane-8,10-dione (0.10 g, 0.3 mmol) and triethylamine (0.036 g, 0.36 mmol) in dichloromethane (2 ml) and the reaction mixture is stirred at room temperature overnight. The mixture is washed with saturated aqueous sodium bicarbonate solution and the solvent evaporated in vacuo. The residue is further purified by column chromatography on silica gel to give the desired product.

$\delta_H$(CDCl$_3$) 6.87 (s, 2H), 3.75 (m, 4H), 2.78 (s 2H), 2.64 (s, 2H), 2.33 (m, 4H), 2.28 (s, 3H), 1.74 (m, 4H), 1.07 (t, 6H), 0.79 (s, 9H)

EXAMPLE 8

Preparation of 9-(2,6-diethyl-4-methylphenyl)-10-prop-2-ynyloxy-3-oxaspiro[5.5]undec-9-en-8-one (Compound Number P31 in Table T2)

A solution of propargyl bromide (0.043 g, 0.36 mmol) in acetone (2 ml) is added dropwise to a mixture of 9-(2,6-diethyl-4-methylphenyl)-3-oxaspiro[5.5]undecane-8,10-dione (0.10 g, 0.3 mmol) and potassium carbonate (0.05 g, 0.36 mmol) in acetone (3 ml) and the reaction is refluxed overnight. The solvent is evaporated in vacuo, and the residue is taken up in ethyl acetate and washed with 2 N aqueous sodium hydroxide solution. The organic phase is concentrated in vacuo, and the residue is further purified by column chromatography on silica gel to give the desired compound as a colourless gum.

$\delta_H$ (CDCl$_3$) 6.92 (s, 2H), 4.50 (s, 2H), 3.76 (t, 4H), 2.85 (s, 2H), 2.60 (s, 2H), 2.56 (t, 1H), 2.32 (m, 7H), 1.74 (t, 4H), 1.07 (t, 6H)

Additional compounds in Table T2 below were prepared by similar methods using appropriate starting materials.

TABLE T2

| Compound Number | Structure | ¹H nmr (CDCl₃ unless stated) or other physical data |
|---|---|---|
| P1 | 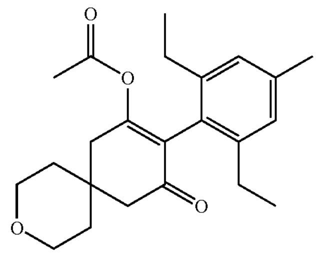 | δ 6.89 (s, 2H), 3.75 (m, 4H), 2.80 (s, 2H), 2.64 (s, 2H), 2.35-2.28 (m, 7H), 1.89 (s, 3H), 1.74 (m, 4H), 1.07 (t, 6H) |
| P2 | 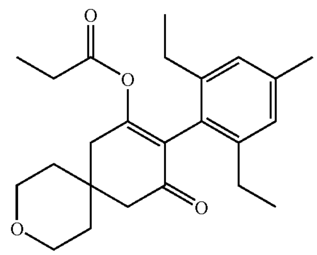 | δ 6.88 (s, 2H), 3.75 (m, 4H), 2.80 (s, 2H), 2.64 (s, 2H), 2.35-2.29 (m, 7H), 2.14 (q, 2H), 1.75 (m, 4H), 1.06 (t, 6H), 0.84 (t, 3H) |
| P3 | 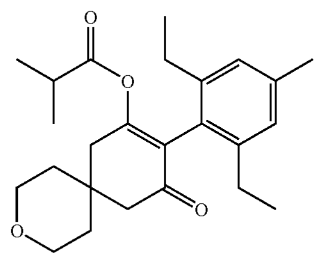 | δ 6.88 (s, 2H), 3.75 (m, 4H), 2.79 (s, 2H), 2.65 (s, 2H), 2.40-2.26 (m, 8H), 1.75 (m, 4H), 1.06 (t, 6H), 0.82 (d, 6H) |
| P4 | 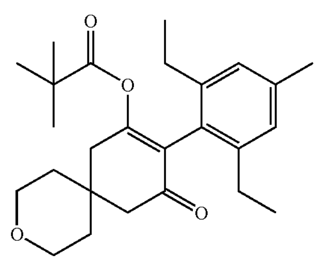 | δ 6.87 (s, 2H), 3.76 (t, 4H), 2.78 (s, 2H), 2.65 (s, 2H), 2.39-2.25 (m, 4H), 2.28 (s, 3H), 1.83-1.67 (m, 4H), 1.07 (t, 6H), 0.88 (s, 9H) |
| P5 | 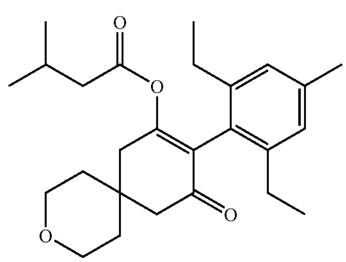 | δ 6.87 (s, 2H), 3.75 (m, 4H), 2.78 (s 2H), 2.64 (s, 2H), 2.37-2.27 (m, 7H), 2.03 (d, 2H), 1.75 (m, 5H), 1.07 (t, 6H), 0.67 (d, 6H) |
| P6 | 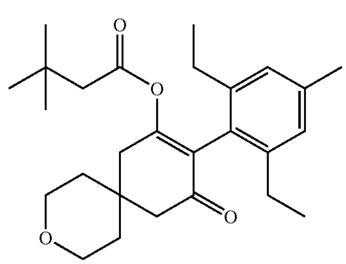 | δ 6.87 (s, 2H), 3.75 (m, 4H), 2.78 (s 2H), 2.64 (s, 2H), 2.33 (m, 4H), 2.28 (s, 3H), 1.74 (m, 4H), 1.07 (t, 6H), 0.79 (s, 9H) |

TABLE T2-continued

| Compound Number | Structure | $^1$H nmr (CDCl$_3$ unless stated) or other physical data |
|---|---|---|
| P7 | 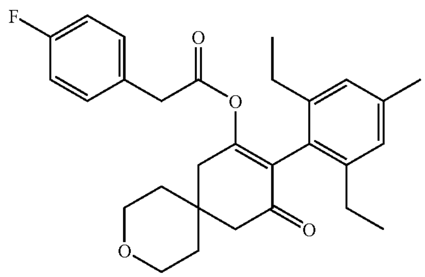 | δ 6.84-6.74 (m, 6H), 3.74 (m, 4H), 3.41 (s, 2H), 2.79 (s, 2H), 2.62 (s, 2H), 2.34 (s, 3H), 2.31-2.13 (m, 4H), 1.73 (m, 4H), 0.98 (t, 3H) |
| P8 | 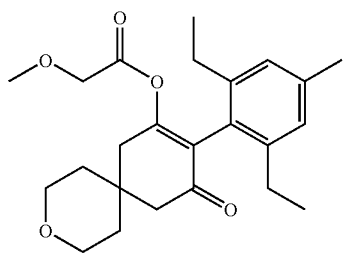 | δ 6.89 (s, 2H), 3.79 (s, 2H), 3.76 (m, 4H), 3.13 (s, 3H), 2.82 (s, 2H), 2.66 (s, 2H), 2.37-2.27 (m, 7H), 1.76 (m, 4H), 1.07 (t, 6H) |
| P9 | 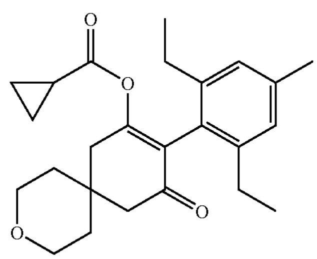 | δ 6.90 (s, 2H), 3.75 (m, 4H), 2.82 (s, 2H), 2.63 (s, 2H), 2.38-2.23 (m, 7H), 1.74 (m, 4H), 1.42 (m, 1H), 1.06 (t, 6H), 0.78-0.65 (m, 4H) |
| P10 | 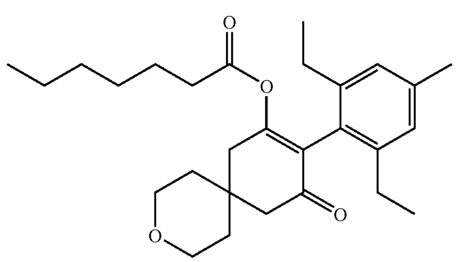 | δ 6.88 (s, 2H), 3.76 (m, 4H), 2.79 (s, 2H), 2.64 (s, 2H), 2.37-2.27 (m, 7H), 1.75 (m, 4H), 1.40-1.15 and 1.07 (m and t, 10H), 0.85 (t, 3H) |
| P11 | 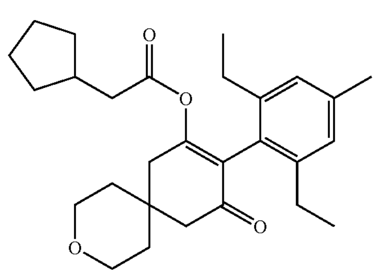 | δ 6.88 (s, 2H), 3.76 (m, 4H), 2.79 (s, 2H), 2.64 (s, 2H), 2.38-2.25 (m, 7H), 2.15 (d, 2H), 1.75 (m, 6H), 1.44 (m, 6H), 1.07 (t, 6H), 0.84 (m, 2H) |

TABLE T2-continued

| Compound Number | Structure | ¹H nmr (CDCl₃ unless stated) or other physical data |
|---|---|---|
| P12 | 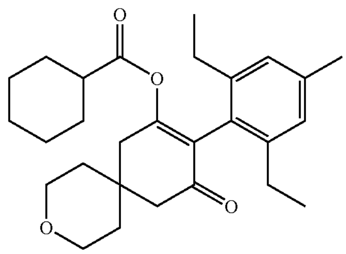 | δ 6.88 (s, 2H), 3.75 (m, 4H), 2.78 (s, 2H), 2.64 (s, 2H), 2.38-2.24 (m, 7H), 2.15 (m, 1H), 1.75 (m, 4H), 1.53-1.41 (br m, 6H), 1.15-1.03 (m and t, 10H) |
| P13 | 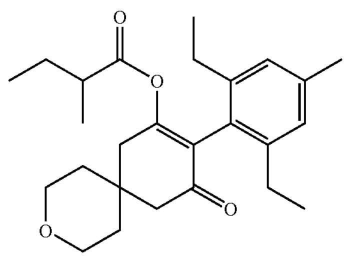 | δ 6.87 (s, 2H), 3.75 (m, 4H), 2.75 (s, 2H), 2.65 (s, 2H), 2.32 (m, 4H), 2.29 (s, 3H), 2.20 (m, 1H), 1.75 (m, 4H), 1.30 (m, 1H), 1.18 (m, 1H), 1.07 (t, 6H), 0.82 (d, 3H), 0.62 (t, 3H) |
| P14 | 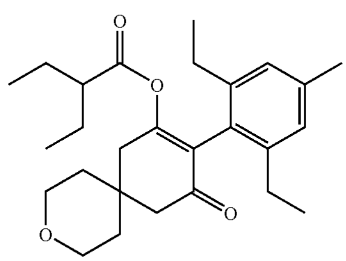 | δ 6.86 (s, 2H), 3.76 (m, 4H), 2.77 (s, 2H), 2.65 (s, 2H), 2.33 (m, 4H), 2.28 (s, 3H), 2.05 (m, 1H), 1.75 (m, 4H), 1.30 (m, 4H), 1.07 (t, 6H), 0.60 (t, 6H) |
| P15 | 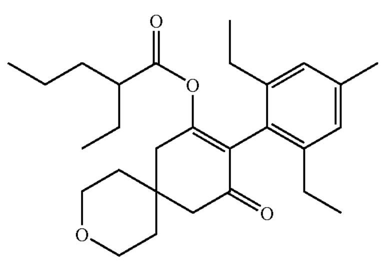 | δ 6.87 (s, 2H), 3.76 (m, 4H), 2.76 (s, 2H), 2.65 (s, 2H), 2.60-2.15 (m, 8H), 1.85-0.70 (m, 24H) |
| P16 | 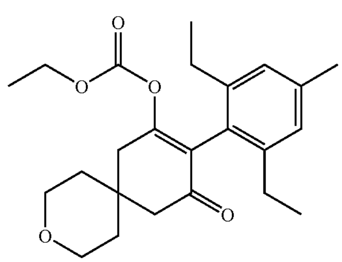 | δ 6.90 (s, 2H), 4.11 (q, 2H), 3.76 (m, 4H), 2.84 (s, 2H), 2.65 (s, 2H), 2.32 (m, 7H), 1.75 (m, 4H), 1.20 (t, 3H), 1.07 (t, 6H) |
| P17 | 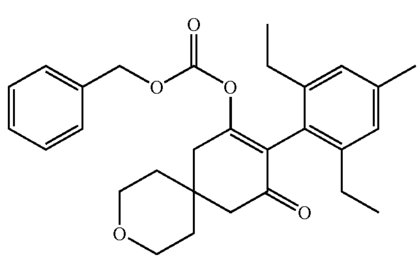 | δ 7.34 (m, 3H), 7.19 (m, 2H), 6.88 (s, 2H), 5.06 (s, 2H), 3.74 (m, 4H), 2.82 (s, 2H), 2.64 (s, 2H), 2.34-2.24 (m, 7H), 1.74 (m, 4H), 1.04 (t, 6H) |

TABLE T2-continued

| Compound Number | Structure | $^1$H nmr (CDCl$_3$ unless stated) or other physical data |
|---|---|---|
| P18 | 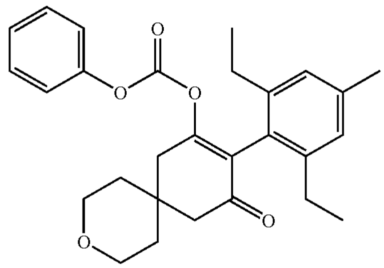 | δ 7.30-7.20 (m, 3H), 6.95 (s, 2H), 6.85 (m, 2H), 3.76 (m, 4H), 2.91 (s, 2H), 2.67 (s, 2H), 2.37-2.31 (m, 7H), 1.76 (m, 4H), 1.07 (t, 6H) |
| P19 | 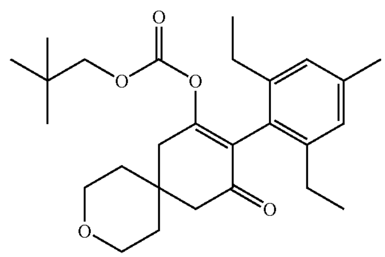 | δ 6.89 (s, 2H), 3.75 (m, 4H), 3.72 (s, 2H), 2.82 (s, 2H), 2.62 (s, 2H), 2.33 (m, 4H), 2.30 (s, 3H), 1.75 (m, 4H), 1.08 (s, 6H), 0.79 (9H) |
| P20 | 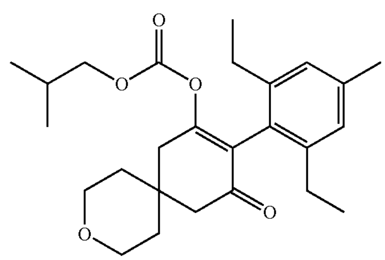 | δ 6.90 (s, 2H), 3.81 (d, 2H), 3.76 (m, 4H), 2.83 (s, 2H), 2.65 (s, 2H), 2.38-2.30 (m, 7H), 1.90-1.70 (m, 5H), 1.07 (t, 6H), 0.80 (d, 6H) |
| P21 | 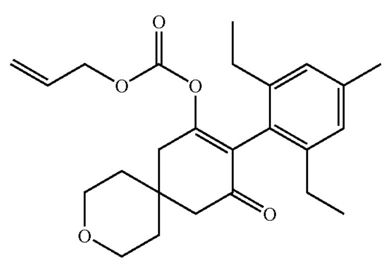 | δ 6.90 (s, 2H), 5.81-5.72 (m, 1H), 5.22-5.16 (m, 2H), 4.53 (d, 2H), 3.76 (m, 4H), 2.84 (s, 2H), 2.65 (s, 2H), 2.35-2.29 (m, 7H), 1.75 (m, 4H), 1.07 (t, 6H) |
| P22 | 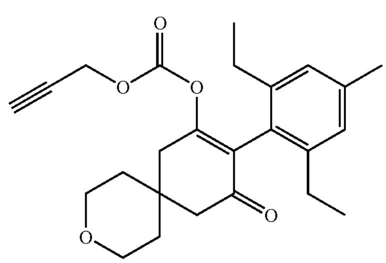 | δ 6.90 (s, 2H), 4.62 (s, 2H), 3.76 (m, 4H), 2.86 (s, 2H), 2.65 (s, 2H), 2.52 (m, 1H), 2.35-2.29 (m, 7H), 1.75 (m, 4H), 1.07 (t, 6H) |
| P23 | 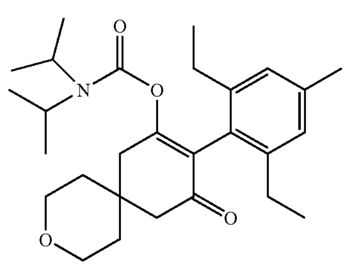 | δ 6.86 (s, 2H), 3.76 (m, 5H), 3.49 (m, 1H), 2.91 (s, 2H), 2.64 (s, 2H), 2.36 (m, 4H), 2.27 (s, 3H), 1.75 (m, 4H), 1.14 (d, 6H), 1.06 (t, 6H), 0.77 (d, 6H) |

TABLE T2-continued

| Compound Number | Structure | ¹H nmr (CDCl₃ unless stated) or other physical data |
|---|---|---|
| P24 | 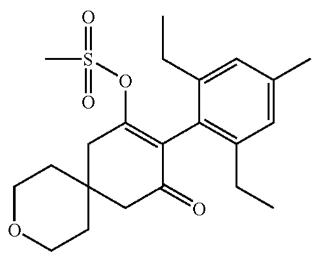 | δ 6.94 (s, 2H), 3.76 (m, 4H), 2.96 (s, 2H), 2.65 (s, 2H), 2.44 (s, 3H), 2.36 (m, 4H), 2.31 (s, 3H), 1.73 (m, 4H), 1.11 (t, 6H) |
| P25 | 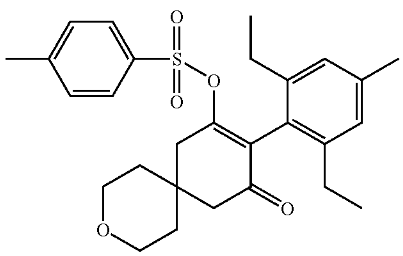 | δ 7.10 (ABq, 4H), 6.79 (s, 2H), 3.77 (m, 4H), 2.76 (s, 2H), 3.06 (s, 2H), 2.65 (s, 2H), 2.39 (s, 3H), 2.31 (s, 3H), 2.25 (q, 4H), 1.75 (m, 4H), 1.02 (t, 6H) |
| P26 | 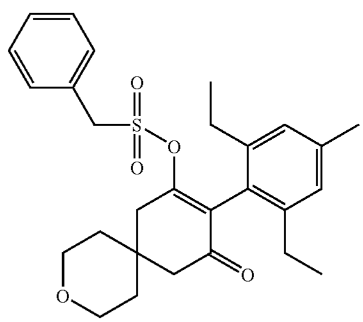 | δ 7.35-7.23 (m, 2H), 7.00 (s, 2H), 6.82 (d, 2H), 3.86 (s, 2H), 3.72 (m, 4H), 2.93 (s, 2H), 2.62 (s, 2H), 2.38-2.31 (m, 7H), 1.69 (m, 4H), 1.08 (t, 6H) |
| P27 | 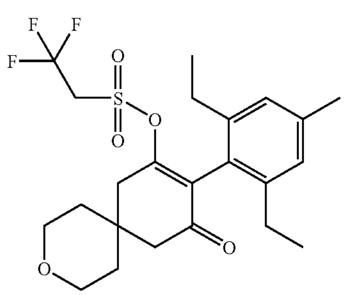 | δ 6.98 (s, 2H), 3.76 (m, 4H), 2.92 (s, 2H), 2.88 (q, 2H), 2.67 (s, 2H), 2.45-2.27 (m and s, 7H), 1.74 (m, 4H), 1.11 (t, 6H) |
| P28 | 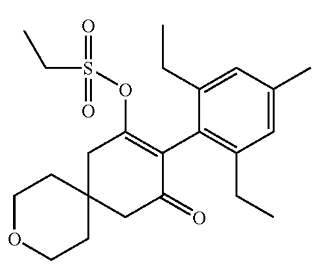 | δ 6.92 (s, 2H), 3.76 (m, 4H), 3.02 (s, 2H), 2.65 (m, 4H), 2.34 (m, 4H), 2.31 (s, 3H), 1.74 (m, 4H), 1.10 (t, 6H), 0.89 (t, 3H) |

TABLE T2-continued

| Compound Number | Structure | $^1$H nmr (CDCl$_3$ unless stated) or other physical data |
|---|---|---|
| P29 | 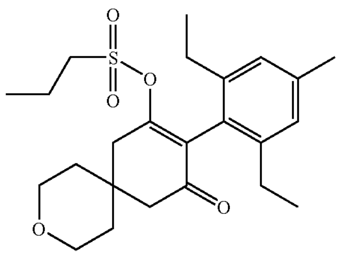 | δ 6.93 (s, 2H), 3.76 (t, 4H), 2.99 (s, 2H), 2.64 (s, 2H), 2.49 (m, 2H), 2.36 (m, 4H), 2.32 (s, 3H), 1.73 (m, 4H), 1.33 (m, 2H), 1.10 (t, 6H), 0.71 (t, 3H) |
| P30 | 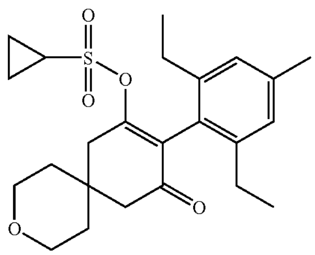 | δ 6.92 (s, 2H), 3.76 (t, 4H), 2.99 (s, 2H), 2.65 (s, 2H), 2.38 (m, 4H), 2.30 (s, 3H), 1.83-1.72 (m, 5H), 1.11 (t, 6H), 0.96 (m, 2H), 0.71 (m, 2H) |
| P31 | 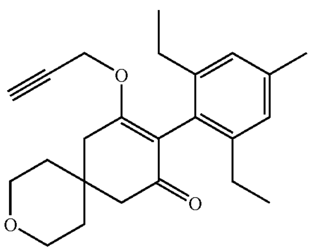 | δ 6.92 (s, 2H), 4.50 (s, 2H), 3.76 (t, 4H), 2.85 (s, 2H), 2.60 (s, 2H), 2.56 (t, 1H), 2.32 (m, 7H), 1.74 (t, 4H), 1.07 (t, 6H) |
| P32 | 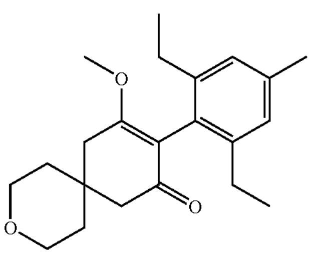 | δ 6.91 (s, 2H), 3.76 (m, 4H), 3.64 (s, 3H), 2.66 (s, 2H), 2.60 (s, 2H), 2.31 (m, 7H), 1.73 (m, 4H), 1.07 (t, 6H) |
| P33 | 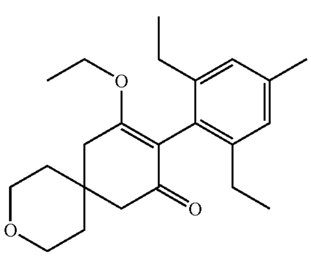 | δ 6.89 (s, 2H), 3.87 (q, 2H), 3.76 (m, 4H), 2.65 (s, 2H), 2.59 (s, 2H), 2.31 (m, 7H0, 1.72 (m, 4H), 1.14 (t, 3H), 1.06 (t, 6H) |
| P34 | 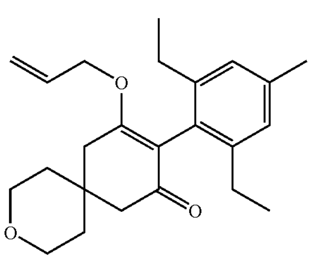 | δ 6.90 (s, 2H), 5.83-5.73 (m, 1H), 5.20-5.13 (m, 2H), 4.39 (d, 2H), 3.74 (m, 4H), 2.69 (s, 2H), 2.58 (s, 2H), 2.31 (m, 7H), 1.71 (m, 4H), 1.07 (t, 6H) |

TABLE T2-continued

| Compound Number | Structure | [1]H nmr (CDCl$_3$ unless stated) or other physical data |
|---|---|---|
| P35 | 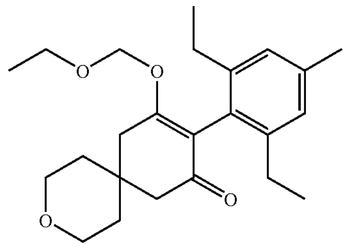 | δ 6.91 (s, 2H), 5.02 (s, 2H), 3.76 (m, 4H), 3.55 (q, 2H), 2.83 (s, 2H), 2.59 (s, 2H), 2.32 (s, 7H), 1.73 (t, 4H), 1.16 (t, 3H), 1.06 (t, 6H) |
| P36 | 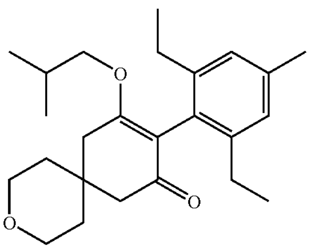 | δ 6.87 (s, 2H), 3.76 (m, 4H), 3.56 (d, 2H), 2.64 (s, 2H), 2.59 (s, 2H), 2.30 (m, 7H), 1.72 (m, 4H), 1.05 (m and t, 7H), 0.73 (d, 6H) |
| P37 | 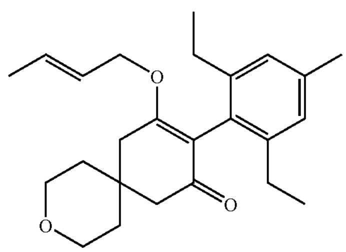 | δ 6.90 (s, 2H), 5.67-5.39 (2 × m, 2H), 4.43 (d, 1H), 4.29 (d, 1H), 3.74 (m, 4H), 2.68 (s, 2H), 2.57 (s, 2H), 2.31 (m, 7H), 1.69 (m, 6H), 1.60 (m, 1H), 1.07 (t, 6H) |
| P38 | 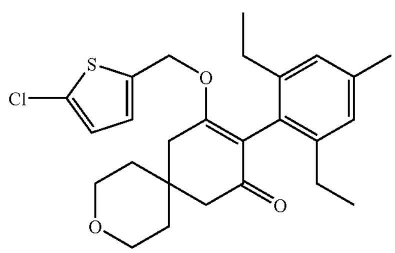 | δ 6.92 (s, 2H), 6.68 (ABq 2H), 4.80 (s, 2H), 3.71 (m, 4H), 2.69 (s, 2H), 2.58 (s, 2H), 2.33 (m, 7H), 1.69 (m, 4H), 1.08 (t, 6H) |
| P41 | 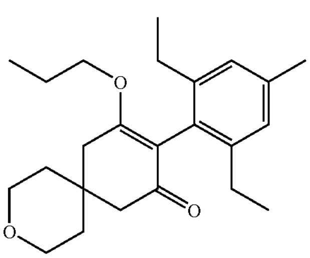 | δ 6.87 (s, 2H), 3.75 (m, 4H), 2.64 (s, 2H), 2.59 (s, 2H), 2.30 (m, 7H), 1.71 (m, 4H), 1.50 (m, 2H), 1.05 (t, 6H), 0.76 (t, 3H) |
| P42 | 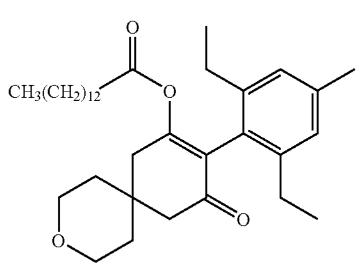 | δ 6.88 (s, 2H), 3.76 (m, 4H), 2.79 (s, 2H), 2.64 (s, 2H), 2.30 (m, 7H), 2.12 (t, 2H), 1.74 (m, 4H), 1.40-1.05 (br m, 22H); 1.07 (t, 6H), 0.88 (t, 3H) |

TABLE T2-continued

| Compound Number | Structure | ¹H nmr (CDCl₃ unless stated) or other physical data |
|---|---|---|
| P43 | CH₃(CH₂)₈—C(=O)O— [spiro tetrahydropyran cyclohexenone with 2,6-diethyl-4-methylphenyl] | δ 6.88 (s, 2H), 3.76 (m, 4H), 2.79 (s, 2H), 2.64 (s, 2H), 2.30 (m, 7H), 2.12 (t, 2H), 1.75 (m, 4H), 1.35-095 (br m, 14H); 1.07 (t, 6H), 0.89 (t, 3H) |
| P44 | CH₃(CH₂)₁₀—C(=O)O— [spiro tetrahydropyran cyclohexenone with 2,6-diethyl-4-methylphenyl] | δ 6.88 (s, 2H), 3.76 (m, 4H), 2.79 (s, 2H), 2.64 (s, 2H), 2.30 (m, 7H), 2.12 (t, 2H), 1.75 (m, 4H), 1.35-0.95 (br m, 18H); 1.07 (t, 6H), 0.89 (t, 3H) |
| P45 | CH₃(CH₂)₁₄—C(=O)O— [spiro tetrahydropyran cyclohexenone with 2,6-diethyl-4-methylphenyl] | δ 6.88 (s, 2H), 3.75 (m, 4H), 2.79 (s, 2H), 2.64 (s, 2H), 2.30 (m, 7H), 2.12 (t, 2H), 1.75 (m, 4H), 1.35-0.95 (br m, 26H); 1.07 (t, 6H), 0.89 (t, 3H) |
| P46 | MeO₂C—(CH₂)₆—C(=O)O— [spiro tetrahydropyran cyclohexenone with 2,6-diethyl-4-methylphenyl] | δ 6.88 (s, 2H), 3.76 (m, 4H), 3.67 (s, 3H), 2.79 (s, 2H), 2.64 (s, 2H), 2.35-2.24 (m, 9H), 2.13 (t, 2H), 1.74 (m, 4H), 1.56-1.51 (m, 2H), 1.25 (m, 2H), 1.16-0.98 (t and m, 10H) |
| P47 | CH₂=CH—(CH₂)₈—C(=O)O— [spiro tetrahydropyran cyclohexenone with 2,6-diethyl-4-methylphenyl] | δ 6.88 (s, 2H), 5.84-5.76 (m, 1H), 5.02-4.92 (m, 2H), 3.76 (m, 4H), 2.79 (s, 2H), 2.29 (s, 2H), 2.29 (m, 7H), 2.12 (t, 2H), 2.05 (m, 2H), 1.76 (m, 4H), 1.40-0.96 (t and m, 18H) |
| P48 | CH₃(CH₂)₇CH=CH—(CH₂)₇—C(=O)O— [spiro tetrahydropyran cyclohexenone with 2,6-diethyl-4-methylphenyl] | δ 6.88 (s, 2H), 5.34 (m, 2H), 3.76 (m, 4H), 2.79 (s, 2H), 2.64 (s, 2H), 2.35-2.24 (m, 9H), 2.01 (br m, 4H), 1.75 (m, 4H), 1.4-0.95 (t and m, 28H), 0.88 (t, 3H) |

US 8,084,649 B2

TABLE T2-continued

| Compound Number | Structure | $^1$H nmr (CDCl$_3$ unless stated) or other physical data |
|---|---|---|
| P49 | 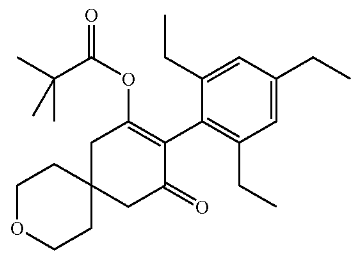 | δ 6.88 (s, 2H), 3.76 (m, 4H), 2.78 (s, 2H), 2.65 (s, 2H), 2.58 (q, 2H), 2.33 (m, 4H), 1.76 (m, 4H), 1.18 (t, 3H), 1.07 (t, 6H), 0.85 (s, 9H) |
| P50 | 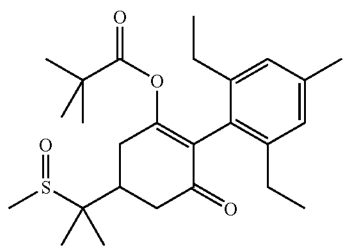 | δ 6.88 (s, 2H), 3.11-2.49 (m, 5H), 2.47 (s, 3H), 2.40-2.21 (m, 4H), 2.28 (s, 3H), 1.37 (s, 3H), 1.21 and 1.19 (s, 3H), 1.14-1.02 (m, 6H), 0.87 (s, 9H) |
| P51 | 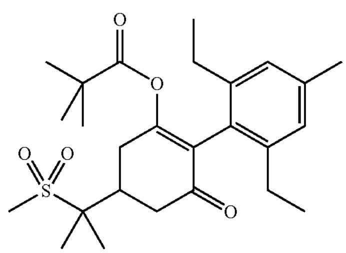 | δ 6.88 (s, 2H), 3.08-2.80 (m, 4H), 2.90 (s, 3H), 2.64-2.52 (m, 1H), 2.40-2.24 (m, 4H), 2.28 (s, 3H), 1.51 (s, 3H), 1.50 (s, 3H), 1.15-1.02 (m, 6H), 0.86 (s, 9H) |
| P52 | 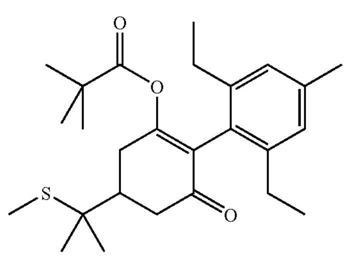 | δ 6.87 (s, 2H), 2.94-2.71 (m, 3H), 2.56-2.25 (m, 6H), 2.28 (s, 3H), 2.07 (s, 3H), 1.38 (s, 3H), 1.35 (s, 3H), 1.14-1.02 (m, 6H), 0.87 (s, 9H) |
| P53 | 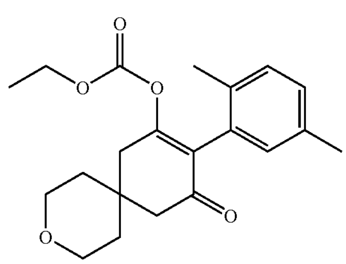 | δ 7.08 (d, 1H), 7.03 (d, 1H), 6.76 (s, 1H), 4.18-4.02 (m, 2H), 3.74 (t, 4H), 2.77 (d, 1H), 2.75 (d, 1H), 2.63 (s, 2H), 2.27 (s, 3H), 2.04 (s, 3H), 1.82-1.63 (m, 4H), 1.17 (t, 3H) |
| P54 | 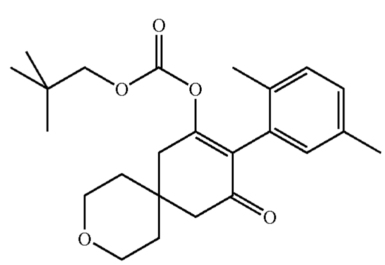 | δ 7.05 (d; 1H), 6.99 (d, 1H), 6.73 (s, 1H), 3.74 (m, 4H), 2.76 (d, 1H), 2.67 (d, 1H), 2.62 (m, 2H), 2.24 (s, 3H), 2.07 (s, 2H), 2.04 (s, 3H), 1.83-1.64 (m, 4H), 0.76 (s, 9H) |

TABLE T2-continued

| Compound Number | Structure | ¹H nmr (CDCl₃ unless stated) or other physical data |
|---|---|---|
| P55 | 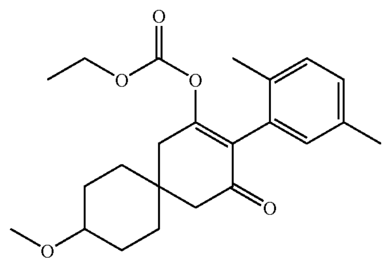 | δ 7.07 (d, 1H), 7.02 (d, 1H), 6.77 (s, 1H), 4.17-4.01 (m, 2H), 3.35 and 3.33 (2 × s, 3H), 3.26 (m, 1H), 2.75-2.50 (m, 4H), 2.26 (s, 3H), 2.05 (s, 3H), 1.97-1.70 (m, 4H), 1.70-1.34 (m, 4H), 1.17 (t, 3H) |
| P56 | 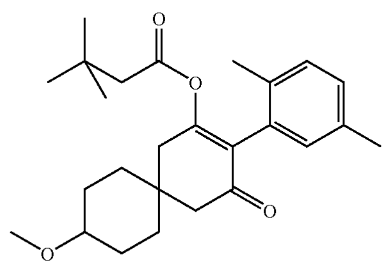 | δ 7.04 (d, 1H), 6.97 (d, 1H), 6.74 (s, 1H), 3.35 and 3.33 (2 × s, 3H), 3.26 (m, 1H), 2.69-2.48 (m, 4H), 2.24 (s, 3H), 2.05 (s, 2H), 2.04 (s, 3H), 1.98-1.73 (m, 4H), 1.69-1.36 (m, 4H), 0.75 (s, 9H) |
| P57 | 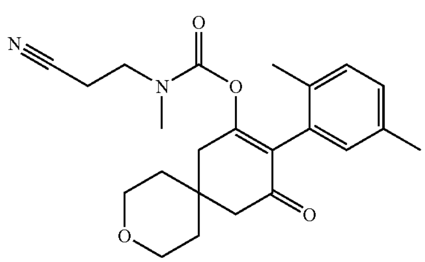 | M.p. 108-114° C.<br>MS (electrospray ES+): 397 (M + H)⁺ |
| P58 | 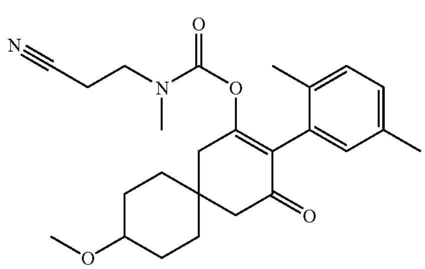 | Oil<br>MS (electrospray ES+): 425 (M + H)⁺ |
| P59 | 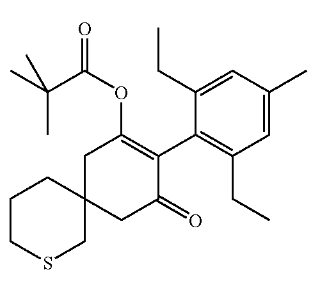 | δ 6.87 (s, 2H), 2.98 (m, 2H), 2.71 (m, 4H), 2.58 (m, 2H), 2.31 (m, 7H), 1.93 (m, 2H), 1.81 (m, 1H), 1.56 (m, 1H), 1.08 (t, 6H), 0.80 (s, 9H) |

TABLE T2-continued

| Compound Number | Structure | ¹H nmr (CDCl₃ unless stated) or other physical data |
|---|---|---|
| P60 | 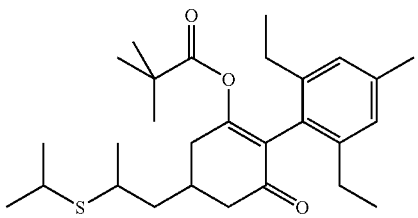 | δ 6.87 (d, 2H), 3.02 (m, 1H), 2.91 (m, 1H), 2.55-2.79 (m, 4H), 2.23-2.45 (m, 5H), 2.28 (s, 3H), 1.61-1.77 (m, 2H), 1.33 (dd, 3H), 1.28 (m, 6H), 1.08 (m, 6H), 0.88 (s, 9H) |

Experimental procedures to key intermediates.

EXAMPLE 1A

Preparation of 2,6-diethyl-4-methylphenylboronic acid

To a solution at −78° C. of 25 g (110 mmol) of 2,6-diethyl-4-methylbromobenzene (preparation described in WO 2000078712) in 240 ml of tetrahydrofuran is added a ~1.6 M solution of butyllithium in hexanes (75 ml, 120 mmol) dropwise over 10 minutes. The mixture is stirred for 10 minutes at −78° C., then trimethylborate (24.6 ml, 22.9 g; 220 mmol) is added at once and stirring is continued at −78° C. for 30 minutes. The cooling bath is removed and the solution is allowed to warm up to room temperature over 1 hour and quenched with 2N aqueous hydrochloric acid (140 ml).

The organic layer is separated, and the aqueous phase is extracted three times with diethyl ether:hexane 1:1. The organic extracts are combined, dried over anhydrous sodium sulfate, filtered and the filtrate concentrated in vacuo. The oily residue is taken up in hexane under stirring, and the white solid is collected by filtration to give 2,6-diethyl-4-methylphenylboronic acid. The filtrate is concentrated and purified by column chromatography on silica gel give a further quantity of desired product. A combined yield of 16.6 g (78%) of 2,6-diethyl-4-methylphenylboronic acid is obtained.

EXAMPLE 1B

Preparation of 5-(4-chlorophenyl)-2-methylphenylboronic acid

Step 1

4-Chlorophenylboronic acid (20.2 g, 0.13 mol) and tetrakis(triphenylphosphine)palladium (0) (3.7 g, 0.003 mol) are added to a solution of 5-bromo-2-methylaniline (20 g, 0.1 mol) in 1,2-dimethoxyethane (200 ml). After stirring the reaction mixture for 15 minutes at 20° C., a solution of 20% aqueous sodium carbonate (300 ml) is added to the mixture, and the resulting mixture is refluxed for 24 hours. The reaction mixture is cooled to room temperature, diluted with water (600 ml) and extracted using ethyl acetate. The combined organic extracts are dried over anhydrous sodium sulfate, filtered and the filtrate evaporated in vacuo. The residue is further purified by column chromatography on silica gel, eluting with 7% ethyl acetate in hexane to give 5-(4-chlorophenyl)-2-methylaniline (21.0 g).

Step 2

Hydrobromic acid (48% wt. in water, 120 ml) is added dropwise to a suspension of 5-(4-chlorophenyl)-2-methylaniline (21 g, 0.09 mol) in water (80 ml), and the mixture stirred until the solid is dissolved. The mixture is cooled to −5° C. and a solution of sodium nitrite (10.12 g, 0.14 mol) in water (50 ml) is added dropwise, maintaining the temperature at 0-5° C. The reaction mixture is stirred for 1 hour, then added to a pre-cooled solution of cuprous bromide (17.9 g, 0.12 mol) in hydrobromic acid (48% wt. in water, 120 ml) at 0° C. The reaction mixture is stirred and allowed to warm to room temperature overnight. The mixture is extracted with ethyl acetate, and the organic extracts are combined, dried over anhydrous sodium sulfate, filtered and the filtrate concentrated in vacuo. The residue is further purified by column chromatography on silica gel, eluting with 2% ethyl acetate in hexane to give 5-(4-chlorophenyl)-2-methyl-1-bromobenzene (15.0 g).

Step 3

5-(4-chlorophenyl)-2-methyl-1-bromobenzene (5.0 g, 0.02 mol) is dissolved in THF (125 ml), and the temperature is brought to −78° C. n-Butyllithium (1.33 molar solution in hexanes, 17.3 ml,) is added dropwise over 30 minutes, maintaining the temperature at around −78° C. The reaction mixture is stirred for one and half hours at −78° C., then trimethylborate (2.58 g, 0.024 mol) is added dropwise and the reaction mixture stirred for three and half hours, allowing it to warm to 0° C. A solution of 2N aqueous hydrochloric acid (50 ml) is then added dropwise, and once the addition is complete the mixture is stirred for 2 hours. The mixture is concentrated in vacuo to remove most of the tetrahydrofuran, then diluted with water (~80 ml) and extracted with diethyl ether. The organic extracts are combined, dried over anhydrous sodium sulfate, filtered and the filtrate evaporated in vacuo. The residue is further purified by flash column chromatography on silica gel, eluting with 7% ethyl acetate in hexane to give 5-(4-chlorophenyl)-2-methylphenylboronic acid (2.5 g).

EXAMPLE 1C

Preparation of 5-(4-chlorophenyl)-2-ethylphenylboronic acid

Step 1

Ammonium nitrate (39.6 g, 0.49 mol) is added portionwise to a chilled (ice-bath) solution of 4-ethylaniline (20 g, 0.16 mol) in concentrated sulfuric acid (100 ml, maintaining the temperature −10° to 0° C. by external cooling. The reaction mixture is stirred for two hours, then poured onto crushed ice, and the precipitate is collected by filtration. The solid is taken up in water, the solution made neutral by addition of dilute aqueous sodium hydroxide solution and the extracted with ethyl acetate. The organic extracts are combined, dried over anhydrous sodium sulfate, filtered and the filtrate evaporated in vacuo to give 4-ethyl-3-nitroaniline (20 g).

Step 2

Hydrobromic acid (48% wt. in water, 240 ml) is added dropwise to a suspension of 4-ethyl-3-nitroaniline (20 g, 0.12 mol) in water (80 ml), and the mixture stirred until the solid is dissolved. The mixture is cooled to −5° C. and a solution of sodium nitrite (19.8 g, 0.28 mol) in water (100 ml) is added dropwise, maintaining the temperature at 0-5° C. Once the addition is complete, the cooling bath is removed and the reaction mixture is stirred for one hour at room temperature. The mixture is added dropwise to a pre-cooled solution of cuprous bromide (22.4 g, 0.16 mol) in hydrobromic acid (48% wt. in water) at 0° C. The reaction mixture is stirred and allowed to warm to room temperature over three hours. The mixture is extracted with diethyl ether, and the organic extracts are combined, dried over anhydrous sodium sulfate, filtered and the filtrate concentrated in vacuo. The residue is further purified by column chromatography on silica gel, eluting with hexane to give 4-bromo-1-ethyl-2-nitrobenzene (18 g)

Step 3

A solution of ammonium chloride (12.5 g, 0.2 mol) in water (30 ml) is added to a mixture of zinc dust (35.7 g, 0.5 mol) and 4-bromo-1-ethyl-2-nitrobenzene (18 g, 0.07 mol) in methanol (720 ml) and water (180 ml). The reaction mixture is refluxed for one hour, then cooled to room temperature and filtered through a plug of diatomaceous earth. The filtrate is concentrated in vacuo, then diluted with water and extracted with ethyl acetate. The combined organic extracts are washed with water and brine, dried over anhydrous sodium sulfate, filtered and the filtrate concentrated in vacuo to yield 5-bromo-2-ethylaniline (14 g), used without further purification in the next step.

Step 4

4-Chlorophenylboronic acid (13.2 g, 0.08 mol) and tetrakis (triphenylphosphine) palladium (0) (2.4 g, 0.002 mol) are added to a solution of 5-bromo-2-ethylaniline (14.1 g, 0.07 mol) in 1,2-dimethoxyethane (140 ml). After stirring the reaction mixture for 15 minutes at 20° C., a solution of 20% aqueous sodium carbonate (300 ml) is added to the mixture, and the resulting mixture is refluxed for 24 hours. The reaction mixture is cooled to room temperature, diluted with water and extracted using ethyl acetate. The combined organic extracts are dried over anhydrous sodium sulfate, filtered and the filtrate evaporated in vacuo. The residue is further purified by column chromatography on silica gel, eluting with 5% ethyl acetate in hexane to give 5-(4-chlorophenyl)-2-ethylaniline (14.3 g).

Step 5

Hydrobromic acid (48% wt. in water, 85 ml) is added dropwise to a suspension of 5-(4-chlorophenyl)-2-ethylaniline (14.3 g, 0.062 mol) in water (57 ml), and the mixture stirred. The mixture is cooled to −5° C. and a solution of sodium nitrite (5.07 g, 0.072 mol) in water (25 ml) is added dropwise, maintaining the temperature at 0-5° C. The reaction mixture is stirred for 1 hour, then added to a pre-cooled solution of cuprous bromide (9 g, 0.062 mol) in hydrobromic acid (48% wt. in water, 64 ml) at 0° C. The reaction mixture is stirred and allowed to warm to room temperature overnight. The mixture is diluted with water, extracted with diethyl ether, and the organic extracts are combined, dried over anhydrous sodium sulfate, filtered and the filtrate concentrated in vacuo. The residue is further purified by column chromatography on silica gel, eluting with 2% ethyl acetate in hexane to give 5-(4-chlorophenyl)-2-ethyl-1-bromobenzene (10 g).

Step 6

5-(4-chlorophenyl)-2-ethyl-1-bromobenzene (10 g, 0.03 mol) is dissolved in THF (250 ml), and the temperature is brought to −78° C. n-Butyllithium (1.33 molar solution in hexanes, 34.6 ml,) is added dropwise over 30 minutes, maintaining the temperature at around −78° C. The reaction mixture is stirred for one and half hours, then trimethylborate (4.9 g, 0.05 mol) is added dropwise and the reaction mixture stirred for two hours. A solution of 2N aqueous hydrochloric acid (100 ml) is added dropwise, and once the addition is complete the mixture is stirred for two hours. The mixture is concentrated to remove most of the tetrahydrofuran, then diluted with water and extracted with diethyl ether. The organic extracts are washed with water and brine, combined, dried over anhydrous sodium sulfate, filtered and the filtrate evaporated in vacuo. The residue is further purified by flash column chromatography on silica gel, eluting with 7% ethyl acetate in hexane to give 5-(4-chloro-phenyl)-2-methylphenylboronic acid (5.4 g).

EXAMPLE 1D

Preparation of 3,5-dimethylbiphenylboronic acid tert-Butyllithium (1.7 M solution in hexanes, 36.2 ml, 62.6 mmol) is added dropwise to a solution of 3,5-dimethylbiphenyl (7.27 g; 28 mmol) in dry tetrahydrofuran (150 ml) at −78° C. and stirred under an atmosphere of nitrogen for 30 minutes. Trimethyl borate (9.54 ml; 84 mmol) is added and the resulting mixture is stirred at −78° C. for 30 min and then allowed to warm to room temperature. The reaction mixture is acidified with aqueous hydrochloric acid and extracted with ether (2×150 ml). The organic layers are combined, dried over anhydrous magnesium sulfate, filtered and the filtrate evaporated in vacuo to give a yellow solid. The crude product is triturated with iso-hexane and filtered to give 3,5-dimethylbiphenylboronic acid (5.89 g) as a white powder.

EXAMPLE 1E

Preparation of 3,5-dimethylbiphen-4-yllead triacetate

To a solution of lead tetraacetate (4.3 g, 9.7 mmol) in dry chloroform (15 ml) at 40° C. is added 3,5-dimethylbiphen-4-ylboronic acid (2.0 g; 8.8 mmol) in one portion under an atmosphere of nitrogen. The mixture is stirred at 40° C. for 4 hours, and then is cooled to room temperature. The precipitate is removed by filtration, and the filtrate is then passed through a plug of potassium carbonate supported on diatomaceous earth to remove acetic acid. The filtrate is evaporated in vacuo to afford 3,5-dimethylbiphen-4-yllead triacetate (3.37 g).

BIOLOGICAL EXAMPLES

Monocotyledonous and dicotyledonous test plants were sown in sterilised standard soil in pots. After cultivation for one day (pre-emergence) or after 10 days cultivation (post-emergence) under controlled conditions in a glasshouse, the plants were sprayed with an aqueous spray solution derived from the formulation of the technical active ingredient in 0.6 ml acetone and 45 ml formulation solution containing 10.6% Emulsogen EL (Registry number 61791-12-6), 42.2% N-methylpyrrolidone, 42.2% dipropylene glycol monomethyl ether (Registry number 34590-94-8) and 0.2% X-77 (Registry number 11097-66-8). The test plants were then grown in a greenhouse under optimum conditions until, 14 or 15 days later for post-emergence and 20 days for pre-emergence, the test was evaluated (100=total damage to plant; 0=no damage to plant).

Test Plants:

*Alopecurus myosuroides* (ALOMY), *Avena fatua* (AVEFA), *Lolium perenne* (LOLPE), *Setaria faberi* (SETFA), *Digitaria sanguinalis* (DIGSA), *Echinochloa crus-galli* (ECHCG)

Pre-Emergence Activity

| Compound Number | Rate g/ha | ALOMY | AVEFA | LOLPE | SETFA | DIGSA | ECHCG |
|---|---|---|---|---|---|---|---|
| T1 | 500 | 60 | 30 | 70 | 70 | 70 | 100 |
| T2 | 500 | 80 | 70 | 100 | 90 | 100 | 100 |
| T3 | 500 | 40 | 50 | 60 | 100 | 100 | 100 |
| T4 | 500 | 70 | 70 | 70 | 100 | 100 | 100 |
| T5 | 500 | 70 | 10 | 60 | 30 | 70 | 40 |
| T6 | 500 | 20 | 30 | 0 | 10 | 10 | 10 |
| T7 | 500 | 100 | 100 | 100 | 100 | 100 | 100 |
| T8 | 500 | 100 | 80 | 100 | 100 | — | 100 |
| T9 | 500 | 30 | 30 | 0 | — | 40 | — |
| T10 | 500 | 100 | 70 | 100 | 100 | 100 | 100 |
| T11 | 500 | 80 | — | 100 | 90 | 90 | 80 |
| T12 | 500 | 70 | 20 | 40 | 0 | 0 | 30 |
| T13 | 500 | 100 | 70 | 100 | 80 | 100 | 80 |
| T14 | 500 | 90 | 100 | 100 | 100 | 100 | 100 |
| T15 | 500 | 100 | 80 | 100 | 90 | 100 | 100 |
| T16 | 500 | 90 | 70 | 100 | 100 | 100 | 90 |
| T17 | 500 | 90 | 90 | 100 | 100 | 100 | 100 |
| T18 | 500 | 20 | 10 | 10 | 40 | 60 | 70 |
| T19 | 250 | 70 | 70 | 80 | 50 | 90 | 80 |
| T20 | 500 | 100 | 100 | 100 | 100 | 100 | 100 |
| T21 | 500 | 100 | 100 | 100 | 100 | 100 | 100 |
| T22 | 500 | 100 | 100 | 100 | 100 | 100 | 100 |
| T23 | 500 | 80 | 70 | 80 | 70 | 100 | 100 |
| T24 | 500 | 100 | 80 | 100 | 100 | 100 | 100 |
| T25 | 500 | 100 | 100 | 100 | 100 | 100 | 100 |
| T26 | 500 | 90 | 20 | 90 | 70 | 100 | 100 |
| T27 | 500 | 100 | 100 | 100 | 100 | 100 | 100 |
| T28 | 500 | 70 | 100 | 100 | 100 | 100 | 100 |
| T29 | 500 | 100 | 90 | 100 | 100 | 100 | 100 |
| T30 | 500 | 80 | 80 | 90 | 100 | 100 | 100 |
| T31 | 500 | 80 | 80 | 100 | 100 | 100 | 100 |
| T32 | 500 | 90 | 80 | 100 | 100 | 100 | 100 |
| T35 | 500 | 90 | 80 | 80 | 80 | 90 | 70 |
| T36 | 500 | 100 | 90 | 100 | 100 | 100 | — |
| T37 | 500 | 100 | 90 | 100 | 100 | 100 | 100 |
| T38 | 500 | 90 | 70 | 100 | 60 | 70 | 70 |
| T39 | 500 | 70 | 70 | 80 | 70 | 90 | 60 |
| T40 | 500 | 80 | 50 | 90 | 60 | 50 | 70 |
| T41 | 500 | 90 | 60 | 100 | 80 | 100 | 80 |
| T52 | 500 | 90 | 100 | 100 | 70 | 70 | 10 |
| T53 | 500 | 60 | 80 | 90 | 30 | 100 | 100 |
| T54 | 500 | 100 | 80 | 100 | 80 | 100 | 100 |
| T55 | 500 | 100 | 90 | 100 | 90 | 100 | 100 |
| T65 | 500 | 90 | 60 | 70 | 100 | 100 | 100 |
| T68 | 500 | 90 | 70 | 100 | 30 | 100 | 70 |
| T69 | 500 | 0 | 30 | 60 | 70 | 100 | 70 |
| P1 | 500 | 100 | 100 | 100 | 100 | 100 | 100 |
| P2 | 500 | 100 | 100 | 100 | 100 | 100 | 100 |
| P3 | 500 | 100 | 100 | 100 | 100 | 100 | 100 |
| P4 | 500 | 100 | 100 | 100 | 100 | 100 | 90 |
| P5 | 500 | 100 | 100 | 100 | 100 | 100 | 100 |
| P6 | 500 | 100 | 90 | 100 | 70 | 100 | 70 |
| P7 | 500 | 40 | 80 | 100 | 100 | 100 | 70 |
| P8 | 500 | 100 | 90 | 100 | 100 | 100 | 100 |
| P9 | 500 | 100 | 100 | 100 | 100 | 100 | 100 |
| P10 | 500 | 100 | 100 | 100 | 100 | 100 | 100 |
| P11 | 500 | 100 | 90 | 90 | 100 | 100 | 90 |
| P12 | 500 | 100 | 100 | 100 | 100 | 100 | 100 |
| P13 | 500 | 100 | 100 | 100 | 100 | 100 | 100 |
| P14 | 500 | 100 | 100 | 100 | 100 | 100 | 90 |
| P15 | 500 | 0 | 90 | 100 | 70 | 90 | 60 |
| P16 | 500 | 100 | 100 | 100 | 100 | 100 | 100 |
| P17 | 500 | 100 | 100 | 100 | 100 | 100 | 100 |
| P18 | 500 | 100 | 100 | 100 | 100 | 100 | 80 |
| P19 | 500 | 100 | 100 | 100 | 100 | 100 | 100 |
| P20 | 500 | 100 | 100 | 100 | 100 | 100 | 100 |
| P21 | 500 | 100 | 100 | 100 | 100 | 100 | 100 |
| P22 | 500 | 100 | 100 | 100 | 100 | 100 | 100 |
| P24 | 500 | 80 | 80 | 80 | 90 | 70 | 50 |

| Compound Number | Rate g/ha | ALOMY | AVEFA | LOLPE | SETFA | DIGSA | ECHCG |
|---|---|---|---|---|---|---|---|
| P26 | 500 | 80 | 80 | 90 | 70 | 60 | 40 |
| P27 | 500 | 100 | 100 | 100 | 100 | 100 | 100 |
| P28 | 500 | 80 | 30 | 80 | 70 | 70 | 10 |
| P29 | 500 | 60 | 60 | 60 | 60 | 80 | 10 |
| P31 | 500 | 100 | 100 | 100 | 90 | 100 | 100 |
| P32 | 500 | 100 | 100 | 100 | 10 | 50 | 20 |
| P33 | 500 | 90 | 30 | 50 | 10 | 70 | 10 |
| P34 | 500 | 100 | 70 | 100 | 30 | — | 30 |
| P35 | 500 | 100 | 100 | 100 | 100 | — | — |
| P41 | 500 | 70 | 10 | 0 | 10 | 90 | 40 |
| P42 | 500 | 100 | 90 | 100 | — | — | 100 |
| P43 | 500 | 100 | 100 | 100 | — | — | 100 |
| P44 | 500 | 100 | 100 | 100 | 100 | 100 | 100 |
| P45 | 500 | 80 | 100 | 100 | 100 | 100 | 100 |
| P46 | 500 | 100 | 100 | 100 | 100 | 100 | 100 |
| P47 | 500 | 100 | 100 | 100 | 100 | 100 | 100 |
| P48 | 500 | 100 | 90 | 100 | 100 | 100 | 100 |
| P49 | 500 | 100 | 60 | 100 | 100 | 100 | 100 |
| P52 | 500 | 100 | 100 | — | 100 | 100 | 100 |
| P56 | 500 | 100 | 60 | 60 | 100 | 100 | 80 |
| P59 | 500 | 20 | 10 | 10 | 70 | 100 | 50 |
| P60 | 500 | 80 | 0 | 100 | 90 | 100 | 90 |

Post-Emergence Activity

| Compound Number | Rate g/ha | ALOMY | AVEFA | LOLPE | SETFA | DIGSA | ECHCG |
|---|---|---|---|---|---|---|---|
| T1 | 500 | 70 | 70 | 70 | 80 | 90 | 90 |
| T2 | 500 | 80 | 80 | 80 | 80 | 100 | 100 |
| T3 | 500 | 80 | 80 | 80 | 100 | 100 | 100 |
| T4 | 500 | 90 | 80 | 70 | 90 | 100 | 100 |
| T5 | 500 | 70 | 20 | 70 | 70 | 70 | 60 |
| T6 | 500 | 20 | 10 | 10 | 80 | 90 | 80 |
| T7 | 500 | 100 | 90 | 100 | 100 | 90 | 90 |
| T8 | 500 | 100 | 90 | 100 | 90 | 90 | 100 |
| T9 | 500 | 50 | 50 | 50 | 80 | 90 | 80 |
| T10 | 500 | 100 | 100 | 100 | 90 | 90 | 90 |
| T11 | 500 | 80 | 80 | 70 | 90 | 90 | 90 |
| T12 | 500 | 80 | 30 | 60 | 90 | 90 | 80 |
| T13 | 500 | 90 | 80 | 80 | 90 | 100 | 90 |
| T14 | 500 | 90 | 90 | 90 | 100 | 100 | 100 |
| T15 | 500 | 90 | 80 | 100 | 80 | 100 | 100 |
| T16 | 500 | 100 | 80 | 90 | 90 | 100 | 70 |
| T17 | 500 | 0 | 90 | 100 | 90 | 100 | 90 |
| T18 | 500 | 60 | 60 | 70 | 80 | 80 | 70 |
| T19 | 250 | 80 | 80 | 80 | 80 | 80 | 80 |
| T20 | 500 | 100 | 100 | 100 | 100 | 100 | 100 |
| T21 | 500 | 90 | 100 | 90 | 90 | 100 | 90 |
| T22 | 125 | 100 | 90 | 90 | 100 | 100 | 100 |
| T23 | 500 | 90 | 80 | 90 | 100 | 90 | 100 |
| T24 | 500 | 90 | 80 | 90 | 100 | 90 | 100 |
| T25 | 500 | 100 | 100 | 90 | 100 | 100 | 80 |
| T26 | 500 | 60 | 10 | 50 | 80 | 80 | 100 |
| T27 | 500 | 80 | 90 | 80 | 100 | 90 | 100 |
| T28 | 500 | 90 | 100 | 80 | 90 | 100 | 100 |
| T29 | 500 | 90 | 100 | 90 | 90 | 100 | 100 |
| T30 | 500 | 70 | 90 | 80 | 100 | 100 | 100 |
| T31 | 500 | 80 | 60 | 90 | 100 | 100 | 100 |
| T32 | 500 | 80 | 80 | 90 | 100 | 100 | 100 |
| T35 | 500 | 90 | 70 | 80 | 50 | 70 | 70 |
| T36 | 500 | 90 | 90 | 90 | 50 | 70 | 100 |
| T37 | 500 | 90 | 90 | 90 | 50 | 80 | 100 |
| T38 | 500 | 90 | 100 | 90 | 80 | 70 | 70 |
| T39 | 125 | 10 | 0 | 0 | 10 | 30 | 20 |
| T40 | 125 | 80 | 30 | 80 | 50 | 50 | 60 |
| T41 | 125 | 90 | 70 | 80 | 50 | 80 | 70 |
| T52 | 125 | 60 | 60 | 40 | 20 | 60 | 30 |
| T53 | 125 | 80 | 80 | 70 | 60 | 90 | 100 |
| T54 | 125 | 80 | 60 | 80 | 50 | 70 | 80 |
| T55 | 125 | 90 | 80 | 80 | 60 | 80 | 90 |
| T65 | 125 | 90 | 90 | 70 | 90 | 90 | 100 |
| T68 | 125 | 80 | 40 | 80 | 20 | 30 | 20 |

-continued

| Compound Number | Rate g/ha | ALOMY | AVEFA | LOLPE | SETFA | DIGSA | ECHCG |
|---|---|---|---|---|---|---|---|
| T69 | 125 | 20 | 10 | 50 | 0 | 0 | 0 |
| P1 | 125 | 50 | 60 | 30 | 30 | 50 | 50 |
| P2 | 125 | 80 | 90 | 80 | 70 | 100 | — |
| P3 | 125 | 100 | 100 | 100 | 90 | 90 | 100 |
| P4 | 500 | 100 | 90 | 100 | 80 | 80 | 100 |
| P5 | 125 | 100 | 100 | 100 | 90 | 100 | 100 |
| P6 | 125 | 60 | 80 | 10 | 0 | 30 | — |
| P7 | 125 | 80 | 80 | 100 | 80 | 80 | 80 |
| P8 | 125 | 90 | 100 | 90 | 90 | 100 | 100 |
| P9 | 125 | 80 | 100 | 90 | 90 | 90 | 100 |
| P10 | 125 | 100 | 100 | 90 | 70 | 80 | — |
| P11 | 125 | 90 | 100 | 90 | 70 | 70 | 70 |
| P12 | 125 | 80 | 90 | 100 | 90 | 90 | 100 |
| P13 | 125 | 90 | 100 | 90 | 90 | 100 | 100 |
| P14 | 125 | 80 | 80 | 80 | 60 | 70 | 60 |
| P15 | 125 | 10 | 70 | 0 | 40 | 70 | — |
| P16 | 125 | 100 | 90 | 100 | 70 | 100 | 100 |
| P17 | 125 | 90 | 80 | 80 | 70 | 70 | 70 |
| P18 | 125 | 80 | 100 | 90 | 50 | 70 | 100 |
| P19 | 125 | 90 | 90 | 90 | 70 | 70 | 100 |
| P20 | 125 | 90 | 100 | 90 | 70 | 70 | 100 |
| P21 | 125 | 100 | 100 | 90 | 90 | 100 | 100 |
| P22 | 125 | 90 | 100 | 90 | 90 | 100 | 90 |
| P24 | 125 | 0 | 0 | 0 | 0 | 0 | 0 |
| P26 | 125 | 10 | 0 | 0 | 0 | 10 | 0 |
| P27 | 125 | 70 | 50 | 70 | 50 | 70 | 70 |
| P28 | 125 | 0 | 10 | 0 | 0 | 10 | — |
| P29 | 125 | 30 | 0 | 10 | 30 | 50 | 30 |
| P31 | 125 | 70 | 70 | 50 | 60 | 20 | — |
| P32 | 125 | 20 | 0 | 0 | 0 | 0 | 0 |
| P33 | 125 | 20 | 0 | 0 | 0 | 30 | 0 |
| P34 | 125 | 0 | 0 | 0 | 0 | 30 | 0 |
| P35 | 125 | 100 | 100 | 90 | 50 | 50 | 100 |
| P41 | 125 | 10 | 10 | 0 | 0 | 50 | — |
| P42 | 125 | 60 | 40 | 50 | 50 | 30 | 30 |
| P43 | 125 | 100 | 100 | 80 | 70 | 70 | 70 |
| P44 | 125 | 80 | 90 | 90 | 90 | 100 | 90 |
| P45 | 125 | 30 | 60 | 0 | 10 | 20 | 10 |
| P46 | 125 | 90 | 100 | 90 | 90 | 90 | 100 |
| P47 | 125 | 70 | 60 | 50 | 60 | 70 | 70 |
| P48 | 125 | 80 | 80 | 80 | 80 | 80 | — |
| P49 | 500 | 60 | 10 | 50 | 80 | 90 | 90 |
| P52 | 500 | 100 | 90 | 100 | 90 | 90 | 90 |
| P56 | 500 | 70 | 10 | 70 | 70 | 80 | 80 |
| P59 | 125 | 40 | 0 | 20 | 60 | 80 | 30 |
| P60 | 125 | 70 | 50 | 70 | 60 | 60 | 70 |

What is claimed is:

1. A compound of formula (I)

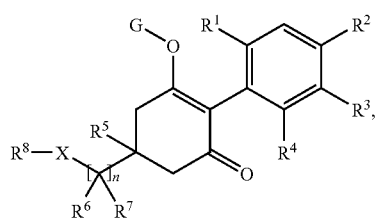

wherein
R$^1$ is methyl, ethyl, n-propyl, iso-propyl, cyclopropyl, halomethyl, haloethyl, halogen, vinyl, ethynyl, methoxy, ethoxy, halomethoxy or haloethoxy,
R$^2$ and R$^3$ are, independently of each other hydrogen, halogen, C$_1$-C$_6$alkyl, C$_1$-C$_6$haloalkyl, C$_1$-C$_6$alkoxy, C$_1$-C$_6$haloalkoxy, C$_2$-C$_6$alkenyl, C$_2$-C$_6$haloalkenyl, C$_2$-C$_6$alkynyl, C$_3$-C$_6$alkenyloxy, C$_3$-C$_6$haloalkenyloxy, C$_3$-C$_6$alkynyloxy, C$_3$-C$_6$cycloalkyl, C$_1$-C$_6$alkylthio, C$_1$-C$_6$alkylsulfinyl, C$_1$-C$_6$alkylsulfonyl, C$_1$-C$_6$alkylsulfonyloxy, C$_1$-C$_6$haloalkylsulfonyloxy, cyano, nitro; phenyl or phenyl substituted by C$_1$-C$_4$alkyl, C$_1$-C$_3$haloalkyl, C$_1$-C$_3$alkoxy, C$_1$-C$_3$haloalkoxy, cyano, nitro, halogen, C$_1$-C$_3$alkylthio, C$_1$-C$_3$alkylsulfinyl or C$_1$-C$_3$alkylsulfonyl; or heteroaryl or heteroaryl substituted by C$_1$-C$_4$alkyl, C$_1$-C$_3$haloalkyl, C$_1$-C$_3$alkoxy, C$_1$-C$_3$haloalkoxy, cyano, nitro, halogen, C$_1$-C$_3$alkylthio, C$_1$-C$_3$alkylsulfinyl or C$_1$-C$_3$alkylsulfonyl;
R$^4$ is hydrogen, methyl, ethyl, n-propyl, iso-propyl, halomethyl, haloethyl, halogen, vinyl, ethynyl, methoxy, ethoxy, halomethoxy or haloethoxy,
n is 0, 1, 2 or 3,
X is O, S, S(O) or S(O)$_2$,
R$^5$ is hydrogen or methyl,
R$^6$ and R$^7$ are independently of each other hydrogen, methyl or ethyl, where, when n is 2 or 3, the meanings of the 4 or 6 substituents R$^6$ and R$^7$ do not have to be the same,
R$^8$ is C$_1$-C$_{18}$alkyl, C$_1$-C$_{18}$haloalkyl, C$_3$-C$_7$cycloalkyl, C$_3$-C$_7$cycloalkyl substituted by methyl or ethyl, C$_1$-C$_6$alkoxyC$_1$-C$_{12}$alkyl, C$_1$-C$_6$alkylthioC$_1$-C$_{12}$alkyl, $C_3$-$C_{18}$alkenyl or $C_3$-$C_{18}$alkenyl substituted by halogen, or $C_3$-$C_{18}$alkynyl or $C_3$-$C_{18}$alkynyl substituted by halogen, or $R^5$, when n denotes 1 or 2, and $R^8$ together form a $C_2$-$C_5$ alkylene chain, which is unsubstituted or substituted by methyl or ethyl, or an $C_2$-$C_5$alkenylene chain, which is unsubstituted or substituted by methyl or ethyl, where, when n is 2, the meanings of the 4 substituents $R^6$ and $R^7$ do not have to be the same, or $R^6$, when n denotes 1, and one of $R^5$, $R^7$ and $R^8$ together form a $C_2$-$C_5$alkylene chain, which is unsubstituted or substituted by methyl or ethyl, or an $C_2$-$C_5$alkenylene chain, which is unsubstituted or substituted by methyl or ethyl, and G is hydrogen, an alkali metal, alkaline earth metal, sulfonium, ammonium or a latentiating group;

and wherein, when G is a latentiating group then G is $C_1$-$C_8$alkyl, $C_2$-$C_8$ haloalkyl, phenyl$C_1$-$C_8$alkyl (wherein the phenyl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$ alkylsulfonyl, halogen, cyano or by nitro), heteroaryl$C_1$-$C_8$alkyl (wherein the heteroaryl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$ alkylsulfonyl, halogen, cyano or by nitro), $C_3$-$C_8$ alkenyl, $C_3$-$C_8$ haloalkenyl, $C_3$-$C_8$ alkynyl, $C(X^a)$—$R^a$, $C(X^b)$—$X^c$—$R^b$, $C(X^d)$—N$(R^c)$—$R^d$, —$SO_2$—$R^e$, —$P(X^e)(R^f)$—$R^g$ or $CH_2$—$X^f$—$R^h$;

wherein $X^a$, $X^b$, $X^c$, $X^d$, $X^e$ and $X^f$ are independently of each other oxygen or sulfur; and wherein $R^a$ is hydrogen, $C_1$-$C_{18}$alkyl, $C_2$-$C_{18}$alkenyl, $C_2$-$C_{18}$alkynyl, $C_1$-$C_{10}$haloalkyl, $C_1$-$C_{10}$cyanoalkyl, $C_1$-$C_{10}$nitroalkyl, $C_1$-$C_{10}$aminoalkyl, $C_1$-$C_5$alkylamino$C_1$-$C_5$alkyl, $C_2$-$C_8$dialkylamino$C_1$-$C_5$alkyl, $C_3$-$C_7$cycloalkyl$C_1$-$C_5$alkyl, $C_1$-$C_5$alkoxy$C_1$-$C_5$alkyl, $C_3$-$C_5$alkenyloxy$C_1$-$C_5$alkyl, $C_3$-$C_5$alkynyloxy$C_1$-$C_5$alkyl, $C_1$-$C_5$alkylthio$C_1$-$C_5$alkyl, $C_1$-$C_5$alkylsulfinyl$C_1$-$C_5$alkyl, $C_1$-$C_5$alkylsulfonyl$C_1$-$C_5$alkyl, $C_2$-$C_8$alkylideneaminoxy$C_1$-$C_5$alkyl, $C_1$-$C_5$alkylcarbonyl$C_1$-$C_5$alkyl, $C_1$-$C_5$alkoxycarbonyl$C_1$-$C_5$alkyl, aminocarbonyl$C_1$-$C_5$alkyl, $C_1$-$C_5$alkylaminocarbonyl$C_1$-$C_5$alkyl, $C_2$-$C_8$dialkylaminocarbonyl$C_1$-$C_5$alkyl, $C_1$-$C_5$alkylcarbonylamino$C_1$-$C_5$alkyl, N—$C_1$-$C_5$alkylcarbonyl-N—$C_1$-$C_5$alkylamino$C_1$-$C_5$alkyl, $C_3$-$C_6$trialkylsilyl$C_1$-$C_5$alkyl, phenyl$C_1$-$C_5$alkyl (wherein the phenyl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), heteroaryl$C_1$-$C_5$alkyl (wherein the heteroaryl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), $C_2$-$C_5$haloalkenyl, $C_3$-$C_8$cycloalkyl; phenyl or phenyl substituted by $C_1$-$C_3$alkyl, $C_1$-$C_3$haloalkyl, $C_1$-$C_3$alkoxy, $C_1$-$C_3$haloalkoxy, halogen, cyano or nitro; or heteroaryl or heteroaryl substituted by $C_1$-$C_3$ alkyl, $C_1$-$C_3$haloalkyl, $C_1$-$C_3$alkoxy, $C_1$-$C_3$haloalkoxy, halogen, cyano or nitro;

$R^b$ is $C_1$-$C_{18}$alkyl, $C_3$-$C_{18}$alkenyl, $C_3$-$C_{18}$alkynyl, $C_2$-$C_{10}$haloalkyl, $C_1$-$C_{10}$cyanoalkyl, $C_1$-$C_{10}$nitroalkyl, $C_2$-$C_{10}$aminoalkyl, $C_1$-$C_5$alkylamino$C_1$-$C_5$alkyl, $C_2$-$C_8$dialkylamino$C_1$-$C_5$alkyl, $C_3$-$C_7$cycloalkyl$C_1$-$C_5$alkyl, $C_1$-$C_5$alkoxy$C_1$-$C_5$alkyl, $C_3$-$C_5$alkenyloxy$C_1$-$C_5$alkyl, $C_3$-$C_5$alkynyloxy$C_1$-$C_5$alkyl, $C_1$-$C_5$alkylthio$C_1$-$C_5$alkyl, $C_1$-$C_5$alkylsulfinyl$C_1$-$C_5$alkyl, $C_1$-$C_5$alkylsulfonyl$C_1$-$C_5$alkyl, $C_2$-$C_8$alkylideneaminoxy$C_1$-$C_5$alkyl, $C_1$-$C_5$alkylcarbonyl$C_1$-$C_5$alkyl, $C_1$-$C_5$alkoxycarbonyl$C_1$-$C_5$alkyl, aminocarbonyl$C_1$-$C_5$alkyl, $C_1$-$C_5$alkylaminocarbonyl$C_1$-$C_5$alkyl, $C_2$-$C_8$dialkylaminocarbonyl$C_1$-$C_5$alkyl, $C_1$-$C_5$alkylcarbonylamino$C_1$-$C_5$alkyl, N—$C_1$-$C_5$alkylcarbonyl-N—$C_1$-$C_5$alkylamino$C_1$-$C_5$alkyl, $C_3$-$C_6$trialkylsilyl$C_1$-$C_5$alkyl, phenyl$C_1$-$C_5$alkyl (wherein the phenyl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), heteroaryl$C_1$-$C_5$alkyl (wherein the heteroaryl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), $C_3$-$C_5$haloalkenyl, $C_3$-$C_8$cycloalkyl; phenyl or phenyl substituted by $C_1$-$C_3$alkyl, $C_1$-$C_3$haloalkyl, $C_1$-$C_3$alkoxy, $C_1$-$C_3$haloalkoxy, halogen, cyano or nitro; or heteroaryl or heteroaryl substituted by $C_1$-$C_3$ alkyl, $C_1$-$C_3$haloalkyl, $C_1$-$C_3$alkoxy, $C_1$-$C_3$haloalkoxy, halogen, cyano or nitro; and $R^c$ and $R^d$ are each independently of each other hydrogen, $C_1$-$C_{10}$alkyl, $C_3$-$C_{10}$alkenyl, $C_3$-$C_{10}$alkynyl, $C_2$-$C_{10}$haloalkyl, $C_1$-$C_{10}$cyanoalkyl, $C_1$-$C_{10}$nitroalkyl, $C_1$-$C_{10}$aminoalkyl, $C_1$-$C_5$alkylamino$C_1$-$C_5$alkyl, $C_2$-$C_8$dialkylamino$C_1$-$C_5$alkyl, $C_3$-$C_7$cycloalkyl$C_1$-$C_5$alkyl, $C_1$-$C_5$alkoxy$C_1$-$C_5$alkyl, $C_3$-$C_5$alkyenyloxy$C_1$-$C_5$alkyl, $C_3$-$C_5$alkynyloxy$C_1$-$C_5$alkyl, $C_1$-$C_5$alkylthio$C_1$-$C_5$alkyl, $C_1$-$C_5$alkylsulfinyl$C_1$-$C_5$alkyl, $C_1$-$C_5$alkylsulfonyl$C_1$-$C_5$alkyl, $C_2$-$C_8$alkylideneaminoxy$C_1$-$C_5$alkyl, $C_1$-$C_5$alkylcarbonyl$C_1$-$C_5$alkyl, $C_1$-$C_5$alkoxycarbonyl$C_1$-$C_5$alkyl, aminicarbonyl$C_1$-$C_5$alkyl, $C_1$-$C_5$alkylaminocarbonyl$C_1$-$C_5$alkyl, $C_2$-$C_8$dialkylaminocarbonyl$C_1$-$C_5$alkyl, $C_1$-$C_5$alkylcarbonylamino$C_1$-$C_5$alkyl, N—$C_1$-$C_5$alkylcarbonyl-N—$C_2$-$C_5$alkylaminoalkyl, $C_3$-$C_6$trialkylsilyl$C_1$-$C_5$alkyl, phenyl$C_1$-$C_5$alkyl (wherein the phenyl is optionally substituted by $C_1$-$C_3$alkyl, $C_1$-$C_3$haloalkyl, $C_1$-$C_3$alkoxy, $C_1$-$C_5$haloalkoxy, $C_1$-$C_3$alkylthio, $C_1$-$C_3$alkylsulfinyl, $C_1$-$C_3$alkylsulfonyl, halogen, cyano, or by nitro), heteroaryl$C_1$-$C_5$alkyl (wherein the heteroaryl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), $C_2$-$C_5$haloalkenyl, $C_3$-$C_8$cycloalkyl; phenyl or phenyl substituted by $C_1$-$C_3$alkyl, $C_1$-$C_3$haloalkyl, $C_1$-$C_3$alkoxy, $C_1$-$C_3$haloalkoxy, halogen, cyano or nitro; heteroaryl or heteroaryl substituted by $C_1$-$C_3$alkyl, $C_1$-$C_3$haloalkyl, $C_1$-$C_3$alkoxy, $C_1$-$C_3$haloalkoxy, halogen, cyano or nitro; heteroarylamino or heteroarylamino substituted by $C_1$-$C_3$ alkyl, $C_1$-$C_3$haloalkyl, $C_1$-$C_3$alkoxy, $C_1$-$C_3$haloalkoxy, halogen, cyano or nitro; diheteroarylamino or diheteroarylamino substituted by $C_1$-$C_3$ alkyl, $C_1$-$C_3$haloalkyl, $C_1$-$C_3$alkoxy, $C_1$-$C_3$haloalkoxy, halogen, cyano or nitro; phenylamino or phenylamino substituted by $C_1$-$C_3$alkyl, $C_1$-$C_3$haloalkyl, $C_1$-$C_3$alkoxy, $C_1$-$C_3$haloalkoxy, halogen, cyano or by nitro; diphenylamino or diphenylamino substituted by $C_1$-$C_3$alkyl, $C_1$-$C_3$haloalkyl, $C_1$-$C_3$alkoxy, $C_1$-$C_3$haloalkoxy, halogen, cyano or by nitro; or $C_3$-$C_7$cycloalkylamino, di-$C_3$-$C_7$cycloalkylamino or $C_3$-$C_7$cycloalkoxy;

or $R^c$ and $R^d$ may join together to form a 3-7 membered ring, optionally containing one heteroatom selected from O or S; and $R^e$ is $C_1$-$C_{10}$alkyl, $C_2$-$C_{10}$alkenyl, $C_2$-$C_{10}$alkynyl, $C_1$-$C_{10}$haloalkyl, $C_1$-$C_{10}$cyanoalkyl, $C_1$-$C_{10}$nitroalkyl, $C_1$-$C_{10}$aminoalkyl, $C_1$-$C_5$alkylamino$C_1$-$C_5$alkyl, $C_2$-$C_8$dialkylamino$C_1$-$C_5$alkyl, $C_3$-$C_7$cycloalkyl$C_1$-$C_5$alkyl, $C_1$-$C_5$alkoxy$C_1$-$C_5$alkyl, $C_3$-$C_5$alkenyloxy$C_1$-$C_5$alkyl, $C_3$-$C_5$alkynyloxy$C_1$-$C_5$alkyl, $C_1$-$C_5$alkylthio$C_1$-$C_5$alkyl, $C_1$-$C_5$alkylsulfinyl$C_1$-$C_5$alkyl, $C_1$-$C_5$alkylsulfonyl$C_1$-$C_5$alkyl, $C_2$-$C_8$alkylideneaminoxy$C_1$-$C_5$alkyl, $C_1$-$C_5$alkylcarbonyl$C_1$-$C_5$alkyl, $C_1$-$C_5$alkoxycarbonyl$C_1$-$C_5$alkyl, aminocarbonyl$C_1$-$C_5$alkyl, $C_1$-$C_5$alkylaminocarbonyl$C_1$-$C_5$alkyl, $C_2$-$C_8$dialkylaminocarbonyl$C_1$-$C_5$alkyl, $C_1$-$C_5$alkylcarbonylamino$C_1$-$C_5$alkyl, N—$C_1$-$C_5$alkylcarbonyl-N—$C_1$-$C_5$alkylamino$C_1$-$C_5$alkyl, $C_3$-$C_6$trialkylsilyl$C_1$-$C_5$alkyl, phenyl$C_1$-$C_5$alkyl (wherein the phenyl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), heteroaryl$C_1$-$C_5$alkyl (wherein the heteroaryl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), $C_2$-$C_5$haloalkenyl, $C_3$-$C_8$cycloalkyl; phenyl or phenyl substituted by $C_1$-$C_3$alkyl, $C_1$-$C_3$haloalkyl, $C_1$-$C_3$alkoxy, $C_1$-$C_3$haloalkoxy, halogen, cyano or nitro; heteroaryl or heteroaryl substituted by $C_1$-$C_3$alkyl, $C_1$-$C_3$haloalkyl, $C_1$-$C_3$alkoxy, $C_1$-$C_3$haloalkoxy, halogen, cyano or by nitro; heteroarylamino or heteroarylamino substituted by $C_1$-$C_3$alkyl, $C_1$-$C_3$haloalkyl, $C_1$-$C_3$alkoxy, $C_1$-$C_3$haloalkoxy, halogen, cyano or by nitro; diheteroarylamino or diheteroarylamino substituted by $C_1$-$C_3$alkyl, $C_1$-$C_3$haloalkyl, $C_1$-$C_3$alkoxy, $C_1$-$C_3$haloalkoxy, halogen, cyano or nitro; phenylamino or phenylamino substituted by $C_1$-$C_3$alkyl, $C_1$-$C_3$haloalkyl, $C_1$-$C_3$alkoxy, $C_1$-$C_3$haloalkoxy, halogen, cyano or nitro; diphenylamino or diphenylamino substituted by $C_1$-$C_3$alkyl, $C_1$-$C_3$haloalkyl, $C_1$-$C_3$alkoxy, $C_1$-$C_3$haloalkoxy, halogen, cyano or nitro; or $C_3$-$C_7$cycloalkylamino, di$C_3$-$C_7$cycloalkylamino, $C_3$-$C_7$cycloalkoxy, $C_1$-$C_{10}$alkoxy, $C_1$-$C_{10}$haloalkoxy, $C_1$-$C_5$alkylamino or $C_2$-$C_8$dialkylamino;

$R^f$ and $R^g$ are each independently of each other $C_1$-$C_{10}$alkyl, $C_2$-$C_{10}$alkenyl, $C_2$-$C_{10}$alkynyl, $C_1$-$C_{10}$alkoxy, $C_1$-$C_{10}$haloalkyl, $C_1$-$C_{10}$cyanoalkyl, $C_1$-$C_{10}$nitroalkyl, $C_1$-$C_{10}$aminoalkyl, $C_1$-$C_5$alkylamino$C_1$-$C_5$alkyl, $C_2$-$C_8$dialkylamino$C_1$-$C_5$alkyl, $C_3$-$C_7$cycloalkyl$C_1$-$C_5$alkyl, $C_1$-$C_5$alkoxy$C_1$-$C_5$alkyl, $C_3$-$C_5$alkenyloxy$C_1$-$C_5$alkyl, $C_3$-$C_5$alkynyloxy$C_1$-$C_5$alkyl, $C_1$-$C_5$alkylthio$C_1$-$C_5$alkyl, $C_1$-$C_5$alkylsulfinyl$C_1$-$C_5$alkyl, $C_1$-$C_5$alkylsulfonyl$C_1$-$C_5$alkyl, $C_2$-$C_8$alkylideneaminoxy$C_1$-$C_5$alkyl, $C_1$-$C_5$alkylcarbonyl$C_1$-$C_5$alkyl, $C_1$-$C_5$alkoxycarbonyl$C_1$-$C_5$alkyl, aminocarbonyl$C_1$-$C_5$alkyl, $C_1$-$C_5$alkylaminocarbonyl$C_1$-$C_5$alkyl, $C_2$-$C_8$dialkylaminocarbonyl$C_1$-$C_5$alkyl, $C_1$-$C_5$alkylcarbonylamino$C_1$-$C_5$alkyl, N—$C_1$-$C_5$alkylcarbonyl-N—$C_2$-$C_5$alkylaminoalkyl, $C_3$-$C_6$trialkylsilyl$C_1$-$C_5$alkyl, phenyl$C_1$-$C_5$alkyl (wherein the phenyl is optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), heteroaryl$C_1$-$C_5$alkyl (wherein the heteroaryl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), $C_2$-$C_5$haloalkenyl, $C_3$-$C_8$cycloalkyl; phenyl or phenyl substituted by $C_1$-$C_3$alkyl, $C_1$-$C_3$haloalkyl, $C_1$-$C_3$alkoxy, $C_1$-$C_3$haloalkoxy, halogen, cyano or nitro; heteroaryl or heteroaryl substituted by $C_1$-$C_3$alkyl, $C_1$-$C_3$haloalkyl, $C_1$-$C_3$alkoxy, $C_1$-$C_3$haloalkoxy, halogen, cyano or by nitro; heteroarylamino or heteroarylamino substituted by $C_1$-$C_3$alkyl, $C_1$-$C_3$haloalkyl, $C_1$-$C_3$haloalkoxy, halogen, cyano or by nitro; diheteroarylamino or diheteroarylamino substituted by $C_1$-$C_3$ alkyl, $C_1$-$C_3$haloalkyl, $C_1$-$C_3$alkoxy, $C_1$-$C_3$haloalkoxy, halogen, cyano or nitro; phenylamino or phenylamino substituted by $C_1$-$C_3$alkyl, $C_1$-$C_3$haloalkyl, $C_1$-$C_3$alkoxy, $C_1$-$C_3$haloalkoxy, halogen, cyano or nitro; diphenylamino or diphenylamino substituted by $C_1$-$C_3$alkyl, $C_1$-$C_3$haloalkyl, $C_1$-$C_3$alkoxy, $C_1$-$C_3$haloalkoxy, halogen, cyano or nitro; or $C_3$-$C_7$cycloalkylamino, di$C_3$-$C_7$cycloalkylamino, $C_3$-$C_7$cycloalkoxy, $C_1$-$C_{10}$haloalkoxy, $C_1$-$C_5$alkylamino or $C_2$-$C_8$dialkylamino; or benzyloxy or phenoxy, wherein the benzyl and phenyl groups may in turn be substituted by $C_1$-$C_3$alkyl, $C_1$-$C_3$haloalkyl, $C_1$-$C_3$alkoxy, $C_1$-$C_3$haloalkoxy, halogen, cyano or nitro; and $R^h$ is $C_1$-$C_{10}$alkyl, $C_3$-$C_{10}$alkenyl, $C_3$-$C_{10}$alkynyl, $C_1$-$C_{10}$haloalkyl, $C_1$-$C_{10}$cyanoalkyl, $C_1$-$C_{10}$nitroalkyl, $C_2$-$C_{10}$aminoalkyl, $C_1$-$C_5$alkylamino$C_1$-$C_5$alkyl, $C_2$-$C_8$dialkylamino$C_1$-$C_5$alkyl, $C_3$-$C_7$cycloalkyl$C_1$-$C_5$alkyl, $C_1$-$C_5$alkoxy$C_1$-$C_5$alkyl, $C_3$-$C_5$alkenyloxy$C_1$-$C_5$alkyl, $C_3$-$C_5$alkynyloxy$C_1$-$C_5$alkyl, $C_1$-$C_5$alkylthio$C_1$-$C_5$alkyl, $C_1$-$C_5$alkylsulfinyl$C_1$-$C_5$alkyl, $C_1$-$C_5$alkylsulfonyl$C_1$-$C_5$alkyl, $C_2$-$C_8$alkylideneaminoxy$C_1$-$C_5$alkyl, $C_1$-$C_5$alkylcarbonyl$C_1$-$C_5$alkyl, $C_1$-$C_5$alkoxycarbonyl$C_1$-$C_5$alkyl, aminocarbonyl$C_1$-$C_5$alkyl, $C_1$-$C_5$alkylaminocarbonyl$C_1$-$C_5$alkyl, $C_2$-$C_8$dialkylaminocarbonyl$C_1$-$C_5$alkyl, $C_1$-$C_5$alkylcarbonylamino$C_1$-$C_5$alkyl, N—$C_1$-$C_5$alkylcarbonyl-N—$C_1$-$C_5$alkylamino$C_1$-$C_5$alkyl, $C_3$-$C_6$trialkylsilyl$C_1$-$C_5$alkyl, phenyl$C_1$-$C_5$alkyl (wherein the phenyl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano or by nitro), heteroaryl$C_1$-$C_5$alkyl (wherein the heteroaryl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$ alkylsulfonyl, halogen, cyano or by nitro), phenoxy$C_1$-$C_5$alkyl (wherein the phenyl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano or by nitro), heteroaryloxy$C_1$-$C_5$alkyl (wherein the heteroaryl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano or by nitro), $C_3$-$C_5$haloalkenyl, $C_3$-$C_8$cycloalkyl; phenyl or phenyl substituted by $C_1$-$C_3$alkyl, $C_1$-$C_3$haloalkyl, $C_1$-$C_3$alkoxy, $C_1$-$C_3$haloalkoxy, halogen or by nitro; or heteroaryl or heteroaryl substituted by $C_1$-$C_3$alkyl, $C_1$-$C_3$haloalkyl, $C_1$-$C_3$alkoxy, $C_1$-$C_3$haloalkoxy, halogen, cyano or by nitro.

2. A compound according to claim 1, wherein $R^1$ is methyl, ethyl, vinyl, ethynyl, methoxy or halogen.

3. A compound according to claim 2, wherein $R^1$ is methyl, ethyl, methoxy or halogen.

4. A compound according to claim 3, wherein $R^1$ is methyl or ethyl.

5. A compound according to claim 1, wherein $R^2$ is hydrogen, halogen, methyl, ethyl, phenyl or phenyl substituted by $C_1$-$C_3$alkyl, $C_1$-$C_3$haloalkyl, $C_1$-$C_3$alkoxy, $C_1$-$C_3$haloalkoxy, cyano, nitro, halogen, $C_1$-$C_3$alkylthio, $C_1$-$C_3$alkylsulfinyl or $C_1$-$C_3$alkylsulfonyl.

6. A compound according to claim 5, wherein $R^2$ is methyl.

7. A compound according to claim 1, wherein $R^3$ is hydrogen, halogen, methyl, ethyl, phenyl or phenyl substituted by $C_1$-$C_3$alkyl, $C_1$-$C_3$haloalkyl, $C_1$-$C_3$alkoxy, $C_1$-$C_3$haloalkoxy, cyano, nitro, halogen, $C_1$-$C_3$alkylthio, $C_1$-$C_3$alkylsulfinyl or $C_1$-$C_3$alkylsulfonyl.

8. A compound according to claim 1, wherein $R^2$ and $R^3$ idependently of each other are hydrogen, methyl, ethyl, halogen, optionally substituted phenyl or optionally substituted heteroaryl.

9. A compound according to claim 1, wherein $R^4$ is hydrogen, methyl, ethyl, vinyl or ethynyl.

10. A compound according to claim 9, wherein $R^4$ is hydrogen, methyl or ethyl.

11. A compound according to claim 1, wherein $R^5$ is hydrogen.

12. A compound according to claim 1, wherein $R^6$ and $R^7$ are each hydrogen.

13. A compound according to claim 1, wherein $R^6$ and $R^7$ are methyl or ethyl.

14. A compound according to claim 1, wherein $R^6$ is hydrogen and $R^7$ is methyl or ethyl.

15. A compound according to claim 1, wherein X denotes $S(O)$ or $S(O)_2$; and $R^8$ is $C_1$-$C_{18}$alkyl, $C_3$-$C_7$cycloalkyl, $C_3$-$C_7$cycloalkyl substituted by methyl or ethyl, $C_1$-$C_6$alkoxy$C_1$-$C_{12}$alkyl, $C_1$-$C_6$alkylthio$C_1$-$C_{12}$alkyl, $C_3$-$C_{18}$ alkenyl, $C_3$-$C_{18}$alkynyl or $C_3$-$C_{18}$alkynyl substituted by halogen.

16. A compound according to claim 15, wherein $R^8$ is $C_1$-$C_6$alkyl or $C_3$-$C_7$cycloalkyl.

17. A compound according to claim 16, wherein $R^8$ is methyl, ethyl or propyl.

18. A compound according to claim 1, wherein X denotes O or S; and $R^8$ is methyl, ethyl, propyl, butyl, pentyl or hexyl, $C_7$-$C_{18}$alkyl, $C_3$-$C_7$cycloalkyl, $C_3$-$C_7$cycloalkyl substituted by methyl or ethyl, $C_1$-$C_6$alkoxy$C_1$-$C_{12}$alkyl, $C_1$-$C_6$alkylthio$C_1$-$C_{12}$alkyl, $C_3$-$C_{18}$ alkenyl, $C_3$-$C_{18}$alkynyl or $C_3$-$C_{18}$alkynyl substituted by halogen.

19. A compound according to claim 18, wherein $R^8$ is methyl, ethyl or propyl.

20. A compound according to claim 19, wherein $R^8$ is ethyl or propyl.

21. A compound according to claim 1, wherein
X denotes $S(O)$ or $S(O)_2$;
$R^8$ is $C_1$-$C_{18}$alkyl, $C_3$-$C_7$cycloalkyl, $C_3$-$C_7$cycloalkyl substituted by methyl or ethyl, $C_1$-$C_6$alkoxy$C_1$-$C_{12}$alkyl, $C_1$-$C_6$alkylthio$C_1$-$C_{12}$alkyl, $C_3$-$C_{18}$alkenyl, $C_3$-$C_{18}$alkynyl or $C_3$-$C_{18}$alkynyl substituted by halogen; and $R^6$ and $R^7$ are methyl or ethyl, or $R^6$ is hydrogen and $R^7$ is methyl or ethyl.

22. A compound according to claim 1, wherein $R^8$—X—$[CR^6R^7]_1$- is different from $CH_3OCH_2$- and $CH_3SCH_2$—.

23. A compound according to claim 1, wherein G is $C(X^a)$—$R^a$ or $C(X^b)$—$X^c$—$R^b$.

24. A compound according to claim 1, wherein G is hydrogen, an alkali metal or alkaline earth metal.

25. A compound according to claim 24, wherein G is hydrogen.

26. A compound according to claim 1, wherein n is 1 or 2.

27. A compound according to claim 1, wherein $R^5$, when n denotes 1 or 2, and $R^8$ together form a $C_2$-$C_5$ alkylene chain.

28. A compound according to claim 1, wherein $R^5$, when n denotes 1, and $R^8$ together form a propylene chain and $R^6$ and $R^7$ are each hydrogen.

29. A compound according to claim 1, wherein $R^5$, when n denotes 1 or 2, and $R^8$ together form an ethylene chain and $R^6$ and $R^7$ are each hydrogen.

30. A compound according to claim 29, wherein n denotes 2.

31. A compound according to claim 1, wherein $R^5$, when n denotes 1 or 2, and $R^8$ together form an ethylene chain and $R^6$ and $R^7$ are each hydrogen and X is O.

32. A compound according to claim 1, wherein $R^5$, when n denotes 1 or 2, and $R^8$ together form an ethylene chain and $R^6$ and $R^7$ are each hydrogen and X is $S(O)$ or $S(O)_2$.

33. A compound according to claim 1, wherein $R^1$, $R^2$ and $R^4$ are independently of each other methyl or ethyl and $R^3$ is hydrogen.

34. A compound according to claim 1, wherein $R^1$ is methyl or ethyl, $R^2$ is hydrogen, $R^3$ is phenyl or phenyl substituted by $C_1$-$C_4$alkyl, $C_1$-$C_3$haloalkyl, $C_1$-$C_3$alkoxy, $C_1$-$C_3$haloalkoxy, cyano, nitro or halogen, or heteroaryl or heteroaryl substituted by $C_1$-$C_4$alkyl, $C_1$-$C_3$haloalkyl, $C_1$-$C_3$alkoxy, $C_1$-$C_3$haloalkoxy, cyano, nitro or halogen.

35. A compound according to claim 1, wherein $R^1$ is methyl or ethyl, $R^2$ is phenyl or phenyl substituted by $C_1$-$C_4$alkyl, $C_1$-$C_3$haloalkyl, $C_1$-$C_3$alkoxy, $C_1$-$C_3$haloalkoxy, cyano, nitro or halogen, or heteroaryl or heteroaryl substituted by $C_1$-$C_4$alkyl, $C_1$-$C_3$haloalkyl, $C_1$-$C_3$alkoxy, $C_1$-$C_3$haloalkoxy, cyano, nitro or halogen, $R^3$ is hydrogen and $R^4$ is hydrogen, methyl or ethyl.

36. A process for the preparation of a compound of formula (I) according to claim 1, wherein G is hydrogen, which comprises reacting a compound of the formula (Y)

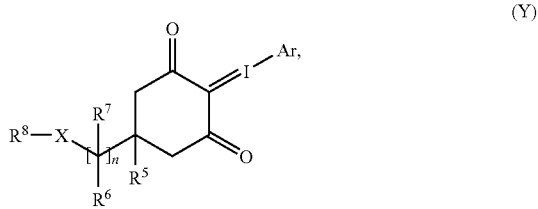

(Y)

wherein $R^5$, $R^6$, $R^7$, $R^8$ and X and n have the meanings assigned to them in claim 1, and Ar is an optionally substituted aromatic ring with an aryl boronic acid of the formula (Z)

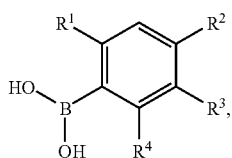

wherein $R^1$, $R^2$, $R^3$ and $R^4$ have the meanings assigned to them in claim 1, in the presence of a palladium catalyst, a base and a solvent.

37. A process for the preparation of a compound of formula (I) according to claim 1, wherein G is hydrogen, which comprises cyclisation of the compound of the formula (B)

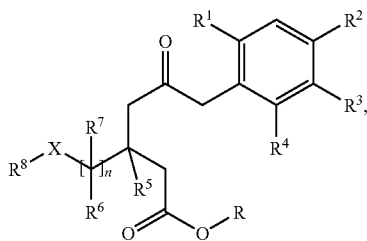

wherein $R^1$, $R^2$, $R^3$, $R^4$, $R^5$, $R^6$, $R^7$, $R^8$ and X and n have the meanings assigned to them in claim 1 and R is alkyl, under acidic or basic conditions.

38. A process for the preparation of a compound of formula (I) according to claim 1, wherein G is hydrogen, which comprises cyclisation of the compound of the formula (B)

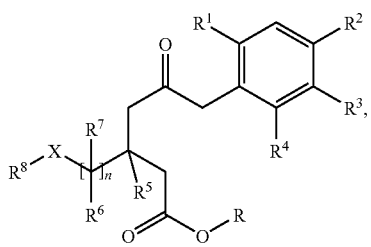

wherein $R^1$, $R^2$, $R^3$, $R^4$, $R^5$, $R^6$, $R^7$, $R^8$ and X and n have the meanings assigned to them in claim 1 and R is hydrogen, under acidic conditions.

39. A process for the preparation of a compound of formula (I) according to claim 1, wherein G is an alkyl, acyl, phosphoryl or sulfonyl group, which comprises treating the compound of the formula (A)

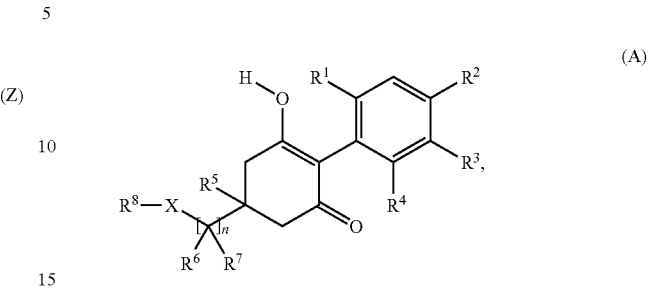

wherein $R^1$, $R^2$, $R^3$, $R^4$, $R^5$, $R^6$, $R^7$, $R^8$ and X and n have the meanings assigned to them in claim 1 with a compound of the formula G-Z, wherein G represents the alkyl, acyl, phosphoryl or sulfonyl group to be incorporated and Z is a suitable nucleofuge, in the presence of at least one equivalent of a base.

40. A process for the preparation of a compound of formula (1) according to claim 1, which comprises treating a compound of formula (JJ)

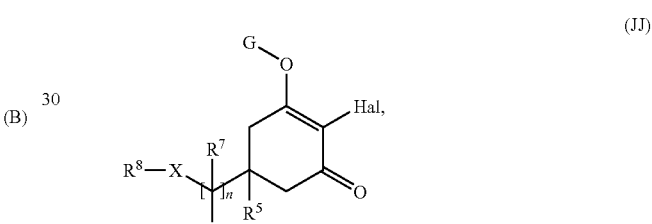

wherein G is $C_1$-$C_4$ alkyl, Hal is chlorine, bromine or iodine and $R^5$, $R^6$, $R^7$ and $R^8$ have the meanings assigned to them in claim 1 with an aryl boronic acid of formula (Z)

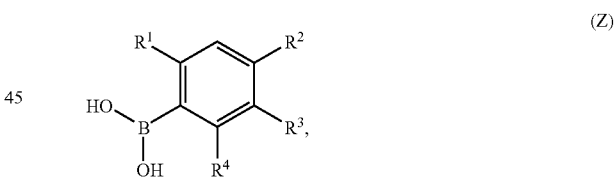

wherein $R^1$, $R^2$, $R^3$ and $R^4$ have the meanings assigned to them in claim 1, in the presence of a base, a solvent and a palladium catalyst.

41. A method of controlling grasses and weeds in crops of useful plants, which comprises applying a herbicidally effective amount of a compound of formula (I) as defined in claim 1, or of a composition comprising such a compound, to the plants or to the locus thereof.

42. A herbicidal composition, which, in addition to comprising formulation adjuvants, comprises a herbicidally effective amount of a compound of formula (I) as defined in claim 1.

43. A composition according to claim 42, which, in addition to comprising the compound of formula (I), comprises a further herbicide as mixing partner.

44. A composition according to claim 42, which, in addition to comprising the compound of formula (I), comprises a safener.

45. A composition according to claim 42, which, in addition to comprising the compound of formula (I), comprises a further herbicide as mixing partner and a safener.

46. A compound according to claim 1, wherein when G is a latentiating group then G is a group $-C(X^a)-R^a$ or $-C(X^b)-X^c-R^b$, and the meanings of $X^a$, $R^a$, $X^b$, $X^c$ and $R^b$ are as defined in claim 1.

47. A method as claimed in claim 41, in which a herbicidally effective amount of the composition comprising the compound of formula (I) as defined in claim 1 is applied to the plants or to the locus thereof, and wherein the crops of useful plants are cereals, cotton, soybeans, sugar beet, sugar cane, plantation crops, rape, maize or rice.

* * * * *